US012618081B2

(12) United States Patent　　　(10) Patent No.: US 12,618,081 B2
Tholl et al.　　　　　　　　　　　　(45) Date of Patent: May 5, 2026

(54) BROWN MARMORATED AND HARLEQUIN STINK BUG PHEROMONE ENZYME SYNTHESIS AND USES THEREOF

(71) Applicant: VIRGINIA TECH INTELLECTUAL PROPERTIES, INC., Blacksburg, VA (US)

(72) Inventors: Dorothea Tholl, Blacksburg, VA (US); Jason Lancaster, Blacksburg, VA (US)

(73) Assignee: VIRGINIA TECH INTELLECTUAL PROPERTIES, INC., Blacksburg, VA (US)

( * ) Notice: Subject to any disclaimer, the term of this patent is extended or adjusted under 35 U.S.C. 154(b) by 674 days.

(21) Appl. No.: 17/637,627

(22) PCT Filed: Aug. 21, 2020

(86) PCT No.: PCT/US2020/047538
§ 371 (c)(1),
(2) Date: Feb. 23, 2022

(87) PCT Pub. No.: WO2021/041270
PCT Pub. Date: Mar. 4, 2021

(65) Prior Publication Data
US 2022/0372509 A1　　Nov. 24, 2022

Related U.S. Application Data

(60) Provisional application No. 62/891,148, filed on Aug. 23, 2019.

(51) Int. Cl.
| C12N 15/82 | (2006.01) |
| C12N 9/00 | (2006.01) |
| C12N 9/02 | (2006.01) |
| C12N 9/88 | (2006.01) |
| C12N 9/90 | (2006.01) |

(52) U.S. Cl.
CPC ....... *C12N 15/8286* (2013.01); *C12N 9/0081* (2013.01); *C12N 9/88* (2013.01); *C12N 9/90* (2013.01)

(58) Field of Classification Search
CPC ..... C12N 15/8286; C12N 9/0081; C12N 9/90
See application file for complete search history.

(56) References Cited

FOREIGN PATENT DOCUMENTS

WO　　　2020096711 A1　　9/2019

OTHER PUBLICATIONS

Lancaster et al. (Published : Aug. 6, 2018, Database: NCBI GenBank),locus MG662378 as Murgantia histrionica terpene synthase (TPS) mRNA, complete cds, (Year: 2018).*

Lancaster'2 et al. (Published : Aug. 6, 2018, Database: NCBI GenBank). locus AVZ23977 as terpene synthase from Murgantia histrionica. (Year: 2018).*
Khrimian et al. (Published 2014, Journal: Journal of Natural Products, vol. 77, pp. 1708-1717) (Year: 2014).*
Khrimian et al. (Published 2014, Journal: J. Chem Ecol., vol. 40, pp. 1260-1268) (Year: 2014).*
Sparks et al. (Published 2017, Journal: Insects, vol. 8, 55, pp. 1-22). (Year: 2017).*
Ding et al. (Published 2013, Journal: Nature communications, vol. 5:3353, pp. 1-7). (Year: 2013).*
Guo et al. (Published Year: 2004, Journal: Proceedings of the National Academy of Sciences, vol. 101(25), pp. 9205-9210) (Year: 2004).*
Bruce et al.(Published Year: 2015, Journal: Scientific reports, vol. 5:11183, pp. 1-9). (Year: 2015).*
Beran et al. (Published Year: 2016, Journal: PNAS, vol. 113, pp. 2922-2927). (Year: 2016).*
Ludwig et al. (Published Year: 2016, Journal: PNAS, vol. 113, pp. 2922-2927). (Year: 2016).*
Anderson, et al., "Terpenes and sesquiterpenes of Chamaecyparis nootkatensis leaf oil," Phytochemistry, vol. 9 1970.
Beran, et al., "Novel family of terpene synthases evolved from trans-isoprenyl diphosphate synthases in a flea beetle," Proc. Natl. Acad. Sci. USA, vol. 113 Mar. 15, 2016.
Blassioli-Moraes, et al., "ex pheromone communication in two sympatric neotropical stink bug species *Chinavia ubica* and *Chinavia impicticornis*," J. Chem. Ecol., vol. 38 Jun. 13, 2012.
Blomquist, et al., "Gary J. Blomquist, Rubi Figueroa-Teran, Mory Aw, Minmin Song, Andrew Gorzalski, Nicole L. Abbott, Eric Chang, Claus Tittiger," Insect Biochemistry and Molecular Bio., vol. 40 2010.
Bohlmann, et al., "Sesquiterpenes and acetylenes from *Argyranthemum adauctum* ssp *jacobaeifolium*," Phytochemistry, vol. 23 1984.
Borges, et al., Sex attractant pheromone from the rice stalk stink bug, *Tibraca limbativentris* Stal. J. Chem. Ecol., vol. 32 Nov. 7, 2006.
Borges, et al., "A male-produced sex pheromone from the neotropical redbanded stink bug, *Piezodorus guildinii*," J Chem Ecol., vol. 33 Apr. 24, 2007.
Burse, et al., "Always being well prepared for defense: The production of deterrents by juvenile Chrysomelina beetles (Chrysomelidae)," Phytochemistry, vol. 70 Sep. 4, 2009.
Byers, et al., "Floral volatile alleles can contribute to pollinator-mediated reproductive isolation in monkeyflowers (Mimulus)," Plant J., vol. 80 Dec. 2014.

(Continued)

*Primary Examiner* — Amjad Abraham
*Assistant Examiner* — Santosh Sharma
(74) *Attorney, Agent, or Firm* — Carin R. Miller; Lex Generalis, LLC

(57)　　　　　　ABSTRACT

Described herein are engineered polynucleotides and vectors capable of encoding one or more engineered harlequin and/or brown marmorated stink bug pheromone synthesis enzymes. Also described herein are engineered harlequin and/or brown marmorated stink bug pheromone synthesis enzymes. Also described herein are methods of making modified plants capable of expressing one or more harlequin and/or brown marmorated stink bug pheromone synthesis enzymes.

2 Claims, 40 Drawing Sheets

Specification includes a Sequence Listing.

(56) References Cited

OTHER PUBLICATIONS

Cai, et al., "A cDNA clone for beta-caryophyllene synthase from Artemisia annua," Phytochemistry, vol. 61 2002.

Cantin, et al., "Isolation, structural assignment and insecticidal activity of (−)-(1S,2R,3R,4S)-1,2-epoxy-1-methyl-4-(1-methylethyl)-cyclohex-3-yl acetate, a natural product from Minthostachys tomentosa," Tetrahedron-Asymmetry, vol. 12 2001.

Cool, Laurence G., "Sesquiterpene alcohols from foliage of Fitzroya cupressoides," Phytochemistry, vol. 42 1996.

Cribb, et al., "Unicellular pheromone glands of the pentatomid bug Nezara viridula (Heteroptera: Insecta): ultrastructure, classification, and proposed function," J Morphol., vol. 267 2006.

Crooks, et al., "WebLogo: a sequence logo generator," Genome Res., vol. 14 2004.

Ditengou, et al., "Volatile signalling by sesquiterpenes from ectomycorrhizal fungi reprogrammes root architecture," Nat. Commun., vol. 6 Feb. 23, 2015.

Frater, et al., "Synthesis of (+)-(4S,8R)-8-epi-beta-bisabolol and (−)-(4R,8S)-4-epi-beta-bisabolol," Helv Chim Acta, vol. 72 1989.

Hagiwara, et al., "Total synthesis of bisabolane sesquiterpenoids, alpha-bisabol-1-one, curcumene, curcuphenol and elvirol: utility of catalytic enamine reaction in cyclohexenone synthesis," J Chem Soc Perk T., vol. 1 Mar. 1, 2002.

Harris, C.S., "The anatomy and histology of the alimentary system of the harlequin cabbage bug, Murgantia histrionica Hahn. (Hemiptera: Pentatomidae)," Ohio J Sci. vol. 38, No. 6 1938.

Huang, et al., "The major volatile organic compound emitted from Arabidopsis thaliana flowers, the sesquiterpene (E)-β-caryophyllene, is a defense against a bacterial pathogen," New Phytol., vol. 193 2012.

Huang, et al., "Sesquiterpenes produced by truncated taxadiene synthase," Tetrahedron Letters, vol. 41 2000.

Jia, et al., "Microbial-type terpene synthase genes occur widely in nonseed land plants, but not in seed plants," Proc. Natl. Acad. Sci. USA, vol. 113 Oct. 25, 2016.

Junker, et al., "Covariation and phenotypic integration in chemical communication displays: biosynthetic constraints and ecoevolutionary implications," New Phytol., vol. 220 2017.

Junker, et al., "Volatile organic compound mediated interactions at the plantmicrobe interface," J. Chem. Ecol., vol. 39 2013.

Khrimian, et al., "Discovery of the aggregation pheromone of the brown marmorated stink bug (Halyomorpha halys) through the creation of stereoisomeric libraries of 1-bisabolen-3-ols," J. Nat. Prod., vol. 77 2014.

Kong, et al., "Btrim: a fast, lightweight adapter and quality trimming program for nextgeneration sequencing technologies," Genomics, vol. 98 May 30, 2011.

Kumar, et al., "Molecular diversity of terpene synthases in the liverwort Marchantia polymorpha," Plant Cell, vol. Oct. 28, 2016.

Lai, et al., "quemao, a Drosophila bristle locus, encodes geranylgeranyl pyrophosphate synthase," Genetics, vol. 149 Jun. 1998.

Leskey, et al., "Behavioral responses of the invasive Halyomorpha halys (Stal) to traps baited with stereoisomeric mixtures of 10,11-epoxy-1-bisabolen-3-ol," J Chem Ecol., vol. 41 Apr. 9, 2015.

Martins, et al., "Oenocytes in insects," Invert Surviv J., vol. 9 Aug. 17, 2012.

Millar, et al., "Rapid and simple isolation of zingiberene from ginger essential Oil," J Nat Prod., vol. 61 Mar. 4, 1998.

Moraes, et al., "The chemical volatiles (semiochemicals) produced by neotropical stink bugs (Hemiptera: Pentatomidae)," Neotrop. Entomol., vol. 37 Oct. 2008.

Muller, et al., "Essential oil components as pheromones. A review," Flavour Frag J., vol. 26, Apr. 28, 2011.

Osbourn, et al., "The saponins - polar isoprenoids with important and diverse biological activities," Nat. Prod. Rep., vol. 28 2011.

Pickett, et al., "The semiochemistry of aphids," Nat. Prod. Rep., vol. 30 Apr. 22, 2013.

Qiu, et al., "An insect-specific P450 oxidative decarbonylase for cuticular hydrocarbon biosynthesis," Proc Natl Acad Sci USA, vol. 109, No. 37 Sep. 11, 2012.

Quin, et al., "Traversing the fungal terpenome," Nat. Prod. Rep., vol. 31 Oct. 2014.

Raguso, et al., "More lessons from linalool: insights gained from a ubiquitous floral volatile," Curr. Opin. Plant Biol., vol. 32 2016.

Rasmann, et al., "Recruitment of entomopathogenic nematodes by insect-damaged maize roots," Nature, vol. 434 Apr. 7, 2005.

Robert, et al., "Herbivore-induced plant volatiles mediate host selection by a root herbivore," New Phytol., vol. 194 2012.

Sandstrom, et al., "Functional expression of a bark beetle cytochrome P450 that hydroxylates myrcene to ipsdienol," Insect Biochem Mol Biol., vol. 36 Aug. 4, 2006.

Schneider, et al., "Sequence logos: a new way t display consensus sequences," Nucleic Acids Res., vol. 18, No. 20 1990.

Sobotnik, et al., "Chemical warfare in termites," J. Insect Physiol., vol. 56, Feb. 22, 2010.

Song, et al., "Functional characterization of myrcene hydroxylases from two geographically distinct Ips pini populations," Insect Biochem Mol Biol., vol. 43 Jan. 15, 2013.

Sparks, et al., "Transcriptome of the invasive brown marmorated stink bug, Halyomorpha halys (Stal) (Heteroptera: Pentatomidae)," Plos One, vol. 9, No. 11, e111646 Nov. 2014.

Staddon, et al., "Gland Regional and Spatial Patterns in the Abdominal Sternites of Some Pentatomoid Heteroptera," Annls Soc. ent. Fr., vol. 27, No. 2 1991.

Sy, et al., "Oxygenated bisabolanes from Alpinia densibracteata," Phytochemistry, vol. 45, No. 3 1997.

Tarshis, et al., Regulation of product chain length by isoprenyl diphosphate synthases. Proc. Natl. Acad. Sci. USA, vol. 93 Dec. 1996.

Tarshis, et al., "Crystal structure of recombinant farnesyl diphosphate synthase at 2.6 Angstrom resolution," Biochemistry, vol. 33 Aug. 15, 1994.

Tholl, et al., "Two sesquiterpene synthases are responsible for the complex mixture of sesquiterpenes emitted from Arabidopsis flowers," Plant J., vol. 42 Mar. 18, 2005.

Vaughan, et al., "Formation of the unusual semivolatile diterpene rhizathalene by the Arabidopsis class I terpene synthase TPS08 in the root stele is involved in defense against belowground herbivory," Plant Cell, vol. 25 Mar. 2013.

Millar, Jocelyn G., "Pheromones of True Bugs," Topics in Current Chemistry, vol. 2005 2005.

Paiero, S.M., et al., "Stink bugs (Pentatomidae) and parent bugs (Acanthosomatidae) of Ontario and adjacent areas: A key to species and a review of the fauna," Canadian Journal of Arthropod Identification, vol. No. 24 Aug. 2013.

Ramirez, et al., "Morphometric Analysis of the Host Effect on Phenotypical Variation of Belminus ferroae (Hemiptera: Triatominae)," Psyche, Article ID 613614, vol. 2015, No. 1 Nov. 5, 2015.

Froeschner, Richard C., "Family Pentatomidae Leach, 1815: The Stink Bugs." In Catalog of the Heteroptera, or True Bugs, of Canada and the Continental United States 1988.

Arnett, Jeffrey Jensen, "Emerging adulthood: A theory of development from the late teens through the twenties," American Psychologist, vol. 55, No. May 5, 2000.

Leskey, et al., "Pest Status of the Brown Marmorated Stink Bug, Halyomorpha halys in the USA," Outlooks on Pest Management, vol. 23 Oct. 2012.

Agrawal, et al., "A Role for Isothiocyanates in Plant Resistance Against the Specialist Herbivore Pieris rapae," Journal of Chemical Ecology, vol. 29, No. 6, Jun. 2003.

Aliabadi, et al., "Sequestration of Glucosinolates By Harlequin Bug Murgantia histrionica," Journal of Chemical Ecology, vol. 28, No. 9, Sep. 2002.

Aldrich, et al., "Chemical Ecology of the Heteroptera," Ann. Rev. Entomol., vol. 33 1988.

Ishiwatari, Taketoshi, "Studies on the Scent of Stink Bugs (Hemiptera : Pentatomidae) II. Aggregation Pheromone Activity," Appl. Ent. Zool. vol. 11, No. 1 1976.

Stokl, et al., "Evolutionary origin of insect pheromones," Current Opinion in Insect Science, vol. 24 2017.

Blomquist, et al., "Biosynthesis and detection of pheromones and plant volatiles—introduction and overview," PNAS, vol. 113 2003.

Jurenka, et al., "Insect Pheromone Biosynthesis," vol. 239 2004.

(56)         References Cited

OTHER PUBLICATIONS

Yew, et al., "Insect pheromones: An overview of function, form, and discovery," Prog Lipid Res., vol. 59 Jun. 15, 2015.

Tillman, et al., "Insect pheromones—an overview of biosynthesis and endocrine regulation," Insect Biochem Mol Biol., vol. 29 Feb. 1999.

Bartelt, et al., "Male-Specific Sesquiterpenes From Phyllotreta and Aphthona Flea Beetles," Journal of Chemical Ecology, vol. 27, No. 12, Dec. 2001.

Brown, et al., "Identification of (−)-β-Caryophyllene as a Gender-Specific Terpene Produced by the Multicolored Asian Lady Beetle," J Chem Ecol., vol. 32 Oct. 5, 2006.

Dewhirst, et al., "Aphid Pheromones," Vitamins and Hormones, vol. 83 2010.

Sillam-Dusses, et al., "Identification by GC-EAD of the two-component trail-following pheromone of Prorhinotermes simplex (Isoptera, Rhinotermitidae, Prorhinotermitinae)," Journal of Insect Physiology, vol. 55 Apr. 14, 2009.

Tholl, et al., "Biosynthesis and Biological Functions of Terpenoids in Plants," Adv Biochem Eng Biotechnol., vol. 148 Jan. 13, 2015.

Chen, et al., "The family of terpene synthases in plants: a mid-size family of genes for specialized metabolism that is highly diversified throughout the kingdom," The Plant Journal, vol. 66 Jan. 31, 2011.

Christianson, et al., "Structural and Chemical Biology of Terpenoid Cyclases," Chemical Reviews, vol. 117 Aug. 25, 2017.

Degenhardt, et al., "Monoterpene and sesquiterpene synthases and the origin of terpene skeletal diversity in plants," Phytochemistry, vol. 70 Sep. 28, 2009.

Dickschat, et al., "Bacterial terpene cyclases," Natural Product Reports, The Royal Society, vol. 33 2016.

Noriega, Fernando G., "Juvenile Hormone Biosynthesis in Insects: What Is New, What Do We Know, and What Questions Remain?" ISRN Zoology Oct. 19, 2014.

Cusson et al., "Characterization and Tissue-Specific Expression of Two Lepidopteran Farnesyl Diphosphate Synthase Homologs: Implications for the Biosynthesis of Ethyl-Substituted Juvenile Hormones," vol. 65 2006.

Ma, et al., "Molecular cloning and characterization of a prenyltransferase from the cotton aphid, Aphis gossypii," Insect Biochemistry and Molecular Biology, vol. 40 May 18, 2010.

Sen, et al., "Purification, properties and heteromeric association of type-1 and type-2 lepidopteran farnesyl diphosphate synthases," Insect Biochemistry and Molecular Biology, vol. 37 May 15, 2007.

Taban, et al., "Isolation and Characterization of Farnesyl Diphosphate Synthase From the Cotton Boll Weevil, Anthonomus grandis," Archives of Insect Biochemistry and Physiology, vol. 71, No. 2 2009.

Vandermoten, et al., "Characterization of a novel aphid prenyltransferase displaying dual geranyl/farnesyl diphosphate synthase activity," FEBS Letters, vol. 582 May 6, 2008.

Frick, et al., "Metal ions control product specificity of isoprenyl diphosphate synthases in the insect terpenoid pathway," PNAS, vol. 110, No. 11 Mar. 3, 2013.

Lewis, et al., "Cloning and characterisation of a prenyltransferase from the aphid Myzus persicae with potential involvement in alarm pheromone biosynthesis," Insect Molecular Biology, vol. 17, No. 4 2008.

Gilg, et al., "Unique animal prenyltransferase with monoterpene synthase activity," Naturwissenschaften, vol. 96 Mar. 10, 2009.

Beran, et al., "Novel family of terpene synthases evolved from trans-isoprenyl diphosphate synthases in a flea beetle," PNAS, vol. 113, No. 11 Mar. 15, 2016.

Beran, et al., "The Aggregation Pheromone of Phyllotreta striolata (Coleoptera: Chrysomelidae) Revisited," J Chem Ecol., vol. 42 Aug. 12, 2016.

Weber, et al., "Semiochemistry of Pentatomoidea In: McPherson, J.E., editor. Invasive Stink Bugs and Related Species (Pentatomoidea): Biology, Higher Systematics, Semiochemistry, and Management. Boca Raton, FL. CRC Press. ," 2018.

Borges, et al., "Long-range mate location and close-range courtship behaviour of Green Stink Bug, Nezara viridula and its mediation by sex pheromones," Entomol. exp. appl., vol. 44 1987.

Cokl, et al., "Comparison of Substrate-Borne Vibrational Signals of Two Stink Bug Species, Acrosternum hilare and Nezara viridula (Heteroptera: Pentatomidae)," Entomological Society of America, vol. 94, No. 3 2001.

Miklas, et al., "Variability of vibratory signals and mate choice selectivity in the southern green stink bug," Behavioural Processes, vol. 61 2003.

Borges, et al., "Field responses of stink bugs to the natural and synthetic pheromone of the Neotropical brown stink bug, Euschistus heros (Heteroptera: Pentatomidae)," Physiological Entomology, vol. 23 1998.

Zahn, et al., "Identification, Synthesis, and Bioassay of a Male-Specific Aggregation Pheromone from the Harlequin Bug, Murgantia histrionica," J Chem Ecol., vol. 34, No. 2 Jan. 19, 2008.

Tillman, et al., Pheromone Attraction and Cross-Attraction of Nezara, Acrosternum, and Euschistus spp. Stink Bugs (Heteroptera: Pentatomidae) in the Field, Chemical Ecology, vol. 39, No. 2 Apr. 2010.

Khrimian, et al., "Determination of the Stereochemistry of the Aggregation Pheromone of Harlequin Bug, Murgantia histrionica," J Chem Ecol., vol. 40 Nov. 19, 2014.

McBrien, et al., "Sex Attractant Pheromone of the Red-Shouldered Stink Bug Thyanta pallidovirens: A Pheromone Blend With Multiple Redundant Components," J Chem Ecol., vol. 28, No. 9 Sep. 2002.

Sparks, et al., "A Transcriptome Survey Spanning Life Stages and Sexes of the Harlequin Bug, Murgantia histrionica," Insects, vol. 8, No. 55 May 25, 2017.

Bansal, et al., "Expansion of cytochrome P450 and cathepsin genes in the generalist herbivore brown marmorated stink bug," BMC Genomics, vol. 19, No. 60 2018.

Gershenzon, et al., "The function of terpene natural products in the natural world," Nature Chemical Biology, vol. 3, No. Jul. 7, 2007.

Aldrich, et al., "Artifacts and pheromone blends from Nezara spp. and other stink bugs (Heteroptera, Pentatomidae)," Z. Naturforsch. C Bio. Sci., vol. 48 1993.

Aldrich, et al., Pheromone strains of the cosmopolitan pest, Nezara viridula (Heteroptera, vol. 244 1987.

Lundgren, Jonathan G., "Reproductive ecology of predaceous Heteroptera," Biological Control 59, Feb. 23, 2011.

Gilg, et al., "Isolation and functional expression of an animal geranyl diphosphate synthase and its role in bark beetle pheromone biosynthesis," PNAS, vol. 102, No. 28, Jul. 12, 2005.

De Oliveira, et al., "Zingiberenol, (1S,4R,1'S)-4-(1',5'-Dimethylhex-4'-enyl)-1-methylcyclohex-2-en-1-ol, Identified as the Sex Pheromone Produced by Males of the Rice Stink Bug Oebalus poecilus (Heteroptera: Pentatomidae)," Journal of Agricultural and Food Chemistry, Jul. 24, 2013.

Zeilinger, et al., "Competition between stink bug and heliothine caterpillar pests on cotton at within-plant spatial scales," Entomologia Experimentalis et Applicata, vol. 141, Jul. 28, 2011.

Wallrapp, et al., "Prediction of function for the polyprenyl transferase subgroup in the isoprenoid synthase superfamily," Proc. Natl. Acad. Sci. USA, vol. 110 Mar. 14, 2013.

Weber, et al., "Attractiveness of harlequin bug, Murgantia histrionica, aggregation pheromone: Field response to isomers, ratios, and dose," J. Chem. Ecol., vol. 40 Nov. 8, 2014.

Zhou, et al., "Tissue-Specific Emission of (E)-alpha-Bergamotene Helps Resolve the Dilemma When Pollinators Are Also Herbivores," Curr Biol., vol. 27 May 8, 2017.

Zi, et al., "To gibberellins and beyond! Surveying the evolution of (di)terpenoid metabolism," Annu. Rev. Plant Biol., vol. 65 2014.

Christianson, et al., "Structural biology and chemistry of the terpenoid cyclases," Chem Rev., vol. 106 Jun. 1, 2006.

Haye, et al., "Range expansion of the invasive brown marmorated stinkbug, Halyomorpha halys: an increasing threat to field, fruit and vegetable crops worldwide," J Pest Sci., vol. 88 May 5, 2015.

Hoebeke, et al., "Halyomorpha halys (Stal) (Heteroptera : Pentatomidae): A polyphagous plant pest from Asia newly detected in North America," P Entomol Soc Wash., vol. 105 Jan. 13, 2003.

(56)  References Cited

OTHER PUBLICATIONS

Kellogg, et al., "Chain elongation in the isoprenoid biosynthetic pathway," Curr Opin Chem Biol., vol. 1 1997.

McPherson, et al., "Comparison of male genitalia of Murgantia histrionica, M. varicolor, and M. violascens (Hemiptera: Heteroptera: Pentatomidae)," P Entomol Soc Wash. vol. 110, No. 4 2008.

Sacchettini, et al., "Biochemistry—Creating isoprenoid diversity," Science, vol. 277 1997.

Sen, et al., "Purification, properties and heteromeric association of type-1 and type-2 lepidopteran farnesyl diphosphate synthases," Insect Biochem Mol Biol., vol. 37 2007.

Thulasiram, et al., "Chimeras of two isoprenoid synthases catalyze all four coupling reactions in isoprenoid biosynthesis," Science, vol. 316 2007.

Vandermoten, et al., "New insights into short-chain prenyltransferases: structural features, evolutionary history and potential for selective inhibition," Cell Mol Life Sci., vol. 66 Jul. 26, 2009.

Xu et al., "Tracing the origin of US brown marmorated stink bug, *Halyomorpha halys*," Biol Inv., vol. 16 Jul. 17, 2013.

Zahn, et al., Annals of the Entomological Society of America, vol. 101, Issue 1 2008.

Tillman, et al., "Trap Cropping Systems and a Physical Barrier for Suppression of Stink Bugs (Hemiptera: Pentatomidae) in Cotton," Entomological Society of America, vol. 108, No. 5 Oct. 2015.

Laskowski, R. A., "PDBsum: summaries and analyses of PDB structures," Nucleic Acids Res., vol. 29, No. 1 Aug. 31, 2001.

Livak, et al., "Analysis of relative gene expression data using realtime quantitative PCR and the 2(-Delta Delta C(T))," Method. Methods, vol. 25 2001.

* cited by examiner

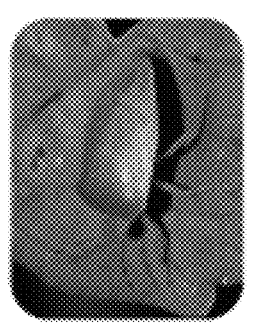
Southern Green
Stink Bug
*Nezara viridula*
cis-(2Z)-(6S)-bisabolene epoxide
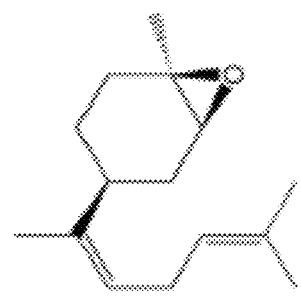
Brown Marmorated
Stink Bug
*Halyomorpha halys*
(SSRS/RSRS)-murgantiol
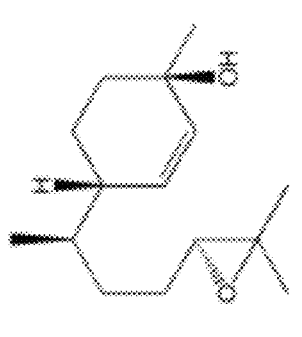
Harlequin Bug
*Murgantia histrionica*
(SSRS/SSRR)-murgantiol
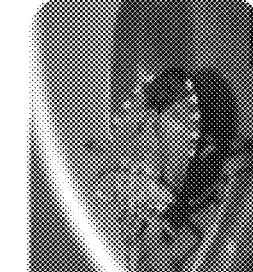
FIG. 1

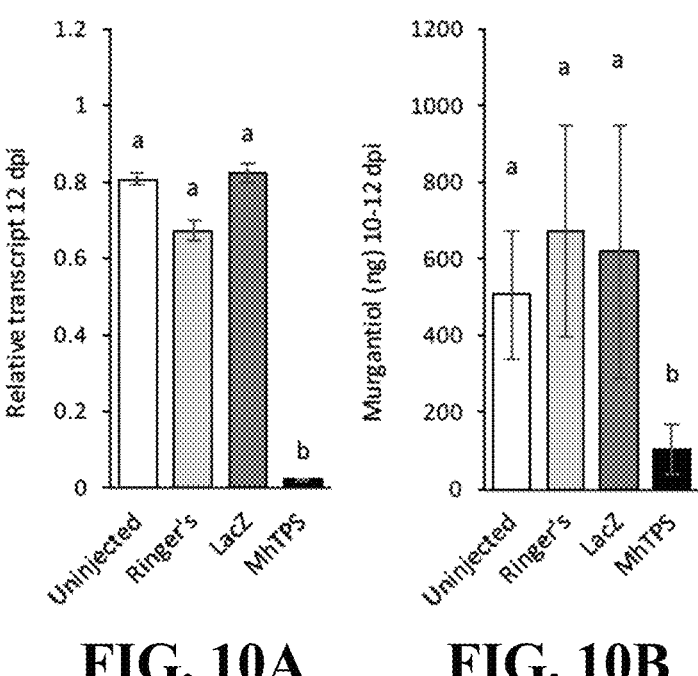
FIG. 10A     FIG. 10B
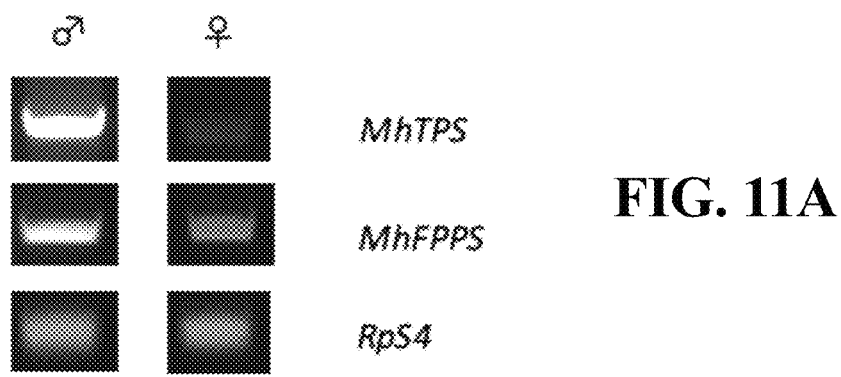
FIG. 11A
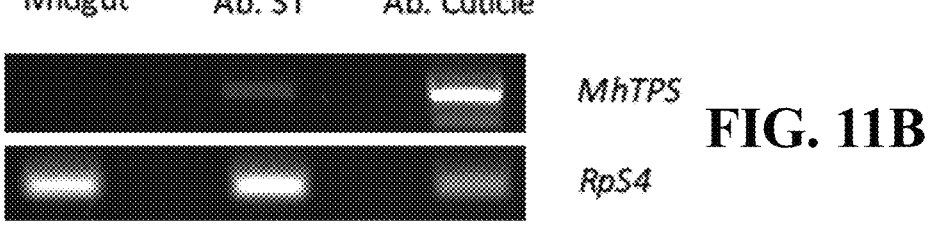
FIG. 11B

Retention time (min)

Retention time (min)

1S,6S,7R-sesquipiperitol 3          1R,6S,7R-sesquipiperitol 4

TPS and atypical IDS proteins
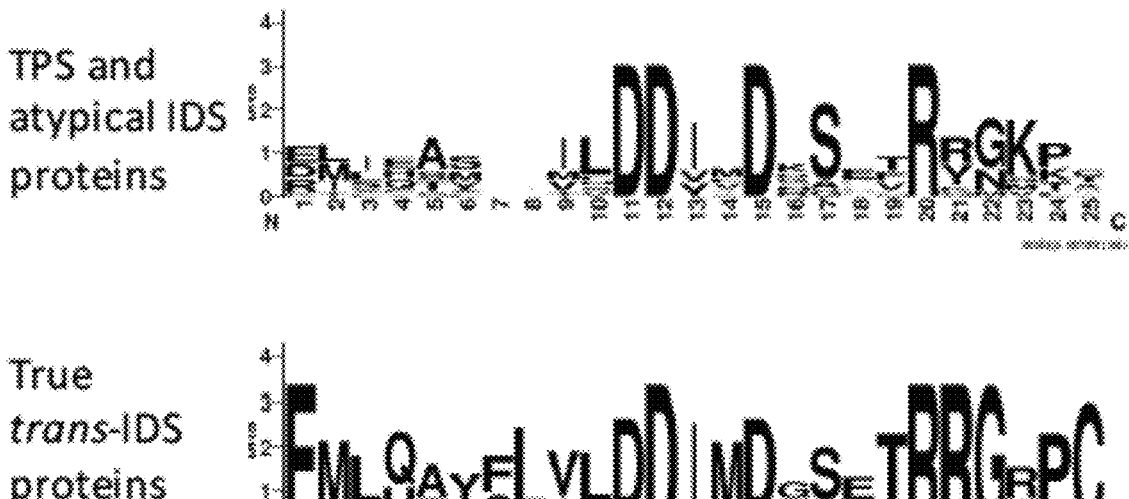
True *trans*-IDS proteins
TPS and atypical IDS proteins
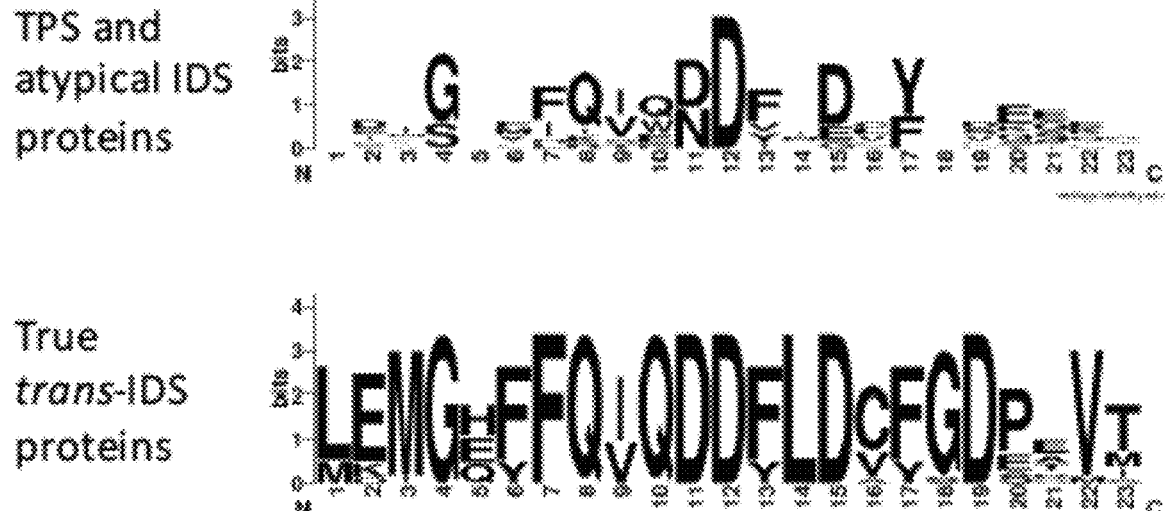
True *trans*-IDS proteins
FIG. 15B

| Position | 3 | | 4 | |
|---|---|---|---|---|
| | δ $^1$H (600 MHz, $J$ in Hz) | δ $^{13}$C (151 MHz) | δ $^1$H (600 MHz, $J$ in Hz) | δ $^{13}$C (151 MHz) |
| 1 | 4.01 m; OH ~1.20 m | 69.2 | 4.12 m; OH 1.07 br d, 6.6 | 65.4 |
| 2 | 5.37 br s | 125.7 | 5.60 br d, 5.4 | 123.7 |
| 3 | | 137.4 | | 139.7 |
| 4 | 4a, 1.87 m | 30.5 | 4a, 1.93 m | 30.9 |
| | 4b, 1.93 m | | 4b, 1.98 dd, 18.0, 5.4 | |
| 5 | 5a, 1.27 m | 20.8 | 5a, 1.34, dddd, 13.2, 12.6, 5.4 | 20.3 |
| | 5b, 1.60 m | | 5b, 1.66 m | |
| 6 | 1.30 m | 46.5 | 1.13 m | 44.2 |
| 7 | 1.89 m | 31.0 | 1.55 m | 32.9 |
| 8 | 1.29 m | 35.5 | 8a, 1.17 m | 34.3 |
| | | | 8b, 1.57 m | |
| 9 | 9a, 1.95 m | 26.2 | 9a, 1.92 m | 25.2 |
| | 9b, 2.00 m | | 9b, 2.02 m | |
| 10 | 5.10 tm, 6.0 | 124.8 | 5.11 tm, 6.0 | 125.0 |
| 11 | | 131.2 | | 131.2 |
| 12 | 1.58 br s | 17.7 | 1.58 br s | 17.7 |
| 13 | 1.656 br s | 25.7 | 1.66 br s | 25.7 |
| 14 | 0.80 d, 6.6 | 14.4 | 0.94 d, 6.6 | 17.2 |
| 15 | 1.660 br s | 23.1 | 1.67 br s | 23.4 |

Assignments were aided by DEPT, COSY, and HSQC recordings

FIG. 17

| Gene | Query Sequences (tblastn) | *M. histrionica* Acc. Nos. |
|---|---|---|
| *MhTPS* | *Ips pini* FPPS (AAX55631.1) | MG662378.1; GECQ01420512.1 |
| | *Ips pini* GPPS/TPS (AY953508) | |
| | *Bombyx mori* FPPS (NP_001036889) | |
| | *Bombyx mori* FPPS2 (NP_001093301) | |
| | *Drosophila melanogaster* FPPS (NP_477380) | |
| *MhFPPS* | *Ips pini* FPPS (AAX55631.1) | MG662379.1; GECQ01414919.1 |
| | *Ips pini* GPPS/TPS (AY953508) | |
| | *Bombyx mori* FPPS (NP_001036889) | |
| | *Bombyx mori* FPPS2 (NP_001093301) | |
| | *Drosophila melanogaster* FPPS (NP_477380) | |

FIG. 18

| Gene | Primers (5'-3') | Amplicon size (bp) | Purpose |
|---|---|---|---|
| MhTPS | MhTPS_1F<br>ATGGTCTCCATTGCTGCTAAG SEQ ID NO: 40<br>MhTPS_1158R<br>TTACCCACTAATGTTCAAACATAAAGC SEQ ID NO: 41 | 1158 | Blunt-end cloning into pGEM |
| | MhTPS_FusF1 SEQ ID NO: 42<br>TCAGTCGACTGGATCCGG (ATGGTCTCCATTGCTGCTAAGT)* SEQ ID NO: 114<br>MhTPS_FusR1<br>CTAGATATCTCGAGTGCGGCC SEQ ID NO: 43<br>(CTACCCACTAATGTTCAAACATAAAGCA)* SEQ ID NO: 44 | 1197 | Gibson assembly into F4/F5 amplified pENTR4<sup>Ncos</sup> |
| | NtagMhTPS_FusF<br>GGATCCGTGGTCTCCATTGCTGC SEQ ID NO: 45<br>NtagMhTPS_FusR<br>GGAGACCACGGATCCAGTCGACTG SEQ ID NO: 46 | 1195 | Gibson assembly into F4/F5 amplified pENTR4<sup>Ncos</sup><br>with N-terminal His tag |
| | MhTPS_QF<br>ACGATGTCAGCAGTTCTAGATG SEQ ID NO: 47<br>MhTPS_QR<br>AGCAGTACTTTCACCCCCTTG SEQ ID NO: 48 | 99 | qRT-PCR |
| | MhTPS_dsRNA1F<br>AAGGTTGGCATATGATCTGTC SEQ ID NO: 49<br>MhTPS_dsRNA1R<br>CGCAACAAATTGTCCTGC SEQ ID NO: 50 | 260 | Generate DNA template for synthesis of dsRNA |
| | MhTPS_dsRNA1F_T7<br>TAATACGACTCACTATAGGGAGAAAGGTTGGCATATGATCTGTC SEQ ID NO: 51<br>MhTPS_dsRNA1R_T7<br>TAATACGACTCACTATAGGGAGACGCAACAAATTGTCCTGC SEQ ID NO: 52 | 306 | Add T7 sites to DNA template for synthesis of dsRNA |
| MhFPPS | MhFPPS_1F<br>ATGCCGTTTACCAAAATGTGC SEQ ID NO: 53<br>MhFPPS_1218R<br>TTACTGCTTTCTACCATATAACTTATGGAGT SEQ ID NO: 54 | 1218 | Blunt-end cloning into pGEM |
| | tMhFPPS_1F<br>GGAGTTGCAATACGTCCAC SEQ ID NO: 55<br>MhFPPS_1218R<br>TTACTGCTTTCTACCATATAACTTATGGAGT SEQ ID NO: 56 | 1045 | Truncation of MhFPPS to remove putative transit peptide (bp 175-1218) |
| 18S | Mh18S_448F<br>TTAAGTCGAACAGCCCGAGC SEQ ID NO: 57<br>Mh18S_546R<br>TCCGAAAAACCCCGCTTTTG SEQ ID NO: 58 | 99 | qRT-PCR |
| pENTR4<sup>Ncos</sup> | pENTR4_F4<br>GGCCGCACTCGAGATATCTA SEQ ID NO: 59<br>pENTR4_R5<br>CCGGATCCAGTCGACTGAAT SEQ ID NO: 60 | 2280 | Linearize pENTR4<sup>Ncos</sup> for Gibson Assembly |

* brackets denote gene specific sequence

FIG. 19

Midgut    Fat body    Ab. St.

*HhTPS1*

*Hh18S*

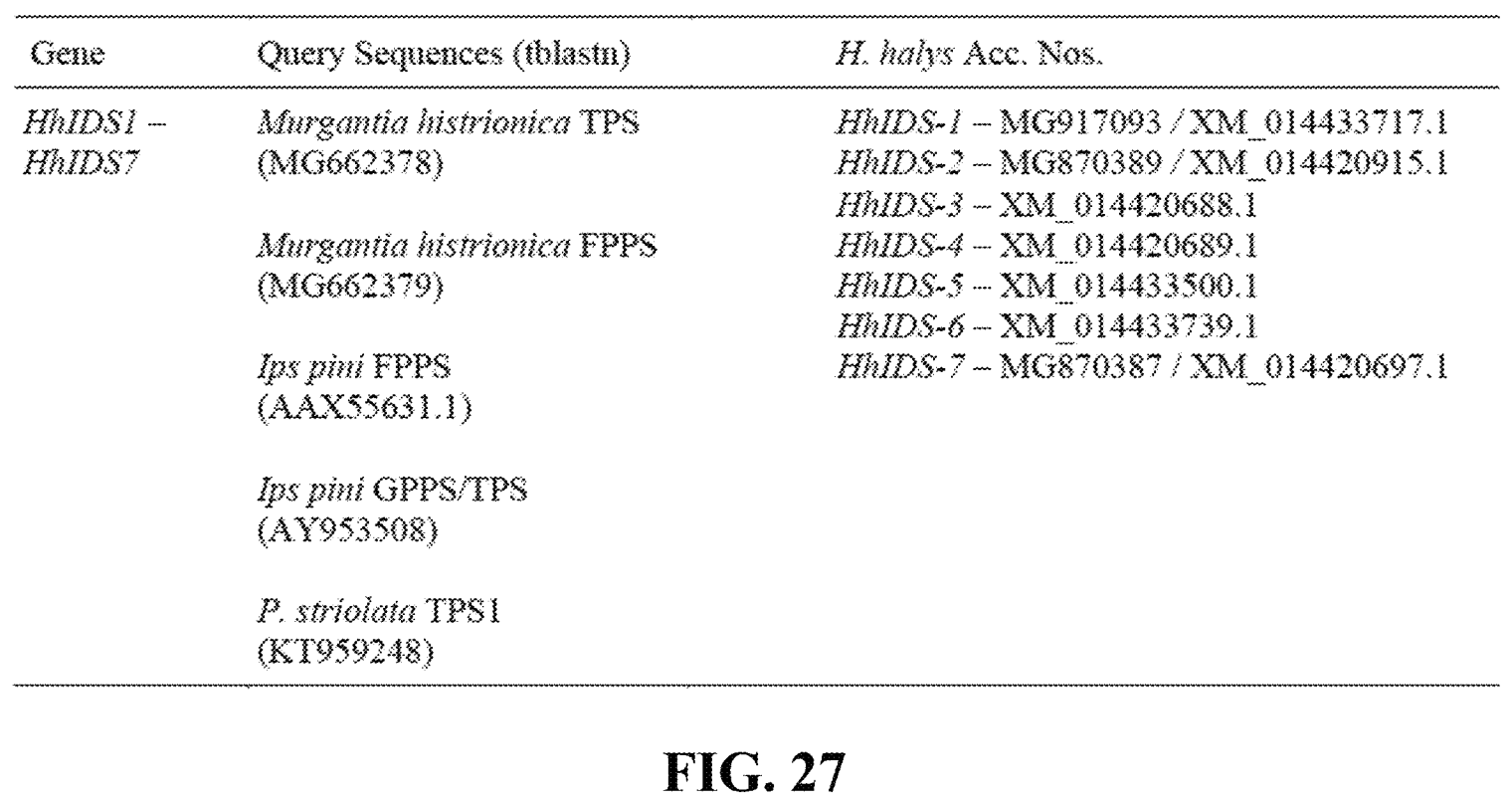

| Gene | Query Sequences (tblastn) | H. halys Acc. Nos. |
|---|---|---|
| HhIDS1 – HhIDS7 | *Murgantia histrionica* TPS (MG662378) | *HhIDS-1* – MG917003 / XM_014433717.1 |
| | | *HhIDS-2* – MG870389 / XM_014420915.1 |
| | *Murgantia histrionica* FPPS (MG662379) | *HhIDS-3* – XM_014420688.1 |
| | | *HhIDS-4* – XM_014420689.1 |
| | | *HhIDS-5* – XM_014433500.1 |
| | *Ips pini* FPPS (AAX55631.1) | *HhIDS-6* – XM_014437739.1 |
| | | *HhIDS-7* – MG870387 / XM_014420697.1 |
| | *Ips pini* GPPS/TPS (AY953508) | |
| | *P. striolata* TPS1 (KT959248) | |

FIG. 27

| Gene | Primers (5'-3') | Amplicon size (bp) | Purpose |
|---|---|---|---|
| HhIDS1/ HhTPS2 | HhIDS1_1F ATGATACCGAAGACGCTTGG SEQ ID NO: 64 HhIDS1_1134R TTATGGAGCTTTTAGGATCTCCAATTC SEQ ID NO: 65 | 1134 | Blunt-end cloning into pGEM |
| | HhIDS1_QF GCCAAGAAGCAGCCATCTATG SEQ ID NO: 66 HhIDS1_QR CACATCTTGGTGAAACCTGGATC SEQ ID NO: 67 | 100 | qRT-PCR |
| HhIDS2/ HhFPPS | HhFPPS_1F ATGCCTTTTGCAAAACTGTG SEQ ID NO: 68 HhFPPS_1212R CTACTGCTTTCTACCATACATCTTATG SEQ ID NO: 69 | 1212 | Blunt-end cloning into pGEM |
| HhIDS3 | HhIDS3_1F ATGGCGTTCGTGTCTGC SEQ ID NO: 70 HhIDS3_1125R TTAATCTAAATTTTCATCAGGAGTTTCTC SEQ ID NO: 71 | 1125 | Blunt-end cloning into pGEM |
| HhIDS4 | HhIDS4_1F ATGGCGAACATGGCTGG SEQ ID NO: 72 HhIDS4_1143R TCAAACATTCGTAACTTTAGGGTCSEQ ID NO: 73 | 1143 | Blunt-end cloning into pGEM |
| HhIDS5 | HhIDS5_1F ATGGCGTCAAAGGTGTCG SEQ ID NO: 74 HhIDS5_1131R TCAGAATGATTCTAATCTTTCAAGTTGAA SEQ ID NO: 75 | 1131 | Blunt-end cloning into pGEM |
| HhIDS6 | HhIDS6_1F ATGGCAGCGAAGGCATC SEQ ID NO: 76 HhIDS6_1131R TCAGAATGATTTTAATCGTTCAAGTTG SEQ ID NO: 77 | 1131 | Blunt-end cloning into pGEM |
| HhIDS7/ HhTPS1 | HhIDS7_1F ATGGCGTCCGTGGCTAC SEQ ID NO: 78 HhIDS7_1107R TCACTCTTCTCGAATCACGAGC SEQ ID NO: 79 | 1107 | Blunt-end cloning into pGEM |
| 18S | Hh18S_320F TCCCCTTTCGAGCAGGTATG SEQ ID NO: 80 Hh18S_419R AGCCTTTTCGCAGGTTTATGAG SEQ ID NO: 81 | 100 | RT-PCR and qRT-PCR |

FIG. 28

| Annotation | Transcript ID | Overall |
|---|---|---|
| Acetoacetyl-CoA thiolase | HBug_USDA-ARS_HBBL_267134 | 233.99 |
| Acetoacetyl-CoA thiolase | HBug_USDA-ARS_HBBL_63170 | 30.56 |
| HMG-CoA reductase | HBug_USDA-ARS_HBBL_421604 | 20.60 |
| HMG-CoA synthase | HBug_USDA-ARS_HBBL_575421 | 0.85 |
| Mevalonate kinase | HBug_USDA-ARS_HBBL_237208 | 0.19 |
| Phosphomevalonate kinase | HBug_USDA-ARS_HBBL_270718 | 4.15 |
| Diphosphomevalonate decarboxylase | HBug_USDA-ARS_HBBL_438030 | 0.19 |
| IDP Isomerase | HBug_USDA-ARS_HBBL_92242 | 14.92 |
| FDP Synthase | HBug_USDA-ARS_HBBL_420352 | 15.29 |
| FDP Synthase | HBug_USDA-ARS_HBBL_414919 | 27.98 |
| Farnesal dehydrogenase | HBug_USDA-ARS_HBBL_414990 | 0.08 |
| Farnesal dehydrogenase | HBug_USDA-ARS_HBBL_328297 | 0.08 |
| Farnesal dehydrogenase | HBug_USDA-ARS_HBBL_576500 | 9.65 |
| Farnesal dehydrogenase | HBug_USDA-ARS_HBBL_14716 | 5.20 |
| Farnesal dehydrogenase | HBug_USDA-ARS_HBBL_79640 | 5.75 |
| Juvenile hormone acid methyltransferase | HBug_USDA-ARS_HBBL_519494 | 0.08 |
| Juvenile hormone acid methyltransferase | HBug_USDA-ARS_HBBL_485406 | 17.85 |
| Juvenile hormone acid methyltransferase | HBug_USDA-ARS_HBBL_346622 | 0.45 |
| Methyl farnesoate epoxidase | HBug_USDA-ARS_HBBL_537163 | 0.23 |

FIG. 31

Figure 31:
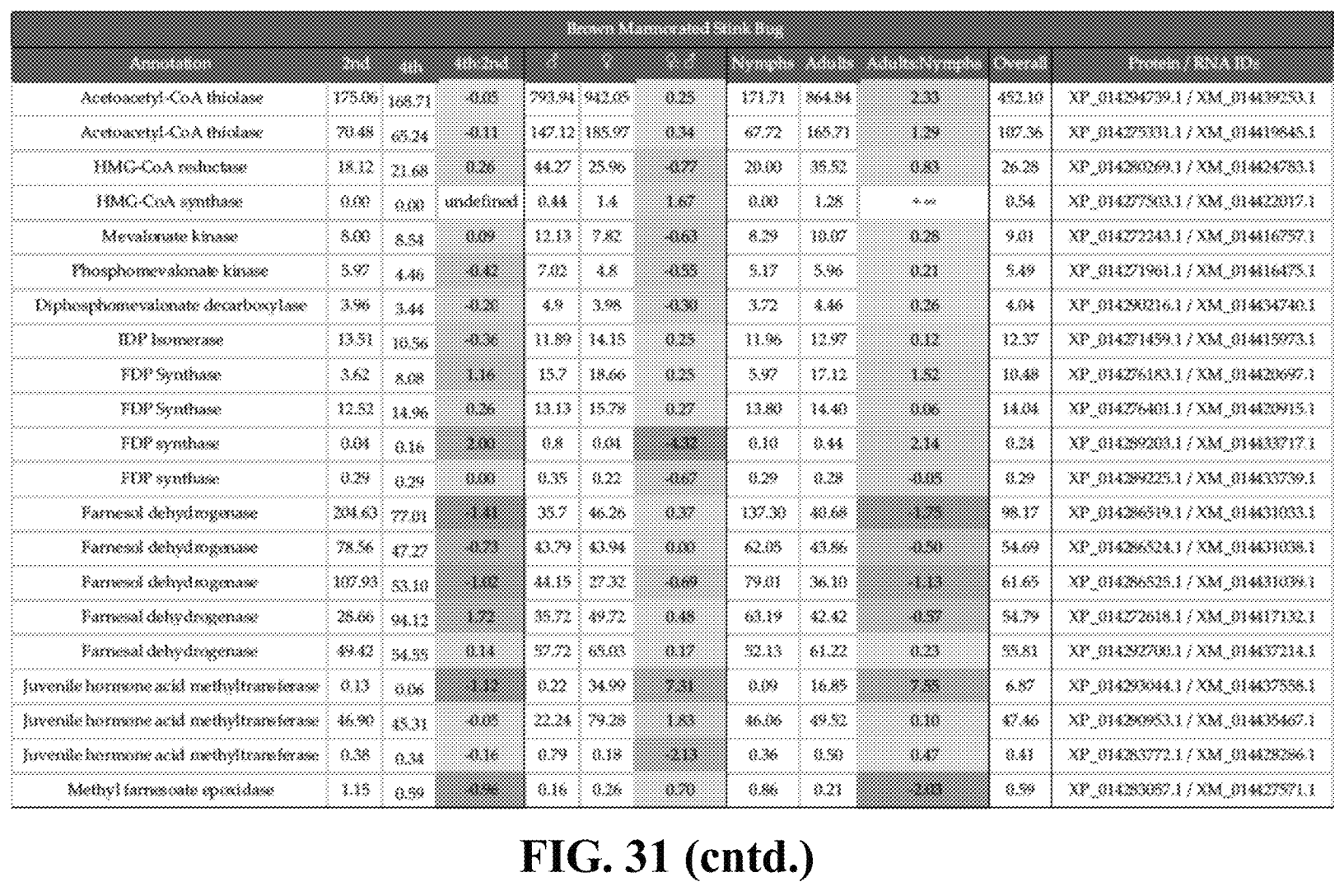

| Annotation | | | | | | | | Coverage | Protein ID/RNA ID |
|---|---|---|---|---|---|---|---|---|---|
| Acetoacetyl-CoA thiolase | 175.86 | 168.71 | 4.69 | 793.94 | 942.05 | 0.25 | 171.71 | 864.94 | 2.53 | 452.10 | XP_0142947299.1 / XM_0144098283.1 |
| Acetoacetyl-CoA thiolase | 70.68 | 65.24 | 4.51 | 147.12 | 185.97 | 0.54 | 69.72 | 165.77 | 1.59 | 107.36 | XP_0142975831.1 / XM_0144190485.1 |
| HMG-CoA reductase | 18.12 | 21.68 | 0.26 | 44.27 | 25.96 | 4.77 | 29.00 | 30.52 | 0.61 | 26.28 | XP_0142862669.1 / XM_0144247863.1 |
| HMG-CoA synthase | 0.00 | 0.00 | undetected | 0.44 | 1.4 | 1.67 | 0.00 | 1.29 | -∞ | 0.54 | XP_0142977803.1 / XM_0144223917.1 |
| Mevalonate kinase | 8.00 | 8.54 | 0.09 | 13.13 | 7.82 | 4.00 | 8.59 | 10.97 | 0.26 | 9.03 | XP_0142722343.1 / XM_0144160797.1 |
| Phosphomevalonate kinase | 5.97 | 4.46 | 4.06 | 7.03 | 4.8 | 4.00 | 5.17 | 5.96 | 0.21 | 5.49 | XP_0142718061.1 / XM_0144184475.1 |
| Diphosphomevalonate decarboxylase | 3.96 | 3.44 | 4.06 | 4.9 | 3.98 | 4.06 | 3.72 | 4.46 | 0.66 | 4.04 | XP_0142862836.1 / XM_0144247840.1 |
| FDP Isomerase | 13.51 | 16.56 | 4.08 | 11.89 | 14.16 | 0.15 | 11.96 | 12.97 | 0.13 | 12.37 | XP_0142714898.1 / XM_0144159973.1 |
| FDP Synthase | 3.62 | 8.08 | 3.16 | 15.7 | 18.66 | 0.25 | 5.97 | 17.12 | 1.56 | 10.48 | XP_0142760401.1 / XM_0144206697.1 |
| FDP Synthase | 12.52 | 14.96 | 0.36 | 13.13 | 15.79 | 4.17 | 13.80 | 14.40 | 0.06 | 14.04 | XP_0142764851.1 / XM_0144208915.1 |
| FDP synthase | 8.04 | 0.16 | 2.66 | 0.8 | 0.64 | 5.55 | 0.10 | 0.44 | 2.14 | 8.23 | XP_0142892203.1 / XM_0144237777.1 |
| FDP synthase | 0.29 | 0.29 | 1.00 | 0.35 | 0.22 | 4.60 | 0.29 | 0.29 | 4.08 | 0.29 | XP_0142892225.1 / XM_0144237789.1 |
| Farnesol dehydrogenase | 204.63 | 77.01 | 5.00 | 35.7 | 46.26 | 0.37 | 137.30 | 40.68 | 3.86 | 98.17 | XP_0142863619.1 / XM_0144318053.1 |
| Farnesol dehydrogenase | 78.56 | 47.27 | 4.69 | 43.79 | 43.94 | 0.08 | 62.95 | 43.86 | 1.86 | 54.69 | XP_0142865824.1 / XM_0144319386.1 |
| Farnesol dehydrogenase | 107.98 | 53.10 | 5.00 | 44.15 | 37.32 | 4.00 | 79.01 | 36.10 | 4.85 | 61.65 | XP_0142865221.1 / XM_0144310396.1 |
| Farnesal dehydrogenase | 28.66 | 94.13 | 1.76 | 88.72 | 49.72 | 0.48 | 63.19 | 42.42 | 4.05 | 34.79 | XP_0142726181.1 / XM_0144177132.1 |
| Farnesal dehydrogenase | 49.42 | 54.55 | 0.14 | 57.72 | 65.03 | 0.17 | 52.13 | 61.22 | 0.23 | 55.81 | XP_0142877081.1 / XM_0144357234.1 |
| Juvenile hormone acid methyltransferase | 0.13 | 0.06 | 0.66 | 0.22 | 34.99 | 7.58 | 0.08 | 16.05 | 7.06 | 6.97 | XP_0142959444.1 / XM_0144375556.1 |
| Juvenile hormone acid methyltransferase | 46.00 | 45.31 | 4.09 | 22.24 | 79.28 | 1.63 | 46.06 | 49.52 | 0.10 | 47.46 | XP_0142869653.1 / XM_0144036667.1 |
| Juvenile hormone acid methyltransferase | 0.36 | 0.34 | 40.16 | 0.79 | 0.19 | 5.56 | 0.36 | 0.59 | 0.67 | 0.43 | XP_0142866772.1 / XM_0144205596.1 |
| Methyl farnesoate epoxidase | 1.15 | 0.59 | 4.96 | 0.16 | 0.26 | 0.78 | 0.06 | 0.23 | 2.61 | 0.59 | XP_0142830057.1 / XM_0144275971.1 |

FIG. 31 (cntd.)

| *H. halys* Genome Wide Shotgun Assembly Hhal_1.0 (GCF_000696795.1) | |
| --- | --- |
| NW_014466702.1 (unplaced scaffold 286) | |
| XM_014420688.1 (*HhIDS3*) | Location 607,298..620,861 |
| XM_014420689.1 (*HhIDS4*) | Location 625,390..639,949 |
| XM_014420697.1 (*HhIDS7*) | Location 647,526..660,901 |
| NW_014466461.1 (unplaced scaffold 45) | |
| XM_014433717.1 (*HhIDS1*) | Location 56,095..66,498 |
| XM_014433500.1 (*HhIDS5*) | Location 75,481..90,135 |
| XM_014433739.1 (*HhIDS6*) | Location 93,509..107,973 |
| NW_014466714.1 (unplaced scaffold 298) | |
| XM_014420915.1 (*HhIDS2*) | Location 43,640..76,838 |

FIG. 32

```
                        SEQUENCE LISTING

<160> NUMBER OF SEQ ID NOS: 114

<210> SEQ ID NO 1
<211> LENGTH: 385
<212> TYPE: PRT
<213> ORGANISM: Artificial
<220> FEATURE:
<223> OTHER INFORMATION: Murgantia histrionica "harlequin bug" Terpene
      Synthase (TPS)

<400> SEQUENCE: 1

Met Val Ser Ile Ala Ala Lys Ser Leu Pro Lys Leu Ser Gly Ala Val
1               5                   10                  15

Phe Gly Gln Phe Ser Arg Arg Lys Gln Leu Ile Gln Arg His Trp Leu
            20                  25                  30

Asp Thr Arg Thr Asp Gln Tyr Tyr Asp Val Leu Arg Arg Ile Val Val
        35                  40                  45

Pro Glu Cys Lys Asn Ile Ala Ser Asp Val Pro Glu Tyr Pro Glu Arg
    50                  55                  60

Ile Glu Lys Leu Leu Tyr Tyr Thr Asn Pro Ala Phe Ser Asp Ala Trp
65                  70                  75                  80
```

-continued

Asn Phe Thr Thr Glu Leu Ile Tyr Arg Thr Val Ala Asp Glu Ser His
                85                  90                  95

Gln Thr Glu Glu Asn Ile Thr Lys Met Tyr Leu Ile Arg Ala Thr Met
            100                 105                 110

Asp Leu Leu Phe Thr Met Ser Ala Val Leu Asp Asp Ile Ser Asp Arg
        115                 120                 125

Ser Glu Phe Arg Lys Gly Lys Lys Gly Trp His Met Ile Cys Gln Gly
    130                 135                 140

Gly Glu Ser Thr Ala Leu Tyr Asp Gly Thr Gln Met Gly Leu Phe Pro
145                 150                 155                 160

Leu Tyr Leu Leu Lys Gln Tyr Phe Lys Asn Asp Pro Gly Tyr Ser Arg
                165                 170                 175

Leu Leu Glu Thr Val Val Met Thr Tyr Ile Lys Leu Thr Ile Gly Gln
            180                 185                 190

Thr Ile Asp Val Leu Gly Gln Phe Lys Lys Ser Pro Ser Met Ala Glu
        195                 200                 205

Tyr Lys Arg Ile Asn Tyr Tyr Lys Ala Gly Gln Phe Val Ala Ala Gly
    210                 215                 220

Ser Glu Leu Ala Val Ile His Ala Gly Ile Thr Ser Gln Asp Leu Ile
225                 230                 235                 240

Asp Lys Thr Val Glu Ile Phe Thr Ile Ala Gly Gln Ile Ile Gln Thr
                245                 250                 255

Trp Asp Asp Phe Asn Asp Tyr Tyr Ser Ser Ser Glu Gln Asn Gly Lys
                260                 265                 270

Leu Ser Cys Asp Phe Met Asn Ala Gly Thr Thr Trp Val Ser Ala Lys
            275                 280                 285

Ala Met Glu Val Phe Thr Pro Ser Gln Ala Val Lys Phe Met Glu Cys
        290                 295                 300

Tyr Gly Ser Asp Asp Gln Ser Lys Met Lys Thr Val Gln Glu Leu Tyr
305                 310                 315                 320

Asp Glu Ile Asp Met Pro Lys Leu Tyr Thr Glu Tyr Val Leu Glu Asn
                325                 330                 335

Tyr Asn Arg Cys Glu Thr Leu Ile Lys Glu Leu Pro His Asp Arg Leu
            340                 345                 350

Arg Glu Ala Cys Ser Ser Tyr Met Glu Trp Leu Val Val Arg Glu Thr
        355                 360                 365

Pro Asp Glu Asp Ser Glu His Lys Val Ala Leu Cys Leu Asn Ile Ser
    370                 375                 380

Gly
385

<210> SEQ ID NO 2
<211> LENGTH: 377
<212> TYPE: PRT
<213> ORGANISM: Artificial
<220> FEATURE:
<223> OTHER INFORMATION: Halyomorpha halys "brown marmorated stink bug"
      Terpene Synthase (TPS)

<400> SEQUENCE: 2

Met Ile Pro Lys Thr Leu Gly Asn Phe Thr Gly Tyr Val Leu Arg Ile
1               5                   10                  15

Ala Leu Asn Lys Lys His Val Asn Val Arg His Lys Leu Asp Thr Asp
            20                  25                  30

Ile Gly Lys Tyr Tyr Gln Thr Leu Asn Asp Val Val Ile Pro Glu Cys

```
           35                    40                    45
Met Glu Phe Val Lys Asp Ala Gln Gly Leu Pro Gln Arg Met Lys Glu
    50                    55                    60

Cys Ile Gly Tyr Thr Thr Pro Tyr Cys Tyr Glu Gly Trp Asn Phe Cys
65                    70                    75                    80

Val Glu Leu Leu Tyr Lys Thr Val Ala Asp Lys Pro His Gln Thr Glu
                  85                    90                    95

Glu Asn Leu Lys Lys Met Arg Ile Leu Arg Val Leu Ser Asp Met Ser
                  100                   105                   110

His Ser Met His Phe Ile Leu Asp Asp Tyr Ala Asp Lys Ala Glu Phe
                  115                   120                   125

Arg Gln Gly Lys Lys Ile Trp Ala Ser Ile Cys Glu Gly Gly Gln Glu
                  130                   135                   140

Ala Ala Ile Tyr Asp Thr Phe Thr Val Asn Tyr Leu Ile Asn Cys Met
145                   150                   155                   160

Leu Gln Arg His Phe Arg Asn Asp Pro Gly Phe Thr Lys Met Cys Glu
                  165                   170                   175

Met Phe Ser Trp Val Asn Gly Asn Ser Gly Ile Gly Gln Val Leu Asp
                  180                   185                   190

Ile Leu Asp His Lys Asn Ser Asp Phe Ser Asp Tyr Ala Ser Trp Lys
                  195                   200                   205

Asn Lys Val Glu Tyr Lys Ser Arg Asn Thr Met Cys Ala Phe Pro Val
    210                   215                   220

Leu Gly Leu Leu His Ala Gly Leu Thr Cys Asn Asp Leu Ile His Lys
225                   230                   235                   240

Thr Met Asp Ile Phe Gly Asp Tyr Gly Leu Met Phe Gln Val Trp Asn
                  245                   250                   255

Asp Phe Met Asp Phe Tyr Ser Val Gln Glu Glu Ser Gly Lys Gly Asn
                  260                   265                   270

Tyr Asp Cys Lys Asn Asn Val Lys Thr Trp Ala Thr Ile Thr Ala Met
                  275                   280                   285

Ser His Phe Asn Pro Ala Gln Ala Lys Glu Phe Arg Asp Cys Tyr Gly
    290                   295                   300

Thr Asn Asp Pro Ala Lys Arg Ser Arg Val Arg Glu Leu Phe Asp Glu
305                   310                   315                   320

Ile Asp Leu Pro Arg Lys Tyr Leu Asp Tyr Leu Arg Asn Ile Arg Val
                  325                   330                   335

Thr Val Glu Lys Lys Ile Ser Glu Leu Ser Asp Ala Arg Val Arg Asp
                  340                   345                   350

Ala Ser Thr Ser Tyr Leu Glu Trp Leu His Gly Asn Gly His His Asp
                  355                   360                   365

Val Glu Leu Glu Ile Leu Lys Ala Pro
    370                   375

<210> SEQ ID NO 3
<211> LENGTH: 1158
<212> TYPE: DNA
<213> ORGANISM: Artificial
<220> FEATURE:
<223> OTHER INFORMATION: Harlequin bug terpene synthase (TPS) encoding
      polynucleotide

<400> SEQUENCE: 3
atggtctcca ttgctgctaa gtctctaccc aagctgagtg gtgctgtctt cggccagttt        60
tcgaggagaa agcagttgat ccaaaggcat tggctggaca ctagaacaga tcaatactat       120
```

```
gatgttctga ggcgtattgt ggtaccagaa tgtaaaaata ttgcatcaga tgtaccagaa        180
tatccggaga gaatagagaa gttactttac tacaccaacc cagcattcag tgatgcttgg        240
aattttacga ctgaactgat ttacagaaca gtggctgatg agagtcacca aacagaagag        300
aacattacca agatgtacct aattagagct acaatggatt tgttatttac gatgtcagca        360
gttctagatg atatcagtga taggtcggag tttaggaaag gtaagaaagg ttggcatatg        420
atctgtcaag ggggtgaaag tactgcttta tacgacggaa ctcaaatggg attattccct        480
ctctatctat taaaacagta tttcaaaaat gatcctggct actcacgact tttggaaact        540
gttgtgatga cctacataaa gctgacaatt gggcaaacaa tagatgtcct aggacagttt        600
aagaaatcac catcaatggc tgaatataag cgtataaatt attacaaagc aggacaattt        660
gttgcggctg gttcagagct tgcggttatt catgctggaa taacatctca agatttgatt        720
gataaaactg tggagatatt tactattgcc ggtcaaatta tacagacatg ggatgacttc        780
aatgattact acagctcctc agaacagaat ggtaagctat catgtgattt catgaacgca        840
ggaacaactt gggttagtgc caaagcaatg gaggtcttca ctccttccca agcagtaaaa        900
tttatggagt gttatggctc agatgatcaa tccaagatga agacagtaca agaattatat        960
gatgagatcg acatgccgaa gttatacacc gagtatgtac tagaaaatta caatcgctgt       1020
gaaactctga taaaagaact accacatgac agattgcggg aggcctgttc cagttatatg       1080
gagtggcttg tagttcgaga aacgcctgat gaagattcgg aacataaagt tgctttatgt       1140
ttgaacatta gtgggtaa                                                      1158
```

```
<210> SEQ ID NO 4
<211> LENGTH: 1134
<212> TYPE: DNA
<213> ORGANISM: Artificial
<220> FEATURE:
<223> OTHER INFORMATION: Brown marmorated stink bug terpene synthase
      (TPS) encoding polynucleotide

<400> SEQUENCE: 4
```

```
atgataccga agacgcttgg gaattttaca ggatatgtat tgagaattgc actaaataag         60
aagcatgtta atgtaagaca caaattagac actgatatcg gcaagtatta tcaaacactg        120
aacgatgtcg tgatccctga gtgtatggaa ttcgttaagg atgcacaagg tcttccacaa        180
aggatgaaag agtgtatagg atacactact ccctattgct acgaaggttg gaacttctgc        240
gttgagttac tctacaaaac ggtggccgac aaacccatc agacagaaga aaacttgaaa         300
aaaatgagaa tactcagagt tttatcggat atgagccatt caatgcactt tatattagat        360
gactacgctg acaaagcaga gtttagacag ggtaagaaga tttgggcttc gatatgtgaa        420
ggaggccaag aagcagccat ctatgacact ttcactgtca actacttgat aaaattgcatg       480 cttcagcgtc actttaggaa tgatccaggt ttcaccaaga tgtgtgaaat gttttcttgg       540
gttaatggca attcagggat aggacaagta ttggatatcc tggaccataa gaattcagat       600
ttcagtgatt atgctagttg gaagaacaaa gttgaataca aatcaaggaa tacaatgtgt       660
gcttttccag tactgggtct tctacatgca ggactgacct gtaacgacct tattcataaa       720
actatggaca tatttggtga ttatggactt atgtttcaag tatggaatga tttcatggat       780
ttctattcag tgcaagagga atctggtaaa ggaaattatg attgcaagaa caatgtaaaa       840
acttgggcaa ctataacagc aatgagtcac tttaatccgg cccaagctaa agagttcagg       900
gactgctatg ggaccaacga tccagctaaa agatctagag tacgcgaact gtttgacgag       960
```
atagatttac ccaggaaata cttggattat ttaaggaata tccgtgttac tgttgaaaaa    1020
aaaatcagtg aacttagtga tgccagagta cgtgatgctt ctactagcta cttagaatgg    1080
ctgcatggaa acggacatca tgatgttgaa ttggagatcc taaaagctcc ataa    1134

<210> SEQ ID NO 5
<211> LENGTH: 15
<212> TYPE: PRT
<213> ORGANISM: Artificial
<220> FEATURE:
<223> OTHER INFORMATION: Linker

<400> SEQUENCE: 5

Gly Gly Gly Gly Gly Gly Gly Gly Gly Gly Gly Gly Gly Gly Gly
1               5                   10                  15

<210> SEQ ID NO 6
<211> LENGTH: 15
<212> TYPE: PRT
<213> ORGANISM: Artificial
<220> FEATURE:
<223> OTHER INFORMATION: Linker

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 405
<212> TYPE: PRT
<213> ORGANISM: Artificial
<220> FEATURE:
<223> OTHER INFORMATION: MhDS-2

<400> SEQUENCE: 7

Met Pro Phe Thr Lys Met Cys Thr Ser Lys Leu Ala Asn Pro Leu Met
1               5                   10                  15

Lys Tyr Tyr Leu Asn Leu Asn Gly Lys Ser Pro Leu Ser Lys Leu Ser
            20                  25                  30

Asn Ser Leu Asn Ser Ser Ser Phe Lys Phe Ile Ser Cys Ser Pro His
        35                  40                  45

Ile Val Cys Arg Glu Leu Asn Thr Val Ser Gly Val Ala Ile Arg Pro
    50                  55                  60

Gln Thr Ile Thr Lys Asp Asp Lys Arg Asp Phe Ala Val Phe Pro Asp
65                  70                  75                  80

Ile Val Arg Asp Leu Thr Gln Leu Asn Pro Gly Ile Ser Asp Leu Ser
                85                  90                  95

Thr Leu Ile Ser Lys Leu Met Gln Tyr Asn Val Ser Gly Gly Lys Lys
            100                 105                 110

Val Arg Gly Leu Thr Val Val Tyr Ser Tyr Arg Met Leu Ala Pro Asp
        115                 120                 125

His Ala Leu Thr Pro Glu Asn Ile Arg Leu Ala Gln Ile Leu Gly Trp
        130                 135                 140

Cys Val Glu Met Leu Gln Gly Phe Phe Val Val Ile Asp Asp Leu Ala
145                 150                 155                 160

Asp Gln Ser Val Thr Arg Arg Gly Arg Pro Cys Trp Tyr Arg Leu Pro
                165                 170                 175

Gly Val Gly Leu Arg Ala Ser Ser Asp Ala Leu Leu Ile Gln Ser Gly
            180                 185                 190

```
Cys Phe Gln Leu Leu Gln Gln His Cys Lys Asp Lys Glu Phe Tyr Val
        195                 200                 205

Asp Leu Val Glu Leu Phe Leu Leu Asp Ala Leu Arg Arg Thr Thr Tyr
    210                 215                 220

Gly Gln Thr Leu Asp Tyr Val Ser Ser Phe Pro Asn Ile Asn His Leu
225                 230                 235                 240

Thr Met Asp Arg Tyr Asn Phe Ile Thr Lys Tyr Lys Thr Ala Tyr Tyr
                245                 250                 255

Thr Tyr His Leu Pro Val Ala Thr Ala Met Thr Met Ala Gly Ile Tyr
            260                 265                 270

Asn Ala Glu Leu His Arg Gln Ala Lys Ser Val Leu Leu Glu Met Gly
            275                 280                 285

His Tyr Phe Gln Val Gln Asp Asp Tyr Leu Asp Val Phe Gly Asp Glu
    290                 295                 300

Glu Met Ile Gly Lys Lys Gly Thr Asp Ile Gln Glu Gly Lys Cys Thr
305                 310                 315                 320

Trp Leu Ala Ile Ile Ala Phe Gln Arg Ala Ser Pro Pro Gln Arg Glu
                325                 330                 335

Val Leu Glu Ser Cys Tyr Gly Thr Lys Glu Pro Glu Lys Ile Lys Lys
            340                 345                 350

Val Lys Asp Ile Phe Ile Glu Leu Ser Leu Pro Ala Val Tyr His Ala
            355                 360                 365

Tyr Glu Glu Glu Thr Tyr Asn Leu Ile Thr Arg Gln Ile Gln Gln Leu
    370                 375                 380

Ser Gln Gly Leu Pro His Glu Leu Phe Leu Thr Leu Leu His Lys Leu
385                 390                 395                 400

Tyr Gly Arg Lys Gln
                405
```

```
<210> SEQ ID NO 8
<211> LENGTH: 399
<212> TYPE: PRT
<213> ORGANISM: Artificial
<220> FEATURE:
<223> OTHER INFORMATION: HhIDS-2

<400> SEQUENCE: 8
```

```
Met Pro Phe Ala Lys Leu Cys Val Gln Lys Leu Ser Asn Pro Leu Met
1                   5                   10                  15

Lys Leu Cys Tyr Pro Asn Leu Asn Gly Arg Leu Ser Leu Ser Lys Phe
                20                  25                  30

Ser Asn Ser Leu Asp Asn Ser Thr Phe Lys Phe Leu Ser Cys Asn Pro
            35                  40                  45

His Thr Ile Cys Arg Glu His Asn Thr Val Ala Ile Arg Pro Gln Thr
    50                  55                  60

Ile Thr Lys Asp Asp Lys Arg Asp Phe Ala Val Phe Pro Asp Ile Val
65                  70                  75                  80

Arg Asp Leu Thr Gln Gln Asp Pro Gly Ile Ser Asp Leu Ser Thr Leu
                85                  90                  95

Ile Ser Lys Leu Met Gln Tyr Asn Val Ser Gly Gly Lys Lys Val Arg
                100                 105                 110

Gly Leu Thr Val Val Tyr Ser Tyr Arg Met Leu Ala Pro Asp His Asp
            115                 120                 125

Leu Thr Pro Glu Asn Ile Arg Leu Ala Gln Ile Leu Gly Trp Cys Val
    130                 135                 140
```

-continued

```
Glu Met Leu Gln Gly Phe Phe Val Val Ile Asp Asp Leu Thr Asp Gln
145                 150                 155                 160

Ser Val Thr Arg Arg Gly Arg Pro Cys Trp Tyr Arg Leu Pro Gly Ile
                165                 170                 175

Gly Leu Arg Ala Ser Ser Asp Ala Leu Leu Ile Gln Ala Gly Thr Phe
                180                 185                 190

Gln Leu Leu Gln Gln His Cys Lys Asp Lys Glu Phe Tyr Val Asp Leu
                195                 200                 205

Val Glu Leu Phe Leu Asp Ala Thr Arg Arg Thr Thr Tyr Gly Gln Thr
        210                 215                 220

Leu Asp Leu Val Ser Ser Phe Pro Asn Ile Thr His Leu Thr Met Asp
225                 230                 235                 240

Arg Tyr Asn Phe Ile Thr Lys Tyr Lys Thr Ser Tyr Tyr Thr Phe His
                245                 250                 255

Leu Pro Val Ala Ile Ala Met Tyr Met Ala Gly Ile Tyr Asn Thr Glu
                260                 265                 270

Leu His Arg Gln Ala Lys Ser Val Leu Leu Glu Met Gly His Tyr Phe
                275                 280                 285

Gln Val Gln Asp Asp Tyr Leu Asp Val Phe Ser Asp Glu Glu Val Ser
        290                 295                 300

Lys Lys Gly Thr Asp Ile Gln Glu Gly Lys Cys Thr Trp Leu Ala Ile
305                 310                 315                 320

Ile Ala Phe Gln Arg Ala Ser Pro Ser Gln Arg Glu Ile Leu Glu Ser
                325                 330                 335

Cys Tyr Gly Ser Lys Asp Pro Glu Lys Ile Gln Lys Val Lys Asp Ile
                340                 345                 350

Phe Ile Glu Ile Gly Pro Ala Val Phe His Ala Tyr Glu Glu Glu Thr
                355                 360                 365

Tyr Asn Leu Ile Thr Arg Gln Ile Gln Gln Leu Ser Gln Gly Leu Pro
        370                 375                 380

His Glu Leu Phe Leu Thr Leu Leu His Lys Tyr Gly Arg Lys Gln
385                 390                 395
```

```
<210> SEQ ID NO 9
<211> LENGTH: 428
<212> TYPE: PRT
<213> ORGANISM: Artificial
<220> FEATURE:
<223> OTHER INFORMATION: DjFPPS

<400> SEQUENCE: 9
```

```
Met Phe Ser Met Lys Leu Cys Arg Asn Arg Ser Cys Arg Glu Phe Leu
1                   5                   10                  15

Arg Glu Ala Arg Arg Thr Ile Ser Lys Thr Ser Thr Asp Lys Asn Ser
                20                  25                  30

Gly Ala Ile Ser Arg Ala Pro Asp His Leu Asn Val Glu Ser Asp Ser
            35                  40                  45

Thr Gly Ser Tyr Ser Arg Trp Lys Lys Gln Met His His Asn Asn Ile
        50                  55                  60

Arg Ala Leu Ser Thr Ile Gln Gln Ser Met Ile Arg Pro Val Gln Ser
65                  70                  75                  80

Ser Ala Leu Val Thr Lys Glu Gln Ser Arg Asp Phe Met Ala Leu Phe
                85                  90                  95

Pro Asp Leu Val Arg Glu Leu Thr Glu Val Gly Lys Ser Gln Glu Leu
            100                 105                 110
```

```
His Asp Val Met Arg Arg Phe Ala Arg Val Leu Gln Tyr Asn Thr Pro
        115                 120                 125

Thr Gly Lys Lys Asn Arg Gly Leu Ile Ile Leu Ser Thr Tyr Arg Met
    130                 135                 140

Leu Glu Asp Pro Glu Lys Leu Thr Pro Glu Asn Ile Arg Leu Ala Ser
145                 150                 155                 160

Ile Leu Gly Trp Cys Ala Glu Met Val His Ala Tyr Val Leu Ile Leu
                165                 170                 175

Asp Asp Ile Met Asp Gly Ser Glu Thr Arg Arg Gly Ala Leu Cys Trp
            180                 185                 190

Phe Arg Gln Ser Gly Ile Gly Leu Thr Ala Val Asn Asp Ala Val Met
            195                 200                 205

Ile Glu Asn Ala Val Tyr Leu Leu Ile Lys Arg His Leu Lys Asp His
        210                 215                 220

Pro Met Tyr Val Pro Leu Met Glu Leu Phe His Glu Gly Asn Leu Lys
225                 230                 235                 240

Thr Thr Leu Gly Gln Ser Leu Asp Ala Met Cys Leu Asp Thr Asn Gly
                245                 250                 255

Lys Pro Lys Leu Asp Met Phe Thr Met Ser Arg Tyr Thr Ser Ile Val
            260                 265                 270

Lys Tyr Lys Thr Ala Phe Tyr Ser Phe Gln Met Pro Val Ala Ile Ala
        275                 280                 285

Met Tyr Leu Ala Gly Met Ser Asp Glu Glu Gln His Arg Gln Ala Lys
        290                 295                 300

Thr Ile Leu Met Glu Met Gly Gln Phe Phe Gln Ile Gln Asp Asp Phe
305                 310                 315                 320

Leu Asp Cys Phe Gly Asp Pro Thr Val Thr Gly Lys Val Gly Thr Asp
            325                 330                 335

Ile Gln Asp Gly Lys Cys Ser Trp Leu Ala Val Val Ala Leu Gln Arg
            340                 345                 350

Ala Ala Ser Pro Ala Gln Arg Lys Ile Met Glu Glu His Tyr Gly Arg
            355                 360                 365

Pro Glu Pro Glu Ser Ile Ala Arg Ile Lys Asn Leu Tyr Val Asp Leu
    370                 375                 380

Cys Leu Pro Asn Thr Tyr Ala Ile Tyr Glu Glu Glu Ser Phe Asn Ile
385                 390                 395                 400

Ile Lys Thr His Ile Gln Gln Ile Ser Lys Gly Leu Arg His Asp Leu
            405                 410                 415

Phe Lys Ile Met Glu Asn Ile Tyr Lys Arg Glu Cys
            420                 425
```

```
<210> SEQ ID NO 10
<211> LENGTH: 429
<212> TYPE: PRT
<213> ORGANISM: Artificial
<220> FEATURE:
<223> OTHER INFORMATION: DpGPPS/FPPS

<400> SEQUENCE: 10
```

```
Met Phe Ser Met Lys Leu Cys Arg Asn Arg Ser Cys Arg Glu Phe Leu
1               5                   10                  15

Arg Glu Ala Arg Arg Thr Ile Ser Lys Thr Ser Thr Asp Lys Asn Ser
            20                  25                  30

Gly Ala Ile Ser Arg Ala Pro Asp His Lys Leu Asn Val Glu Ser Asp
        35                  40                  45
```

```
Ser Thr Gly Ser Tyr Ser Arg Trp Lys Lys Gln Met His His Asn Asn
    50              55                  60

Ile Arg Ala Leu Ser Thr Ile Gln Gln Ser Met Ile Arg Pro Val Gln
65              70                  75                  80

Ser Ser Ala Leu Val Thr Lys Glu Gln Ser Arg Asp Phe Met Ala Leu
            85                  90                  95

Phe Pro Asp Leu Val Arg Glu Leu Thr Glu Val Gly Lys Ser Gln Glu
            100                 105                 110

Leu Pro Asp Val Met Arg Arg Phe Ala Arg Val Leu Gln Tyr Asn Thr
            115                 120                 125

Pro Thr Gly Lys Lys Asn Arg Gly Leu Ile Val Leu Ser Thr Tyr Arg
    130                 135                 140

Met Leu Glu Asp Pro Glu Lys Leu Thr Pro Glu Asn Ile Arg Leu Ala
145                 150                 155                 160

Ser Ile Leu Gly Trp Cys Val Glu Met Val His Ala Tyr Phe Leu Ile
                165                 170                 175

Leu Asp Asp Ile Met Asp Gly Ser Glu Thr Arg Arg Gly Ala Leu Cys
            180                 185                 190

Trp Phe Arg Gln Ser Gly Ile Gly Leu Thr Ala Val Asn Asp Ala Val
            195                 200                 205

Met Ile Glu Asn Ala Val Tyr Leu Leu Ile Lys Arg His Leu Lys Asp
    210                 215                 220

His Pro Met Tyr Val Pro Leu Met Glu Leu Phe His Glu Gly Asn Leu
225                 230                 235                 240

Lys Thr Thr Leu Gly Gln Ser Leu Asp Ala Met Cys Leu Asp Thr Asn
                245                 250                 255

Gly Lys Pro Lys Leu Asp Met Phe Thr Met Ser Arg Tyr Thr Ser Ile
            260                 265                 270

Val Lys Tyr Lys Thr Ala Phe Tyr Ser Phe Gln Met Pro Val Ala Ile
            275                 280                 285

Ala Met Tyr Leu Ala Gly Met Ser Asp Glu Glu Gln His Arg Gln Ala
    290                 295                 300

Lys Thr Ile Leu Met Glu Met Gly Gln Phe Phe Gln Ile Gln Asp Asp
305                 310                 315                 320

Phe Leu Asp Cys Phe Gly Asp Pro Thr Val Thr Gly Lys Val Gly Thr
            325                 330                 335

Asp Ile Gln Asp Gly Lys Cys Ser Trp Leu Ala Val Val Ala Leu Gln
            340                 345                 350

Arg Ala Ser Pro Ala Gln Arg Lys Ile Met Glu Glu His Tyr Gly Arg
            355                 360                 365

Pro Glu Pro Glu Ser Ile Ala Arg Ile Lys Asn Leu Tyr Val Asp Leu
    370                 375                 380

Cys Leu Pro Asn Thr Tyr Ala Ile Tyr Glu Glu Glu Ser Phe Asn Ile
385                 390                 395                 400

Ile Lys Thr His Ile Gln Gln Ile Ser Lys Gly Leu Arg His Asp Leu
                405                 410                 415

Phe Phe Lys Ile Met Glu Lys Ile Tyr Lys Arg Glu Cys
            420                 425
```

<210> SEQ ID NO 11
<211> LENGTH: 434
<212> TYPE: PRT
<213> ORGANISM: Artificial
<220> FEATURE:
<223> OTHER INFORMATION: PsFPPS1

<400> SEQUENCE: 11

Met Phe Ser Phe Asn Lys Leu Pro Ile Asn Arg Ala Ser Arg Glu Leu
1               5                   10                  15

Arg Asn Ser Leu Lys Arg Gln Ile Ser Lys Thr Ser Ser Ala Pro Asn
                20                  25                  30

Ser Asp Ala Val Ser Arg Lys Asp Gly Gln Leu Gly Val Asn Ala Asp
            35                  40                  45

Leu Lys Pro Phe Ser Asn Val Arg Ala Ala Asn Asp Lys Trp Thr Ile
        50                  55                  60

His Ser Lys His Asn Asn Ser Arg Ala Leu Ser Thr Ile Gln Thr Lys
65                  70                  75                  80

Val Leu Pro Asn Val Ser Asn Ala Pro Phe Ala Thr Lys Glu Glu Ser
                85                  90                  95

Arg Glu Phe Met Ala Ile Phe Pro Asp Ile Val Arg Asp Leu Thr Asp
                100                 105                 110

Ala Gly Arg His Thr Asp Ile Pro Glu Val Thr Lys Arg Phe Ala His
            115                 120                 125

Val Leu Gln Tyr Asn Val Pro Asn Gly Lys Lys Thr Arg Gly Leu Thr
        130                 135                 140

Thr Val Ile Ala Tyr Lys Met Leu Glu Lys Pro Glu Asn Leu Thr Pro
145                 150                 155                 160

Glu Asn Ile Arg Leu Ala Asn Ile Leu Gly Trp Cys Val Glu Leu Leu
                165                 170                 175

Gln Ala Tyr Phe Ile Val Ala Asp Asp Ile Met Asp His Ser Val Ser
                180                 185                 190

Arg Arg Gly Arg Pro Cys Trp Tyr Arg Thr Glu Gly Val Gly Leu Ile
            195                 200                 205

Ala Val Asn Asp Gly Ile Leu Leu Glu Asn Ser Ile Tyr Leu Leu Leu
        210                 215                 220

Lys Lys His Leu Ser Ser Leu Pro Cys Tyr Val Pro Ile Met Glu Leu
225                 230                 235                 240

Phe Arg Asp Ile Thr Phe Lys Thr Ser Leu Gly Gln Ser Leu Asp Cys
                245                 250                 255

Leu Cys Leu Ala Asn Gly Lys Pro Val Leu Asp Leu Phe Thr Met Lys
            260                 265                 270

Arg Tyr Lys Thr Ile Val Lys Tyr Lys Thr Ser Tyr Tyr Ser Ile Gln
        275                 280                 285

Leu Pro Val Ala Leu Gly Met Tyr Leu Ala Asn Met Thr Asp Gln Glu
        290                 295                 300

Gln His Arg Gln Ala Lys Thr Ile Leu Leu Glu Met Gly Glu Phe Phe
305                 310                 315                 320

Gln Ile Gln Asp Asp Phe Leu Asp Val Phe Gly Asp Ser Asp Val Thr
                325                 330                 335

Gly Lys Ile Gly Thr Asp Ile Lys Asp Gly Lys Cys Ser Trp Leu Ala
            340                 345                 350

Val Leu Ala Leu Gln Arg Ala Thr Pro Ala Gln Arg Lys Val Met Asp
            355                 360                 365

Glu His Tyr Gly Lys Asp Asn Asp Glu Ser Val Arg Leu Val Lys Asn
        370                 375                 380

Leu Phe Glu Glu Leu Gly Leu Pro Ala Thr Phe Ala Val Tyr Glu Glu
385                 390                 395                 400

Glu Ser Phe Asn Ile Thr Arg Thr His Ile Gln Gln Ile Ser Lys Gly

-continued

```
                    405             410             415
Leu Pro His Asp Leu Phe Phe Lys Ile Leu Arg Lys Phe Tyr Lys Arg
            420             425             430

Asp Cys

<210> SEQ ID NO 12
<211> LENGTH: 416
<212> TYPE: PRT
<213> ORGANISM: Artificial
<220> FEATURE:
<223> OTHER INFORMATION: IpGPPS/TPS

<400> SEQUENCE: 12

Met Phe Lys Leu Ala Gln Arg Leu Pro Lys Ser Val Ser Ser Leu Gly
1               5                   10                  15

Ser Gln Leu Ser Lys Asn Ala Pro Asn Gln Leu Ala Ala Ala Thr Thr
            20                  25                  30

Ser Gln Leu Ile Asn Thr Pro Gly Ile Arg Lys His Ser Arg Ser Ser
        35                  40                  45

Ala Val Pro Ser Ser Leu Ser Lys Ser Met Tyr Asp His Asn Glu Glu
    50                  55                  60

Met Lys Ala Ala Met Lys Tyr Met Asp Glu Ile Tyr Pro Glu Val Met
65                  70                  75                  80

Gly Gln Ile Glu Lys Val Pro Gln Tyr Glu Glu Ile Lys Pro Ile Leu
                85                  90                  95

Val Arg Leu Arg Glu Ala Ile Asp Tyr Thr Val Pro Tyr Gly Lys Arg
            100                 105                 110

Phe Lys Gly Val His Ile Val Ser His Phe Lys Leu Leu Ala Asp Pro
        115                 120                 125

Lys Phe Ile Thr Pro Glu Asn Val Lys Leu Ser Gly Val Leu Gly Trp
    130                 135                 140

Cys Ala Glu Ile Ile Gln Ala Tyr Phe Cys Met Leu Asp Asp Ile Met
145                 150                 155                 160

Asp Asp Ser Asp Thr Arg Arg Gly Lys Pro Thr Trp Tyr Lys Leu Pro
            165                 170                 175

Gly Ile Gly Leu Asn Ala Val Thr Asp Val Cys Leu Met Glu Met Phe
            180                 185                 190

Thr Phe Glu Leu Leu Lys Arg Tyr Phe Pro Lys His Pro Ser Tyr Ala
            195                 200                 205

Asp Ile His Glu Ile Leu Arg Asn Leu Leu Phe Leu Thr His Met Gly
        210                 215                 220

Gln Gly Tyr Asp Phe Thr Phe Ile Asp Pro Val Thr Arg Lys Ile Asn
225                 230                 235                 240

Phe Asn Asp Phe Thr Glu Glu Asn Tyr Thr Lys Leu Cys Arg Tyr Lys
            245                 250                 255

Ile Ile Phe Ser Thr Phe His Asn Thr Leu Glu Leu Thr Ser Ala Met
            260                 265                 270

Ala Asn Val Tyr Asp Pro Lys Lys Ile Lys Gln Leu Asp Pro Val Leu
            275                 280                 285

Met Arg Ile Gly Met Met His Gln Ser Gln Asn Asp Phe Lys Asp Leu
        290                 295                 300

Tyr Arg Asp Gln Gly Glu Val Leu Lys Gln Ala Glu Lys Ser Val Leu
305                 310                 315                 320

Gly Thr Asp Ile Lys Thr Gly Gln Leu Thr Trp Phe Ala Gln Lys Ala
            325                 330                 335
```

```
Leu Ser Ile Cys Asn Asp Arg Gln Arg Lys Ile Ile Met Asp Asn Tyr
            340                 345                 350

Gly Lys Glu Asp Asn Lys Asn Ser Glu Ala Val Arg Glu Val Tyr Glu
            355                 360                 365

Glu Leu Asp Leu Lys Gly Lys Phe Met Glu Phe Glu Glu Glu Ser Phe
        370                 375                 380

Glu Trp Leu Lys Lys Glu Ile Pro Lys Ile Asn Asn Gly Ile Pro His
385                 390                 395                 400

Lys Val Phe Gln Asp Tyr Thr Tyr Gly Val Phe Lys Arg Arg Pro Glu
                405                 410                 415

<210> SEQ ID NO 13
<211> LENGTH: 377
<212> TYPE: PRT
<213> ORGANISM: Artificial
<220> FEATURE:
<223> OTHER INFORMATION: PsTPS1

<400> SEQUENCE: 13

Met Phe Leu Leu Pro Arg Leu Lys Asn Phe Thr Arg Ser Asn Ser Pro
1               5                   10                  15

Ala Arg Lys Leu Phe Ser Pro Lys Ser Asn Ser Phe Ser Ser Thr Pro
            20                  25                  30

His Asp Asp Gly Phe Phe Lys His Glu Met Asp Glu Leu Lys Thr Tyr
            35                  40                  45

Tyr Pro Leu Met Val Gln Asp Leu Thr Asp Ala Ile Ser Gln Tyr Lys
        50                  55                  60

Gln Phe Pro Gly Leu Leu Glu Arg Phe Pro Val Leu Met Asp Tyr Thr
65                  70                  75                  80

Val Thr His Asp Asp Pro Tyr Phe Leu Ser Ser Ala Val Leu Pro Leu
                85                  90                  95

Tyr Phe Tyr Lys Ala Val Glu Glu Ser Asp Lys Leu Thr Glu Glu Asn
            100                 105                 110

Ile Lys Arg Ala Cys Leu Met Ser Trp Ala Tyr Arg Thr Leu Glu Thr
            115                 120                 125

Ser Gln Ile Ile Val Asp Asp Ile Leu Asp Lys Ser Glu Val Arg Tyr
        130                 135                 140

Asn Lys Pro Ala Trp Tyr Lys Lys Asp Gly Val Ser Met Glu Leu Thr
145                 150                 155                 160

Ile Leu Leu Asp Ser His Tyr Leu Ala Thr Gly Ala Tyr Met Val Leu
                165                 170                 175

Thr Lys Arg Leu Ala Gly His Pro Cys Cys Leu Asp Ile Leu Asp Leu
            180                 185                 190

Tyr Ala Glu Glu Met Phe Val Met Ile Ile Ala Gln Tyr Met Asp Ile
            195                 200                 205

Lys Lys Leu Asp Leu Lys Asp Phe Gln Lys Leu Val Arg His Arg Phe
        210                 215                 220

Asp Lys Ala Leu Tyr Val Phe Asn Gly Ser Ala Arg Ser Gly Leu Tyr
225                 230                 235                 240

Leu Ala Asn Val Arg Asp Arg Glu Thr His Asp Cys Met Lys Lys Phe
                245                 250                 255

Ser Val Pro Met Ser Arg Phe Phe Gln Val Gln Asn Asp Phe Ser Gly
            260                 265                 270

Phe Glu Glu Glu Ser Lys Phe Gln Asn Ser Cys Pro Asp Ile Val Asn
            275                 280                 285
```

-continued

```
Gly Arg Asn Ser Trp Leu Val Thr Thr Ala Leu Lys Met Ala Asn Pro
    290                 295                 300

Ala Gln Arg Lys Val Ile Glu Asn Tyr Gly Asn Gly Ala Glu Ser Ala
305                 310                 315                 320

Arg Lys Val Met Gln Val Tyr Glu Asp Leu Lys Leu Lys Asp Val His
                325                 330                 335

Asp Arg Arg Thr Glu Glu Phe Leu Gly Glu Met Arg Glu Ile Val Glu
                340                 345                 350

Asn Phe Pro Glu Arg Ile Pro Lys Gln Pro Phe His Asp Ile Val Arg
            355                 360                 365

Gln Leu Ala Leu Asn Lys Leu Tyr Ser
    370                 375
```

```
<210> SEQ ID NO 14
<211> LENGTH: 376
<212> TYPE: PRT
<213> ORGANISM: Artificial
<220> FEATURE:
<223> OTHER INFORMATION: HhIDS-1

<400> SEQUENCE: 14
```

```
Met Ile Pro Lys Thr Leu Gly Asn Phe Thr Gly Tyr Val Leu Arg Ile
1                   5                   10                  15

Ala Leu Asn Lys Lys His Val Asn Val Arg His Lys Leu Asp Thr Asp
            20                  25                  30

Ile Gly Lys Tyr Tyr Gln Thr Leu Asn Asp Val Val Ile Pro Glu Cys
            35                  40                  45

Met Glu Phe Val Lys Asp Ala Gln Gly Leu Pro Gln Arg Met Lys Glu
    50                  55                  60

Cys Ile Gly Tyr Thr Thr Pro Tyr Cys Tyr Glu Gly Trp Asn Phe Cys
65                  70                  75                  80

Val Glu Leu Leu Tyr Lys Thr Val Ala Asp Lys Pro His Gln Thr Glu
                85                  90                  95

Glu Asn Leu Lys Lys Met Arg Ile Leu Arg Val Leu Ser Asp Met Ser
            100                 105                 110

His Ser Met His Phe Ile Leu Asp Asp Tyr Ala Lys Ala Glu Phe Arg
            115                 120                 125

Gln Gly Lys Lys Ile Trp Ala Ser Ile Cys Glu Gly Gly Gln Glu Ala
    130                 135                 140

Ala Ile Tyr Asp Thr Phe Thr Val Asn Tyr Leu Ile Asn Cys Met Leu
145                 150                 155                 160

Gln Arg His Phe Arg Asn Asp Pro Gly Phe Thr Lys Met Cys Glu Met
                165                 170                 175

Phe Ser Trp Val Asn Gly Asn Ser Gly Ile Gly Gln Val Leu Asp Ile
            180                 185                 190

Leu Asp His Lys Asn Ser Asp Phe Ser Asp Tyr Ala Ser Trp Lys Asn
            195                 200                 205

Lys Val Glu Tyr Lys Ser Arg Asn Thr Met Cys Ala Phe Pro Val Leu
    210                 215                 220

Gly Leu Leu His Ala Gly Leu Thr Cys Asn Asp Leu Ile His Lys Thr
225                 230                 235                 240

Met Asp Ile Phe Gly Asp Tyr Gly Leu Met Phe Gln Val Trp Asn Asp
                245                 250                 255

Phe Met Asp Phe Tyr Ser Val Gln Glu Glu Ser Gly Lys Gly Asn Tyr
            260                 265                 270
```

```
Asp Cys Lys Asn Asn Val Lys Thr Trp Ala Thr Ile Thr Ala Met Ser
        275               280               285

His Phe Asn Pro Ala Gln Ala Lys Glu Phe Arg Asp Cys Tyr Gly Thr
    290               295               300

Asn Asp Pro Ala Lys Arg Ser Arg Val Arg Glu Leu Phe Asp Glu Ile
305               310               315               320

Asp Leu Pro Arg Lys Tyr Leu Asp Tyr Leu Arg Asn Ile Arg Val Thr
                325               330               335

Val Glu Lys Lys Ile Ser Glu Leu Ser Asp Ala Arg Val Arg Asp Ala
                340               345               350

Ser Thr Ser Tyr Leu Glu Trp Leu His Gly Asn Gly His His Asp Val
        355               360               365

Glu Leu Glu Ile Leu Lys Ala Pro
    370               375

<210> SEQ ID NO 15
<211> LENGTH: 384
<212> TYPE: PRT
<213> ORGANISM: Artificial
<220> FEATURE:
<223> OTHER INFORMATION: MhIDS-1

<400> SEQUENCE: 15

Met Val Ser Ile Ala Ala Lys Ser Leu Pro Lys Leu Ser Gly Ala Val
1               5               10               15

Phe Gly Gln Phe Ser Arg Arg Lys Gln Leu Ile Gln Arg His Trp Leu
            20               25               30

Asp Thr Arg Thr Asp Gln Tyr Tyr Asp Val Leu Arg Arg Ile Val Val
        35               40               45

Pro Glu Cys Lys Asn Ile Ala Ser Asp Val Pro Glu Tyr Pro Glu Arg
    50               55               60

Ile Glu Lys Leu Leu Tyr Tyr Thr Asn Pro Ala Phe Ser Asp Ala Trp
65               70               75               80

Asn Phe Thr Thr Glu Leu Ile Tyr Arg Thr Val Ala Asp Glu Ser His
            85               90               95

Gln Thr Glu Glu Asn Ile Thr Lys Met Tyr Leu Ile Arg Ala Thr Met
            100               105               110

Asp Leu Leu Phe Thr Met Ser Ala Val Leu Asp Asp Ile Ser Asp Arg
        115               120               125

Ser Glu Phe Arg Lys Gly Lys Lys Gly Trp His Met Ile Cys Gln Gly
    130               135               140

Gly Glu Ser Thr Ala Leu Tyr Asp Gly Thr Gln Met Gly Leu Phe Pro
145               150               155               160

Leu Tyr Leu Leu Lys Gln Tyr Phe Lys Asn Asp Pro Gly Tyr Ser Arg
            165               170               175

Leu Leu Glu Thr Val Val Met Thr Tyr Ile Lys Leu Thr Ile Gly Gln
            180               185               190

Thr Ile Asp Val Leu Gly Gln Phe Lys Lys Ser Pro Ser Met Ala Glu
        195               200               205

Tyr Lys Arg Ile Asn Tyr Tyr Lys Ala Gly Gln Phe Val Ala Ala Gly
    210               215               220

Ser Glu Leu Ala Val Ile His Ala Gly Ile Thr Ser Gln Asp Leu Ile
225               230               235               240

Asp Lys Thr Val Glu Ile Phe Thr Ile Ala Gly Gln Ile Ile Gln Thr
            245               250               255
```

-continued

```
Trp Asp Asp Phe Asn Asp Tyr Tyr Ser Ser Ser Glu Gln Asn Gly Lys
        260                 265             270

Leu Ser Cys Asp Phe Met Asn Ala Gly Thr Thr Trp Val Ser Ala Lys
        275                 280             285

Ala Met Glu Val Phe Thr Pro Ser Gln Ala Val Lys Phe Met Glu Cys
        290                 295             300

Tyr Gly Ser Asp Asp Gln Ser Lys Met Lys Thr Val Gln Glu Leu Tyr
305                 310             315                 320

Asp Glu Ile Asp Met Pro Lys Leu Tyr Thr Glu Tyr Val Leu Glu Asn
                325             330             335

Tyr Asn Arg Cys Glu Thr Leu Ile Lys Glu Leu Pro His Asp Arg Leu
        340             345             350

Arg Glu Ala Cys Ser Ser Tyr Met Glu Trp Leu Val Val Arg Glu Thr
        355             360             365

Pro Asp Glu Asp Ser Glu His Val Ala Leu Cys Leu Asn Ile Ser Gly
    370             375             380
```

```
<210> SEQ ID NO 16
<211> LENGTH: 25
<212> TYPE: PRT
<213> ORGANISM: Artificial
<220> FEATURE:
<223> OTHER INFORMATION: M. histrionica IDS-1 FARM containing region

<400> SEQUENCE: 16

Asp Leu Leu Phe Thr Met Ser Ala Val Leu Asp Asp Ile Ser Asp Arg
1               5               10              15

Ser Glu Phe Arg Lys Gly Lys Lys Gly
            20              25
```

```
<210> SEQ ID NO 17
<211> LENGTH: 25
<212> TYPE: PRT
<213> ORGANISM: Artificial
<220> FEATURE:
<223> OTHER INFORMATION: H. halys IDS-1 FARM containing region

<400> SEQUENCE: 17

Asp Met Ser His Ser Met His Phe Ile Leu Asp Asp Tyr Ala Asp Lys
1               5               10              15

Ala Glu Phe Arg Gln Gly Lys Lys Ile
            20              25
```

```
<210> SEQ ID NO 18
<211> LENGTH: 25
<212> TYPE: PRT
<213> ORGANISM: Artificial
<220> FEATURE:
<223> OTHER INFORMATION: I. pini GPPS/TPS FARM containing region

<400> SEQUENCE: 18

Glu Ile Ile Gln Ala Tyr Phe Cys Met Leu Asp Asp Ile Met Asp Asp
1               5               10              15

Ser Asp Thr Arg Arg Gly Lys Pro Thr
            20              25
```

```
<210> SEQ ID NO 19
<211> LENGTH: 25
<212> TYPE: PRT
<213> ORGANISM: Artificial
<220> FEATURE:
```

```
<223> OTHER INFORMATION: P. striolata FPPS3 FARM containing region

<400> SEQUENCE: 19

Glu Leu Ile Glu Ala Ala Val Val Ile Phe Asp Asp Val Met Asp Asn
1               5                   10                  15

Ser Phe Thr Arg Arg Gly Gly Leu Cys
            20                  25

<210> SEQ ID NO 20
<211> LENGTH: 24
<212> TYPE: PRT
<213> ORGANISM: Artificial
<220> FEATURE:
<223> OTHER INFORMATION: P. striolata TPS1 FARM containing region

<400> SEQUENCE: 20

Arg Thr Leu Glu Thr Ser Ile Ile Val Asp Asp Ile Leu Asp Lys Ser
1               5                   10                  15

Glu Val Arg Tyr Asn Lys Pro Ala
            20

<210> SEQ ID NO 21
<211> LENGTH: 25
<212> TYPE: PRT
<213> ORGANISM: Artificial
<220> FEATURE:
<223> OTHER INFORMATION: P. striolata TPS2 FARM containing region

<400> SEQUENCE: 21

Arg Met Ala Glu Ala Ser Gln Leu Thr Leu Asp Asp Val Leu Asp Asn
1               5                   10                  15

Ser Leu Thr Arg Tyr Met Lys Pro Ala
            20                  25

<210> SEQ ID NO 22
<211> LENGTH: 25
<212> TYPE: PRT
<213> ORGANISM: Artificial
<220> FEATURE:
<223> OTHER INFORMATION: P. striolata TPS3 FARM containing region

<400> SEQUENCE: 22

Lys Leu Ile His Ser Ser Ile Asn Ile Asn Asp Asp Ile Ile Asp Arg
1               5                   10                  15

Ser Asn Ile Arg Tyr Asn Lys Thr Thr
            20                  25

<210> SEQ ID NO 23
<211> LENGTH: 25
<212> TYPE: PRT
<213> ORGANISM: Artificial
<220> FEATURE:
<223> OTHER INFORMATION: P. striolata TPS4 FARM containing region

<400> SEQUENCE: 23

Arg Leu Ile His Ala Ser Val Ile Ile Ser Asp Asp Ile Val Asp Asp
1               5                   10                  15

Ser Glu Met Arg Tyr Asn Lys Thr Thr
            20                  25

<210> SEQ ID NO 24
<211> LENGTH: 25
<212> TYPE: PRT
<213> ORGANISM: Artificial
```

-continued

```
<220> FEATURE:
<223> OTHER INFORMATION: B. mori FPPS2 FARM containing region

<400> SEQUENCE: 24

Glu Met Phe Gln Ala Tyr Cys Ile Val Leu Asp Asp Ile Met Asp Gly
1               5                   10                  15

Ser Ser Val Arg Arg Gly Met Pro Cys
            20                  25

<210> SEQ ID NO 25
<211> LENGTH: 25
<212> TYPE: PRT
<213> ORGANISM: Artificial
<220> FEATURE:
<223> OTHER INFORMATION: C. fumiferana FPPS2 FARM containing region

<400> SEQUENCE: 25

Glu Ile Leu Gln Gly Phe Leu Val Met Leu Asp Asp Ile Met Asp Gly
1               5                   10                  15

Ser Thr Thr Arg Arg Gly Val Pro Cys
            20                  25

<210> SEQ ID NO 26
<211> LENGTH: 25
<212> TYPE: PRT
<213> ORGANISM: Artificial
<220> FEATURE:
<223> OTHER INFORMATION: M. histrionica IDS-2 FARM containing region

<400> SEQUENCE: 26

Glu Met Leu Gln Gly Phe Phe Val Val Ile Asp Asp Leu Ala Asp Gln
1               5                   10                  15

Ser Val Thr Arg Arg Gly Arg Pro Cys
            20                  25

<210> SEQ ID NO 27
<211> LENGTH: 25
<212> TYPE: PRT
<213> ORGANISM: Artificial
<220> FEATURE:
<223> OTHER INFORMATION: H. halys IDS-2 FARM containing region

<400> SEQUENCE: 27

Glu Met Leu Gln Gly Phe Phe Val Val Ile Asp Asp Leu Thr Asp Gln
1               5                   10                  15

Ser Val Thr Arg Arg Gly Arg Pro Cys
            20                  25

<210> SEQ ID NO 28
<211> LENGTH: 25
<212> TYPE: PRT
<213> ORGANISM: Artificial
<220> FEATURE:
<223> OTHER INFORMATION: A. ipsilon FPPS FARM containing region

<400> SEQUENCE: 28

Glu Met Phe His Thr His Gln Leu Leu Leu Asn Asp Ile Met Glu Gly
1               5                   10                  15

Ala Glu Met Arg Arg Gly Ala Pro Cys
            20                  25

<210> SEQ ID NO 29
<211> LENGTH: 25
<212> TYPE: PRT
```

```
<213> ORGANISM: Artificial
<220> FEATURE:
<223> OTHER INFORMATION: B. mori FPPS1 FARM containing region

<400> SEQUENCE: 29

Glu Met Phe His Thr His Gln Leu Leu Leu Asn Asp Ile Met Glu Gly
1               5                   10                  15

Thr Thr Met Arg Arg Gly Val Pro Cys
            20                  25

<210> SEQ ID NO 30
<211> LENGTH: 25
<212> TYPE: PRT
<213> ORGANISM: Artificial
<220> FEATURE:
<223> OTHER INFORMATION: C. fumiferana FPPS1 FARM containing region

<400> SEQUENCE: 30

Glu Met Phe His Thr His Gln Leu Leu Leu Asn Asp Ile Met Glu Gly
1               5                   10                  15

Thr Glu Met Arg Arg Gly Ala Pro Ala
            20                  25

<210> SEQ ID NO 31
<211> LENGTH: 24
<212> TYPE: PRT
<213> ORGANISM: Artificial
<220> FEATURE:
<223> OTHER INFORMATION: P. striolata FPPS1 FARM containing region

<400> SEQUENCE: 31

Glu Leu Gln Ala Tyr Phe Ile Val Ala Asp Asp Ile Met Asp His Ser
1               5                   10                  15

Val Ser Arg Arg Gly Arg Pro Cys
            20

<210> SEQ ID NO 32
<211> LENGTH: 25
<212> TYPE: PRT
<213> ORGANISM: Artificial
<220> FEATURE:
<223> OTHER INFORMATION: I. pini FPPS FARM containing region

<400> SEQUENCE: 32

Glu Met Leu His Thr Tyr Phe Leu Ile Ile Asp Asp Ile Ile Asp His
1               5                   10                  15

Ser Asp Thr Arg Arg Gly Ala Ile Cys
            20                  25

<210> SEQ ID NO 33
<211> LENGTH: 25
<212> TYPE: PRT
<213> ORGANISM: Artificial
<220> FEATURE:
<223> OTHER INFORMATION: A. fabae FPPS FARM containing region

<400> SEQUENCE: 33

Glu Ile Leu Gln Ala Tyr Gln Leu Val Leu Asp Asp Ile Met Asp Asn
1               5                   10                  15

Ala Ile Thr Arg Arg Gly Arg Pro Cys
            20                  25

<210> SEQ ID NO 34
<211> LENGTH: 25
```

<212> TYPE: PRT
<213> ORGANISM: Artificial
<220> FEATURE:
<223> OTHER INFORMATION: A. gossypii FPPS FARM containing region

<400> SEQUENCE: 34

Glu Ile Leu Gln Ala Tyr Gln Leu Val Leu Asp Asp Ile Met Asp Asn
1               5                   10                  15

Ala Ile Thr Arg Arg Gly Arg Pro Cys
            20                  25

<210> SEQ ID NO 35
<211> LENGTH: 25
<212> TYPE: PRT
<213> ORGANISM: Artificial
<220> FEATURE:
<223> OTHER INFORMATION: P. cochleariae FPPS FARM containing region

<400> SEQUENCE: 35

Glu Leu Leu Gln Ala Ser Leu Leu Ile Met Asp Asp Leu Met Asp Arg
1               5                   10                  15

Ser Glu Thr Arg Arg Gly Gln Pro Cys
            20                  25

<210> SEQ ID NO 36
<211> LENGTH: 25
<212> TYPE: PRT
<213> ORGANISM: Artificial
<220> FEATURE:
<223> OTHER INFORMATION: M. persicae GPPS/FPPS FARM containing region

<400> SEQUENCE: 36

Glu Ile Leu Gln Ala Tyr Gln Leu Val Leu Asp Asp Ile Met Asp Asn
1               5                   10                  15

Ala Ile Thr Arg Arg Gly Arg Pro Cys
            20                  25

<210> SEQ ID NO 37
<211> LENGTH: 25
<212> TYPE: PRT
<213> ORGANISM: Artificial
<220> FEATURE:
<223> OTHER INFORMATION: D. ponderosae FPPS FARM containing region

<400> SEQUENCE: 37

Glu Met Val His Ala Tyr Phe Leu Ile Leu Asp Asp Ile Met Asp Gly
1               5                   10                  15

Ser Glu Thr Arg Arg Gly Ala Leu Cys
            20                  25

<210> SEQ ID NO 38
<211> LENGTH: 25
<212> TYPE: PRT
<213> ORGANISM: Artificial
<220> FEATURE:
<223> OTHER INFORMATION: D. jeffreyi FPPS FARM containing region

<400> SEQUENCE: 38

Glu Met Val His Ala Tyr Val Leu Ile Leu Asp Asp Ile Met Asp Gly
1               5                   10                  15

Ser Glu Thr Arg Arg Gly Ala Leu Cys
            20                  25

<210> SEQ ID NO 39

-continued

```
<211> LENGTH: 25
<212> TYPE: PRT
<213> ORGANISM: Artificial
<220> FEATURE:
<223> OTHER INFORMATION: A. grandis FFPS FARM containing region

<400> SEQUENCE: 39

Glu Met Ile His Ser Cys Phe Leu Val Leu Asp Asp Ile Met Asp Asn
1               5                   10                  15

Ser Glu Thr Arg Arg Gly Ser Leu Cys
            20                  25

<210> SEQ ID NO 40
<211> LENGTH: 21
<212> TYPE: DNA
<213> ORGANISM: Artificial
<220> FEATURE:
<223> OTHER INFORMATION: Primer

<400> SEQUENCE: 40
atggtctcca ttgctgctaa g                                               21

<210> SEQ ID NO 41
<211> LENGTH: 27
<212> TYPE: DNA
<213> ORGANISM: Artificial
<220> FEATURE:
<223> OTHER INFORMATION: Primer

<400> SEQUENCE: 41
ttacccacta atgttcaaac ataaagc                                         27

<210> SEQ ID NO 42
<211> LENGTH: 18
<212> TYPE: DNA
<213> ORGANISM: Artificial
<220> FEATURE:
<223> OTHER INFORMATION: Primer

<400> SEQUENCE: 42
tcagtcgact ggatccgg                                                   18

<210> SEQ ID NO 43
<211> LENGTH: 21
<212> TYPE: DNA
<213> ORGANISM: Artificial
<220> FEATURE:
<223> OTHER INFORMATION: Primer

<400> SEQUENCE: 43
ctagatatct cgagtgcggc c                                               21

<210> SEQ ID NO 44
<211> LENGTH: 28
<212> TYPE: DNA
<213> ORGANISM: Artificial
<220> FEATURE:
<223> OTHER INFORMATION: Primer

<400> SEQUENCE: 44
ctacccacta atgttcaaac ataaagca                                        28

<210> SEQ ID NO 45
<211> LENGTH: 23
<212> TYPE: DNA
<213> ORGANISM: Artificial
```

-continued

```
<220> FEATURE:
<223> OTHER INFORMATION: Primer

<400> SEQUENCE: 45
ggatccgtgg tctccattgc tgc                                              23

<210> SEQ ID NO 46
<211> LENGTH: 24
<212> TYPE: DNA
<213> ORGANISM: Artificial
<220> FEATURE:
<223> OTHER INFORMATION: Primer

<400> SEQUENCE: 46
ggagaccacg gatccagtcg actg                                             24

<210> SEQ ID NO 47
<211> LENGTH: 22
<212> TYPE: DNA
<213> ORGANISM: Artificial
<220> FEATURE:
<223> OTHER INFORMATION: Primer

<400> SEQUENCE: 47
acgatgtcag cagttctaga tg                                               22

<210> SEQ ID NO 48
<211> LENGTH: 21
<212> TYPE: DNA
<213> ORGANISM: Artificial
<220> FEATURE:
<223> OTHER INFORMATION: Primer

<400> SEQUENCE: 48
agcagtactt tcaccccctt g                                                21

<210> SEQ ID NO 49
<211> LENGTH: 21
<212> TYPE: DNA
<213> ORGANISM: Artificial
<220> FEATURE:
<223> OTHER INFORMATION: Primer

<400> SEQUENCE: 49
aaggttggca tatgatctgt c                                                21

<210> SEQ ID NO 50
<211> LENGTH: 18
<212> TYPE: DNA
<213> ORGANISM: Artificial
<220> FEATURE:
<223> OTHER INFORMATION: Primer

<400> SEQUENCE: 50
cgcaacaaat tgtcctgc                                                    18

<210> SEQ ID NO 51
<211> LENGTH: 44
<212> TYPE: DNA
<213> ORGANISM: Artificial
<220> FEATURE:
<223> OTHER INFORMATION: Primer

<400> SEQUENCE: 51
taatacgact cactataggg agaaaggttg gcatatgatc tgtc                       44
```

<210> SEQ ID NO 52
<211> LENGTH: 41
<212> TYPE: DNA
<213> ORGANISM: Artificial
<220> FEATURE:
<223> OTHER INFORMATION: Primer

<400> SEQUENCE: 52
taatacgact cactataggg agacgcaaca aattgtcctg c                    41

<210> SEQ ID NO 53
<211> LENGTH: 21
<212> TYPE: DNA
<213> ORGANISM: Artificial
<220> FEATURE:
<223> OTHER INFORMATION: Primer

<400> SEQUENCE: 53
atgccgttta ccaaaatgtg c                                          21

<210> SEQ ID NO 54
<211> LENGTH: 31
<212> TYPE: DNA
<213> ORGANISM: Artificial
<220> FEATURE:
<223> OTHER INFORMATION: Primer

<400> SEQUENCE: 54
ttactgcttt ctaccatata acttatggag t                              31

<210> SEQ ID NO 55
<211> LENGTH: 19
<212> TYPE: DNA
<213> ORGANISM: Artificial
<220> FEATURE:
<223> OTHER INFORMATION: Primer

<400> SEQUENCE: 55
ggagttgcaa tacgtccac                                            19

<210> SEQ ID NO 56
<211> LENGTH: 31
<212> TYPE: DNA
<213> ORGANISM: Artificial
<220> FEATURE:
<223> OTHER INFORMATION: Primer

<400> SEQUENCE: 56
ttactgcttt ctaccatata acttatggag t                              31

<210> SEQ ID NO 57
<211> LENGTH: 20
<212> TYPE: DNA
<213> ORGANISM: Artificial
<220> FEATURE:
<223> OTHER INFORMATION: Primer

<400> SEQUENCE: 57
ttaagtcgaa cagcccgagc                                           20

<210> SEQ ID NO 58
<211> LENGTH: 20
<212> TYPE: DNA
<213> ORGANISM: Artificial
<220> FEATURE:
<223> OTHER INFORMATION: Primer -continued

<400> SEQUENCE: 58
tccgaaaaac cccgcttttg                                                    20

<210> SEQ ID NO 59
<211> LENGTH: 20
<212> TYPE: DNA
<213> ORGANISM: Artificial
<220> FEATURE:
<223> OTHER INFORMATION: Primer

<400> SEQUENCE: 59
ggccgcactc gagatatcta                                                    20

<210> SEQ ID NO 60
<211> LENGTH: 20
<212> TYPE: DNA
<213> ORGANISM: Artificial
<220> FEATURE:
<223> OTHER INFORMATION: Primer

<400> SEQUENCE: 60
ccggatccag tcgactgaat                                                    20

<210> SEQ ID NO 61
<211> LENGTH: 403
<212> TYPE: PRT
<213> ORGANISM: Artificial
<220> FEATURE:
<223> OTHER INFORMATION: HhFPPS

<400> SEQUENCE: 61

Met Pro Phe Ala Lys Leu Cys Val Gln Lys Leu Ser Asn Pro Leu Met
1               5                   10                  15

Lys Leu Cys Tyr Pro Asn Leu Asn Gly Arg Leu Ser Leu Ser Lys Phe
                20                  25                  30

Ser Asn Ser Leu Asp Asn Ser Thr Phe Lys Phe Leu Ser Cys Asn Pro
            35                  40                  45

His Thr Ile Cys Arg Glu His Asn Thr Val Ala Ile Arg Pro Gln Thr
        50                  55                  60

Ile Thr Lys Asp Asp Lys Arg Asp Phe Met Ala Val Phe Pro Asp Ile
65                  70                  75                  80

Val Arg Asp Leu Thr Gln Gln Asp Pro Gly Ile Ser Asp Leu Ser Thr
                85                  90                  95

Leu Ile Ser Lys Leu Met Gln Tyr Asn Val Ser Gly Gly Lys Lys Val
            100                 105                 110

Arg Gly Leu Thr Val Val Tyr Ser Tyr Arg Met Leu Ala Pro Asp His
        115                 120                 125

Asp Leu Thr Pro Glu Asn Ile Arg Leu Ala Gln Ile Leu Gly Trp Cys
        130                 135                 140

Val Glu Met Leu Gln Gly Phe Phe Val Val Ile Asp Asp Leu Thr Asp
145                 150                 155                 160

Gln Ser Val Thr Arg Arg Gly Arg Pro Cys Trp Tyr Arg Leu Pro Gly
                165                 170                 175

Ile Gly Leu Arg Ala Ser Ser Asp Ala Leu Leu Ile Gln Ala Gly Thr
            180                 185                 190

Phe Gln Leu Leu Gln Gln His Cys Lys Asp Lys Glu Phe Tyr Val Asp
        195                 200                 205

Leu Val Glu Leu Phe Leu Asp Ala Thr Arg Arg Thr Thr Tyr Gly Gln

-continued

```
            210                 215                 220
Thr Leu Asp Leu Val Ser Ser Phe Pro Asn Ile Thr His Leu Thr Met
225                 230                 235                 240

Asp Arg Tyr Asn Phe Ile Thr Lys Tyr Lys Thr Ser Tyr Tyr Thr Phe
                245                 250                 255

His Leu Pro Val Ala Ile Ala Met Tyr Met Ala Gly Ile Tyr Asn Thr
                260                 265                 270

Glu Leu His Arg Gln Ala Lys Ser Val Leu Leu Glu Met Gly His Tyr
                275                 280                 285

Phe Gln Val Gln Asp Asp Tyr Leu Asp Val Phe Ser Asp Glu Glu Val
        290                 295                 300

Ser Gly Lys Lys Gly Thr Asp Ile Gln Glu Gly Lys Cys Thr Trp Leu
305                 310                 315                 320

Ala Ile Ile Ala Phe Gln Arg Ala Ser Pro Ser Gln Arg Glu Ile Leu
                325                 330                 335

Glu Ser Cys Tyr Gly Ser Lys Asp Pro Glu Lys Ile Gln Lys Val Lys
                340                 345                 350

Asp Ile Phe Ile Glu Ile Gly Leu Pro Ala Val Phe His Ala Tyr Glu
                355                 360                 365

Glu Glu Thr Tyr Asn Leu Ile Thr Arg Gln Ile Gln Gln Leu Ser Glu
        370                 375                 380

Gly Leu Pro His Glu Leu Phe Leu Thr Leu Leu His Lys Met Tyr Gly
385                 390                 395                 400

Arg Lys Gln
```

<210> SEQ ID NO 62
<211> LENGTH: 368
<212> TYPE: PRT
<213> ORGANISM: Artificial
<220> FEATURE:
<223> OTHER INFORMATION: HhTPS1

<400> SEQUENCE: 62

```
Met Ala Ser Val Ala Thr Lys Ser Leu Pro Lys Leu Ser Gly Ala Val
1               5                   10                  15

Phe Gly Gln Phe Ser Arg Arg Lys Gln Leu Ile Lys Arg His Trp Leu
                20                  25                  30

Asp Thr Lys Thr Asp Gln Tyr Tyr Asp Val Leu Arg Arg Ile Val Ile
            35                  40                  45

Pro Glu Cys Lys Asn Ile Ala Ser Asp Val Pro Gly Tyr Pro Glu Arg
        50                  55                  60

Ile Glu Glu Leu Leu Thr Tyr Thr Asn Pro Ala Phe Ser Asp Ala Trp
65                  70                  75                  80

Asn Phe Thr Thr Glu Leu Val Tyr Arg Ile Val Ala Asp Glu Ser His
                85                  90                  95

Gln Thr Glu Glu Asn Ile Asn Lys Met Tyr Ile Ile Arg Ala Ser Met
                100                 105                 110

Asp Leu Leu Phe Thr Met Ser Ala Val Leu Asp Asp Ile Ser Asp Lys
            115                 120                 125

Ser Asp Ser Arg Arg Gly Lys Lys Ser Trp His Ile Ile Cys Gln Gly
        130                 135                 140

Gly Glu Gly Ala Ala Leu Phe Asp Gly Ala Gln Ile Gly Leu Phe Pro
145                 150                 155                 160

Leu Tyr Leu Leu Lys Lys Phe Phe Arg Asn Asp Pro Gly Tyr Ile Pro
                165                 170                 175
```

-continued

```
Leu Met Glu Thr Ala Leu Met Ala Tyr Ile Lys Val Ala Ile Gly Gln
        180                 185                 190

Thr Ile Asp Val Leu Gly Gln Ser Asn Lys Thr Pro Val Met Ala Glu
        195                 200                 205

Tyr Lys Arg Ile Asn Tyr Tyr Lys Ala Gly Gln Phe Val Ala Ala Gly
        210                 215                 220

Pro Ala Leu Ala Ala Ile His Ala Gly Ile Leu Ser Glu Asp Leu Ile
225                 230                 235                 240

Glu Lys Thr Val Glu Ile Phe Thr Ile Ala Gly Arg Met Ile Gln Thr
                245                 250                 255

Trp Asp Asp Phe Asn Asp Tyr Tyr Ser Ser Ser Asp Gln Asn Gly Lys
                260                 265                 270

Pro Ser Cys Asp Leu Ile Asn Gly Gly Thr Thr Trp Val Ser Ala Lys
        275                 280                 285

Ala Met Glu Thr Phe Thr Pro Ser Gln Ala Ala Glu Phe Met Glu Cys
        290                 295                 300

Tyr Gly Ser Ala Asp Pro Asn Lys Asn Arg Arg Val Ile Glu Leu Tyr
305                 310                 315                 320

Asp Glu Ile Asp Met Pro Asn Leu Tyr Thr Glu Tyr Met Leu Glu Asn
                325                 330                 335

Tyr Asn Tyr Cys Gln Thr Leu Ile Lys Arg Leu Pro His Glu Arg Leu
                340                 345                 350

Arg Glu Ala Cys Ser Ser Tyr Leu Glu Trp Leu Val Ile Arg Glu Glu
        355                 360                 365
```

```
<210> SEQ ID NO 63
<211> LENGTH: 377
<212> TYPE: PRT
<213> ORGANISM: Artificial
<220> FEATURE:
<223> OTHER INFORMATION: HhTPS2

<400> SEQUENCE: 63
```

```
Met Ile Pro Lys Thr Leu Gly Asn Phe Thr Gly Tyr Val Leu Arg Ile
1               5                   10                  15

Ala Leu Asn Lys Lys His Val Asn Val Arg His Lys Leu Asp Thr Asp
                20                  25                  30

Ile Gly Lys Tyr Tyr Gln Thr Leu Asn Asp Val Val Ile Pro Glu Cys
        35                  40                  45

Met Glu Phe Val Lys Asp Ala Gln Gly Leu Pro Gln Arg Met Lys Glu
        50                  55                  60

Cys Ile Gly Tyr Thr Thr Pro Tyr Cys Tyr Glu Gly Trp Asn Phe Cys
65                  70                  75                  80

Val Glu Leu Leu Tyr Lys Thr Val Ala Asp Lys Pro His Gln Thr Glu
                85                  90                  95

Glu Asn Leu Lys Lys Met Arg Ile Leu Arg Val Leu Ser Asp Met Ser
        100                 105                 110

His Ser Met His Phe Ile Leu Asp Asp Tyr Ala Asp Lys Ala Glu Phe
        115                 120                 125

Arg Gln Gly Lys Lys Ile Trp Ala Ser Ile Cys Glu Gly Gly Gln Glu
        130                 135                 140

Ala Ala Ile Tyr Asp Thr Phe Thr Val Asn Tyr Leu Ile Asn Cys Met
145                 150                 155                 160

Leu Gln Arg His Phe Arg Asn Asp Pro Gly Phe Thr Lys Met Cys Glu
                165                 170                 175
```

```
Met Phe Ser Trp Val Asn Gly Asn Ser Gly Ile Gly Gln Val Leu Asp
            180                 185                 190

Ile Leu Asp His Lys Asn Ser Asp Phe Ser Asp Tyr Ala Ser Trp Lys
            195                 200                 205

Asn Lys Val Glu Tyr Lys Ser Arg Asn Thr Met Cys Ala Phe Pro Val
            210                 215                 220

Leu Gly Leu Leu His Ala Gly Leu Thr Cys Asn Asp Leu Ile His Lys
225                 230                 235                 240

Thr Met Asp Ile Phe Gly Asp Tyr Gly Leu Met Phe Gln Val Trp Asn
                245                 250                 255

Asp Phe Met Asp Phe Tyr Ser Val Gln Glu Glu Ser Gly Lys Gly Asn
                260                 265                 270

Tyr Asp Cys Lys Asn Asn Val Lys Thr Trp Ala Thr Ile Thr Ala Met
            275                 280                 285

Ser His Phe Asn Pro Ala Gln Ala Lys Glu Phe Arg Asp Cys Tyr Gly
            290                 295                 300

Thr Asn Asp Pro Ala Lys Arg Ser Arg Val Arg Glu Leu Phe Asp Glu
305                 310                 315                 320

Ile Asp Leu Pro Arg Lys Tyr Leu Asp Tyr Leu Arg Asn Ile Arg Val
                325                 330                 335

Thr Val Glu Lys Lys Ile Ser Glu Leu Ser Asp Ala Arg Val Arg Asp
            340                 345                 350

Ala Ser Thr Ser Tyr Leu Glu Trp Leu His Gly Asn Gly His His Asp
            355                 360                 365

Val Glu Leu Glu Ile Leu Lys Ala Pro
        370                 375
```

```
<210> SEQ ID NO 64
<211> LENGTH: 20
<212> TYPE: DNA
<213> ORGANISM: Artificial
<220> FEATURE:
<223> OTHER INFORMATION: Primer

<400> SEQUENCE: 64
atgataccga agacgcttgg                                    20

<210> SEQ ID NO 65
<211> LENGTH: 27
<212> TYPE: DNA
<213> ORGANISM: Artificial
<220> FEATURE:
<223> OTHER INFORMATION: Primer

<400> SEQUENCE: 65
ttatggagct tttaggatct ccaattc                            27

<210> SEQ ID NO 66
<211> LENGTH: 21
<212> TYPE: DNA
<213> ORGANISM: Artificial
<220> FEATURE:
<223> OTHER INFORMATION: Primer

<400> SEQUENCE: 66
gccaagaagc agccatctat g                                  21

<210> SEQ ID NO 67
<211> LENGTH: 23
```

-continued

```
<212> TYPE: DNA
<213> ORGANISM: Artificial
<220> FEATURE:
<223> OTHER INFORMATION: Primer

<400> SEQUENCE: 67
cacatcttgg tgaaacctgg atc                                              23

<210> SEQ ID NO 68
<211> LENGTH: 20
<212> TYPE: DNA
<213> ORGANISM: Artificial
<220> FEATURE:
<223> OTHER INFORMATION: Primer

<400> SEQUENCE: 68
atgccttttg caaaactgtg                                                 20

<210> SEQ ID NO 69
<211> LENGTH: 27
<212> TYPE: DNA
<213> ORGANISM: Artificial
<220> FEATURE:
<223> OTHER INFORMATION: Primer

<400> SEQUENCE: 69
ctactgcttt ctaccataca tcttatg                                         27

<210> SEQ ID NO 70
<211> LENGTH: 17
<212> TYPE: DNA
<213> ORGANISM: Artificial
<220> FEATURE:
<223> OTHER INFORMATION: Primer

<400> SEQUENCE: 70
atggcgttcg tgtctgc                                                    17

<210> SEQ ID NO 71
<211> LENGTH: 29
<212> TYPE: DNA
<213> ORGANISM: Artificial
<220> FEATURE:
<223> OTHER INFORMATION: Primer

<400> SEQUENCE: 71
ttaatctaaa ttttcatcag gagtttctc                                       29

<210> SEQ ID NO 72
<211> LENGTH: 17
<212> TYPE: DNA
<213> ORGANISM: Artificial
<220> FEATURE:
<223> OTHER INFORMATION: Primer

<400> SEQUENCE: 72
atggcgaaca tggctgg                                                    17

<210> SEQ ID NO 73
<211> LENGTH: 24
<212> TYPE: DNA
<213> ORGANISM: Artificial
<220> FEATURE:
<223> OTHER INFORMATION: Primer

<400> SEQUENCE: 73
```
tcaaacattc gtaactttag ggtc                                                              24

<210> SEQ ID NO 74
<211> LENGTH: 18
<212> TYPE: DNA
<213> ORGANISM: Artificial
<220> FEATURE:
<223> OTHER INFORMATION: Primer

<400> SEQUENCE: 74
atggcgtcaa aggtgtcg                                                                     18

<210> SEQ ID NO 75
<211> LENGTH: 29
<212> TYPE: DNA
<213> ORGANISM: Artificial
<220> FEATURE:
<223> OTHER INFORMATION: Primer

<400> SEQUENCE: 75
tcagaatgat tctaatcttt caagttgaa                                                         29

<210> SEQ ID NO 76
<211> LENGTH: 17
<212> TYPE: DNA
<213> ORGANISM: Artificial
<220> FEATURE:
<223> OTHER INFORMATION: Primer

<400> SEQUENCE: 76
atggcagcga aggcatc                                                                      17

<210> SEQ ID NO 77
<211> LENGTH: 27
<212> TYPE: DNA
<213> ORGANISM: Artificial
<220> FEATURE:
<223> OTHER INFORMATION: Primer

<400> SEQUENCE: 77
tcagaatgat tttaatcgtt caagttg                                                           27

<210> SEQ ID NO 78
<211> LENGTH: 17
<212> TYPE: DNA
<213> ORGANISM: Artificial
<220> FEATURE:
<223> OTHER INFORMATION: Primer

<400> SEQUENCE: 78
atggcgtccg tggctac                                                                      17

<210> SEQ ID NO 79
<211> LENGTH: 22
<212> TYPE: DNA
<213> ORGANISM: Artificial
<220> FEATURE:
<223> OTHER INFORMATION: Primer

<400> SEQUENCE: 79
tcactcttct cgaatcacga gc                                                                22

<210> SEQ ID NO 80
<211> LENGTH: 20
<212> TYPE: DNA
<213> ORGANISM: Artificial

-continued

```
<220> FEATURE:
<223> OTHER INFORMATION: Primer

<400> SEQUENCE: 80 tccccttttcg agcaggtatg                                                    20

<210> SEQ ID NO 81
<211> LENGTH: 22
<212> TYPE: DNA
<213> ORGANISM: Artificial
<220> FEATURE:
<223> OTHER INFORMATION: Primer

<400> SEQUENCE: 81
agccttttcg caggtttatg ag                                                  22

<210> SEQ ID NO 82
<211> LENGTH: 384
<212> TYPE: PRT
<213> ORGANISM: Artificial
<220> FEATURE:
<223> OTHER INFORMATION: MhTPS

<400> SEQUENCE: 82

Met Val Ser Ile Ala Ala Lys Ser Leu Pro Lys Leu Ser Gly Ala Val
1               5                   10                  15

Phe Gly Gln Phe Ser Arg Arg Lys Gln Leu Ile Gln Arg His Trp Leu
            20                  25                  30

Asp Thr Arg Thr Asp Gln Tyr Tyr Asp Val Leu Arg Arg Ile Val Val
        35                  40                  45

Pro Glu Cys Lys Asn Ile Ala Ser Asp Val Pro Glu Tyr Pro Glu Arg
    50                  55                  60

Ile Glu Lys Leu Leu Tyr Tyr Thr Asn Pro Ala Phe Ser Asp Ala Trp
65                  70                  75                  80

Asn Phe Thr Thr Glu Leu Ile Tyr Arg Thr Ala Asp Glu Ser His Gln
                85                  90                  95

Thr Glu Glu Asn Ile Thr Lys Met Tyr Leu Ile Arg Ala Thr Met Asp
            100                 105                 110

Leu Leu Phe Thr Met Ser Ala Val Leu Asp Asp Ile Ser Asp Arg Ser
        115                 120                 125

Glu Phe Arg Lys Gly Lys Lys Gly Trp His Met Ile Cys Gln Gly Gly
    130                 135                 140

Glu Ser Thr Ala Leu Tyr Asp Gly Thr Gln Met Gly Leu Phe Pro Leu
145                 150                 155                 160

Tyr Leu Leu Lys Gln Tyr Phe Lys Asn Asp Pro Gly Tyr Ser Arg Leu
                165                 170                 175

Leu Glu Thr Val Val Met Thr Tyr Ile Lys Leu Thr Ile Gly Gln Thr
            180                 185                 190

Ile Asp Val Leu Gly Gln Phe Lys Lys Ser Pro Ser Met Ala Glu Tyr
        195                 200                 205

Lys Arg Ile Asn Tyr Tyr Lys Ala Gly Gln Phe Val Ala Ala Gly Ser
    210                 215                 220

Glu Leu Ala Val Ile His Ala Gly Ile Thr Ser Gln Asp Leu Ile Asp
225                 230                 235                 240

Lys Thr Val Glu Ile Phe Thr Ile Ala Gly Gln Ile Ile Gln Thr Trp
                245                 250                 255

Asp Asp Phe Asn Asp Tyr Tyr Ser Ser Ser Glu Gln Asn Gly Lys Leu
                260                 265                 270
```

```
Ser Cys Asp Phe Met Asn Ala Gly Thr Thr Trp Val Ser Ala Lys Ala
        275             280             285

Met Glu Val Phe Thr Pro Ser Gln Ala Val Lys Phe Met Glu Cys Tyr
    290             295             300

Gly Ser Asp Asp Gln Ser Lys Met Lys Thr Val Gln Glu Leu Tyr Asp
305             310             315             320

Glu Ile Asp Met Pro Lys Leu Tyr Thr Glu Tyr Val Leu Glu Asn Tyr
            325             330             335

Asn Arg Cys Glu Thr Leu Ile Lys Glu Leu Pro His Asp Arg Leu Arg
        340             345             350

Glu Ala Cys Ser Ser Tyr Met Glu Trp Leu Val Val Arg Glu Thr Pro
        355             360             365

Asp Glu Asp Ser Glu His Lys Val Ala Leu Cys Leu Asn Ile Ser Gly
    370             375             380
```

```
<210> SEQ ID NO 83
<211> LENGTH: 368
<212> TYPE: PRT
<213> ORGANISM: Artificial
<220> FEATURE:
<223> OTHER INFORMATION: HhTPS1

<400> SEQUENCE: 83
```

```
Met Ala Ser Val Ala Thr Lys Ser Leu Pro Lys Leu Ser Gly Ala Val
1               5               10              15

Phe Gly Gln Phe Ser Arg Arg Lys Gln Leu Ile Lys Arg His Trp Leu
            20              25              30

Asp Thr Lys Thr Asp Gln Tyr Tyr Asp Val Leu Arg Arg Ile Val Ile
        35              40              45

Pro Glu Cys Lys Asn Ile Ala Ser Asp Val Pro Gly Tyr Pro Glu Arg
    50              55              60

Ile Glu Glu Leu Leu Thr Tyr Thr Asn Pro Ala Phe Ser Asp Ala Trp
65              70              75              80

Asn Phe Thr Thr Glu Leu Val Tyr Arg Ile Val Ala Asp Glu Ser His
            85              90              95

Gln Thr Glu Glu Asn Ile Asn Lys Met Tyr Ile Ile Arg Ala Ser Met
        100             105             110

Asp Leu Leu Phe Thr Met Ser Ala Val Leu Asp Asp Ile Ser Asp Lys
        115             120             125

Ser Asp Ser Arg Arg Gly Lys Lys Ser Trp His Ile Ile Cys Gln Gly
    130             135             140

Gly Glu Gly Ala Ala Leu Phe Asp Gly Ala Gln Ile Gly Leu Phe Pro
145             150             155             160

Leu Tyr Leu Leu Lys Lys Phe Phe Arg Asn Asp Pro Gly Tyr Ile Pro
            165             170             175

Leu Met Glu Thr Ala Leu Met Ala Tyr Ile Lys Val Ala Ile Gly Gln
        180             185             190

Thr Ile Asp Val Leu Gly Gln Ser Asn Lys Thr Pro Val Met Ala Glu
        195             200             205

Tyr Lys Arg Ile Asn Tyr Tyr Lys Ala Gly Gln Phe Val Ala Ala Gly
    210             215             220

Pro Ala Leu Ala Ala Ile His Ala Gly Ile Leu Ser Glu Asp Leu Ile
225             230             235             240

Glu Lys Thr Val Glu Ile Phe Thr Ile Ala Gly Arg Met Ile Gln Thr
            245             250             255
```

Trp Asp Asp Phe Asn Asp Tyr Tyr Ser Ser Ser Asp Gln Asn Gly Lys
        260                 265                 270

Pro Ser Cys Asp Leu Ile Asn Gly Gly Thr Thr Trp Val Ser Ala Lys
        275                 280                 285

Ala Met Glu Thr Phe Thr Pro Ser Gln Ala Ala Glu Phe Met Glu Cys
        290                 295                 300

Tyr Gly Ser Ala Asp Pro Asn Lys Asn Arg Arg Val Ile Glu Leu Tyr
305                 310                 315                 320

Asp Glu Ile Asp Met Pro Asn Leu Tyr Thr Glu Tyr Met Leu Glu Asn
                325                 330                 335

Tyr Asn Tyr Cys Gln Thr Leu Ile Lys Arg Leu Pro His Glu Arg Leu
        340                 345                 350

Arg Glu Ala Cys Ser Ser Tyr Leu Glu Trp Leu Val Ile Arg Glu Glu
        355                 360                 365

<210> SEQ ID NO 84
<211> LENGTH: 369
<212> TYPE: PRT
<213> ORGANISM: Artificial
<220> FEATURE:
<223> OTHER INFORMATION: HhTPS

<400> SEQUENCE: 84

Met Ala Ser Val Ala Thr Lys Ser Leu Pro Lys Leu Ser Gly Ala Val
1               5                   10                  15

Phe Gly Gln Phe Ser Arg Arg Lys Gln Leu Ile Lys Arg His Trp Leu
                20                  25                  30

Asp Thr Lys Thr Asp Gln Tyr Tyr Asp Val Leu Arg Arg Ile Val Ile
        35                  40                  45

Pro Glu Cys Lys Asn Ile Ala Ser Asp Val Pro Gly Tyr Pro Glu Arg
        50                  55                  60

Ile Glu Glu Leu Leu Thr Tyr Thr Asn Pro Ala Phe Ser Asp Ala Trp
65                  70                  75                  80

Asn Phe Thr Thr Glu Leu Val Tyr Arg Ile Ala Val Ala Asp Glu Ser
                85                  90                  95

His Gln Thr Glu Glu Asn Ile Asn Lys Met Tyr Ile Ile Arg Ala Ser
                100                 105                 110

Met Asp Leu Leu Phe Thr Met Ser Ala Val Leu Asp Asp Ile Ser Asp
        115                 120                 125

Lys Ser Asp Ser Arg Arg Gly Lys Lys Ser Trp His Ile Ile Cys Gln
        130                 135                 140

Gly Gly Glu Gly Ala Ala Leu Phe Asp Gly Ala Gln Ile Gly Leu Phe
145                 150                 155                 160

Pro Leu Tyr Leu Leu Lys Lys Phe Phe Arg Asn Asp Pro Gly Tyr Ile
                165                 170                 175

Pro Leu Met Glu Thr Ala Leu Met Ala Tyr Ile Lys Val Ala Ile Gly
                180                 185                 190

Gln Thr Ile Asp Val Leu Gly Gln Ser Asn Lys Thr Pro Val Met Ala
        195                 200                 205

Glu Tyr Lys Arg Ile Asn Tyr Tyr Lys Ala Gly Gln Phe Val Ala Ala
        210                 215                 220

Gly Pro Ala Leu Ala Ala Ile His Ala Gly Ile Leu Ser Glu Asp Leu
225                 230                 235                 240

Ile Glu Lys Thr Val Glu Ile Phe Thr Ile Ala Gly Arg Met Ile Gln
                245                 250                 255

```
Thr Trp Asp Asp Phe Asn Asp Tyr Tyr Ser Ser Ser Asp Gln Asn Gly
        260             265             270

Lys Pro Ser Cys Asp Leu Ile Asn Gly Gly Thr Thr Trp Val Ser Ala
        275             280             285

Lys Ala Met Glu Thr Phe Thr Pro Ser Gln Ala Ala Glu Phe Met Glu
        290             295             300

Cys Tyr Gly Ser Ala Asp Pro Asn Lys Asn Arg Arg Val Ile Glu Leu
305             310             315             320

Tyr Asp Glu Ile Asp Met Pro Asn Leu Tyr Thr Glu Tyr Met Leu Glu
                325             330             335

Asn Tyr Asn Tyr Cys Gln Thr Leu Ile Lys Arg Leu Pro His Glu Arg
        340             345             350

Leu Arg Glu Ala Cys Ser Ser Tyr Leu Glu Trp Leu Val Ile Arg Glu
        355             360             365

Glu

<210> SEQ ID NO 85
<211> LENGTH: 382
<212> TYPE: PRT
<213> ORGANISM: Artificial
<220> FEATURE:
<223> OTHER INFORMATION: MhTPS

<400> SEQUENCE: 85

Met Val Ser Ile Ala Ala Lys Ser Leu Pro Lys Leu Ser Gly Ala Val
1               5               10              15

Phe Gln Phe Ser Arg Arg Lys Gln Leu Ile Gln Arg His Trp Leu Asp
        20              25              30

Thr Arg Thr Gln Tyr Tyr Asp Val Leu Arg Arg Ile Val Val Pro Glu
        35              40              45

Cys Lys Asn Ile Ala Ser Asp Tyr Pro Glu Tyr Pro Glu Arg Ile Glu
        50              55              60

Lys Leu Leu Tyr Tyr Thr Asn Pro Ala Phe Ser Asp Ala Trp Asn Phe
65              70              75              80

Thr Thr Glu Leu Ile Tyr Arg Thr Val Ala Asp Glu Ser His Gln Thr
                85              90              95

Glu Glu Asn Ile Thr Lys Met Tyr Leu Ile Arg Ala Thr Met Asp Leu
        100             105             110

Leu Phe Thr Met Ser Ala Val Leu Asp Asp Ile Ser Asp Arg Ser Glu
        115             120             125

Phe Arg Lys Gly Lys Lys Gly Trp His Met Ile Cys Gln Gly Gly Glu
        130             135             140

Ser Thr Ala Leu Tyr Asp Gly Thr Gln Met Gly Leu Phe Pro Leu Tyr
145             150             155             160

Leu Lys Gln Tyr Phe Lys Asn Asp Pro Gly Tyr Ser Arg Leu Leu Glu
                165             170             175

Thr Val Val Met Thr Tyr Ile Lys Leu Thr Ile Gly Gln Thr Ile Asp
                180             185             190

Val Leu Gly Gln Phe Lys Lys Ser Pro Ser Met Ala Glu Tyr Lys Arg
        195             200             205

Ile Asn Tyr Tyr Lys Ala Gly Gln Phe Val Ala Ala Gly Ser Glu Leu
        210             215             220

Ala Val Ile His Ala Gly Ile Thr Ser Gln Asp Leu Ile Asp Lys Thr
225             230             235             240
```

Val Glu Ile Phe Thr Ile Ala Gly Gln Ile Ile Gln Thr Trp Asp Asp
                245                 250                 255

Phe Asn Asp Tyr Tyr Ser Ser Ser Glu Gln Asn Gly Lys Leu Ser Cys
                260                 265                 270

Asp Phe Met Asn Ala Gly Thr Thr Trp Val Ser Ala Lys Ala Met Glu
            275                 280                 285

Val Phe Thr Pro Ser Gln Ala Val Lys Phe Met Glu Cys Tyr Gly Ser
        290                 295                 300

Asp Asp Gln Ser Lys Met Lys Thr Val Gln Glu Leu Tyr Asp Glu Ile
305                 310                 315                 320

Asp Met Pro Lys Leu Tyr Thr Glu Tyr Val Leu Glu Asn Tyr Asn Arg
                325                 330                 335

Cys Glu Thr Leu Ile Lys Glu Leu Pro His Asp Arg Leu Arg Glu Ala
            340                 345                 350

Cys Ser Ser Tyr Met Glu Trp Leu Val Val Arg Glu Thr Pro Asp Glu
        355                 360                 365

Asp Ser Glu His Lys Val Ala Leu Cys Leu Asn Ile Ser Gly
    370                 375                 380

<210> SEQ ID NO 86
<211> LENGTH: 376
<212> TYPE: PRT
<213> ORGANISM: Artificial
<220> FEATURE:
<223> OTHER INFORMATION: NvTPS

<400> SEQUENCE: 86

Met Ala Ala Arg Ala Pro Val His Leu Arg Gly Phe Ile Ala Arg Val
1               5                   10                  15

Ala Leu Asn Lys Lys Asn Leu His Ala Arg His Lys Leu Asp Thr Asp
                20                  25                  30

Ile Asp Lys Tyr Tyr Thr Leu His Asn Val Ile Ile Pro Asp Phe Met
            35                  40                  45

Asp Met Val Lys Glu Ile Pro Gly Tyr Pro Glu Arg Ile Lys Lys Cys
        50                  55                  60

Val Ala His Thr Thr Pro Ser Tyr Phe Glu Gly Trp Ala Phe Ser Thr
65                  70                  75                  80

Glu Leu Ile Tyr Lys Thr Val Ala Asp Lys Gln His Gln Thr Glu Arg
                85                  90                  95

Asn Leu Glu Lys Cys Arg Ile Ile Arg Ala Leu Met Asp Met Ser Tyr
            100                 105                 110

Ala Met Ala Gly Ile Leu Asp Asp Tyr Val Asp Lys Gly Glu Phe Arg
        115                 120                 125

Arg Gly Lys Lys Val Trp Ala Ser Val Cys Glu Gly Gly Gln Glu Ala
    130                 135                 140

Ala Ile Tyr Asp Ser Ile Ala Val Thr Tyr Leu Met Ser Leu Met Val
145                 150                 155                 160

Lys Arg His Phe Gly Thr Asp Pro Gly Tyr Ser Lys Leu Ile Glu Leu
                165                 170                 175

Phe Asn Met Val Pro Gly Thr Ala Ala Ile Gly Asn Thr Leu Asp Ile
            180                 185                 190

Leu Asp Arg His Asp Thr Asn Tyr Tyr Asp Asp Thr Met Trp Lys His
        195                 200                 205

Ser Val Gln Asn Lys Ala Ala Asn Thr Val Phe Pro Ala Ala Thr Ala
    210                 215                 220

-continued

```
Gly Leu Ile His Ala Gly Val Leu Cys Asp Asp Leu Leu Asp Arg Thr
225             230             235             240

Ser Glu Val Phe Gly Tyr Thr Gly His Leu Phe Gln Val Trp Asp Asp
                245             250             255

Phe Met Glu His Tyr Ala Val Lys Glu Gln Ser Gly Lys Gly Ala Pro
            260             265             270

Asp Thr Lys Tyr Asn Ala Lys Thr Trp Ala Thr Leu Thr Ala Met Ala
        275             280             285

His Phe Asn Glu Gln Ala Lys Glu Phe Lys Ala Cys Tyr Gly Ser Thr
    290             295             300

Asp Pro Ala Lys Arg Ser Val Arg Glu Leu Tyr Asp Glu Val Asn Leu
305             310             315             320

Arg Gly Leu Tyr Ile Asp Tyr Leu Arg Asn Thr Tyr Met Val Val Glu
                325             330             335

Glu Lys Ile Ser Lys Ile Pro Asp Pro Arg Ile Gln Ser Ala Cys Arg
            340             345             350

Ser Tyr Met Asp Trp Leu Leu Val Glu Pro Pro Gln Asp Glu Glu Glu
        355             360             365

Ala Glu Ser Val Leu Asn Asn Val
    370             375

<210> SEQ ID NO 87
<211> LENGTH: 405
<212> TYPE: PRT
<213> ORGANISM: Artificial
<220> FEATURE:
<223> OTHER INFORMATION: HhFPPS

<400> SEQUENCE: 87

Met Pro Phe Ala Lys Leu Cys Val Gln Lys Leu Ser Asn Pro Leu Met
1               5               10              15

Lys Leu Cys Tyr Pro Asn Leu Asn Gly Arg Leu Ser Leu Ser Lys Phe
            20              25              30

Ser Asn Ser Leu Asp Asn Ser Thr Phe Lys Phe Leu Ser Cys Asn Pro
        35              40              45

His Thr Ile Cys Arg Glu His Asn Thr Val Ala Ile Arg Pro Gln Thr
    50              55              60

Ile Thr Lys Asp Asp Lys Arg Asp Phe Met Ala Val Phe Pro Asp Ile
65              70              75              80

Val Arg Asp Leu Thr Gln Gln Asp Pro Gly Ile Ser Asp Leu Ser Thr
                85              90              95

Ile Leu Ile Ser Lys Leu Met Gln Tyr Asn Val Ser Gly Gly Lys Lys
            100             105             110

Val Arg Gly Leu Thr Val Val Tyr Ser Tyr Arg Met Leu Ala Pro Asp
        115             120             125

His Asp Leu Thr Pro Glu Asn Ile Arg Leu Ala Gln Ile Leu Gly Trp
    130             135             140

Cys Val Glu Met Leu Gln Gly Phe Phe Val Val Ile Phe Phe Leu Tyr
145             150             155             160

Phe Trp Asp Asx Tyr Thr Thr His Thr Pro Val Glu Tyr Thr Leu Pro
                165             170             175

His Ile His Leu Thr Ser Asp Asp Phe Ser Leu Leu Ile Gln Ala Gly
            180             185             190

Thr Phe Gln Leu Leu Gln Gln His Cys Lys Asp Lys Glu Phe Tyr Val
        195             200             205
```

```
Asp Leu Val Glu Leu Phe Leu Asp Ala Thr Arg Arg Thr Thr Tyr Gly
    210             215             220

Gln Thr Leu Asp Leu Val Ser Ser Phe Pro Asn Ile Thr His Leu Thr
225             230             235             240

Met Asp Arg Tyr Asn Phe Ile Thr Lys Tyr Lys Thr Ser Tyr Tyr Thr
            245             250             255

Phe His Leu Pro Val Ala Ile Ala Met Tyr Met Ala Gly Ile Tyr Asn
            260             265             270

Thr Glu Leu His Arg Gln Ala Lys Ser Val Leu Leu Glu Met Gly His
            275             280             285

Tyr Phe Gln Val Gln Asp Asp Tyr Leu Asp Val Phe Ser Asp Glu Glu
    290             295             300

Val Ser Gly Lys Lys Gly Thr Asp Ile Gln Glu Gly Lys Cys Thr Trp
305             310             315             320

Leu Ala Ile Ile Ala Phe Gln Arg Ala Ser Pro Ser Gln Arg Glu Ile
            325             330             335

Leu Glu Ser Cys Tyr Gly Ser Lys Asp Pro Glu Lys Ile Ala Gln Lys
            340             345             350

Val Lys Asp Ile Phe Ile Glu Ile Gly Leu Pro Ala Val Phe His Ala
            355             360             365

Tyr Glu Glu Glu Thr Tyr Asn Leu Ile Thr Arg Gln Ile Gln Gln Leu
    370             375             380

Ser Glu Gly Leu Pro His Glu Leu Phe Leu Thr Leu Leu His Lys Met
385             390             395             400

Tyr Gly Arg Lys Gln
                405

<210> SEQ ID NO 88
<211> LENGTH: 403
<212> TYPE: PRT
<213> ORGANISM: Artificial
<220> FEATURE:
<223> OTHER INFORMATION: NvFPPS

<400> SEQUENCE: 88

Met Pro Leu Ala Lys Leu Cys Ala Lys Lys Leu Ser Ser Pro Leu Met
1               5               10              15

Lys Leu Cys Tyr Pro Asn Leu Asn Gly Lys Leu Pro Phe Ser Asn Leu
            20              25              30

Ser Asn Ile Leu Asp Asn Ser Ser Leu Lys Phe His Ser Cys Asn Pro
            35              40              45

Asp His Ile Thr Cys Arg Gly Leu Ser Thr Val Ala Leu Arg Pro Gln
    50              55              60

Thr Ile Thr Lys Asp Asp Lys Arg Asp Phe Met Ala Val Phe Pro Asp
65              70              75              80

Ile Val Arg Asp Leu Thr Gln Leu Asn Pro Gly Ile Ser Asp Leu Ser
            85              90              95

Thr Leu Ile Ser Lys Ile Met Gln Tyr Asn Val Ser Gly Gly Lys Lys
            100             105             110

Val Arg Gly Leu Thr Val Val Tyr Ser Tyr Arg Met Leu Ala Pro Asp
            115             120             125

His Ala Leu Thr Pro Glu Asn Ile Arg Leu Ala Gln Ile Leu Gly Trp
    130             135             140

Cys Val Glu Met Leu Gln Gly Phe Phe Leu Val Ile Asp Asp Leu Ala
145             150             155             160
```

-continued

Asp Gln Ser Ile Thr Arg Arg Gly Arg Pro Cys Trp Tyr Arg Asn Pro
                165                     170                     175

Asp Val Gly Leu Arg Ala Gly Ser Asp Ala Leu Leu Ile Gln Ser Gly
            180                     185                     190

Thr Phe Gln Leu Leu Gln Gln His Cys Lys Asp Arg Glu Phe Tyr Ile
            195                     200                     205

Asp Leu Val Glu Leu Phe Leu Asp Ala Val Arg Arg Thr Thr Tyr Gly
        210                     215                     220

Gln Thr Leu Asp His Val Ser Ser Phe Pro Asn Ile Thr His Leu Thr
225                     230                     235                     240

Met Asp Arg Tyr Asn Phe Ile Thr Lys Tyr Lys Thr Ser Tyr Tyr Thr
                245                     250                     255

Phe His Leu Pro Val Ala Thr Ala Met Tyr Met Ala Gly Ile Tyr Asn
            260                     265                     270

Thr Glu Leu His Arg Gln Ala Lys Ser Val Leu Leu Glu Met Gly His
            275                     280                     285

Tyr Phe Gln Val Gln Asp Asp Tyr Leu Asp Val Phe Gly Asp Glu Glu
        290                     295                     300

Val Ile Gly Lys Ile Gly Thr Asp Ile Gln Glu Gly Lys Cys Thr Trp
305                     310                     315                     320

Leu Ala Ile Val Ala Phe Gln Arg Ala Ser Pro Gln Arg Glu Ile Leu
                325                     330                     335

Glu Ser Cys Tyr Gly Ser Lys Asp Pro Glu Lys Ile Lys Lys Val Lys
                340                     345                     350

Asp Thr Phe Ile Glu Ile Gly Val Pro Ala Val Phe His Ala Tyr Glu
            355                     360                     365

Glu Glu Thr Tyr Asn Leu Ile Thr Arg Gln Ile Gln Gln Leu Ser Gln
        370                     375                     380

Gly Leu Pro His Glu Leu Phe Leu Thr Leu Leu His Lys Thr Tyr Gly
385                     390                     395                     400

Arg Lys Gln

<210> SEQ ID NO 89
<211> LENGTH: 406
<212> TYPE: PRT
<213> ORGANISM: Artificial
<220> FEATURE:
<223> OTHER INFORMATION: MhFPPS

<400> SEQUENCE: 89

Met Pro Phe Thr Lys Met Cys Thr Ser Lys Leu Ala Asn Pro Leu Met
1                   5                       10                      15

Lys Tyr Tyr Leu Asn Leu Asn Gly Lys Ser Pro Leu Ser Lys Leu Ser
                20                      25                      30

Asn Ser Leu Asn Ser Ser Ser Phe Lys Phe Ile Ser Cys Ser Pro His
            35                      40                      45

Ile Val Cys Arg Glu Leu Asn Thr Val Ser Gly Val Ala Ile Arg Pro
        50                      55                      60

Gln Thr Ile Thr Lys Asp Asp Lys Arg Asp Phe Met Ala Val Phe Pro
65                      70                      75                      80

Asp Ile Val Arg Asp Leu Thr Gln Leu Asn Pro Gly Ile Ser Asp Leu
                85                      90                      95

Ser Thr Leu Ile Ser Lys Leu Met Gln Tyr Asn Val Ser Gly Gly Lys
            100                     105                     110

Lys Val Arg Gly Leu Thr Val Val Tyr Ser Tyr Arg Met Leu Ala Pro

```
            115               120               125

Asp His Ala Leu Thr Pro Glu Asn Ile Arg Leu Ala Gln Ile Leu Gly
    130               135               140

Trp Cys Val Glu Met Leu Gln Gly Phe Phe Val Val Ile Asp Asp Leu
145               150               155               160

Ala Asp Asp Gln Ser Val Thr Arg Arg Gly Arg Pro Cys Trp Tyr Arg
                165               170               175

Leu Pro Gly Val Gly Leu Arg Ala Ser Ser Asp Ala Leu Leu Ile Gln
                180               185               190

Ser Gly Cys Phe Gln Leu Leu Gln Gln His Cys Lys Asp Lys Glu Phe
                195               200               205

Tyr Val Asp Leu Val Glu Leu Phe Leu Asp Ala Leu Arg Arg Thr Thr
    210               215               220

Tyr Gly Gln Thr Leu Asp Tyr Val Ser Ser Phe Pro Asn Ile Asn His
225               230               235               240

Leu Thr Met Asp Arg Tyr Asn Phe Ile Thr Lys Tyr Lys Thr Ala Tyr
                245               250               255

Tyr Thr Tyr His Leu Pro Val Ala Thr Ala Met Tyr Met Ala Gly Ile
                260               265               270

Tyr Asn Ala Glu Leu His Arg Gln Ala Lys Ser Val Leu Leu Glu Met
                275               280               285

Gly His Tyr Phe Gln Val Gln Asp Asp Tyr Leu Asp Val Phe Gly Asp
    290               295               300

Glu Glu Met Ile Gly Lys Lys Gly Thr Asp Ile Gln Glu Gly Lys Cys
305               310               315               320

Thr Trp Leu Ala Ile Ile Ala Phe Gln Arg Ala Ser Pro Pro Gln Arg
                325               330               335

Glu Val Leu Glu Ser Cys Tyr Gly Thr Lys Glu Pro Glu Lys Ile Lys
                340               345               350

Lys Val Lys Asp Ile Phe Ile Glu Leu Ser Leu Pro Ala Val Tyr His
                355               360               365

Ala Tyr Glu Glu Glu Thr Tyr Asn Leu Ile Thr Arg Gln Ile Gln Gln
    370               375               380

Leu Ser Gln Gly Leu Pro His Glu Leu Phe Leu Thr Leu Leu His Lys
385               390               395               400

Leu Tyr Gly Arg Lys Gln
                405
```

<210> SEQ ID NO 90
<211> LENGTH: 23
<212> TYPE: PRT
<213> ORGANISM: Artificial
<220> FEATURE:
<223> OTHER INFORMATION: M. histrionica IDS-1 SARM containing region

<400> SEQUENCE: 90

```
Thr Ile Ala Gly Gln Ile Ile Gln Thr Trp Asp Asp Phe Asn Asp Tyr
1               5               10               15

Tyr Ser Ser Ser Glu Gln Asn
            20
```

<210> SEQ ID NO 91
<211> LENGTH: 23
<212> TYPE: PRT
<213> ORGANISM: Artificial
<220> FEATURE:
<223> OTHER INFORMATION: H. halys IDS-1 SARM  containing region -continued

<400> SEQUENCE: 91

Gly Asp Tyr Gly Leu Met Phe Gln Val Trp Asn Asp Phe Met Asp Phe
1               5                   10                  15

Tyr Ser Val Gln Glu Glu Ser
            20

<210> SEQ ID NO 92
<211> LENGTH: 25
<212> TYPE: PRT
<213> ORGANISM: Artificial
<220> FEATURE:
<223> OTHER INFORMATION: I. pini GPPS/TPS SARM containing region

<400> SEQUENCE: 92

Met Arg Ile Gly Met Met His Gln Ser Gln Asn Asp Phe Lys Asp Leu
1               5                   10                  15

Tyr Arg Asp Gln Gly Glu Val Leu Lys
            20                  25

<210> SEQ ID NO 93
<211> LENGTH: 23
<212> TYPE: PRT
<213> ORGANISM: Artificial
<220> FEATURE:
<223> OTHER INFORMATION: P. striolata FPPS3 SARM containing region

<400> SEQUENCE: 93

Phe Asp Met Gly Glu Tyr Phe Gln Ile Lys Asn Asp Ile Asn Asp Cys
1               5                   10                  15

Phe Val Lys Glu Asp Ile Ala
            20

<210> SEQ ID NO 94
<211> LENGTH: 23
<212> TYPE: PRT
<213> ORGANISM: Artificial
<220> FEATURE:
<223> OTHER INFORMATION: P. striolata TPS1 SARM containing region

<400> SEQUENCE: 94

Val Pro Met Ser Arg Phe Phe Gln Val Gln Asn Asp Phe Ser Gly Val
1               5                   10                  15

Phe Glu Glu Glu Ser Lys Phe
            20

<210> SEQ ID NO 95
<211> LENGTH: 23
<212> TYPE: PRT
<213> ORGANISM: Artificial
<220> FEATURE:
<223> OTHER INFORMATION: P. striolata TPS2 SARM containing region

<400> SEQUENCE: 95

Arg Ile Ser Gly Glu Trp Ile Ile Ile Gln Asn Asp Tyr Gln Glu Val
1               5                   10                  15

Phe Leu Pro Thr Ser Glu Asn
            20

<210> SEQ ID NO 96
<211> LENGTH: 23
<212> TYPE: PRT
<213> ORGANISM: Artificial
<220> FEATURE:

-continued

<223> OTHER INFORMATION: P. striolata TPS3 SARM containing region

<400> SEQUENCE: 96

Asn Asp Leu Ser Arg Phe Ile Arg Ile Glu Asp Asp Val Val Asp Leu
1               5                   10                  15

Tyr Asp Ser Glu Gly Asn Ile
            20

<210> SEQ ID NO 97
<211> LENGTH: 23
<212> TYPE: PRT
<213> ORGANISM: Artificial
<220> FEATURE:
<223> OTHER INFORMATION: P. striolata TPS4 SARM containing region

<400> SEQUENCE: 97

Asn Asp Ile Ser Gln Tyr Leu Lys Val Glu Asp Asp Val Ile Asp Leu
1               5                   10                  15

Tyr Asp Ser Lys Gly Lys Ile
            20

<210> SEQ ID NO 98
<211> LENGTH: 23
<212> TYPE: PRT
<213> ORGANISM: Artificial
<220> FEATURE:
<223> OTHER INFORMATION: B. mori FPPS2 SARM containing region

<400> SEQUENCE: 98

Leu Glu Ile Gly Thr Met Phe Gln Ile Gln Asp Asp Phe Ile Asp Cys
1               5                   10                  15

Phe Gly Asp Glu Ile Lys Thr
            20

<210> SEQ ID NO 99
<211> LENGTH: 23
<212> TYPE: PRT
<213> ORGANISM: Artificial
<220> FEATURE:
<223> OTHER INFORMATION: C. fumiferana FPPS2 SARM containing region

<400> SEQUENCE: 99

Leu Glu Ile Gly Lys Phe Phe Gln Ile Gln Asp Asp Tyr Ile Asp Cys
1               5                   10                  15

Tyr Gly Asp Glu Ser Leu Thr
            20

<210> SEQ ID NO 100
<211> LENGTH: 23
<212> TYPE: PRT
<213> ORGANISM: Artificial
<220> FEATURE:
<223> OTHER INFORMATION: M. histrionica IDS-2 SARM containing region

<400> SEQUENCE: 100

Leu Glu Met Gly His Tyr Phe Gln Val Gln Asp Asp Tyr Leu Asp Val
1               5                   10                  15

Phe Gly Asp Glu Glu Met Ile
            20

<210> SEQ ID NO 101
<211> LENGTH: 23
<212> TYPE: PRT
<213> ORGANISM: Artificial

<220> FEATURE:
<223> OTHER INFORMATION: H. halys IDS-2 SARM containing region

<400> SEQUENCE: 101

Leu Glu Met Gly His Tyr Phe Gln Val Gln Asp Asp Tyr Leu Asp Val
1               5                   10                  15

Phe Ser Asp Glu Glu Val Ser
            20

<210> SEQ ID NO 102
<211> LENGTH: 23
<212> TYPE: PRT
<213> ORGANISM: Artificial
<220> FEATURE:
<223> OTHER INFORMATION: A. ipsilon FPPS SARM containing region

<400> SEQUENCE: 102

Leu Lys Met Gly Glu Phe Phe Gln Ile Gln Asp Asp Phe Leu Asp Cys
1               5                   10                  15

Phe Gly Asp Pro Ala Val Thr
            20

<210> SEQ ID NO 103
<211> LENGTH: 23
<212> TYPE: PRT
<213> ORGANISM: Artificial
<220> FEATURE:
<223> OTHER INFORMATION: B. mori FPPS1 SARM containing region

<400> SEQUENCE: 103

Leu Lys Met Gly Glu Phe Phe Gln Ile Gln Asp Asp Phe Leu Asp Cys
1               5                   10                  15

Phe Gly Asp Pro Thr Val Thr
            20

<210> SEQ ID NO 104
<211> LENGTH: 23
<212> TYPE: PRT
<213> ORGANISM: Artificial
<220> FEATURE:
<223> OTHER INFORMATION: C. fumiferana FPPS1 SARM containing region

<400> SEQUENCE: 104

Leu Glu Met Gly Gln Phe Phe Gln Ile Gln Asp Asp Phe Leu Asp Cys
1               5                   10                  15

Phe Gly Asp Pro Ala Val Thr
            20

<210> SEQ ID NO 105
<211> LENGTH: 23
<212> TYPE: PRT
<213> ORGANISM: Artificial
<220> FEATURE:
<223> OTHER INFORMATION: P. striolata FPPS1 SARM containing region

<400> SEQUENCE: 105

Leu Glu Met Gly Glu Phe Phe Gln Ile Gln Asp Asp Phe Leu Asp Val
1               5                   10                  15

Phe Gly Asp Ser Asp Val Thr
            20

<210> SEQ ID NO 106
<211> LENGTH: 23
<212> TYPE: PRT

-continued

<213> ORGANISM: Artificial
<220> FEATURE:
<223> OTHER INFORMATION: I. pini FPPS SARM containing region

<400> SEQUENCE: 106

Leu Asp Met Gly Gln Phe Phe Gln Ile Gln Asp Asp Phe Leu Asp Cys
1               5                   10                  15

Phe Gly Asp Pro Asn Val Thr
            20

<210> SEQ ID NO 107
<211> LENGTH: 23
<212> TYPE: PRT
<213> ORGANISM: Artificial
<220> FEATURE:
<223> OTHER INFORMATION: A. fabae FPPS SARM containing region

<400> SEQUENCE: 107

Leu Glu Met Gly His Phe Phe Gln Val Gln Asp Asp Phe Leu Asp Cys
1               5                   10                  15

Tyr Gly Asp Pro Glu Val Met
            20

<210> SEQ ID NO 108
<211> LENGTH: 23
<212> TYPE: PRT
<213> ORGANISM: Artificial
<220> FEATURE:
<223> OTHER INFORMATION: A. gossypii FPPS SARM containing region

<400> SEQUENCE: 108

Leu Glu Met Gly His Phe Phe Gln Val Gln Asp Asp Phe Leu Asp Cys
1               5                   10                  15

Tyr Gly Asp Pro Glu Val Met
            20

<210> SEQ ID NO 109
<211> LENGTH: 23
<212> TYPE: PRT
<213> ORGANISM: Artificial
<220> FEATURE:
<223> OTHER INFORMATION: P. cochleariae FPPS SARM containing region

<400> SEQUENCE: 109

Met Glu Ile Gly Glu Phe Phe Gln Ile Gln Asp Asp Phe Leu Asp Ala
1               5                   10                  15

Phe Gly Asp Ser Gln Val Thr
            20

<210> SEQ ID NO 110
<211> LENGTH: 23
<212> TYPE: PRT
<213> ORGANISM: Artificial
<220> FEATURE:
<223> OTHER INFORMATION: M. persicae GPPS/FPPS SARM containing region

<400> SEQUENCE: 110

Leu Glu Met Gly His Phe Phe Gln Val Gln Asp Asp Phe Leu Asp Cys
1               5                   10                  15

Tyr Gly Asp Pro Asp Val Met
            20

<210> SEQ ID NO 111
<211> LENGTH: 23

```
<212> TYPE: PRT
<213> ORGANISM: Artificial
<220> FEATURE:
<223> OTHER INFORMATION: D. ponderosae FPPS SARM containing region

<400> SEQUENCE: 111

Met Glu Met Gly Gln Phe Phe Gln Ile Gln Asp Asp Phe Leu Asp Cys
1               5                   10                  15

Phe Gly Asp Pro Thr Val Thr
            20

<210> SEQ ID NO 112
<211> LENGTH: 23
<212> TYPE: PRT
<213> ORGANISM: Artificial
<220> FEATURE:
<223> OTHER INFORMATION: D. jeffreyi FPPS ARM containing region

<400> SEQUENCE: 112

Met Glu Met Gly Gln Phe Phe Gln Ile Gln Asp Asp Phe Leu Asp Cys
1               5                   10                  15

Phe Gly Asp Pro Thr Val Thr
            20

<210> SEQ ID NO 113
<211> LENGTH: 23
<212> TYPE: PRT
<213> ORGANISM: Artificial
<220> FEATURE:
<223> OTHER INFORMATION: A. grandis FFPS SARM containing region

<400> SEQUENCE: 113

Leu Glu Met Gly Glu Phe Phe Gln Ile Gln Asp Asp Phe Leu Asp Cys
1               5                   10                  15

Phe Gly Asp Pro Ala Val Thr
            20

<210> SEQ ID NO 114
<211> LENGTH: 22
<212> TYPE: DNA
<213> ORGANISM: Artificial
<220> FEATURE:
<223> OTHER INFORMATION: Primer

<400> SEQUENCE: 114
atggtctcca ttgctgctaa gt                                            22
```

BROWN MARMORATED AND HARLEQUIN STINK BUG PHEROMONE ENZYME SYNTHESIS AND USES THEREOF

CROSS-REFERENCE TO RELATED APPLICATIONS

This application is the U.S. National Stage Application under 35 U.S.C. § 371 of Patent Cooperation Treaty Application No. PCT/US2020/047538, filed on Aug. 21, 2020, entitled "BROWN MARMORATED AND HARLEQUIN STINK BUG PHEROMONE ENZYME SYNTHESIS AND USES THEREOF," which claims the benefit of and priority to U.S. Provisional Patent Application No. 62/891,148, filed on Aug. 23, 2019, entitled "Production of Stink Bug Pest Aggregation Pheromone Precursors," the contents of which is incorporated by reference herein in their entireties.

STATEMENT REGARDING FEDERALLY SPONSORED RESEARCH

This invention was made with government support under Grant No. 2016-67013-24759 awarded by USDA National Institute of Food and Agriculture. The government has certain rights in the invention.

STATEMENT REGARDING SEQUENCE LISTING

This application contains a sequence listing in electronic form as a .txt file entitled "VTIP-0225US2_2025-09-12_ST25", created on Sep. 12, 2025, and having a size of 96,600 bytes. The content of the sequence listing is herein incorporated by reference in its entirety.

TECHNICAL FIELD

The subject matter disclosed herein is generally directed to engineered terpene synthesis enzymes, and more particularly those related to those present in insects.

BACKGROUND

The brown marmorated (*Halyomorpha halys*) and harlequin (*Murgantia histrionica*) stink bugs pose a threat to many agriculturally important corps grown throughout the world. The brown marmorated stink bug is very invasive particularly in the U.S., Europe, Eurasia, South America, and eastern Asia. The harlequin stink bug is an important embodiment of cabbage and related crops in the southern half of the United States and other parts of the world with similar climates. If not controlled the harlequin stink bug can easily destroy and entire crop by injuring the host plants by sucking their sap and causing them to wilt and die. Current methods to control these stink bug populations include biological control (e.g. wasps and flies that transmit parasites to the brown marmorated and/or harlequin stink bug) and chemical control. Given the need to find alternatives to chemical control of pests in agriculture, there exists a need for alternative methods for control of pests, such as the brown marmorated and harlequin stink bugs, in agriculture.

Citation or identification of any document in this application is not an admission that such a document is available as prior art to the present invention.

SUMMARY

Described in several example embodiments herein are engineered polynucleotides comprising:

one or more polynucleotides that is about 50-100% identical to SEQ ID NO: 3, SEQ ID NO: 4, or both.

In certain example embodiments, the engineered polynucleotide encodes a polypeptide that is about 50-100% identical to SEQ ID NO: 1, SEQ ID NO: 2, or both.

In certain example embodiments, comprising a polynucleotide capable of encoding a cytochrome P450 enzyme.

In certain example embodiments, the cytochrome P450 enzyme is a cytochrome P450 enzyme that is expressed by a brown marmorated stink bug, a harlequin stink bug, or both.

In certain example embodiments, the engineered polynucleotide further comprises a polynucleotide capable of encoding an isomerase.

In certain example embodiments, the isomerase is an isomerase that is expressed by a brown marmorated stink bug, a harlequin stink bug, or both.

Described in several example embodiments herein are engineered polynucleotides capable of encoding two or more of the following polypeptides:

(a) a polypeptide that is about 50-100% identical to SEQ ID NO: 1;

(b) a polypeptide that is about 50-100% identical to SEQ ID NO: 2;

(c) a cytochrome P450 enzyme; and (d) an isomerase.

Described in several example embodiments herein are vector systems comprising:

one or more polynucleotides of the present description; and optionally, one or more regulatory elements, wherein one or more of the one or more regulatory elements is operably coupled to the polynucleotide.

In certain example embodiments, the regulatory element is a plant-specific regulatory element.

In certain example embodiments, the vector system comprises 2 or more vectors, where at least one of the vectors comprises one or more polynucleotides of the present description.

Described in several example embodiments herein are engineered stink bug pheromone synthesis systems comprising:

one or more TPS polypeptides, wherein each TPS polypeptide is about 50-100% identical to SEQ ID NO: 1, SEQ ID NO: 2, or both; and one or both of a cytochrome P450 polypeptide and an isomerase polypeptide.

In certain example embodiments, the system is capable of producing (a) a brown marmorated stink bug pheromone;

(b) a brown marmorated stink bug pheromone intermediate;

(c) a harlequin stink bug pheromone;

(d) a harlequin stink bug pheromone intermediate; or (e) any combination thereof.

In certain example embodiments, system is capable of producing (a) a brown marmorated stink bug sesquipiperitol or isomer thereof;

(b) a harlequin stink bug sesquipiperitol or isomer thereof;

(c) a brown marmorated stink bug zingiberenol;

(d) a harlequin stink bug zingiberenol;

(e) a brown marmorated stink bug murgantiol;

(f) a harlequin stink bug murgantiol; or (g) any combination thereof.

Described in several example embodiments herein are cells comprising:

(a) one or more engineered polynucleotide of the present description;

(b) a vector system of the present description;

(c) an engineered stink bug pheromone synthesis system of the present description; or (d) any combination thereof.

In certain example embodiments, the cell is a plant cell.

In certain example embodiments, the plant cell is of a plant species that is suitable for use as a trap crop for management of a brown marmorated stink bug, a harlequin stink bug, or both.

In certain example embodiments, the cell is capable of producing (a) a brown marmorated stink bug pheromone;

(b) a brown marmorated stink bug pheromone intermediate;

(c) a harlequin stink bug pheromone;

(d) a harlequin stink bug pheromone intermediate; or (e) any combination thereof.

In certain example embodiments, the cell is capable of producing (a) a brown marmorated stink bug sesquipiperitol or isomer thereof;

(b) a harlequin stink bug sesquipiperitol or isomer thereof;

(c) a brown marmorated stink bug zingiberenol;

(d) a harlequin stink bug zingiberenol;

(e) a brown marmorated stink bug murgantiol;

(f) a harlequin stink bug murgantiol; or (g) any combination thereof.

Described in several example embodiments herein are engineered plants comprising:

(a) one or more engineered polynucleotide of the present description;

(b) a vector system of the present description;

(c) an engineered stink bug pheromone synthesis system of the present description;

(d) a cell of the present description; or (e) any combination thereof.

In certain example embodiments, the plant is a plant species effective as a trap crop for management of the brown marmorated stink bug, harlequin stink bug, or both.

In certain example embodiments, the engineered plant expresses in one or more of its cells:

(a) one or more engineered polynucleotide of the present description;

(b) an engineered stink bug pheromone synthesis system of the present description; or (c) both.

In certain example embodiments, the engineered plant is capable of producing a brown marmorated stink bug pheromone, a harlequin stink bug pheromone, or both.

In certain example embodiments, the plant is capable of producing in one, some, or all of it cells;

(a) a brown marmorated stink bug pheromone;

(b) a brown marmorated stink bug pheromone intermediate;

(c) a harlequin stink bug pheromone;

(d) a harlequin stink bug pheromone intermediate; or (e) any combination thereof.

In certain example embodiments, the engineered plant is capable of producing (a) a brown marmorated stink bug sesquipiperitol or isomer thereof;

(b) a harlequin stink bug sesquipiperitol or isomer thereof;

(c) a brown marmorated stink bug zingiberenol;

(d) a harlequin stink bug zingiberenol;

(e) a brown marmorated stink bug murgantiol;

(f) a harlequin stink bug murgantiol; or (g) any combination thereof.

Described in several example embodiments herein are kits comprising:

(a) one or more engineered polynucleotide of the present description;

(b) a vector system of the present description;

(c) an engineered stink bug pheromone synthesis system of the present description;

(d) a cell of the present description;

(e) a plant of the present description; or (f) any combination thereof.

Described in several example embodiments herein are methods of managing brown stink bug infestation, harlequin stink bug infestation, or both of a crop, comprising: planting an engineered plant of the present description.

In certain example embodiments, the engineered plant is planted in a location next to, adjacent to, or with in effective proximity to the crop.

These and other embodiments, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 1—Pheromones from Three Common Stink Bugs. The bisabolene backbone is common in Pentatomidae pheromones and can suggest evolution of a common enzymatic mechanism or pathway in this family.

(FIG. 2A) GC-MS chromatograms of enzyme products. Sf9 control cells express a housefly cytochrome P450 reductase. 1, γ-curcumene; 2, α-zingiberene; 3, β-sesquiphellandrene; 4, (1S, 6S,7R)-sesquipiperitol; 5, (2E,6E)-farnesol; * non-enzyme product. (FIG. 2B) Mass spectra of enzymatic products with (1S,6S,7R)-sesquipiperitol standard. (FIG. 2C) Formation of sesquipiperitol by *M. histrionica* TPS activity (boxed). A putative single or two-step pathway to murgantiol is shown involving isomerization and epoxidation reactions. EV=empty vector, ^=*Musca domestica* cytochrome P450 reductase.

(FIG. 4A) Synthesis and chemical transformations of sesquipiperitols. Reagents: a) pyridinium chlorochromate; b) LiAlH4; c) 1. POCl3/Py 2. H2/PtO2. 1, SSR-zingiberenol; 2, SR-sesquipiperitone; 3, SSR-sesquipiperitol; 4, RSR-sesquipiperitol; 5, bisabolane. (FIG. 4B) GC-MS TIC of a synthetic mixture of SR-sesquipiperitone 2 and RR-sesquipiperitone (top) and individual 2 (bottom). (FIG. 4C) GC-MS TIC of the MhIDS-1/TPS terpene alcohol product upon oxidation with PCC (top) and synthetic SR-sesquipiperitone 2 (bottom); on HP-5 MS column. (FIG. 4D) GC-MS TIC of the MhIDS-1 (MhTPS) terpene alcohol product (top) and synthetic sesquipiperitol isomers 3 (middle) and 4 (bottom); cool-on-column injection on HP-5 MS column; insets represent mass spectra of the corresponding compounds.

(FIG. 5A) TPS assay products before and after cleaving the N-terminal histidine tag using (E,E)-FPP as the substrate. (FIG. 5B) GC-MS analysis of hexane extracts from MhTPS activity assays (protein with N-terminal His-tag) at different injection temperatures. Splitless injection at 260° C. (top). Cool-on-column injection at 70° C. (bottom). (FIG. 5C) Terpene synthase assay products with (E,E)-FPP, (Z,E)-FPP, (Z,Z)-FPP, DMAPP and IPP. Substrates were used at 50 µM except for IPP (100 µM). All assays were overlaid with hexane and extracts were analyzed by GC-MS. 1, sesquipiperitol; 2, (E,E)-farnesol; 3, γ-curcumene; 4, zingiberene; 5, β-sesquiphellandrene; 6, myrcene; 7, a-terpinene; 8, limonene; 9, terpinolene; 10, linalool.

(FIG. 8A) MhTPS transcript abundance at different developmental stages and in different sexes. Young-3 days adult, mature=15 day adult. (n=3, +SD). (FIG. 8B) MhTPS transcript abundance in different tissues of adult males. Ab. ST=Abdominal soft tissue minus midgut. Ab. Cuticle=Tissue lining the abdominal cuticle. (n=3, +SD). Gene expression was normalized against 18S rRNA and transcript abundance is shown relative to that in nymphs (FIG. 8A) or the male head tissue (FIG. 8B) (set to 1). Significance was determined using one-way analysis of variance (ANOVA) and means grouped by Tukey's HSD.

(FIG. 9A) Tissues of the abdominal cuticle of mature male or female M. histrionica were homogenized in assay buffer and assayed with 100 µM (E,E)-FPP. (FIG. 9B) Different tissues from mature male M. histrionica were homogenized in assay buffer and assayed with 50 µM (E,E)-FPP. Volatile products were extracted with an equal volume of hexane and analyzed with GC-MS. 1, sesquipiperitol, 2, (E,E)-farnesol.

FIGS. 10A-10B—Effects of RNA interference on M. histrionica MhTPS expression and murgantiol emission. (FIG. 10A) MhTPS transcript abundance in adult males 12 days post injection (400 ng) normalized to 18S rRNA. LacZ was used as negative control (n=3, +SEM). (FIG. 10B) Amount of murgantiol detected in headspace collections 10-12 days post injection (n=9, +SEM). Bars in each figure with the same letter are not different according to a generalized log-linear model ($\alpha$=0.05). FIG. 10A: $\chi2$=63.13, p<0.0001. FIG. 10B: $\chi2$=4883.3, p<0.0001.

FIGS. 11A-11B—Transcript abundance of MhTPS and MhFPPS in mature M. histrionica males and females determined by RT-PCR. (FIG. 11A) Transcript abundance by sex. (FIG. 11B) Transcript abundance in mature males by tissue. Ab. ST=Abdominal soft tissue, Ab. Cuticle=abdominal cuticle including tissue lining cuticle minus free soft tissue and midgut, RpS4=ribosomal subunit protein S4.

(FIG. 13A) 7R stereo configuration of enzymatically produced sesquipiperitol. Chiral GC analysis of (top) bisabolanes derived from enzymatically produced sesquipiperitol by dehydration/hydrogenation, (middle) bisabolane standard mixture made by dehydration/hydrogenation of (7S)- and (7R)-zingiberenols, (bottom) co-injection of both. Assignment of cis- and trans-isomers is arbitrary. (FIG. 13B) Determination of the configuration of enzymatically derived sesquipiperitol at C-1. Chiral GC analysis of (top) enzymatically produced sesquipiperitol, (middle) RSR-sesquipiperitol 4, (bottom) SSR-sesquipiperitol 3. Separation in (FIG. 13A) and (FIG. 13B) was performed on a on Hydrodex β-6TBDM column. (FIG. 13C) NOESY correlations of H-1 protons in sesquipiperitols 3 and 4 in MM2 minimized energy conformations in ChemBio3D Ultra 11.0. Enhancement between H-1 and H-6 was found for compound 4 but not 3.

FIGS. 15A-15B—Sequence comparison of MhTPS and MhFPS with other insect TPS and IDS proteins. (FIG. 15A) Sequence comparison of the first aspartate-rich motif (FARM) and second aspartate-rich motif (SARM). TPS and IDS-like proteins are separated from the bonafide trans-IDS proteins by a line; FARM and SARM are indicated by bars above sequences. (FIG. 15B) Residue conservation in the FARM and SARM for TPS and IDS-like proteins and for true trans-IDS proteins. Accession nos. M histrionica TPS (MG662378.1); H. halys TPS (XP_014289203.1); I. pini GPPS/TPS (AAX55632.1); P striolata FPPS3 (ALL35406.1); P. striolata TPS1 (ALL35411.1) P. striolata TPS2 (ALL35414); P. striolata TPS3 (ALL35417); P. striolata TPS4 (ALL35420.1); B. mori FPPS2 (NP_001093301.1); C. fumiferana FPPS1 (AAY26574.1); M/ histrionica FPPS (MG662379.1); H. halys FPPS (XP_014276401.1); A. ipsilon FPPS (CAA08918.2); B. mori FPPS1 (001036889.1); C. fumiferana FPPS1 (AAY33486.1); P. striolata FPPS1 (ALL35400.1); P.

*cochleariae* FPPS (AGE89831.1); *M. persicae* GPPS/FPPS (ABY19312.1); *D. ponderosae* FPPS (AFI45068.1); *D. jeffreyi* FPPS (AAX78435.1); *A. grandis* FPPS (AAX78434.1).

FIGS. 16A-16D—Docking simulations with MhTPS, competition assay with DMAPP and proposed mechanism. (FIGS. 16A-16B) Position of (E,E)-FPP (left) and DMAPP (right) in the active site of *G. gallus* FPPS (green) and the *M. histrionica* TPS homology model (blue). (FIG. 16C) Competitive inhibition of MhTPS activity by DMAPP. MhTPS was assayed with 50 μM (E,E)-FPP and various concentrations of DMAPP and IPP (n=3, ±SD). One-way ANOVA P<0.05. (FIG. 16D) Proposed cyclization mechanism for the formation of sesquipiperitol.

FIG. 17—NMR Data for Sesquipiperitols 3 and 4.

FIG. 18—BLAST query sequences.

The figures herein are for illustrative purposes only and are not necessarily drawn to scale.

FIG. 19—Primers sequences used in Example 1.

Figure 20A:
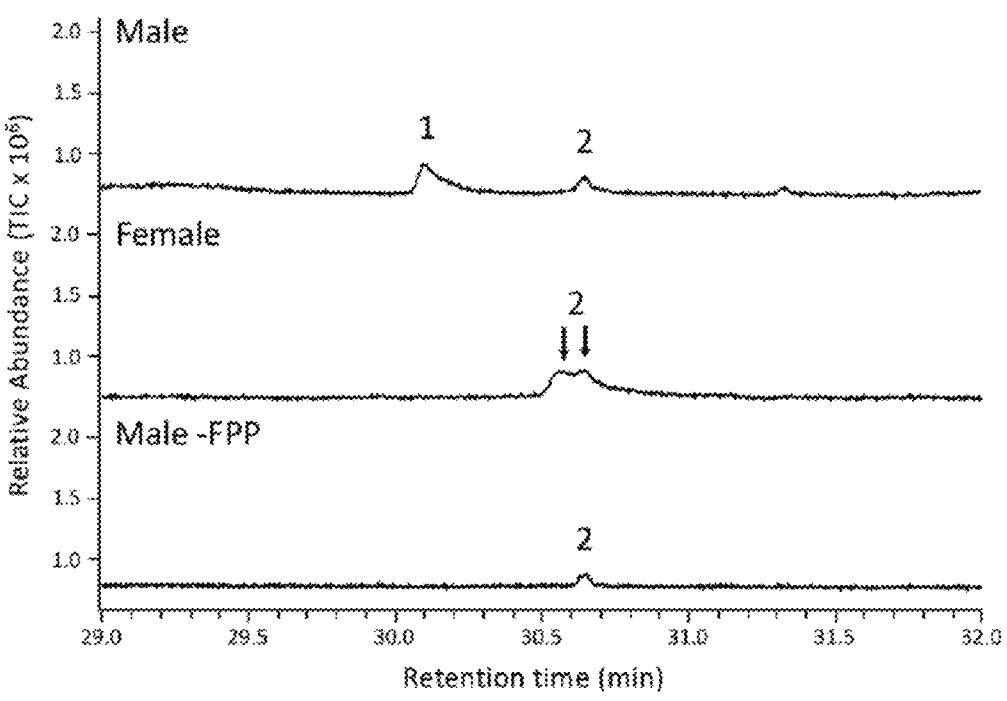
Figure 20B:
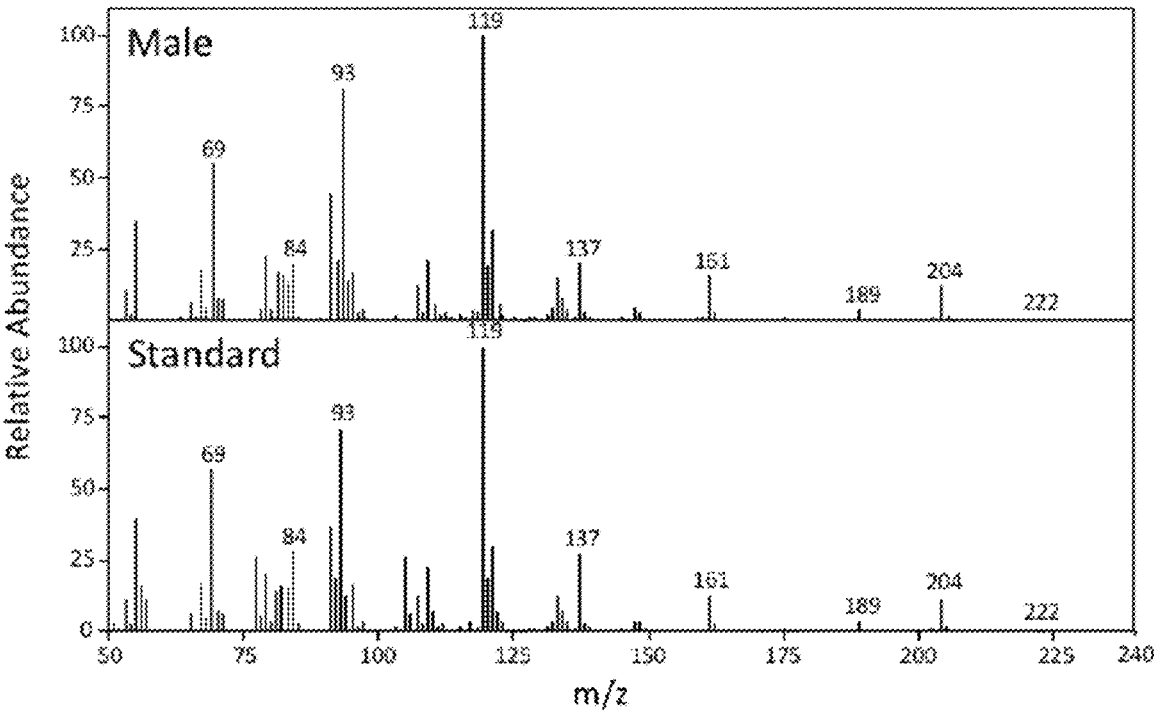

FIGS. 20A-20B—Terpene synthase activity in crude protein extracts from male and female *H. halys*. Whole male and female BMSB were homogenized in assay buffer and assayed with 100 μM (E,E)-FPP. (FIG. 20A) Volatile products were extracted with hexane and analyzed by GC-MS. 1, sesquipiperitol, 2, farnesol isomers. Arrows indicate farnesol isomers in female sample. (FIG. 20B) Mass spectra enzymatic product from male and (1S,6S,7R)-sesquipiperitol standard.

Figure 21:
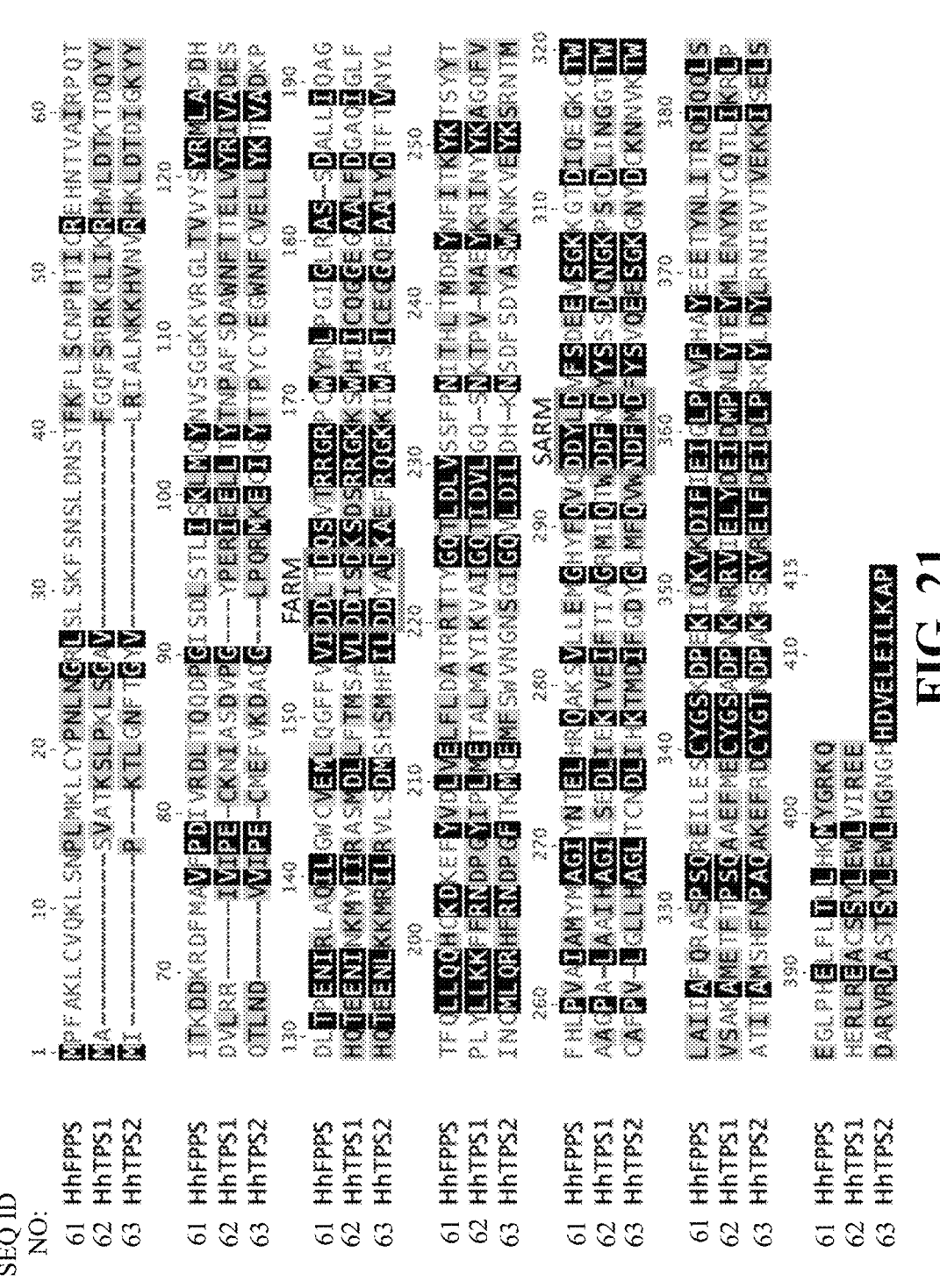

FIG. 21—Amino acid sequence alignment of BMSB IDS and TPS enzymes. Amino acid sequence alignment of BMSB IDS and TPS enzymes. HhFPPS (HhIDS2), HhTPS1 (HhIDS7) and HhTPS2 (HhIDS1) are shown. The conserved first aspartate-rich motif (FARM) and second aspartate-rich motif (SARM) are outlined in red.

Figure 22A:
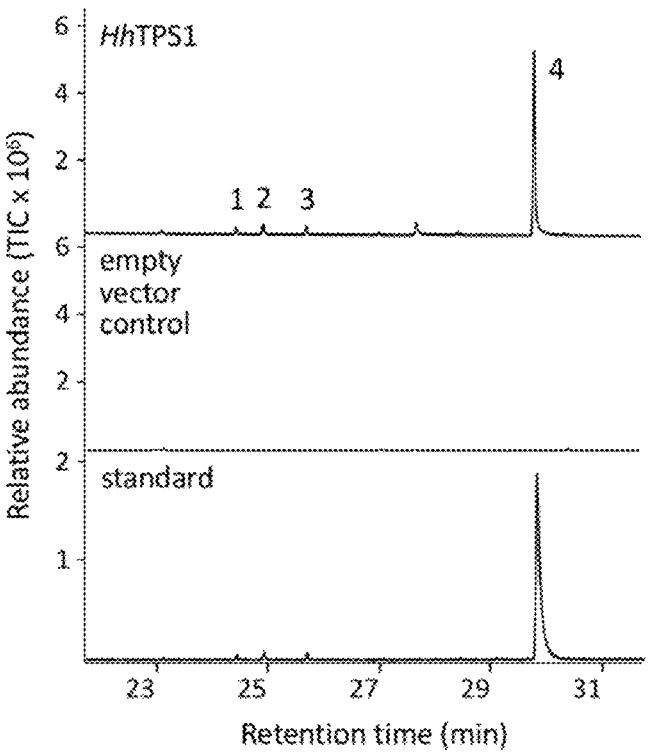
Figure 22B:
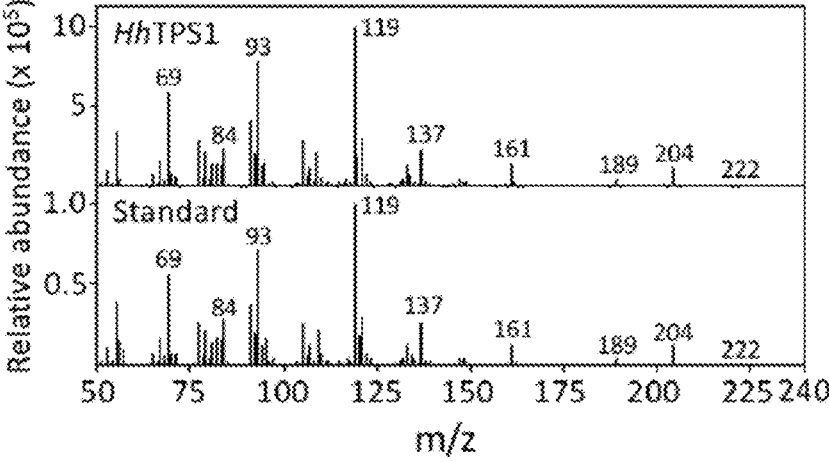

FIGS. 22A-22B—Terpene synthase assay of HhTPS1 from BMSB. (FIG. 22A) GC-MS chromatogram of enzymatic product from HhTPS1. (FIG. 22B) Mass spectra of enzyme product and standard. Standard is synthetic (1S,6S, 7R)-sesquipiperitol. 1, γ-curcumene; 2, α-zingiberene; 3, β-sesquiphellandrene; 4, sesquipiperitol isomer.

Figure 23:
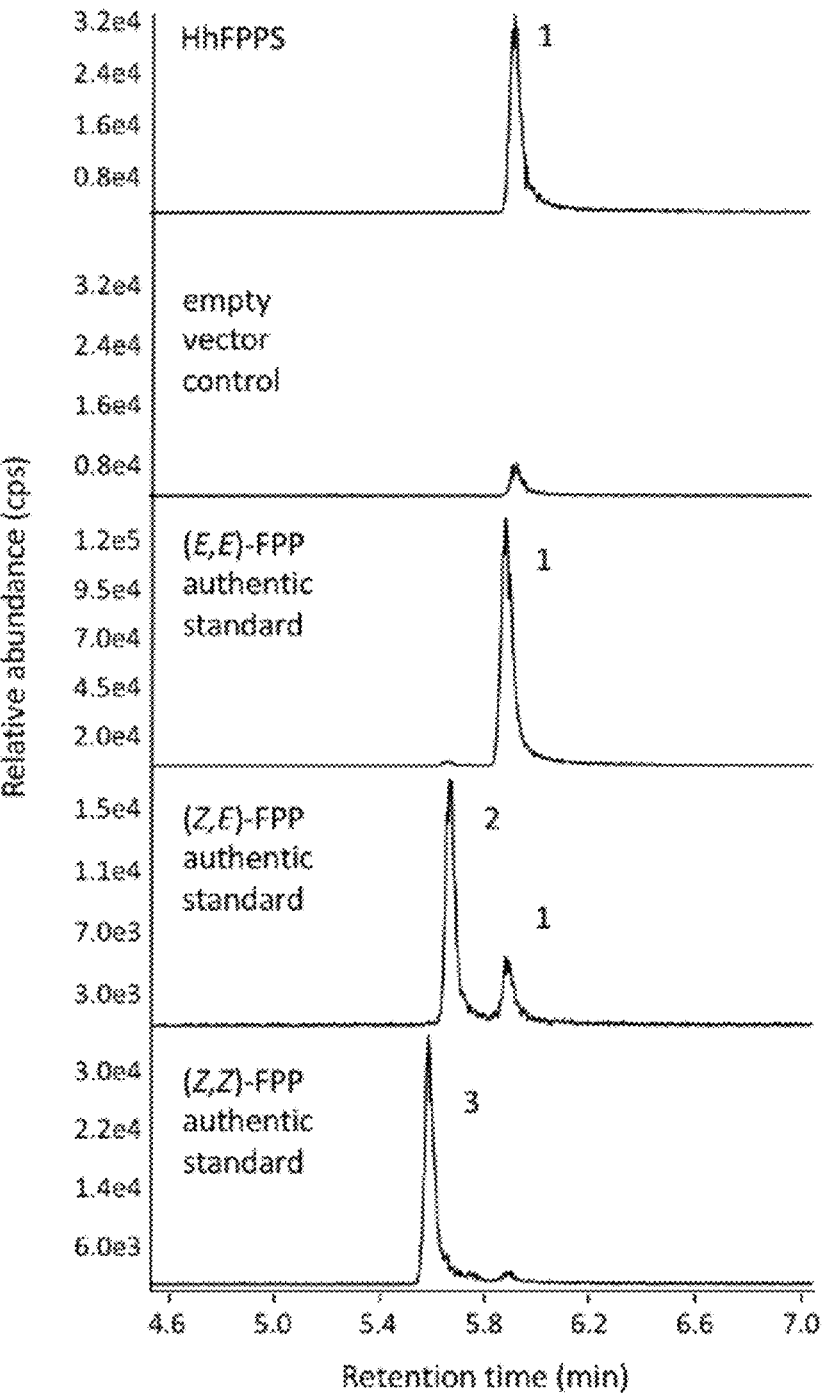

FIG. 23—Prenyltransferase assay of HhFPPS. LC-MS chromatograms after functional assays of HhFPPS. 50 μM IPP and 50 μM DMAPP were provided as substrates. 1, (E,E)-FPP, 2, (Z,E)-FPP, 3, (Z, Z)-FPP.

Figure 24:
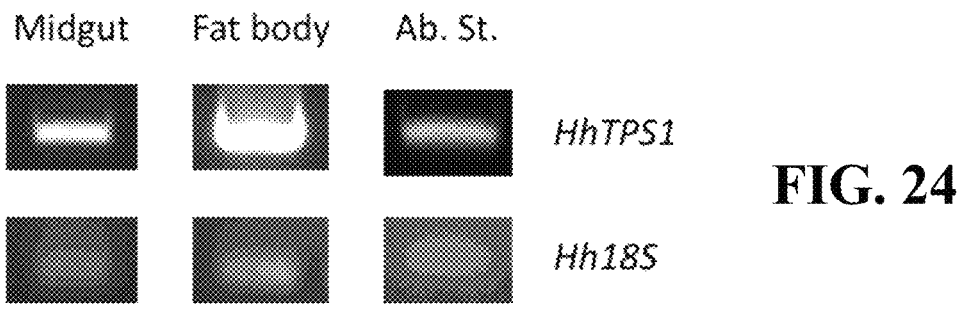

FIG. 24—Transcript abundance of HhTPS1 as determined by RT-PCR. Transcript abundance of HhTPS1 in abdomen of adult male BMSB by tissue type. Fat body includes fat body, testes and all other soft tissues of the abdomen minus the midgut. Ab. St., abdominal sternites includes abdominal cuticle with attached epithelial cells.

Figure 25A:
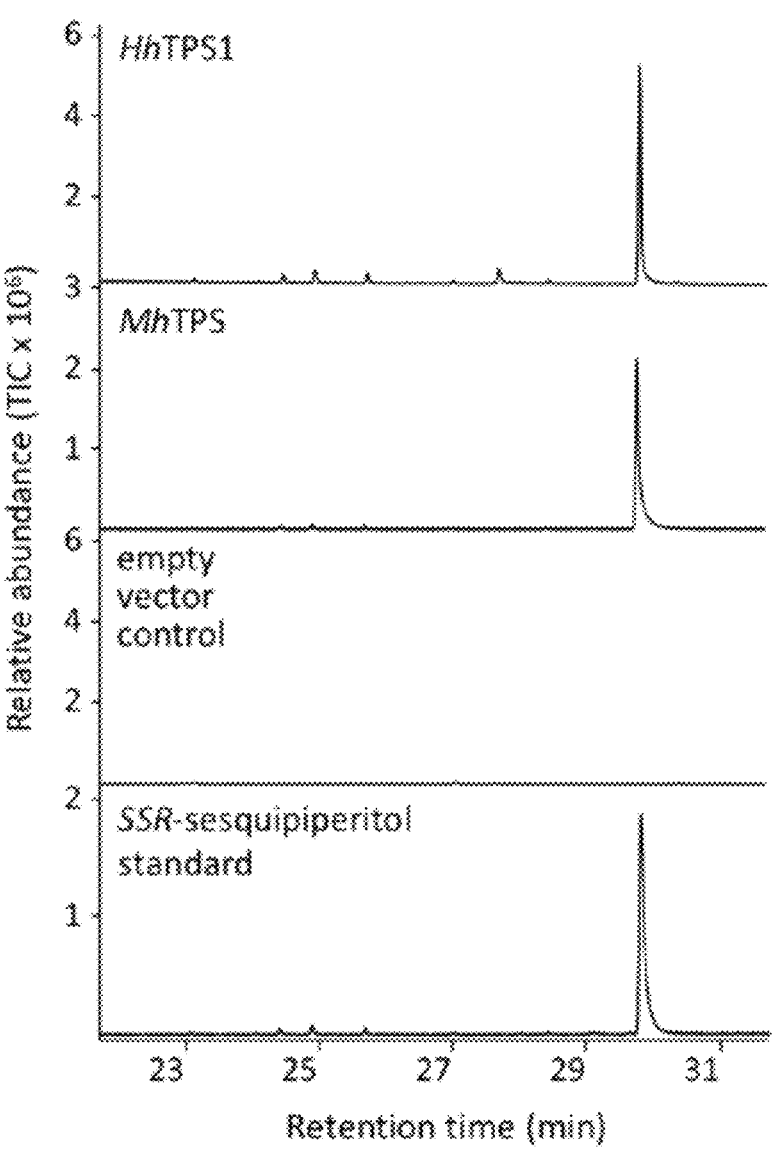
Figure 25B:
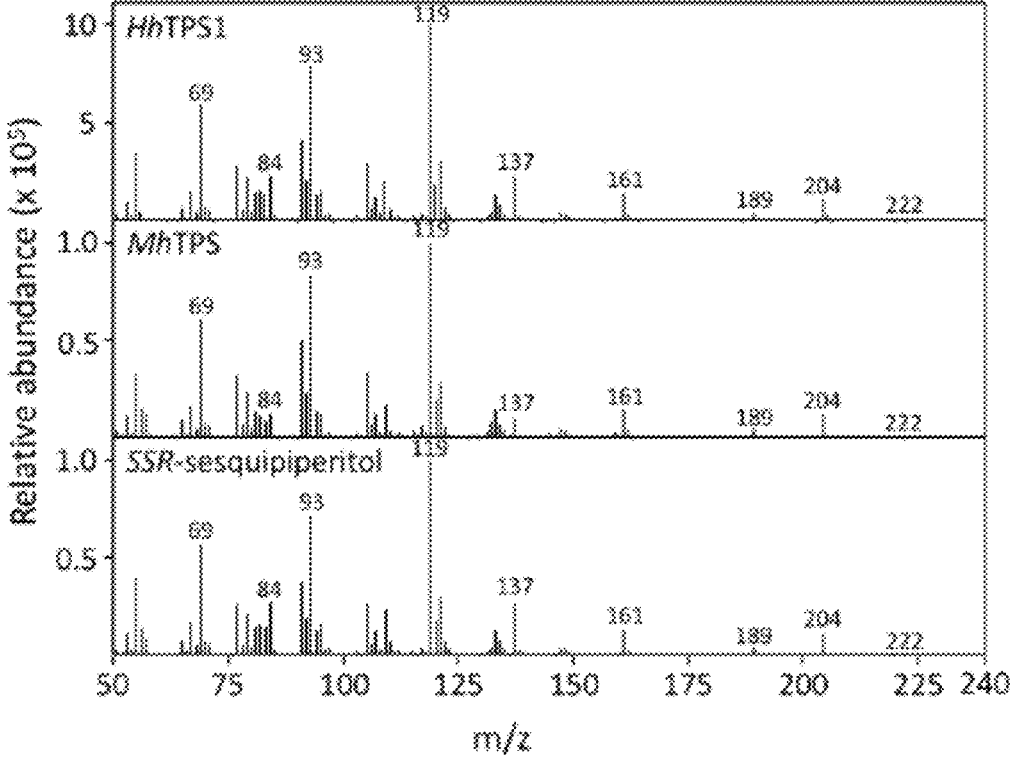

FIGS. 25A-25B—Comparison of enzymatic products from BMSB HhTPS1 and HB MhTPS. (FIG. 25A) GC-MS analysis of enzymatic products from HhTPS1 and MhTPS using 50 μM (E,E)-FPP as substrate. (FIG. 25B) Mass spectra of enzymatic products and standard.

Figure 26:
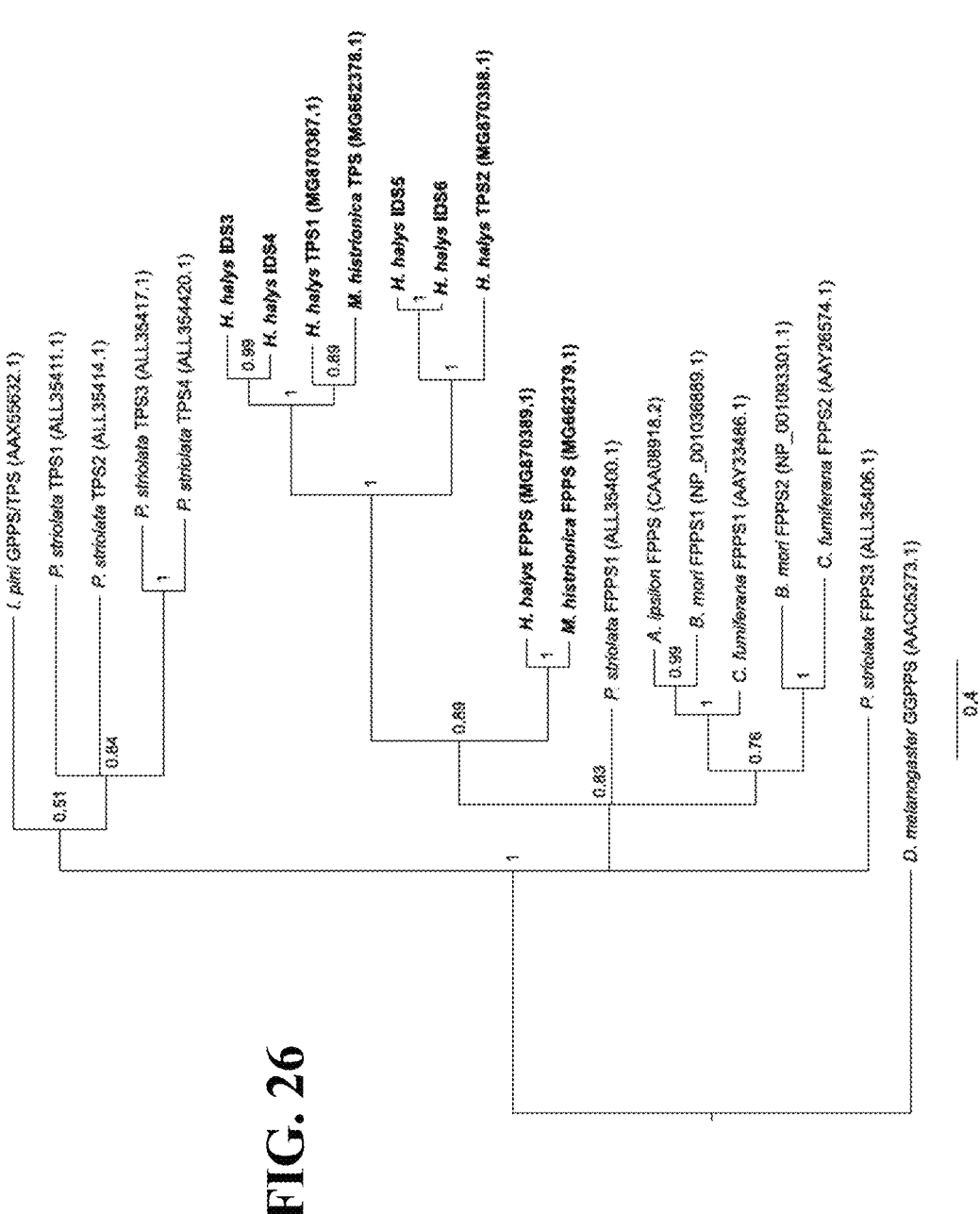

FIG. 26—Phylogenetic analysis of *H. halys* IDS and TPS proteins. Majority-rule phylogenetic analysis of *H. halys* IDS and TPS proteins based on Bayesian posterior probability with other insect IDS and TPS genes. Scale is number of expected number of substitutions per site.

FIG. 27—BLAST query sequences.

FIG. 28—Primers used in Example 2.

Figures 29A, 29B:
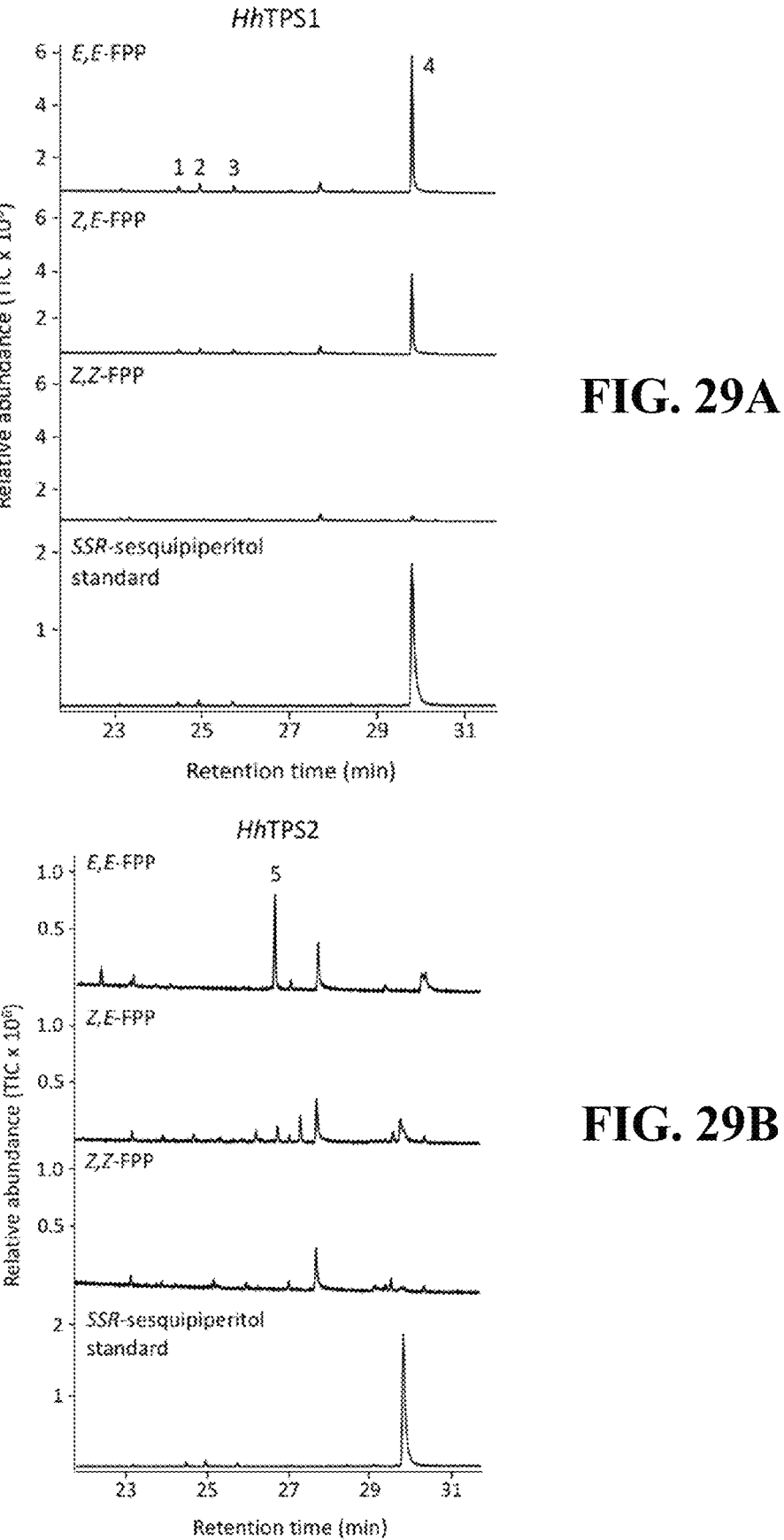

FIGS. 29A-29B—Terpene synthase assay of HhTPS1 and HhTPS2 with various FPP substrates. Partially purified enzymes were assayed with 50 M FPP substrates in assay buffer. (FIG. 29A) HhTPS1 produces an isomer of the pheromone precursor sesquipiperitol (4) along with thermal rearrangement products (1-3). (FIG. 29B) HhTPS2 produces non-specific sesquiterpene products with the most abundant compound being elemol (5). 1, γ-curcumene; 2, α-zingiberene; 3, β-sesquiphellandrene; 4, sesquipiperitol isomer, 5, elemol.

Figure 30:
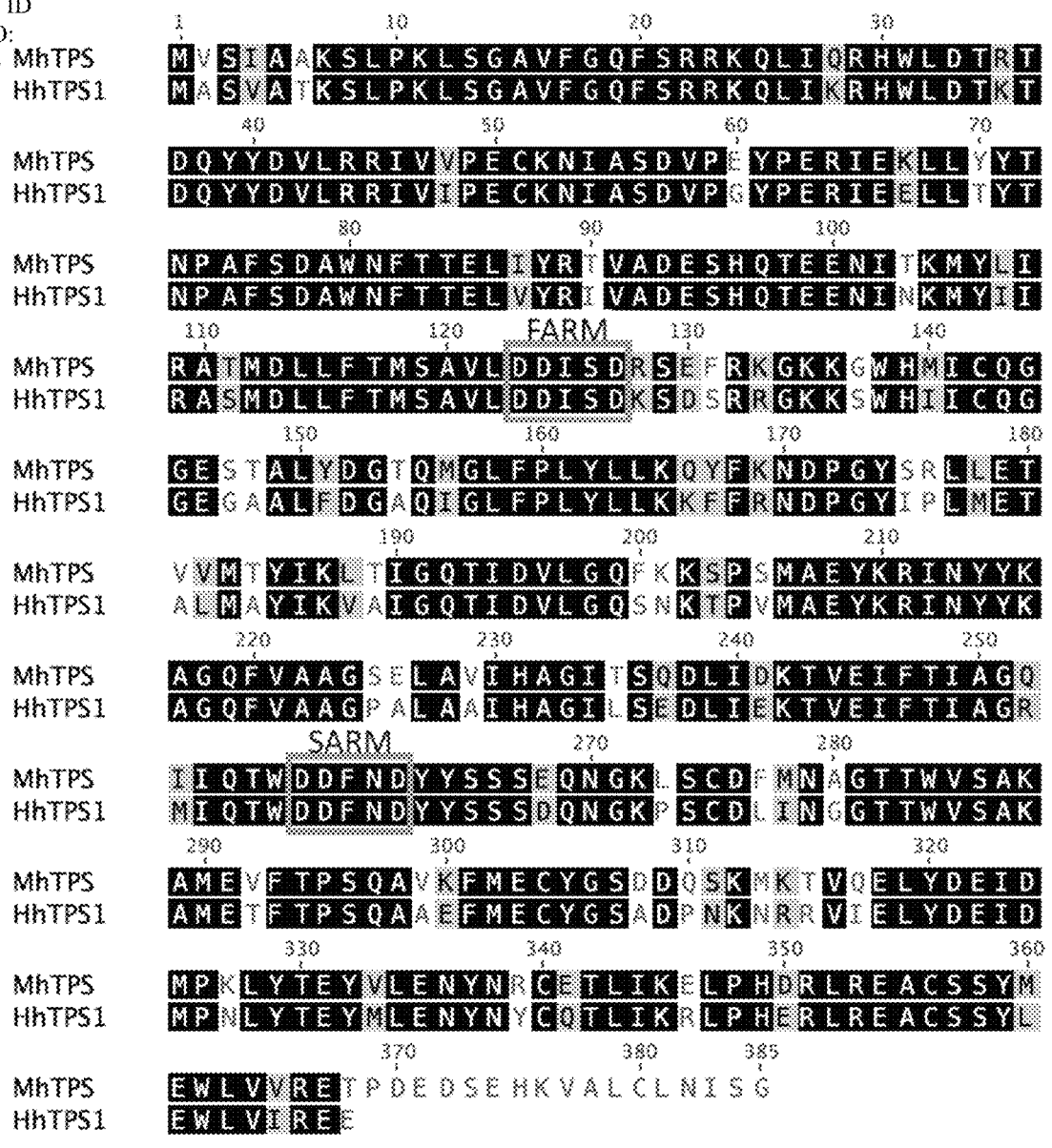

FIG. 30—Amino acid sequence alignment of HhTPS1 and MhTPS. Amino acid sequence alignment of BMSB HhTPS1 and HB MhTPS with the first and second aspartate-rich motifs (FARM, SARM) marked in grey.

FIG. 31—Comparison of expression levels between *Murgantia histrionica* and *Halyomorpha halys* genes involved in terpene biosynthesis. Gene expression levels were calculated in Transcripts per Million (TPM) and comparisons are in binary logs of TPM ratios. Values calculated using RSEM. Table originally printed in Insects (Sparks et al., 2017).

FIG. 32—Placement of *H. halys* IDS and TPS genes in genome scaffolds.

Figure 33:
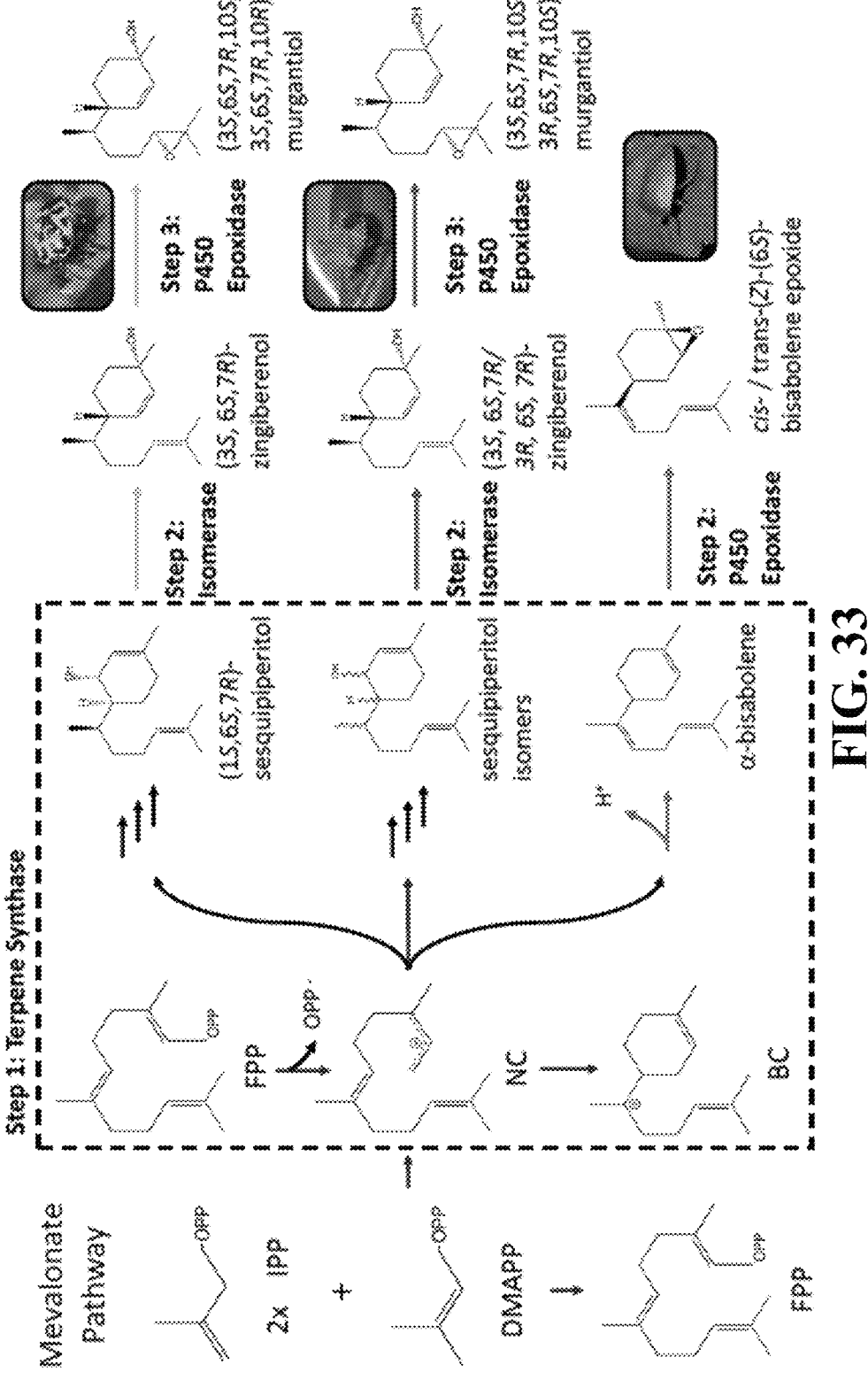

FIG. 33—Pathways for the biosynthesis of sesquiterpenoid pheromone precursors in Harlequin bug, Brown marmorated stink bug, and Southern Green stink bug. TPS enzymes produce an initial sesquiterpene precursor from FPP in all species. In harlequin bug and brown marmorated stink bug this product may then be isomerized to zingiberenol and oxidized to from murgantiol. In southern green stink bug the product may be oxidized to form cis- or trans-(Z)-(6S)-bisabolene epoxide. NC=nerolidyl carbocation; BC=bisabolyl carbocation.

Figure 34:
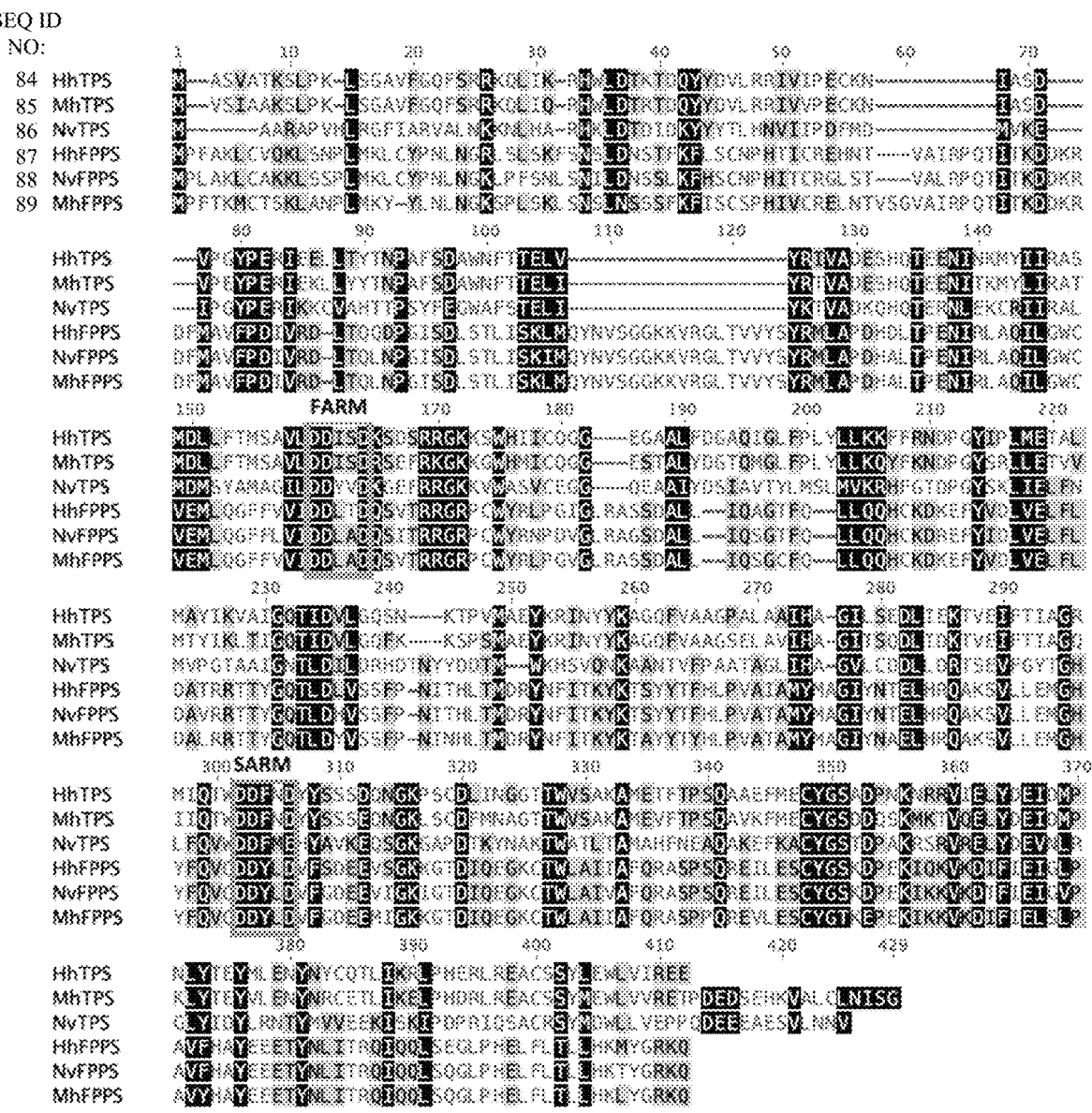

FIG. 34—Amino acid sequence alignment of all functional pentatomid IDS and TPS proteins. Amino acid alignment showing first aspartate-rich motif (FARM) and second aspartate-rich motif (SARM).

Figure 35:
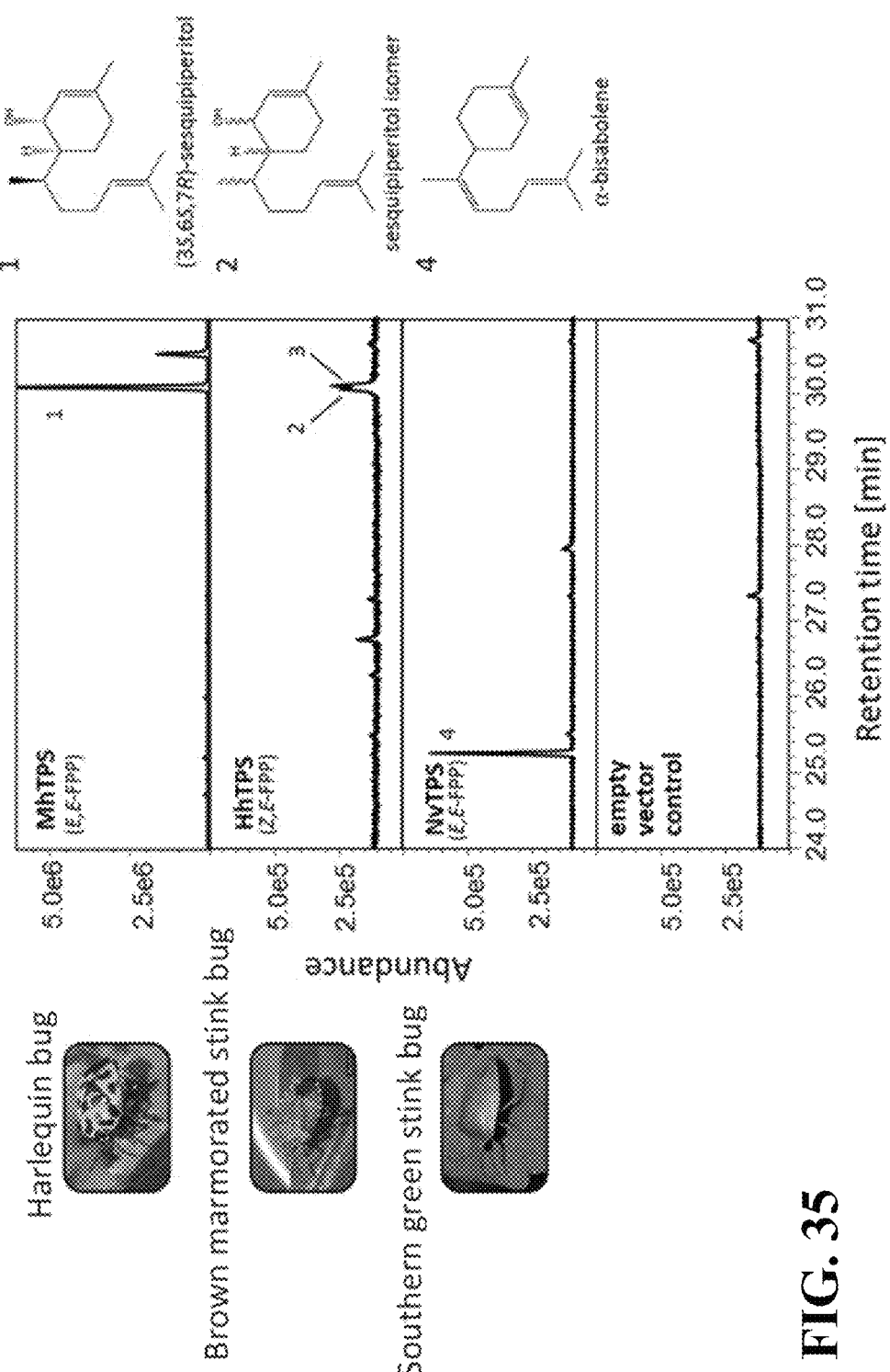

FIG. 35—Gas chromatography-mass spectrometry chromatography of enzymatic products TPS1 recombinant enzymes. MhTSP1 produces the sequiterpene alcohol sesquipiperitol and NvTPS1 produces Z-α-bisabolene from the substrate E,E-FPP. Recombinant HhTPS1 converts Z,E-FPP into a sesquipiperitol isomer and a bisabolol (3) isomer.

DETAILED DESCRIPTION OF THE EXAMPLE EMBODIMENTS

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further embodiment includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges off 'about x', 'about y', and 'about z' as well as the ranges of 'less than x', less than 'y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further embodiment. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosed invention. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein with reference to the relationship between DNA, cDNA, CRNA, RNA, protein/peptides, and the like "corresponding to" or "encoding" (used interchangeably herein) refers to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "deoxyribonucleic acid (DNA)" and "ribonucleic acid (RNA)" can generally refer to any polyribonucleotide or polydeoxyribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA or protein by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins. In some instances, "expression" can also be a reflection of the stability of a given RNA. For example, when one measures RNA, depending on the method of detection and/or quantification of the RNA as well as other techniques used in conjunction with RNA detection and/or quantification, it can be that increased/decreased RNA transcript levels are the result of increased/decreased transcription and/or increased/decreased stability and/or degradation of the RNA transcript. One of ordinary skill in the art will appreciate these techniques and the relation "expression" in these various contexts to the underlying biological mechanisms.

As used herein, "gene" can refer to a hereditary unit corresponding to a sequence of DNA that occupies a specific location on a chromosome and that contains the genetic instruction for a characteristic(s) or trait(s) in an organism. The term gene can refer to translated and/or untranslated regions of a genome. "Gene" can refer to the specific sequence of DNA that is transcribed into an RNA transcript that can be translated into a polypeptide or be a catalytic RNA molecule, including but not limited to, tRNA, siRNA, piRNA, miRNA, long-non-coding RNA and shRNA.

As used herein, "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, in aspects modulation may encompass an increase in the value of the measured variable by about 10 to 500 percent or more. In aspects, modulation can encompass an increase in the value of at least 10%, 20%, 30%, 40%, 50%, 75%, 100%, 150%, 200%, 250%, 300%, 400% to 500% or more, compared to a reference situation or suitable control without said modulation. In aspects, modulation may encompass a decrease or reduction in the value of the measured variable by about 5 to about 100%. In some aspects, the decrease can be about 5%, 10%, 20%, 30%, 40%, 50%, 60%, 70%, 80%, 90%, 95%, 96%, 97%, 98%, 99% to about 100%, compared to a reference situation or suitable control without said modulation. In aspects, modulation may be specific or selective, hence, one or more desired phenotypic aspects of a cell or cell population may be modulated without substantially altering other (unintended, undesired) phenotypic aspect(s).

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

The term "nanoparticle" as used herein includes a nanoscale deposit of a homogenous or heterogeneous material. Nanoparticles may be regular or irregular in shape and may be formed from a plurality of co-deposited particles that form a composite nanoscale particle. Nanoparticles may be generally spherical in shape or have a composite shape formed from a plurality of co-deposited generally spherical particles. Exemplary shapes for the nanoparticles include, but are not limited to, spherical, rod, elliptical, cylindrical, disc, and the like. In some embodiments, the nanoparticles have a substantially spherical shape.

As used herein, "nucleic acid," "nucleotide sequence," and "polynucleotide" can be used interchangeably herein and can generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein can refer to triple-stranded regions comprising RNA or DNA or both RNA and DNA. The strands in such regions can be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide as used herein can include DNAs or RNAs as described herein that contain one or more modified bases. Thus, DNAs or RNAs including unusual bases, such as inosine, or modified bases, such as tritylated bases, to name just two examples, are polynucleotides as the term is used herein. "Polynucleotide", "nucleotide sequences" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotides" as that term is intended herein. As used herein, "nucleic acid sequence" and "oligonucleotide" also encompasses a nucleic acid and polynucleotide as defined elsewhere herein.

As used interchangeably herein, "operatively linked" and "operably linked" in the context of recombinant or engineered polynucleotide molecules (e.g. DNA and RNA) vectors, and the like refers to the regulatory and other sequences useful for expression, stabilization, replication, and the like of the coding and transcribed non-coding sequences of a nucleic acid that are placed in the nucleic acid molecule in the appropriate positions relative to the coding sequence so as to effect expression or other characteristic of the coding sequence or transcribed non-coding sequence. This same term can be applied to the arrangement of coding sequences, non-coding and/or transcription control elements (e.g. promoters, enhancers, and termination elements), and/or selectable markers in an expression vector. "Operatively linked" can also refer to an indirect attachment (i.e. not a direct fusion) of two or more polynucleotide sequences or polypeptides to each other via a linking molecule (also referred to herein as a linker).

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

As used herein, "overexpressed" or "overexpression" refers to an increased expression level of an RNA and/or protein product encoded by a gene as compared to the level of expression of the RNA or protein product in a normal or control cell. The amount of increased expression as compared to a normal or control cell can be about 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.2, 2.4, 2.6, 2.8, 3.0, 3.3, 3.6, 3.9, 4.0, 4.4, 4.8, 5.0, 5.5, 6, 6.5, 7, 7.5, 8.0, 8.5, 9, 9.5, 10, 11, 12, 13, 14, 15, 16, 17, 18, 19, 20, 25, 30, 35, 40, 45, 50, 60, 70, 0, 90, 100 fold or more greater than the normal or control cell.

As used herein, "polypeptides" or "proteins" refers to amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). "Protein" and "Polypeptide" can refer to a molecule composed of one or more chains of amino acids in a specific order. The term protein is used interchangeable with "polypeptide." The order is determined by the base sequence of nucleotides in the gene coding for the protein. Proteins can be required for the structure, function, and regulation of the body's cells, tissues, and organs.

As used herein, "promoter" includes all sequences capable of driving transcription of a coding or a non-coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

As used herein, the term "recombinant" or "engineered" can generally refer to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc. Recombinant or engineered can also refer to the polypeptide encoded by the recombinant nucleic acid. Non-naturally occurring nucleic acids or polypeptides include nucleic acids and polypeptides modified by man.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

Various embodiments are described hereinafter. It should be noted that the specific embodiments are not intended as an exhaustive description or as a limitation to the broader embodiments discussed herein. One embodiment described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Stink bugs and shield bugs belong to the Pentatomidae, a superfamily of insects in the order Hemiptera or true bugs. True bugs are hemimetabolous, which means they develop from nymphs resembling small adults. They are piercing-sucking insects and have a hollow, round "beak" or rostrum to pierce tissues and suck liquids (Millar, 2005; Paiero et al., 2013). They feed on a wide range of hosts including plants ranging from row crops to fruit trees (McPherson and McPherson, 2000) while some feed on other insects (Lundgren, 2011) and still others are blood feeders and can be carriers for disease like Chagas in parts of the world (Otalora-Luna et al., 2015; Schuh and Slater, 1996).

Stink bugs can be found around the world with over 180 species in North America (Froeschner, 1988) and Hemiptera is considered the fourth most economically significant insect order in the United States (Arnett, 2000) and globally. In the United States alone, stink bugs are a considerable economic pest with harlequin bug (*Murgantia histrionica*), brown marmorated stink bug (*Halyomorpha halys*) commonly found on crops in the southeastern United States. Harlequin bugs are specialist pests that feed on cole crops (*Brassica* spp.) such as broccoli and kale, while brown marmorated stink bug are generalists that feed on fruits and vegetables. Stink bugs are often grouped together when reporting damage making accounts of individual stink bugs difficult (McPherson and McPherson, 2000). However, brown marmorated stink bug has gained attention due to its quick spread, heavy crop damage and being a domestic pest. An invasive species that was brought to the United States from China in a shipping container in the mid 1990's, its economic impact totaled over $37 million in 2010 alone (Leskey et al., 2012; McPherson and McPherson, 2000).

Aside from releasing defense compounds with a foul odor, some specialist stink bugs like the harlequin bug sequester plant toxins for their own defense. The sharp taste of arugula and horseradish (both *Brassica* species) comes from isothiocyanates formed when the plant cells are disrupted and myrosinase is released and able to hydrolyze glucosinolates (Agrawal and Kurashige, 2003). This is a key defense of cole crops, the so-called "mustard bomb". In one study, birds learned to associate aposematic (warning) coloration on harlequin bug with a bitter taste and chose the bugs less often versus other insect prey in a choice assay. When the body fluids were analyzed, isothiocyanate breakdown products were identified which match those of plants the bugs were feeding on (Aliabadi et al., 2002).

Current methods to control these stink bug populations include biological control (e.g. wasps and flies that transmit parasites to the southern green stink bug) and chemical control. Given the need to find alternatives to chemical control of pests in agriculture, there exists a need for alternative methods for control of pests, such as the brown marmorated and harlequin stink bugs, in agriculture.

Trap crops are crops that are planted to attract insect pests from another crop, especially one in which the pest fail to survive or reproduce or can be sacrificed to destroy the pests and/or offspring to reduce the population. Trap crops can be planted in an area, usually a small area, adjacent to the cash crops. Trap crops must be intercepted by the stink bug prior to their movement to the cash crop. Currently, the use of trap crops is not widely used or accepted for control of the harlequin or brown marmorated stink bug, which may be due to a variety of reasons such as a strong "edge effect" behavior when moving through landscape, a dislike of crossing open areas where they are more exposed to natural enemies, and a preference for type of plant and plant part that varies with life stage. Further, trap crops are not effective if planted interspersed as it will draw the harlequin or brown marmorated stink bug to the center of the field where they would not naturally bother. In short, correctly placing the trap crop for optimal stink bug control is challenging. As such there also exists a need to improve trap crops, particularly for control of the brown marmorated and/or harlequin stink bug.

With that said, embodiments disclosed herein can provide engineered brown marmorated and/or harlequin stink bug pheromone synthesis enzymes and systems thereof that can be capable of producing an IDS-type TPS or TPS enzyme, a P450 enzyme, and/or an isomerase from a brown marmorated and/or harlequin stink bug. The system can be expressed in a plant such that the plant can be used as a trap crop. Also described herein are engineered polynucleotides and vectors capable of expressing one or more of the engineered brown marmorated and/or harlequin stink bug pheromones described herein. Also described herein are genetically modified cells and/or plants that can express one or more of these engineered brown marmorated and/or harlequin stink bug pheromone synthesis enzymes, polynucleotides, enzymes, and/or vectors. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Engineered Terpene Pheromone Synthases and Systems Thereof

When most people think of stink bugs, they typically think of the unpleasant smell emitted when they are squeezed. These are defense compounds located in the metathoracic scent glands (MTG) and contain primarily aldehydes and esters (Aldrich, 1988). In the majority of stink bugs, however, these defense compounds are completely unrelated to the pheromones released by the bugs. In some cases, such as Miridae (leaf bugs) (Millar, 2005), *Eurydema rugosa* (cabbage bug) (Ishiwatari, 1976), and *Nezara viridula* (southern green stink bug) (Lockwood and Story, 1985) defense compounds may act as pheromones at low concentration although this is controversial.

Insects communicate with pheromones of diverse chemical structure and composition (Müller and Buchbauer. 2011. Flavour Frag J 26:357-377; Stokl and Steiger. 2017. Curr Opp Insct Sci 24:36-42). Many insect pheromones are derived from fatty acids while others arise from terpene (isoprenoid), amino acid, or alkaloid precursors (Blomquist and Vogt. 2003. PNAS 113:2922-2927; Jurenka. 2004. Insect pheromone biosynthesis. In: Schulz (ed.) Chemistry of pheromones and other Semiochemicals I, Vol. 239. Topics in current Chemistry. pp 97-131; Tillman et al. 1999; Yew and Chung. 2015. Prog Lipid Res. 59:88-105). Several studies over the past decades have investigated whether the biosynthesis of insect pheromones depends on the sequestration and conversion of dietary host plant precursors or may occur de novo (Blomquist and Vogt. 2003. PNAS 113:2922-2927; Tillman et al. 1999. Insect Biochem Mol Biol. 29:481-514). Terpenes are released by insects for attraction, aggregation, dispersal, or as trail pheromones (Bartelt et al. 2001. J. Chem Ecol. 27:2397-2423; Brown et al. 2006. J. Chem Ecol. 32:2489-2499; Dewhirst et al. 2010. Aphid pheromones. In: Litwack G. (ed) Vitamins and hormones: pheromones, vol 83. Academic Press, pp 551-574; Sillam-Dusses et al. 2009. J. Insct Physiol 55:751-757). All terpene specialized metabolites are derived from the 5-carbon diphosphate building block isopentenyl diphosphate (IPP) and its allylic isomer dimethylallyl diphosphate (DMAPP) (Tholl. 2015. Adv. Biochem Eng-Biotechnol. 148:63-106). Conjugation of DMAPP with one or several units of IPP by enzymes called isoprenyl diphosphate synthases (IDSs) results in the formation of cis- or trans-isoprenyl diphosphate intermediates such as medium size 10-carbon geranyl diphosphate (GPP) or 15-carbon (E,E)-farnesyl diphosphate (FPP). In plants and microbes these di-phosphates are converted by terpene synthases (TPSs) to monoterpenes (C10) or sesquiterpenes (C15), respectively, in a carbocation-dependent reaction (Chen et al. 2011. Plant J. 66:212-229; Christianson. 2017. Chem Rev. 117-11570-11648; Degenhardt et al. 2009. Phytochemistry. 70:1621-1637; Dickschat. 2016. Nat Prod Rep. 33:87-110).

Insects synthesize isoprenyl diphosphates such as (E,E)-FPP as a precursor of juvenile hormones (Noriega. 2014. Juvenile hormone biosynthesis in insects: what is new, what do we know, and what questions remain? ISRN Zoology 967361). Consequently, FPP synthases or bi-functional GPP/FPP synthases have been identified from a larger number of insects (e.g. Cusson et al. 2006. Proteins. 65:742-758; Ma et al. 2010. Insect Biochem. Mol. Biol. 40:552-561; Sen et al. 2007. Insect Biochem Mol. Biol. 37:819-828; Taban et al. 2009. Arch Insect Biochem Physiol. 71:88-104; Vandermoten et al. 2008. FEBS Lett. 582:1928-1934). Moreover, GPP and FPP synthases have been implicated with providing the pre-cursors of defensive monoterpenoids in leaf beetles and alarm pheromones in aphids (Frick et al. 2013. PNAS. 110:56-61; Lewis et al. 2008. Insect Mol Biol. 17:437-443). However, in most cases insects have been assumed to lack the ability to convert prenyl diphosphate intermediates to terpenes by activity of TPS enzymes because of the absence of plant or microbial type TPS genes in insect genomes.

Only a single study of the bark beetle *Ips pini* (Coleoptera: Curculionidae) by Gilg and co-workers (Gilg et al. 2009. Naturwissenschaften 96:731-735) suggested that the monoterpene myrcene, a precursor of the aggregation pheromone ipsdienol, is synthesized de novo from IPP and DMAPP in a reaction catalyzed by a bi-functional IDS/TPS enzyme. This enzyme first produces GPP as an enzymatic intermediate and subsequently converts it to the monoterpene product (Gilg et al. 2005. PNAS 102:9769-9765 and Gilg et al. 2009. Naturwissenschaften 96:731-735). Recently, a similar biosynthetic route has been detected for the formation of sesquiterpene aggregation pheromones in the striped flea beetle *Phyllotreta striolata* (Coleoptera: Chrysomelidae) (Beran et al. 2016. PNAS. 113:2922-2927) supporting the notion of a TPS-mediated biosynthesis of terpene pheromones in beetles. A family of nine *P. striolata*

IDS-type genes was found, of which four encode functionally active recombinant sesqui-TPSs. Of those, PsTPS1 produces a blend of sesquiterpene olefins similar to that released by male *P. striolata* with (6R,7S)-himachala-9,11-diene as a main compound (Beran et al. 2016. PNAS. 113:2922-2927 and Beran et al. 2016. J Chem Ecol. 42:748-755). Interestingly, PsTPS1 requires a (Z,E)-FPP isomer as substrate, which is made from GPP and IPP by an enzyme with cis-IDS activity.

Only a single study of the bark beetle Ips *pini* (Coleoptera: Curculionidae) by Gilg and co-workers (Gilg et al. 2009. Naturwissenschaften 96:731-735) suggested that the monoterpene myrcene, a precursor of the aggregation pheromone ipsdienol, is synthesized de novo from IPP and DMAPP in a reaction catalyzed by a bi-functional IDS/TPS enzyme. This enzyme first produces GPP as an enzymatic intermediate and subsequently converts it to the monoterpene product (Gilg et al. 2005. PNAS 102:9769-9765 and Gilg et al. 2009. Naturwissenschaften 96:731-735). Recently, a similar biosynthetic route has been detected for the formation of sesquiterpene aggregation pheromones in the striped flea beetle *Phyllotreta striolata* (Coleoptera: Chrysomelidae) (Beran et al. 2016. PNAS. 113:2922-2927) supporting the notion of a TPS-mediated biosynthesis of terpene pheromones in beetles. A family of nine *P. striolata* IDS-type genes was found, of which four encode functionally active recombinant sesqui-TPSs. Of those, PsTPS1 produces a blend of sesquiterpene olefins similar to that released by male *P. striolata* with (6R,7S)-himachala-9,11-diene as a main compound (Beran et al. 2016. PNAS. 113:2922-2927 and Beran et al. 2016. J Chem Ecol. 42:748-755). Interestingly, PsTPS1 requires a (Z,E)-FPP isomer as substrate, which is made from GPP and IPP by an enzyme with cis-IDS activity.

There has been a doubling of the understanding of stink bug pheromones within the past decade or so (Weber et al., 2018). All stink bug pheromones are released by the males which can attract females only (sex pheromone) or all conspecifics (aggregation pheromone) depending on the species (Weber et al., 2018). This is followed with mating calls sent over short distances using leaf surface vibrations (Borges et al., 1987; Cokl et al., 2001; Miklas et al., 2003). Some species of stink bug share the same compound as part of their pheromone blend as in the case of harlequin bug and brown marmorated stink bug which both produce (3S,6S, 7R,10S)-10,11-epoxy-1-bisabolen-3-ol (SSRS-murgantiol; this dissertation) or between *Euschistus heros* and *Piezodorus guildinii* which both produce methyl 2,6,10-trimethyl-dodecanoate and methyl 2,6,10-trimethyltridecanoate (Borges et al., 1998). Other species that don't share compounds can show cross-attractions and can even enhance the attractiveness when presented in a pheromone trap. For instance, adding methyl (E,E,Z)-2,4,6-decatrienoate (MDT) from the stink bug *Plautia stali* to a trap containing the two principle components of the *H. halys* pheromone (3S,6S, 7R,10S)-10,11-epoxy-1-bisabolen-3-ol and (3R,6S,7R, 10S)-10,11-epoxy-1-bisabolen-3-ol) increased the attractiveness to *H. halys* and lead to a 70% increase in captured bugs (Aldrich et al., 2007; Weber et al., 2014b). Bisabolene forms the structural backbone for many stink bug pheromones including *Murgantia histrionica* (Zahn et al., 2008), *Nezara viridula* (Tillman et al., 2010) and *Halyomorpha halys* (Khrimian et al., 2014) among others (McBrien et al., 2002) suggesting there may be a common biosynthetic pathway for these pheromones (FIG. 1). The pheromone composition and the production pathways between different species are quite different (see e.g. FIGS. 1 and 33-35).

Described in several embodiments herein are engineered harlequin stink bug and brown marmorated stink bug terpene pheromone synthases and systems thereof. Also described in several embodiments herein are encoding polynucleotides, vectors and vector systems.

Isoprenyl diphosphate synthases (IDS) are enzymes that combine two or more C5 isoprenyl diphosphate subunits in a head-to-tail condensation reaction to form the diphosphate precursors used by terpene synthase (TPS) to form over 55,000 terpenes known to date. With respect to terpene pheromones, a common question in this area is whether the insect (e.g. harlequin or brown marmorated stink bug) derives the precursors to the pheromones from the host plants on which they feed or if they are made by the insect de novo. As is discussed and demonstrated elsewhere herein, the harlequin and brown marmorated stink bug produces them de novo. Also described and demonstrated herein are various embodiments of engineered harlequin and brown marmorated stink bug synthases that can be involved and capable of producing terpene pheromones of harlequin and brown marmorated stink bugs.

In some embodiments, the enzyme system includes an IDS-type enzyme having TPS activity or a TPS enzyme that is capable of converting (E,E)-FPP into a sesquipiperitol or an isomer thereof. In some embodiments, the enzyme system can also include an isomerase that is capable of converting the sesquipiperitol or an isomer thereof into a zingiberenol. In some embodiments, the enzyme system can also include a p450 enzyme that is capable of converting the zingiberenol or an isomer thereof into a murgantiol. In some embodiments, at least one of the enzymes in a system is an IDS-type enzyme having TPS activity or a TPS enzyme that is capable of converting (E,E)-FPP into (1S,6S,7R)-sesquipiperitol (harlequin stink bug pathway) and/or sesquipiperitol isomers (brown marmorated stink bug pathway) (see e.g. FIG. 33). In some embodiments, the enzyme system can also include an isomerase that is capable of converting the (1S,6S,7R)-sesquipiperitol or sesquipiperitol isomers into a zingiberenol (e.g. 3S,6S,7R)-zingiberenol (harlequin pathway) or 3S,6S,7R/3R, 6S 7R)-zingiberenol (brown marmorated pathway). In some embodiments, the enzyme system can include a p450 enzyme capable of converting the (e.g. 3S,6S,7R)-zingiberenol or 3S,6S,7R/3R, 6S 7R)-zingiberenol into 3S,6S,7R, 10S/3S, 6S, 7R, 10R)-murgantiol.

IDS-Type TPS or TPS Enzymes

In some embodiments, the IDS-type or TPS enzyme can have an amino acid sequence that is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to/or 100 percent identical to SEQ ID NO: 1 or SEQ ID NO: 2. In some embodiments, the IDS-type or TPS enzyme can have an amino acid sequence that is about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to/or 100 percent identical to SEQ ID NO: 1 or SEQ ID NO: 2. In some embodiments, the IDS-type or TPS enzyme can have an amino acid sequence that is about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to/or 100 percent identical to SEQ ID NO: 1 or SEQ ID NO: 2. In some embodiments, the IDS-type or TPS enzyme can have an amino acid sequence that is about 80, 81, 82, 83, 84, 85, 86, 87, 88, 89, 90, 91, 92, 93, 94, 95, 96, 97, 98, 99, to/or 100 percent identical to SEQ ID NO: 1 or SEQ ID NO: 2. In some embodiments, the IDS-type or TPS enzyme can have an amino acid sequence that is about 90, 91, 92, 93, 94, 95, 96, 97, 98, 99, to/or 100 percent identical to SEQ ID NO: 1 or SEQ ID NO: 2. In some embodiments, the IDS-type or TPS enzyme can have an amino acid sequence that is about, 95, 96, 97, 98, 99, to/or 100 percent identical to SEQ ID NO: 1 or SEQ ID NO: 2.

```
(Harlequin Bug Terpene Syntase (TPS))
                                      SEQ ID NO: 1
MVSIAAKSLPKLSGAVFGQFSRRKQLIQRHWLDTRTDQYYDVLRRIVVPE

CKNIASDVPEYPERIEKLLYYTNPAFSDAWNFTTELIYRTVADESHQTEE

NITKMYLIRATMDLLFTMSAVLDDISDRSEFRKGKKGWHMICQGGESTAL

YDGTQMGLFPLYLLKQYFKNDPGYSRLLETVVMTYIKLTIGQTIDVLGQF

KKSPSMAEYKRINYYKAGQFVAAGSELAVIHAGITSQDLIDKTVEIFTIA

GQIIQTWDDFNDYYSSSEQNGKLSCDFMNAGTTWVSAKAMEVFTPSQAVK

FMECYGSDDQSKMKTVQELYDEIDMPKLYTEYVLENYNRCETLIKELPHD

RLREACSSYMEWLVVRETPDEDSEHKVALCLNISG (Harlequin Bug Terpene Syntase (TPS))
                                      SEQ ID NO: 2
MIPKTLGNFTGYVLRIALNKKHVNVRHKLDTDIGKYYQTLNDVVIPECME

FVKDAQGLPQRMKECIGYTTPYCYEGWNFCVELLYKTVADKPHQTEENLK

KMRILRVLSDMSHSMHFILDDYADKAEFRQGKKIWASICEGGQEAAIYDT

FTVNYLINCMLQRHFRNDPGFTKMCEMFSWVNGNSGIGQVLDILDHKNSD

FSDYASWKNKVEYKSRNTMCAFPVLGLLHAGLTCNDLIHKTMDIFGDYGL

MFQVWNDFMDFYSVQEESGKGNYDCKNNVKTWATITAMSHFNPAQAKEFR

DCYGTNDPAKRSRVRELFDEIDLPRKYLDYLRNIRVTVEKKISELSDARV

RDASTSYLEWLHGNGHHDVELEILKAP
```

Isomerases

The enzyme system can include one or more isomerases. In some embodiments, the isomerase(s) is/are from brown marmorated stink bug and/or harlequin stink bug. In some embodiments, the isomerase is a racemase, a cis-trans isomerase, an intramolecular oxidoreductase, and intramolecular transferase, and intramolecular lyase. In some embodiments, the isomerase is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to/or 100 percent identical to amino acid sequences with GenBank Accession No: XP_014270846.1, XP_014272751.1, XP_014286089.1, XP_014282603.1, XP_024218976.1, XP_024217574.1, XP_014273617.1, XP_014284568.1 XP 024214238.1, and/or XP_014247428.1.

P450 Enzymes

Brown Marmorated stink bug has 128 named P450 enzymes in 26 families and 11 fragments that were too short to name (see Sparks et al., 2017. Insects. 8(2):55, particularly at Table 2, FIG. 5; Bansal and Michel. BMC Genomics. 2018. 19:60, particularly at Table 1 FIG. 5, Additional Files 2, 3, 6). Many P450 enzymes are produced by the harlequin stink bug. Harlequin bug has 87 named P450s and 17 fragments in 25 families. Sparks et al. (2017. Insects. 8(2):55, particularly at Table 4, FIG. 5). In some embodiments, the P450 enzyme can be a P450 enzyme as described in Sparks et al. (2017. Insects. 8(2):55, particularly at Tables 2 and 4, FIG. 5). In some embodiments, the P450 enzyme can be a P450 enzyme as set forth in any one or more of Tables 2, 4 or FIG. 5 in Sparks et al. (2017. Insects. 8(2):55)

and/or as set forth in any one or more of Table 1, FIG. 5, or additional files 2, 3, or 6 of Bansal and Michel. BMC Genomics. 2018. 19:60.

In some embodiments, the P450 enzyme is a P450 enzyme from brown marmorated stink bug. In some embodiments, the P450 enzyme is a CYP2 clan, CYP3 clan, CYP4 clan or a mito clan P450 enzyme. In some embodiments, the P450 enzyme can be a CYP9, CYP6, CYP4, CYP395, CYP3230, CYP3231, CRP322, CYP3226, CYP3225, CYP3224, CY3227, CYP3229, CYP315, CYP314, CYP3090, CYP3092, CYP307, CYP306, CYP305, CYP302, CYP303, CYP301, CYP18, CYP15, CYP395. In some embodiments, the P450 enzyme(s) can be selected from the group of CYP9, CYP6, CYP4, CYP395, CYP3230, CYP3231, CRP322, CYP3226, CYP3225, CYP3224, CYP315, CYP314, CYP3092, CYP307, CYP306, CYP305, CYP302, CYP301, CYP18, CYP15 and combinations thereof.

In some embodiments a Southern green stink bug P450 enzyme can be included in the system. In some embodiments, the P450 enzyme can have a sequence that is 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to/or 100 percent identical to any one of those set forth in International Application Publication No. WO 2020/096711, particularly any one of SEQ ID NOs: 6-79 therein.

Engineered Terpene Pheromone Synthesis Enzyme Encoding Polynucleotides and Vector Systems Encoding Polynucleotides In some embodiments one or more enzymes of the engineered terpene pheromone synthase pathway (e.g. the IDS-type TPS or TPS enzyme, isomerase, and/or P450 enzyme) of the brown marmorated and harlequin stink bug can be encoded by one or more polynucleotides.

In some embodiments, a polynucleotide encoding a IDS-type TPS or TPS enzyme can be about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to/or 100 percent identical to SEQ ID NO: 3 or SEQ ID NO: 4. In some embodiments, a polynucleotide encoding a IDS-type TPS or TPS enzyme can be about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to/or 100 percent identical to SEQ ID NO: 3 or SEQ ID NO: 4. In some embodiments, a polynucleotide encoding a IDS-type TPS or TPS enzyme can be about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to/or 100 percent identical to SEQ ID NO: 3 or SEQ ID NO: 4. In some embodiments, a polynucleotide encoding a IDS-type TPS or TPS enzyme can be about 80, 81, 82, 83, 84, 85, 86, 87, 88, 89, 90, 91, 92, 93, 94, 95, 96, 97, 98, 99, to/or 100 percent identical to SEQ ID NO: 3 or SEQ ID NO: 4. In some embodiments, a polynucleotide encoding a IDS-type TPS or TPS enzyme can be about 90, 91, 92, 93, 94, 95, 96, 97, 98, 99, to/or 100 percent identical to SEQ ID NO: 3 or SEQ ID NO: 4. In some embodiments, a polynucleotide encoding a IDS-type TPS or TPS enzyme can be about 95, 96, 97, 98, 99, to/or 100 percent identical to SEQ ID NO: 3 or SEQ ID NO: 4.

In some embodiments, a P450 enzyme can be encoded by a polynucleotide as set forth in Sparks et al., 2017. Insects. 8(2):55, particularly at Table 2, FIG. 5; Bansal and Michel. BMC Genomics. 2018. 19:60, particularly at Table 1 FIG. 5, Additional Files 2, 3, 6) or be about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to/or 100 percent identical to a P450 encoding polynucleotide described therein.

In some embodiments the isomerase can be encoded by a polynucleotide as set forth at GenBank Accession No.: XM_014427117.2, XM_024363208.1, XM_024361806.1, XM_014418131.2, XM_014429082.2, XM_024358470.1, and/or XM_014415973.1. In some embodiments, the isomerase encoding polynucleotide is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to/or 100 percent identical to a polynucleotide at GenBank Accession No.: XM_014427117.2, XM_024363208.1, XM_024361806.1, XM_014418131.2, XM_014429082.2, XM_024358470.1, and/or XM_024415973.1.

One of ordinary skill in the art, based upon at least the polypeptide sequence can generate appropriate polynucleotides capable of encoding said polypeptide sequences using commercially and other wise available software that is capable of determining reading frames, codons, and the like. In some embodiments, the polynucleotides can be codon optimized. Codon optimization is described in greater detail elsewhere herein. In some embodiments, the polynucleotides are codon optimized for expression in a plant cell. The polynucleotides can be naked or included in a vector. Suitable vectors are discussed in greater detail elsewhere herein. The polynucleotide can include one or more modified bases. The modification can modulate (increase or decrease) stability, modulate transcription efficiency, and provide other functionalities. Such modifications that can be applied to the polynucleotides described herein will be appreciated by those of ordinary skill in the art.

Harlequin bug terpene synthase (TPS)
encoding polynucleotide.
SEQ ID NO: 3
ATGGTCTCCATTGCTGCTAAGTCTCTACCCAAGCTGAGTGGTGCTGTCTT

CGGCCAGTTTTCGAGGAGAAAGCAGTTGATCCAAAGGCATTGGCTGGACA

CTAGAACAGATCAATACTATGATGTTCTGAGGCGTATTGTGGTACCAGAA

TGTAAAAATATTGCATCAGATGTACCAGAATATCCGGAGAGAATAGAGAA

GTTACTTTACTACACCAACCCAGCATTCAGTGATGCTTGGAATTTTACGA

CTGAACTGATTTACAGAACAGTGGCTGATGAGAGTCACCAAACAGAAGAG

AACATTACCAAGATGTACCTAATTAGAGCTACAATGGATTTGTTATTTAC

GATGTCAGCAGTTCTAGATGATATCAGTGATAGGTCGGAGTTTAGGAAAG

GTAAGAAAGGTTGGCATATGATCTGTCAAGGGGGTGAAAGTACTGCTTTA

TACGACGGAACTCAAATGGGATTATTCCCTCTCTATCTATTAAAACAGTA

TTTCAAAAATGATCCTGGCTACTCACGACTTTTGGAAACTGTTGTGATGA

CCTACATAAAGCTGACAATTGGGCAAACAATAGATGTCCTAGGACAGTTT

AAGAAATCACCATCAATGGCTGAATATAAGCGTATAAATTATTACAAAGC

AGGACAATTTGTTGCGGCTGGTTCAGAGCTTGCGGTTATTCATGCTGGAA

TAACATCTCAAGATTTGATTGATAAAACTGTGGAGATATTTACTATTGCC

GGTCAAATTATACAGACATGGGATGACTTCAATGATTACTACAGCTCCTC

AGAACAGAATGGTAAGCTATCATGTGATTTCATGAACGCAGGAACAACTT

-continued

GGGTTAGTGCCAAAGCAATGGAGGTCTTCACTCCTTCCCAAGCAGTAAAA

TTTATGGAGTGTTATGGCTCAGATGATCAATCCAAGATGAAGACAGTACA

AGAATTATATGATGAGATCGACATGCCGAAGTTATACACCGAGTATGTAC

TAGAAAATTACAATCGCTGTGAAACTCTGATAAAAGAACTACCACATGAC

AGATTGCGGGAGGCCTGTTCCAGTTATATGGAGTGGCTTGTAGTTCGAGA

AACGCCTGATGAAGATTCGGAACATAAAGTTGCTTTATGTTTGAACATTA

GTGGGTAA

Brown marmorated stink bug terpene synthase
(TPS) encoding polynucleotide.
SEQ ID NO: 4
ATGATACCGAAGACGCTTGGGAATTTTACAGGATATGTATTGAGAATTGC

ACTAAATAAGAAGCATGTTAATGTAAGACACACAAATTAGACACTGATATCG

GCAAGTATTATCAAACACTGAACGATGTCGTGATCCCTGAGTGTATGGAA

TTCGTTAAGGATGCACAAGGTCTTCCACAAAGGATGAAAGAGTGTATAGG

ATACACTACTCCCTATTGCTACGAAGGTTGGAACTTCTGCGTTGAGTTAC

TCTACAAAACGGTGGCCGACAAACCCCATCAGACAGAAGAAAACTTGAAA

AAAATGAGAATACTCAGAGTTTTATCGGATATGAGCCATTCAATGCACTT

TATATTAGATGACTACGCTGACAAAGCAGAGTTTAGACAGGGTAAGAAGA

TTTGGGCTTCGATATGTGAAGGAGGCCAAGAAGCAGCCATCTATGACACT

TTCACTGTCAACTACTTGATAAATTGCATGCTTCAGCGTCACTTTAGGAA

TGATCCAGGTTTCACCAAGATGTGTGAAATGTTTTCTTGGGTTAATGGCA

ATTCAGGGATAGGACAAGTATTGGATATCCTGGACCATAAGAATTCAGAT

TTCAGTGATTATGCTAGTTGGAAGAACAAAGTTGAATACAAATCAAGGAA

TACAATGTGTGCTTTTCCAGTACTGGGTCTTCTACATGCAGGACTGACCT

GTAACGACCTTATTCATAAAACTATGGACATATTTGGTGATTATGGACTT

ATGTTTCAAGTATGGAATGATTTCATGGATTTCTATTCAGTGCAAGAGGA

ATCTGGTAAAGGAAATTATGATTGCAAGAACAATGTAAAAACTTGGGCAA

CTATAACAGCAATGAGTCACTTTAATCCGGCCCAAGCTAAAGAGTTCAGG

GACTGCTATGGGACCAACGATCCAGCTAAAAGATCTAGAGTACGCGAACT

GTTTGACGAGATAGATTTACCCAGGAAATACTTGGATTATTTAAGGAATA

TCCGTGTTACTGTTGAAAAAAAAATCAGTGAACTTAGTGATGCCAGAGTA

CGTGATGCTTCTACTAGCTACTTAGAATGGCTGCATGGAAACGGACATCA

TGATGTTGAATTGGAGATCCTAAAAGCTCCATAA

Vectors and Vector Systems

Also provided herein are vectors that can contain one or more of the engineered stink bug pheromone synthesis enzyme (e.g. an IDS-type TPS or TPS, P450, and/or isomerase) encoding polynucleotides described herein (hereinafter "encoding polynucleotide(s)"). In embodiments, the vector can contain one or more polynucleotides encoding one or more elements of engineered stink bug pheromone synthesis enzyme system described herein. The vectors can be useful in producing bacterial, fungal, yeast, plant cells, animal cells, and transgenic animals that can express one or more components of the engineered stink bug pheromone synthesis enzyme system described herein. Within the scope of this disclosure are vectors containing one or more of the polynucleotide sequences described herein. One or more of the polynucleotides that are part of the engineered stink bug pheromone synthesis enzyme system described herein can be included in a vector or vector system. The vectors and/or vector systems can be used, for example, to express one or more of the polynucleotides in a cell, such as a producer cell, to produce one or more of particles (e.g. viral particles) containing an encoding polynucleotide(s) described elsewhere herein. Other uses for the vectors and vector systems described herein are also within the scope of this disclosure. In general, and throughout this specification, the term "vector" refers to a tool that allows or facilitates the transfer of an entity from one environment to another. In some contexts which will be appreciated by those of ordinary skill in the art, "vector" can be a term of art to refer to a nucleic acid molecule capable of transporting another nucleic acid to which it has been linked. A vector can be a replicon, such as a plasmid, phage, or cosmid, into which another DNA segment may be inserted so as to bring about the replication of the inserted segment. Generally, a vector is capable of replication when associated with the proper control elements.

Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can be composed of a nucleic acid (e.g. a polynucleotide) of the invention in a form suitable for expression of the nucleic acid in a host cell, which means that the recombinant expression vectors include one or more regulatory elements, which can be selected on the basis of the host cells to be used for expression, that is operatively-linked to the nucleic acid sequence to be expressed. Within a recombinant expression vector, "operably linked" and "operatively-linked" are used interchangeably herein and further defined elsewhere herein. In the context of a vector, the term "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). Advantageous vectors include lentiviruses and adeno-associated viruses, and types of such vectors can also be selected for targeting particular types of cells. These and other embodiments of the vectors and vector systems are described elsewhere herein.

In some embodiments, the vector can be a bicistronic vector. In some embodiments, a bicistronic vector can be used for one or more elements of the engineered stink bug pheromone synthesis system described herein. In some embodiments, expression of elements of the engineered stink bug pheromone synthesis system described herein can be driven by a plant specific promoter. Where the element of the engineered stink bug pheromone synthesis system is an RNA, its expression can be driven by a Pol III promoter, such as a U6 promoter. In some embodiments, the two are combined.

Cell-Based Vector Amplification and Expression

Vectors can be designed for expression of one or more elements of the engineered stink bug pheromone synthesis system described herein (e.g. nucleic acid transcripts, proteins, enzymes, and combinations thereof) in a suitable host cell. In some embodiments, the suitable host cell is a prokaryotic cell. Suitable host cells include, but are not limited to, bacterial cells, yeast cells, insect cells, and mammalian cells. The vectors can be viral-based or nonviral based. In some embodiments, the suitable host cell is a eukaryotic cell. In some embodiments, the suitable host cell is a suitable bacterial cell. Suitable bacterial cells include, but are not limited to, bacterial cells from the bacteria of the species *Escherichia coli*. Many suitable strains of *E. coli* are known in the art for expression of vectors. These include, but are not limited to Pir1, Stb12, Stb13, Stb14, TOP10, XL1 Blue, and XL10 Gold. In some embodiments, the host cell is a suitable insect cell. Suitable insect cells include those from *Spodoptera frugiperda*. Suitable strains of *S. frugiperda* cells include, but are not limited to, Sf9 and Sf21. In some embodiments, the host cell is a suitable yeast cell. In some embodiments, the yeast cell can be from *Saccharomyces cerevisiae*. In some embodiments, the host cell is a suitable mammalian cell. Many types of mammalian cells have been developed to express vectors. Suitable mammalian cells include, but are not limited to, HEK293, Chinese Hamster Ovary Cells (CHOs), mouse myeloma cells, HeLa, U2OS, A549, HT1080, CAD, P19, NIH 3T3, L929, N2a, MCF-7, Y79, SO-Rb50, HepG G2, DIKX-X11, J558L, Baby hamster kidney cells (BHK), and chicken embryo fibroblasts (CEFs). Suitable host cells are discussed further in Goeddel, GENE EXPRESSION TECHNOLOGY: METHODS IN ENZYMOLOGY 185, Academic Press, San Diego, Calif. (1990).

In some embodiments, the vector can be a yeast expression vector. Examples of vectors for expression in yeast *Saccharomyces cerevisiae* include pYepSec1 (Baldari, et al., 1987. EMBO J. 6:229-234), pMFa (Kuijan and Herskowitz, 1982. Cell 30:933-943), pJRY88 (Schultz et al., 1987. Gene 54:113-123), pYES2 (Invitrogen Corporation, San Diego, Calif.), and picZ (InVitrogen Corp, San Diego, Calif.). As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeast cell. Many suitable yeast expression vectors and features thereof are known in the art; for example, various vectors and techniques are illustrated in Yeast Protocols, 2nd edition, Xiao, W., ed. (Humana Press, New York, 2007) and Buckholz, R. G. and Gleeson, M. A. (1991) Biotechnology (NY) 9(11): 1067-72. Yeast vectors can contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2u plasmids, yeast integrative plasmids, yeast replicative plasmids, shuttle vectors, and episomal plasmids.

In some embodiments, the vector is a baculovirus vector or expression vector and can be suitable for expression of polynucleotides and/or proteins in insect cells. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39). rAAV (recombinant Adeno-associated viral) vectors are preferably produced in insect cells, e.g., *Spodoptera frugiperda* Sf9 insect cells, grown in serum-free suspension culture. Serum-free insect cells can be purchased from commercial vendors, e.g., Sigma Aldrich (EX-CELL 405).

In some embodiments, the vector is a mammalian expression vector. In some embodiments, the mammalian expression vector is capable of expressing one or more polynucleotides and/or polypeptides in a mammalian cell. Examples of mammalian expression vectors include, but are not limited to, pCDM8 (Seed, 1987. Nature 329: 840) and pMT2PC (Kaufman, et al., 1987. EMBO J. 6: 187-195). The mammalian expression vector can include one or more suitable regulatory elements capable of controlling expression of the one or more polynucleotides and/or proteins in the mammalian cell. For example, commonly used promoters are derived from polyoma, adenovirus 2, cytomegalovirus, simian virus 40, and others disclosed herein and known in the art. More detail on suitable regulatory elements are described elsewhere herein.

For other suitable expression vectors and vector systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the a-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments can utilize viral vectors, with regards to which mention is made of U.S. patent application Ser. No. 13/092, 085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element can be operably linked to one or more elements of an engineered stink bug pheromone synthesis system so as to drive expression of the one or more elements of the engineered stink bug pheromone synthesis system described herein.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism.

In some embodiments, the vector can be a fusion vector or fusion expression vector. In some embodiments, fusion vectors add a number of amino acids to a protein encoded therein, such as to the amino terminus, carboxy terminus, or both of a recombinant protein. Such fusion vectors can serve one or more purposes, such as: (i) to increase expression of recombinant protein; (ii) to increase the solubility of the recombinant protein; and (iii) to aid in the purification of the recombinant protein by acting as a ligand in affinity purification. In some embodiments, expression of polynucleotides (such as non-coding polynucleotides) and proteins in prokaryotes can be carried out in *Escherichia coli* with vectors containing constitutive or inducible promoters directing the expression of either fusion or non-fusion polynucleotides and/or proteins. In some embodiments, the fusion expression vector can include a proteolytic cleavage site, which can be introduced at the junction of the fusion vector backbone or other fusion moiety and the recombinant polynucleotide or protein to enable separation of the recombinant polynucleotide or protein from the fusion vector backbone or other fusion moiety subsequent to purification of the fusion polynucleotide or protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67:31-40), pMAL (New England Biolabs, Beverly, Mass.) and pRIT5-(Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) *Gene* 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, one or more vectors driving expression of one or more elements of an engineered stink bug pheromone synthesis system described herein are introduced into a host cell such that expression of the elements of the engineered delivery system described herein direct formation of an engineered stink bug pheromone synthesis system or component thereof. For example, different elements of the engineered stink bug pheromone synthesis system described herein can each be operably linked to separate regulatory elements on separate vectors. RNA(s) of different elements of the engineered delivery system described herein can be delivered to an animal or mammal or cell thereof to produce an animal or mammal or cell thereof that constitutively or inducibly or conditionally expresses different elements of the engineered stink bug pheromone synthesis system described herein that incorporates one or more elements of the engineered stink bug pheromone synthesis system described herein or contains one or more cells that incorporates and/or expresses one or more elements of the engineered stink bug pheromone synthesis system described herein.

In some embodiments, two or more of the elements expressed from the same or different regulatory element(s), can be combined in a single vector, with one or more additional vectors providing any components of the system not included in the first vector. Engineered encoding and other system polynucleotides that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding one or more engineered stink bug pheromone synthesis system proteins, embedded within one or more intron sequences (e.g., each in a different intron, two or more in at least one intron, or all in a single intron). In some embodiments, the engineered stink bug pheromone synthesis system polynucleotides can be operably linked to and expressed from the same promoter.

Vector Features

The vectors can include additional features that can confer one or more functionalities to the vector, the polynucleotide to be delivered, a virus particle produced there from, or polypeptide expressed thereof. Such features include, but are not limited to, regulatory elements, selectable markers, molecular identifiers (e.g. molecular barcodes), stabilizing elements, and the like. It will be appreciated by those skilled in the art that the design of the expression vector and additional features included can depend on such factors as the choice of the host cell to be transformed, the level of expression desired, etc.

Regulatory Elements

In embodiments, the polynucleotides and/or vectors thereof described herein (such as the engineered stink bug pheromone synthesis system polynucleotides) can include one or more regulatory elements that can be operatively linked to the polynucleotide. The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter can direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (see, e.g., Boshart et al, Cell, 41:521-530 (1985)), the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981).

In some embodiments, the regulatory sequence can be a regulatory sequence described in U.S. Pat. No. 7,776,321, U.S. Pat. Pub. No. 2011/0027239, and PCT publication WO 2011/028929, the contents of which are incorporated by reference herein in their entirety. In some embodiments, the vector can contain a minimal promoter. In some embodiments, the minimal promoter is the Mecp2 promoter, tRNA promoter, or U6. In a further embodiment, the minimal promoter is tissue specific. In some embodiments, the length of the vector polynucleotide the minimal promoters and polynucleotide sequences is less than 4.4 Kb.

To express a polynucleotide, the vector can include one or more transcriptional and/or translational initiation regulatory sequences, e.g. promoters, that direct the transcription of the gene and/or translation of the encoded protein in a cell. In some embodiments a constitutive promoter may be employed. Suitable constitutive promoters for mammalian cells are generally known in the art and include, but are not limited to SV40, CAG, CMV, EF-1α, β-actin, RSV, and PGK. Suitable constitutive promoters for bacterial cells, yeast cells, and fungal cells are generally known in the art, such as a T-7 promoter for bacterial expression and an alcohol dehydrogenase promoter for expression in yeast.

In some embodiments, the regulatory element can be a regulated promoter. "Regulated promoter" refers to promoters that direct gene expression not constitutively, but in a temporally- and/or spatially-regulated manner, and includes tissue-specific, tissue-preferred and inducible promoters. Regulated promoters include conditional promoters and inducible promoters. In some embodiments, conditional promoters can be employed to direct expression of a polynucleotide in a specific cell type, under certain environmental conditions, and/or during a specific state of development. Suitable tissue specific promoters can include, but are not limited to, liver specific promoters (e.g. APOA2, SERPIN A1 (hAAT), CYP3A4, and MIR122), pancreatic cell promoters (e.g. INS, IRS2, Pdx1, Alx3, Ppy), cardiac specific promoters (e.g. Myh6 (alpha MHC), MYL2 (MLC-2v), TNI3 (cTnI), NPPA (ANF), Slc8a1 (Ncx1)), central nervous system cell promoters (SYN1, GFAP, INA, NES, MOBP, MBP, TH, FOXA2 (HNF3 beta)), skin cell specific promoters (e.g. FLG, K14, TGM3), immune cell specific promoters, (e.g. ITGAM, CD43 promoter, CD14 promoter, CD45 promoter, CD68 promoter), urogenital cell specific promoters (e.g. Pbsn, Upk2, Sbp, Fer1l4), endothelial cell specific promoters (e.g. ENG), pluripotent and embryonic germ layer cell specific promoters (e.g. Oct4, NANOG, Synthetic Oct4, T brachyury, NES, SOX17, FOXA2, MIR122), and muscle cell specific promoter (e.g. Desmin). Other tissue and/or cell specific promoters are generally known in the art and are within the scope of this disclosure.

Inducible/conditional promoters can be positively inducible/conditional promoters (e.g. a promoter that activates transcription of the polynucleotide upon appropriate interaction with an activated activator, or an inducer (compound, environmental condition, or other stimulus) or a negative/conditional inducible promoter (e.g. a promoter that is repressed (e.g. bound by a repressor) until the repressor condition of the promotor is removed (e.g. inducer binds a repressor bound to the promoter stimulating release of the promoter by the repressor or removal of a chemical repressor from the promoter environment). The inducer can be a compound, environmental condition, or other stimulus. Thus, inducible/conditional promoters can be responsive to any suitable stimuli such as chemical, biological, or other molecular agents, temperature, light, and/or pH. Suitable inducible/conditional promoters include, but are not limited to, Tet-On, Tet-Off, Lac promoter, pBad, AlcA, LexA, Hsp70 promoter, Hsp90 promoter, pDawn, XVE/OlexA, GVG, and pOp/LhGR.

Where expression in a plant cell is desired, the components of the engineered stink bug pheromone synthesis system described herein are typically placed under control of a plant promoter, i.e. a promoter operable in plant cells. The use of different types of promoters is envisaged.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. Different promoters may direct the expression of a gene in different tissues or cell types, or at different stages of development, or in response to different environmental conditions. In particular embodiments, one or more of the engineered stink bug pheromone synthesis system components are expressed under the control of a constitutive promoter, such as the cauliflower mosaic virus 35S promoter issue-preferred promoters can be utilized to target enhanced expression in certain cell types within a particular plant tissue, for instance vascular cells in leaves or roots or in specific cells of the seed. Examples of particular promoters for use in the engineered stink bug pheromone synthesis system are found in Kawamata et al., (1997) Plant Cell Physiol 38:792-803; Yamamoto et al., (1997) Plant J 12:255-65; Hire et al, (1992) Plant Mol Biol 20:207-18, Kuster et al, (1995) Plant Mol Biol 29:759-72, and Capana et al., (1994) Plant Mol Biol 25:681-91.

Examples of promoters that are inducible and that can allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc), or light inducible systems (Phytochrome, LOV domains, or cryptochrome)., such as a Light Inducible Transcriptional Effector (LITE) that direct changes in transcriptional activity in a sequence-specific manner. The components of a light inducible system may include one or more elements of the engineered stink bug pheromone synthesis system described herein, a light-responsive cytochrome heterodimer (e.g.

from *Arabidopsis thaliana*), and a transcriptional activation/repression domain. In some embodiments, the vector can include one or more of the inducible DNA binding proteins provided in PCT publication WO 2014/018423 and US Publications, 2015/0291966, 2017/0166903, 2019/0203212, which describe e.g. embodiments of inducible DNA binding proteins and methods of use and can be adapted for use with the present invention.

In some embodiments, transient or inducible expression can be achieved by including, for example, chemical-regulated promotors, i.e. whereby the application of an exogenous chemical induces gene expression. Modulation of gene expression can also be obtained by including a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) Plant Cell Physiol 38:568-77), the maize GST promoter (GST-11-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227: 229-37; U.S. Pat. Nos. 5,814,618 and 5,789,156) can also be used herein.

In some embodiments, the vector or system thereof can include one or more elements capable of translocating and/or expressing an engineered stink bug pheromone synthesis system polynucleotide to/in a specific cell component or organelle. Such organelles can include, but are not limited to, nucleus, ribosome, endoplasmic reticulum, golgi apparatus, chloroplast, mitochondria, vacuole, lysosome, cytoskeleton, plasma membrane, cell wall, peroxisome, centrioles, etc.

Selectable Markers and Tags

One or more of the engineered stink bug pheromone synthesis system polynucleotides can be operably linked, fused to, or otherwise modified to include a polynucleotide that encodes or is a selectable marker or tag, which can be a polynucleotide or polypeptide. In some embodiments, the polypeptide encoding a polypeptide selectable marker can be incorporated in the engineered stink bug pheromone synthesis system polynucleotide such that the selectable marker polypeptide, when translated, is inserted between two amino acids between the N- and C-terminus of the engineered stink bug pheromone synthesis system polypeptide or at the N- and/or C-terminus of the engineered stink bug pheromone synthesis system polypeptide. In some embodiments, the selectable marker or tag is a polynucleotide barcode or unique molecular identifier (UMI).

It will be appreciated that the polynucleotide encoding such selectable markers or tags can be incorporated into a polynucleotide encoding one or more components of the engineered stink bug pheromone synthesis system described herein in an appropriate manner to allow expression of the selectable marker or tag. Such techniques and methods are described elsewhere herein and will be instantly appreciated by one of ordinary skill in the art in view of this disclosure. Many such selectable markers and tags are generally known in the art and are intended to be within the scope of this disclosure.

Suitable selectable markers and tags include, but are not limited to, affinity tags, such as chitin binding protein (CBP), maltose binding protein (MBP), glutathione-S-transferase (GST), poly(His) tag; solubilization tags such as thioredoxin (TRX) and poly (NANP), MBP, and GST; chromatography tags such as those consisting of polyanionic amino acids, such as FLAG-tag; epitope tags such as V5-tag, Myc-tag, HA-tag and NE-tag; protein tags that can allow specific enzymatic modification (such as biotinylation by biotin ligase) or chemical modification (such as reaction with FLASH-EDT2 for fluorescence imaging), DNA and/or RNA segments that contain restriction enzyme or other enzyme cleavage sites; DNA segments that encode products that provide resistance against otherwise toxic compounds including antibiotics, such as, spectinomycin, ampicillin, kanamycin, tetracycline, Basta, neomycin phosphotransferase II (NEO), hygromycin phosphotransferase (HPT)) and the like; DNA and/or RNA segments that encode products that are otherwise lacking in the recipient cell (e.g., tRNA genes, auxotrophic markers); DNA and/or RNA segments that encode products which can be readily identified (e.g., phenotypic markers such as B-galactosidase, GUS; fluorescent proteins such as green fluorescent protein (GFP), cyan (CFP), yellow (YFP), red (RFP), luciferase, and cell surface proteins); polynucleotides that can generate one or more new primer sites for PCR (e.g., the juxtaposition of two DNA sequences not previously juxtaposed), DNA sequences not acted upon or acted upon by a restriction endonuclease or other DNA modifying enzyme, chemical, etc.; epitope tags (e.g. GFP, FLAG- and His-tags), and, DNA sequences that make a molecular barcode or unique molecular identifier (UMI), DNA sequences required for a specific modification (e.g., methylation) that allows its identification. Other suitable markers will be appreciated by those of skill in the art.

Selectable markers and tags can be operably linked to one or more components of the engineered stink bug pheromone synthesis system described herein via suitable linker, such as a glycine or glycine serine linkers as short as GS or GG up to (GGGGG)$_3$ (SEQ ID NO: 5) or (GGGGS)$_3$ (SEQ ID NO: 6). Other suitable linkers are described elsewhere herein.

The vector or vector system can include one or more polynucleotides encoding one or more targeting moieties. In some embodiments, the targeting moiety encoding polynucleotides can be included in the vector or vector system, such as a viral vector system, such that they are expressed within and/or on the virus particle(s) produced such that the virus particles can be targeted to specific cells, tissues, organs, etc. In some embodiments, the targeting moiety encoding polynucleotides can be included in the vector or vector system such that the engineered stink bug pheromone synthesis system polynucleotide(s) and/or products expressed therefrom include the targeting moiety and can be targeted to specific cells, tissues, organs, etc. In some embodiments, such as non-viral carriers, the targeting moiety can be attached to the carrier (e.g. polymer, lipid, inorganic molecule etc.) and can be capable of targeting the carrier and any attached or associated engineered stink bug pheromone synthesis system polynucleotide(s) to specific cells, tissues, organs, etc.

Cell-Free Vector and Polynucleotide Expression

In some embodiments, the polynucleotide encoding one or more features of the engineered stink bug pheromone synthesis system can be expressed from a vector or suitable polynucleotide in a cell-free in vitro system. In other words, the polynucleotide can be transcribed and optionally translated in vitro. In vitro transcription/translation systems and appropriate vectors are generally known in the art and commercially available. Generally, in vitro transcription and in vitro translation systems replicate the processes of RNA and protein synthesis, respectively, outside of the cellular environment. Vectors and suitable polynucleotides for in vitro transcription can include T7, SP6, T3, promoter regulatory sequences that can be recognized and acted upon by an appropriate polymerase to transcribe the polynucleotide or vector.

In vitro translation can be stand-alone (e.g. translation of a purified polyribonucleotide) or linked/coupled to transcription. In some embodiments, the cell-free (or in vitro) translation system can include extracts from rabbit reticulocytes, wheat germ, and/or *E. coli*. The extracts can include various macromolecular components that are needed for translation of exogenous RNA (e.g. 70S or 80S ribosomes, tRNAs, aminoacyl-tRNA, synthetases, initiation, elongation factors, termination factors, etc.). Other components can be included or added during the translation reaction, including but not limited to, amino acids, energy sources (ATP, GTP), energy regenerating systems (creatine phosphate and creatine phosphokinase (eukaryotic systems)) (phosphoenol pyruvate and pyruvate kinase for bacterial systems), and other co-factors (Mg$^{2+}$, K+, etc.). As previously mentioned, in vitro translation can be based on RNA or DNA starting material. Some translation systems can utilize an RNA template as starting material (e.g. reticulocyte lysates and wheat germ extracts). Some translation systems can utilize a DNA template as a starting material (e.g. *E coli*-based systems). In these systems transcription and translation are coupled and DNA is first transcribed into RNA, which is subsequently translated. Suitable standard and coupled cell-free translation systems are generally known in the art and are commercially available.

Codon Optimization of Vector Polynucleotides

As described elsewhere herein, the polynucleotide encoding one or more embodiments of the engineered stink bug pheromone synthesis system described herein can be codon optimized. In some embodiments, one or more polynucleotides contained in a vector ("vector polynucleotides") described herein that are in addition to an optionally codon optimized polynucleotide encoding embodiments of the engineered stink bug pheromone synthesis system described herein can be codon optimized. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. As to codon usage in yeast, reference is made to the online Yeast Genome database available atwww.yeastgenome.org, or *Codon selection in yeast*, Bennetzen and Hall, J Biol Chem. 1982 Mar. 25; 257(6):3026-31. As to codon usage in plants including algae, reference is made to *Codon usage in higher plants, green algae, and cyanobacteria*, Campbell and Gowri, Plant Physiol. 1990 January; 92(1):1-11; as well as *Codon usage in plant genes*, Murray et al, Nucleic Acids Res. 1989 Jan. 25; 17(2):477-98; or *Selection on the codon bias of chloroplast and cyanelle genes in different plant and algal lineages*, Morton B R, J Mol Evol. 1998 April; 46(4):449-59.

The vector polynucleotide can be codon optimized for expression in a specific cell-type, tissue type, organ type, and/or subject type. In some embodiments, a codon optimized sequence is a sequence optimized for expression in a eukaryote, e.g., humans (i.e. being optimized for expression in a human or human cell), or for another eukaryote, such as another animal (e.g. a mammal or avian) as is described elsewhere herein. Such codon optimized sequences are within the ambit of the ordinary skilled artisan in view of the description herein. In some embodiments, the polynucleotide is codon optimized for a specific cell type. Such cell types can include, but are not limited to, epithelial cells (including skin cells, cells lining the gastrointestinal tract, cells lining other hollow organs), nerve cells (nerves, brain cells, spinal column cells, nerve support cells (e.g. astrocytes, glial cells, Schwann cells etc.), muscle cells (e.g. cardiac muscle, smooth muscle cells, and skeletal muscle cells), connective tissue cells (fat and other soft tissue padding cells, bone cells, tendon cells, cartilage cells), blood cells, stem cells and other progenitor cells, immune system cells, germ cells, and combinations thereof. Such codon optimized sequences are within the ambit of the ordinary skilled artisan in view of the description herein. In some embodiments, the polynucleotide is codon optimized for a specific tissue type. Such tissue types can include, but are not limited to, muscle tissue, connective tissue, connective tissue, nervous tissue, and epithelial tissue. Such codon optimized sequences are within the ambit of the ordinary skilled artisan in view of the description herein. In some embodiments, the polynucleotide is codon optimized for a specific organ. Such organs include, but are not limited to, muscles, skin, intestines, liver, spleen, brain, lungs, stomach, heart, kidneys, gallbladder, pancreas, bladder, thyroid, bone, blood vessels, blood, and combinations thereof. Such codon optimized sequences are within the ambit of the ordinary skilled artisan in view of the description herein.

In some embodiments, a vector polynucleotide is codon optimized for expression in particular cells, such as prokaryotic or eukaryotic cells. The eukaryotic cells may be those of or derived from a particular organism, such as a plant or a mammal, including but not limited to human, or non-human eukaryote or animal or mammal as discussed herein, e.g., mouse, rat, rabbit, dog, livestock, or non-human mammal or primate.

Non-Viral Vectors and Carriers

In some embodiments, the vector is a non-viral vector or carrier. In some embodiments, non-viral vectors can have the advantage(s) of reduced toxicity and/or immunogenicity and/or increased bio-safety as compared to viral vectors. The terms of art "Non-viral vectors and carriers" and as used herein in this context refers to molecules and/or compositions that are not based on one or more component of a virus or virus genome (excluding any nucleotide to be delivered and/or expressed by the non-viral vector) that can be capable of attaching to, incorporating, coupling, and/or otherwise interacting with an engineered stink bug pheromone synthesis system polynucleotide and can be capable of ferrying the polynucleotide to a cell and/or expressing the polynucleotide. It will be appreciated that this does not exclude the inclusion of a virus-based polynucleotide that is to be delivered. For example, if a gRNA to be delivered is directed against a virus component and it is inserted or otherwise coupled to an otherwise non-viral vector or carrier, this would not make said vector a "viral vector". Non-viral vectors and carriers include naked polynucleotides, chemical-based carriers, polynucleotide (non-viral) based vectors, and particle-based carriers. It will be appreciated that the term "vector" as used in the context of non-viral vectors and carriers refers to polynucleotide vectors and "carriers" used in this context refers to a non-nucleic acid, polynucleotide molecule, or composition that be attached to or otherwise interact with, encapsulate, and/or associate with a polynucleotide to be delivered, such as an engineered stink bug pheromone synthesis system polynucleotide of the present invention.

Naked Polynucleotides

In some embodiments one or more engineered stink bug pheromone synthesis system polynucleotides described elsewhere herein can be included in a naked polynucleotide. The term of art "naked polynucleotide" as used herein refers to polynucleotides that are not associated with another molecule (e.g. proteins, lipids, and/or other molecules) that can often help protect it from environmental factors and/or degradation. As used herein, associated with includes, but is not limited to, linked to, adhered to, adsorbed to, enclosed in, enclosed in or within, mixed with, and the like. Naked polynucleotides that include one or more of the engineered stink bug pheromone synthesis system polynucleotides described herein can be delivered directly to a host cell and optionally expressed therein. The naked polynucleotides can have any suitable two- and three-dimensional configurations. By way of non-limiting examples, naked polynucleotides can be single-stranded molecules, double stranded molecules, circular molecules (e.g. plasmids and artificial chromosomes), molecules that contain portions that are single stranded and portions that are double stranded (e.g. ribozymes), and the like. In some embodiments, the naked polynucleotide contains only the engineered stink bug pheromone synthesis system polynucleotide(s) of the present invention. In some embodiments, the naked polynucleotide can contain other nucleic acids and/or polynucleotides in addition to the engineered stink bug pheromone synthesis system polynucleotide(s) of the present invention. The naked polynucleotides can include one or more elements of a transposon system. Transposons and system thereof are described in greater detail elsewhere herein.

Non-Viral Polynucleotide Vectors

In some embodiments, one or more of the engineered stink bug pheromone synthesis system polynucleotides can be included in a non-viral polynucleotide vector. Suitable non-viral polynucleotide vectors include, but are not limited to, transposon vectors and vector systems, plasmids, bacterial artificial chromosomes, yeast artificial chromosomes, AR (antibiotic resistance)-free plasmids and miniplasmids, circular covalently closed vectors (e.g. minicircles, minivectors, miniknots,), linear covalently closed vectors ("dumb-bell shaped"), MIDGE (minimalistic immunologically defined gene expression) vectors, MiLV (micro-linear vector) vectors, Ministrings, mini-intronic plasmids, PSK systems (post-segregationally killing systems), ORT (operator repressor titration) plasmids, and the like. See e.g. Hardee et al. 2017. Genes. 8(2):65.

In some embodiments, the non-viral polynucleotide vector can have a conditional origin of replication. In some embodiments, the non-viral polynucleotide vector can be an ORT plasmid. In some embodiments, the non-viral polynucleotide vector can have a minimalistic immunologically defined gene expression. In some embodiments, the non-viral polynucleotide vector can have one or more post-segregationally killing system genes. In some embodiments, the non-viral polynucleotide vector is AR-free. In some embodiments, the non-viral polynucleotide vector is a mini-vector. In some embodiments, the non-viral polynucleotide vector includes a nuclear localization signal. In some embodiments, the non-viral polynucleotide vector can include one or more CpG motifs. In some embodiments, the non-viral polynucleotide vectors can include one or more scaffold/matrix attachment regions (S/MARs). See e.g. Mirkovitch et al. 1984. Cell. 39:223-232, Wong et al. 2015. Adv. Genet. 89:113-152, whose techniques and vectors can be adapted for use in the present invention. S/MARs are AT-rich sequences that play a role in the spatial organization of chromosomes through DNA loop base attachment to the nuclear matrix. S/MARs are often found close to regulatory elements such as promoters, enhancers, and origins of DNA replication. Inclusion of one or S/MARs can facilitate a once-per-cell-cycle replication to maintain the non-viral polynucleotide vector as an episome in daughter cells. In embodiments, the S/MAR sequence is located downstream of an actively transcribed polynucleotide (e.g. one or more engineered stink bug pheromone synthesis system poly-nucleotides) included in the non-viral polynucleotide vector. In some embodiments, the S/MAR can be a S/MAR from the beta-interferon gene cluster. See e.g. Verghese et al. 2014. Nucleic Acid Res. 42:e53; Xu et al. 2016. Sci. China Life Sci. 59:1024-1033; Jin et al. 2016. 8:702-711; Koirala et al. 2014. Adv. Exp. Med. Biol. 801:703-709; and Nehlsen et al. 2006. Gene Ther. Mol. Biol. 10:233-244, whose techniques and vectors can be adapted for use in the present invention.

In some embodiments, the non-viral vector is a transpo-son vector or system thereof. As used herein, "transposon" (also referred to as transposable element) refers to a poly-nucleotide sequence that is capable of moving form location in a genome to another. There are several classes of trans-posons. Transposons include retrotransposons and DNA transposons. Retrotransposons require the transcription of the polynucleotide that is moved (or transposed) in order to transpose the polynucleotide to a new genome or polynucle-otide. DNA transposons are those that do not require reverse transcription of the polynucleotide that is moved (or trans-posed) in order to transpose the polynucleotide to a new genome or polynucleotide. In some embodiments, the non-viral polynucleotide vector can be a retrotransposon vector. In some embodiments, the retrotransposon vector includes long terminal repeats. In some embodiments, the retrotrans-poson vector does not include long terminal repeats. In some embodiments, the non-viral polynucleotide vector can be a DNA transposon vector. DNA transposon vectors can include a polynucleotide sequence encoding a transposase. In some embodiments, the transposon vector is configured as a non-autonomous transposon vector, meaning that the transposition does not occur spontaneously on its own. In some of these embodiments, the transposon vector lacks one or more polynucleotide sequences encoding proteins required for transposition. In some embodiments, the non-autonomous transposon vectors lack one or more Ac ele-ments.

In some embodiments a non-viral polynucleotide trans-poson vector system can include a first polynucleotide vector that contains the engineered stink bug pheromone synthesis system polynucleotide(s) of the present invention flanked on the 5' and 3' ends by transposon terminal inverted repeats (TIRs) and a second polynucleotide vector that includes a polynucleotide capable of encoding a transposase coupled to a promoter to drive expression of the transposase. When both are expressed in the same cell the transposase can be expressed from the second vector and can transpose the material between the TIRs on the first vector (e.g. the engineered stink bug pheromone synthesis system poly-nucleotide(s) of the present invention) and integrate it into one or more positions in the host cell's genome. In some embodiments the transposon vector or system thereof can be configured as a gene trap. In some embodiments, the TIRs can be configured to flank a strong splice acceptor site followed by a reporter and/or other gene (e.g. one or more of the engineered stink bug pheromone synthesis system polynucleotide(s) of the present invention) and a strong poly A tail. When transposition occurs while using this vector or system thereof, the transposon can insert into an intron of a gene and the inserted reporter or other gene can provoke a mis-splicing process and as a result it in activates the trapped gene.

Any suitable transposon system can be used. Suitable transposon and systems thereof can include, Sleeping Beauty transposon system (Tc1/mariner superfamily) (see e.g. Ivics et al. 1997. Cell. 91(4): 501-510), piggyBac (piggyBac superfamily) (see e.g. Li et al. 2013 110(25): E2279-E2287 and Yusa et al. 2011. PNAS. 108(4): 1531-1536), Tol2 (superfamily hAT), Frog Prince (Tc1/mariner superfamily) (see e.g. Miskey et al. 2003 Nucleic Acid Res. 31(23):6873-6881) and variants thereof.

Chemical Carriers

In some embodiments the engineered stink bug phero-mone synthesis system polynucleotide(s) can be coupled to a chemical carrier. Chemical carriers that can be suitable for delivery of polynucleotides can be broadly classified into the following classes: (i) inorganic particles, (ii) lipid-based, (iii) polymer-based, and (iv) peptide based. They can be categorized as (1) those that can form condensed complexes with a polynucleotide (such as the engineered stink bug pheromone synthesis system polynucleotide(s) of the pres-ent invention), (2) those capable of targeting specific cells, (3) those capable of increasing delivery of the polynucle-otide (such as the engineered stink bug pheromone synthesis system polynucleotide(s) of the present invention) to the nucleus or cytosol of a host cell, (4) those capable of disintegrating from DNA/RNA in the cytosol of a host cell, and (5) those capable of sustained or controlled release. It will be appreciated that any one given chemical carrier can include features from multiple categories. The term "par-ticle" as used herein, refers to any suitable sized particles for delivery of the e engineered stink bug pheromone synthesis system components described herein. Suitable sizes include macro-, micro-, and nano-sized particles.

In some embodiments, the non-viral carrier can be an inorganic particle. In some embodiments, the inorganic particle, can be a nanoparticle. The inorganic particles can be configured and optimized by varying size, shape, and/or porosity. In some embodiments, the inorganic particles are optimized to escape from the reticulo endothelial system. In some embodiments, the inorganic particles can be optimized to protect an entrapped molecule from degradation., the Suitable inorganic particles that can be used as non-viral carriers in this context can include, but are not limited to, calcium phosphate, silica, metals (e.g. gold, platinum, silver, palladium, rhodium, osmium, iridium, ruthenium, mercury, copper, rhenium, titanium, niobium, tantalum, and combinations thereof), magnetic compounds, particles, and materials, (e.g. supermagnetic iron oxide and magnetite), quantum dots, fullerenes (e.g. carbon nanoparticles, nanotubes, nanostrings, and the like), and combinations thereof. Other suitable inorganic non-viral carriers are discussed elsewhere herein.

In some embodiments, the non-viral carrier can be lipid-based. Suitable lipid-based carriers are also described in greater detail herein. In some embodiments, the lipid-based carrier includes a cationic lipid or an amphiphilic lipid that is capable of binding or otherwise interacting with a negative charge on the polynucleotide to be delivered (e.g. such as an engineered stink bug pheromone synthesis system polynucleotide). In some embodiments, chemical non-viral carrier systems can include a polynucleotide such as the engineered stink bug pheromone synthesis system polynucleotide(s)) and a lipid (such as a cationic lipid). These are also referred to in the art as lipoplexes. Other embodiments of lipoplexes are described elsewhere herein. In some embodiments, the non-viral lipid-based carrier can be a lipid nano emulsion. Lipid nano emulsions can be formed by the dispersion of an immiscible liquid in another stabilized emulsifying agent and can have particles of about 200 nm that are composed of the lipid, water, and surfactant that can contain the polynucleotide to be delivered (e.g. the engineered stink bug pheromone synthesis system polynucleotide(s)). In some embodiments, the lipid-based non-viral carrier can be a solid lipid particle or nanoparticle.

In some embodiments, the non-viral carrier can be peptide-based. In some embodiments, the peptide-based non-viral carrier can include one or more cationic amino acids. In some embodiments, 35 to 40, 45, 50, 55, 60, 65, 70, 75, 80, 85, 90, 95, 99 or 100% of the amino acids are cationic. In some embodiments, peptide carriers can be used in conjunction with other types of carriers (e.g. polymer-based carriers and lipid-based carriers to functionalize these carriers). In some embodiments, the functionalization is targeting a host cell. Suitable polymers that can be included in the polymer-based non-viral carrier can include, but are not limited to, polyethylenimine (PEI), chitosan, poly (DL-lactide) (PLA), poly (DL-Lactide-co-glycoside) (PLGA), dendrimers (see e.g. US Pat. Pub. 2017/0079916 whose techniques and compositions can be adapted for use with the engineered stink bug pheromone synthesis system polynucleotides of the present invention), polymethacrylate, and combinations thereof.

In some embodiments, the non-viral carrier can be configured to release an engineered delivery system polynucleotide that is associated with or attached to the non-viral carrier in response to an external stimulus, such as pH, temperature, osmolarity, concentration of a specific molecule or composition (e.g. calcium, NaCl, and the like), pressure and the like. In some embodiments, the non-viral carrier can be a particle that is configured includes one or more of the engineered stink bug pheromone synthesis system describe herein and a environmental triggering agent response element, and optionally a triggering agent. In some embodiments, the particle can include a polymer that can be selected from the group of polymethacrylates and polyacrylates. In some embodiments, the non-viral particle can include one or more embodiments of the compositions microparticles described in US Pat. Pubs. 20150232883 and 20050123596, whose techniques and compositions can be adapted for use in the present invention.

In some embodiments, the non-viral carrier can be a polymer-based carrier. In some embodiments, the polymer is cationic or is predominantly cationic such that it can interact in a charge-dependent manner with the negatively charged polynucleotide to be delivered (such as the engineered stink bug pheromone synthesis system polynucleotide(s) of the present invention). Polymer-based systems are described in greater detail elsewhere herein.

Viral Vectors

In some embodiments, the vector is a viral vector. The term of art "viral vector" and as used herein in this context refers to polynucleotide based vectors that contain one or more elements from or based upon one or more elements of a virus that can be capable of expressing and packaging a polynucleotide, such as an engineered stink bug pheromone synthesis system polynucleotide of the present invention, into a virus particle and producing said virus particle when used alone or with one or more other viral vectors (such as in a viral vector system). Viral vectors and systems thereof can be used for producing viral particles for delivery of and/or expression of one or more components of the engineered stink bug pheromone synthesis system described herein. The viral vector can be part of a viral vector system involving multiple vectors. In some embodiments, systems incorporating multiple viral vectors can increase the safety of these systems. Suitable viral vectors can include retroviral-based vectors, lentiviral-based vectors, adenoviral-based vectors, adeno-associated vectors, helper-dependent adenoviral (HdAd) vectors, hybrid adenoviral vectors, herpes simplex virus-based vectors, poxvirus-based vectors, and Epstein-Barr virus-based vectors. Other embodiments of viral vectors and viral particles produce therefrom are described elsewhere herein. In some embodiments, the viral vectors are configured to produce replication incompetent viral particles for improved safety of these systems.

Retroviral and Lentiviral Vectors

Retroviral vectors can be composed of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Suitable retroviral vectors for the engineered stink bug pheromone synthesis system can include those based upon murine leukemia virus (MuLV), gibbon ape leukemia virus (GaLV), Simian immunodeficiency virus (SIV), human immunodeficiency virus (HIV), and combinations thereof (see, e.g., Buchscher et al., J. Virol. 66:2731-2739 (1992); Johann et al., J. Virol. 66:1635-1640 (1992); Sommerfelt et al., Virol. 176:58-59 (1990); Wilson et al., J. Virol. 63:2374-2378 (1989); Miller et al., J. Virol. 65:2220-2224 (1991); PCT/US94/05700). Selection of a retroviral gene transfer system may therefore depend on the target tissue.

The tropism of a retrovirus can be altered by incorporating foreign envelope proteins, expanding the potential target population of target cells. Lentiviral vectors are retroviral vectors that are able to transduce or infect non-dividing cells and are described in greater detail elsewhere herein. A retrovirus can also be engineered to allow for conditional expression of the inserted transgene, such that only certain cell types are infected by the lentivirus.

Lentiviruses are complex retroviruses that have the ability to infect and express their genes in both mitotic and post-mitotic cells. Advantages of using a lentiviral approach can include the ability to transduce or infect non-dividing cells and their ability to typically produce high viral titers, which can increase efficiency or efficacy of production and delivery. Suitable lentiviral vectors include, but are not limited to, human immunodeficiency virus (HIV)-based lentiviral vectors, feline immunodeficiency virus (FIV)-based lentiviral vectors, simian immunodeficiency virus (SIV)-based lentiviral vectors, Moloney Murine Leukaemia Virus (Mo-MLV), Visna-maedi virus (VMV)-based lentiviral vector, carpine arthritis-encephalitis virus (CAEV)-based lentiviral vector, bovine immune deficiency virus (BIV)-based lentiviral vector, and Equine infectious anemia (EIAV)-based lentiviral vector. In some embodiments, an HIV-based lentiviral vector system can be used. In some embodiments, a FIV-based lentiviral vector system can be used.

In some embodiments, the lentiviral vector is an EIAV-based lentiviral vector or vector system. EIAV vectors have been used to mediate expression, packaging, and/or delivery in other contexts, such as for ocular gene therapy (see, e.g., Balagaan, J Gene Med 2006; 8: 275-285). In another embodiment, RetinoStat®, (see, e.g., Binley et al., HUMAN GENE THERAPY 23:980-991 (September 2012)), which describes RetinoStat®, an equine infectious anemia virus-based lentiviral gene therapy vector that expresses angiostatic proteins endostatin and angiostatin that is delivered via a subretinal injection for the treatment of the wet form of age-related macular degeneration. Any of these vectors described in these publications can be modified for the elements of the engineered stink bug pheromone synthesis system described herein.

In some embodiments, the lentiviral vector or vector system thereof can be a first-generation lentiviral vector or vector system thereof. First-generation lentiviral vectors can contain a large portion of the lentivirus genome, including the gag and pol genes, other additional viral proteins (e.g. VSV-G) and other accessory genes (e.g. vif, vprm vpu, nef, and combinations thereof), regulatory genes (e.g. tat and/or rev) as well as the gene of interest between the LTRs. First generation lentiviral vectors can result in the production of virus particles that can be capable of replication in vivo, which may not be appropriate for some instances or applications.

In some embodiments, the lentiviral vector or vector system thereof can be a second-generation lentiviral vector or vector system thereof. Second-generation lentiviral vectors do not contain one or more accessory virulence factors and do not contain all components necessary for virus particle production on the same lentiviral vector. This can result in the production of a replication-incompetent virus particle and thus increase the safety of these systems over first-generation lentiviral vectors. In some embodiments, the second-generation vector lacks one or more accessory virulence factors (e.g. vif, vprm, vpu, nef, and combinations thereof). Unlike the first-generation lentiviral vectors, no single second generation lentiviral vector includes all features necessary to express and package a polynucleotide into a virus particle. In some embodiments, the envelope and packaging components are split between two different vectors with the gag, pol, rev, and tat genes being contained on one vector and the envelope protein (e.g. VSV-G) are contained on a second vector. The gene of interest, its promoter, and LTRs can be included on a third vector that can be used in conjunction with the other two vectors (packaging and envelope vectors) to generate a replication-incompetent virus particle.

In some embodiments, the lentiviral vector or vector system thereof can be a third-generation lentiviral vector or vector system thereof. Third-generation lentiviral vectors and vector systems thereof have increased safety over first- and second-generation lentiviral vectors and systems thereof because, for example, the various components of the viral genome are split between two or more different vectors but used together in vitro to make virus particles, they can lack the tat gene (when a constitutively active promoter is included up-stream of the LTRs), and they can include one or more deletions in the 3'LTR to create self-inactivating (SIN) vectors having disrupted promoter/enhancer activity of the LTR. In some embodiments, a third-generation lentiviral vector system can include (i) a vector plasmid that contains the polynucleotide of interest and upstream promoter that are flanked by the 5' and 3' LTRs, which can optionally include one or more deletions present in one or both of the LTRs to render the vector self-inactivating; (ii) a "packaging vector(s)" that can contain one or more genes involved in packaging a polynucleotide into a virus particle that is produced by the system (e.g. gag, pol, and rev) and upstream regulatory sequences (e.g. promoter(s)) to drive expression of the features present on the packaging vector, and (iii) an "envelope vector" that contains one or more envelope protein genes and upstream promoters. In embodiments, the third-generation lentiviral vector system can include at least two packaging vectors, with the gag-pol being present on a different vector than the rev gene.

In some embodiments, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2: 36ra43) can be used and/or adapted to the engineered stink bug pheromone synthesis system of the present invention.

In some embodiments, the pseudotype and infectivity or tropism of a lentivirus particle can be tuned by altering the type of envelope protein(s) included in the lentiviral vector or system thereof. As used herein, an "envelope protein" or "outer protein" means a protein exposed at the surface of a viral particle that is not a capsid protein. For example, envelope or outer proteins typically comprise proteins embedded in the envelope of the virus. In some embodiments, a lentiviral vector or vector system thereof can include a VSV-G envelope protein. VSV-G mediates viral attachment to an LDL receptor (LDLR) or an LDLR family member present on a host cell, which triggers endocytosis of the viral particle by the host cell. Because LDLR is expressed by a wide variety of cells, viral particles expressing the VSV-G envelope protein can infect or transduce a wide variety of cell types. Other suitable envelope proteins can be incorporated based on the host cell that a user desires to be infected by a virus particle produced from a lentiviral vector or system thereof described herein and can include, but are not limited to, feline endogenous virus envelope protein (RD114) (see e.g. Hanawa et al. Molec. Ther. 2002 5(3) 242-251), modified Sindbis virus envelope proteins (see e.g. Morizono et al. 2010. J. Virol. 84(14) 6923-6934; Morizono et al. 2001. J. Virol. 75:8016-8020; Morizono et al. 2009. J. Gene Med. 11:549-558; Morizono et al. 2006 Virology 355:71-81; Morizono et al J. Gene Med. 11:655-663, Morizono et al. 2005 Nat. Med. 11:346-352), baboon retroviral envelope protein (see e.g. Girard-Gagnepain et al. 2014. Blood. 124:1221-1231); Tupaia paramyxovirus glycoproteins (see e.g. Enkirch T. et al., 2013. Gene Ther. 20:16-23); measles virus glycoproteins (see e.g. Funke et al. 2008. Molec. Ther. 16(8): 1427-1436), rabies virus envelope proteins, MLV envelope proteins, Ebola envelope proteins, baculovirus envelope proteins, filovirus envelope proteins, hepatitis E1 and E2 envelope proteins, gp41 and gp120 of HIV, hemagglutinin, neuraminidase, M2 proteins of influenza virus, and combinations thereof.

In some embodiments, the tropism of the resulting lentiviral particle can be tuned by incorporating cell targeting peptides into a lentiviral vector such that the cell targeting peptides are expressed on the surface of the resulting lentiviral particle. In some embodiments, a lentiviral vector can contain an envelope protein that is fused to a cell targeting protein (see e.g. Buchholz et al. 2015. Trends Biotechnol. 33:777-790; Bender et al. 2016. PLOS Pathog. 12 (e1005461); and Friedrich et al. 2013. Mol. Ther. 2013. 21:849-859.

In some embodiments, a split-intein-mediated approach to target lentiviral particles to a specific cell type can be used (see e.g. Chamoun-Emaneulli et al. 2015. Biotechnol. Bioeng. 112:2611-2617, Ramirez et al. 2013. Protein. Eng. Des. Sel. 26:215-233. In these embodiments, a lentiviral vector can contain one half of a splicing-deficient variant of the naturally split intein from *Nostoc punctiforme* fused to a cell targeting peptide and the same or different lentiviral vector can contain the other half of the split intein fused to an envelope protein, such as a binding-deficient, fusion-competent virus envelope protein. This can result in production of a virus particle from the lentiviral vector or vector system that includes a split intein that can function as a molecular Velcro linker to link the cell-binding protein to the pseudotyped lentivirus particle. This approach can be advantageous for use where surface-incompatibilities can restrict the use of, e.g., cell targeting peptides.

In some embodiments, a covalent-bond-forming protein-peptide pair can be incorporated into one or more of the lentiviral vectors described herein to conjugate a cell targeting peptide to the virus particle (see e.g. Kasaraneni et al. 2018. Sci. Reports (8) No. 10990). In some embodiments, a lentiviral vector can include an N-termial PDZ domain of InaD protein (PDZ1) and its pentapeptide ligand (TEFCA) from NorpA, which can conjugate the cell targeting peptide to the virus particle via a covalent bond (e.g. a disulfide bond). In some embodiments, the PDZ1 protein can be fused to an envelope protein, which can optionally be binding deficient and/or fusion competent virus envelope protein and included in a lentiviral vector. In some embodiments, the TEFCA can be fused to a cell targeting peptide and the TEFCA-CPT fusion construct can be incorporated into the same or a different lentiviral vector as the PDZ1-envelope protein construct. During virus production, specific interaction between the PDZ1 and TEFCA facilitates producing virus particles covalently functionalized with the cell targeting peptide and thus capable of targeting a specific cell-type based upon a specific interaction between the cell targeting peptide and cells expressing its binding partner. This approach can be advantageous for use where surface-incompatibilities can restrict the use of, e.g., cell targeting peptides.

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and US Patent No. U.S. Pat. No. 7,259,015. Any of these systems or a variant thereof can be used to deliver an engineered stink bug pheromone synthesis system polynucleotide described herein to a cell.

In some embodiments, a lentiviral vector system can include one or more transfer plasmids. Transfer plasmids can be generated from various other vector backbones and can include one or more features that can work with other retroviral and/or lentiviral vectors in the system that can, for example, improve safety of the vector and/or vector system, increase virial titers, and/or increase or otherwise enhance expression of the desired insert to be expressed and/or packaged into the viral particle. Suitable features that can be included in a transfer plasmid can include, but are not limited to, 5'LTR, 3'LTR, SIN/LTR, origin of replication (Ori), selectable marker genes (e.g. antibiotic resistance genes), Psi (ψ), RRE (rev response element), cPPT (central polypurine tract), promoters, WPRE (woodchuck hepatitis post-transcriptional regulatory element), SV40 polyadenylation signal, pUC origin, SV40 origin, F1 origin, and combinations thereof.

Adenoviral Vectors, Helper-Dependent Adenoviral Vectors, and Hybrid Adenoviral Vectors In some embodiments, the vector can be an adenoviral vector. In some embodiments, the adenoviral vector can include elements such that the virus particle produced using the vector or system thereof can be serotype 2 or serotype 5. In some embodiments, the polynucleotide to be delivered via the adenoviral particle can be up to about 8 kb. Thus, in some embodiments, an adenoviral vector can include a DNA polynucleotide to be delivered that can range in size from about 0.001 kb to about 8 kb. Adenoviral vectors have been used successfully in several contexts (see e.g. Teramato et al. 2000. Lancet. 355:1911-1912; Lai et al. 2002. DNA Cell. Biol. 21:895-913; Flotte et al., 1996. Hum. Gene. Ther. 7:1145-1159; and Kay et al. 2000. Nat. Genet. 24:257-261.

In some embodiments the vector can be a helper-dependent adenoviral vector or system thereof. These are also referred to in the art as "gutless" or "gutted" vectors and are a modified generation of adenoviral vectors (see e.g. Thrasher et al. 2006. Nature. 443: E5-7). In embodiments of the helper-dependent adenoviral vector system one vector (the helper) can contain all the viral genes required for replication but contains a conditional gene defect in the packaging domain. The second vector of the system can contain only the ends of the viral genome, one or more engineered stink bug pheromone synthesis system polynucleotides, and the native packaging recognition signal, which can allow selective packaged release from the cells (see e.g. Cideciyan et al. 2009. N Engl J Med. 361:725-727). Helper-dependent adenoviral vector systems have been successful for gene delivery in several contexts (see e.g. Simonelli et al. 2010. J Am Soc Gene Ther. 18:643-650; Cideciyan et al. 2009. N Engl J Med. 361:725-727; Crane et al. 2012. Gene Ther. 19(4): 443-452; Alba et al. 2005. Gene Ther. 12:18-S27; Croyle et al. 2005. Gene Ther. 12:579-587; Amalfitano et al. 1998. J. Virol. 72:926-933; and Morral et al. 1999. PNAS. 96:12816-12821). The techniques and vectors described in these publications can be adapted for inclusion and delivery of the engineered stink bug pheromone synthesis system polynucleotides described herein. In some embodiments, the polynucleotide to be delivered via the viral particle produced from a helper-dependent adenoviral vector or system thereof can be up to about 37 kb. Thus, in some embodiments, a adenoviral vector can include a DNA polynucleotide to be delivered that can range in size from about 0.001 kb to about 37 kb (see e.g. Rosewell et al. 2011. J. Genet. Syndr. Gene Ther. Suppl. 5:001).

In some embodiments, the vector is a hybrid-adenoviral vector or system thereof. Hybrid adenoviral vectors are composed of the high transduction efficiency of a gene-deleted adenoviral vector and the long-term genome-integrating potential of adeno-associated, retroviruses, lentivirus, and transposon based-gene transfer. In some embodiments, such hybrid vector systems can result in stable transduction and limited integration site. See e.g. Balague et al. 2000. Blood. 95:820-828; Morral et al. 1998. Hum. Gene Ther. 9:2709-2716; Kubo and Mitani. 2003. J. Virol. 77(5): 2964-2971; Zhang et al. 2013. PloS One. 8(10) e76771; and Cooney et al. 2015. Mol. Ther. 23(4): 667-674), whose techniques and vectors described therein can be modified and adapted for use in the engineered stink bug pheromone synthesis system of the present invention. In some embodiments, a hybrid-adenoviral vector can include one or more features of a retrovirus and/or an adeno-associated virus. In some embodiments the hybrid-adenoviral vector can include one or more features of a spuma retrovirus or foamy virus (FV). See e.g. Ehrhardt et al. 2007. Mol. Ther. 15:146-156 and Liu et al. 2007. Mol. Ther. 15:1834-1841, whose techniques and vectors described therein can be modified and adapted for use in the engineered stink bug pheromone synthesis system of the present invention. Advantages of using one or more features from the FVs in the hybrid-adenoviral vector or system thereof can include the ability of the viral particles produced therefrom to infect a broad range of cells, a large packaging capacity as compared to other retroviruses, and the ability to persist in quiescent (non-dividing) cells. See also e.g. Ehrhardt et al. 2007. Mol. Ther. 156:146-156 and Shuji et al. 2011. Mol. Ther. 19:76-82, whose techniques and vectors described therein can be modified and adapted for use in the engineered stink bug pheromone synthesis system of the present invention.

Adeno-Associated Viral (AAV) Vectors

In an embodiment, the vector can be an adeno-associated virus (AAV) vector. See, e.g., West et al., Virology 160:38-47 (1987); U.S. Pat. No. 4,797,368; WO 93/24641; Kotin, Human Gene Therapy 5:793-801 (1994); and Muzyczka, J. Clin. Invest. 94:1351 (1994). Although similar to adenoviral vectors in some of their features, AAVs have some deficiency in their replication and/or pathogenicity and thus can be safer that adenoviral vectors. In some embodiments the AAV can integrate into a specific site on chromosome 19 of a human cell with no observable side effects. In some embodiments, the capacity of the AAV vector, system thereof, and/or AAV particles can be up to about 4.7 kb.

The AAV vector or system thereof can include one or more regulatory molecules. In some embodiments the regulatory molecules can be promoters, enhancers, repressors and the like, which are described in greater detail elsewhere herein. In some embodiments, the AAV vector or system thereof can include one or more polynucleotides that can encode one or more regulatory proteins. In some embodiments, the one or more regulatory proteins can be selected from Rep78, Rep68, Rep52, Rep40, variants thereof, and combinations thereof.

The AAV vector or system thereof can include one or more polynucleotides that can encode one or more capsid proteins. The capsid proteins can be selected from VP1, VP2, VP3, and combinations thereof. The capsid proteins can be capable of assembling into a protein shell of the AAV virus particle. In some embodiments, the AAV capsid can contain 60 capsid proteins. In some embodiments, the ratio of VP1: VP2: VP3 in a capsid can be about 1:1:10.

In some embodiments, the AAV vector or system thereof can include one or more adenovirus helper factors or polynucleotides that can encode one or more adenovirus helper factors. Such adenovirus helper factors can include, but are not limited, E1A, E1B, E2A, E4ORF6, and VA RNAs. In some embodiments, a producing host cell line expresses one or more of the adenovirus helper factors.

The AAV vector or system thereof can be configured to produce AAV particles having a specific serotype. In some embodiments, the serotype can be AAV-1, AAV-2, AAV-3, AAV-4, AAV-5, AAV-6, AAV-8, AAV-9 or any combinations thereof. In some embodiments, the AAV can be AAV1, AAV-2, AAV-5 or any combination thereof. One can select the AAV of the AAV with regard to the cells to be targeted; e.g., one can select AAV serotypes 1, 2, 5 or a hybrid capsid AAV-1, AAV-2, AAV-5 or any combination thereof for targeting brain and/or neuronal cells; and one can select AAV-4 for targeting cardiac tissue; and one can select AAV8 for delivery to the liver. Thus, in some embodiments, an AAV vector or system thereof capable of producing AAV particles capable of targeting the brain and/or neuronal cells can be configured to generate AAV particles having serotypes 1, 2, 5 or a hybrid capsid AAV-1, AAV-2, AAV-5 or any combination thereof. In some embodiments, an AAV vector or system thereof capable of producing AAV particles capable of targeting cardiac tissue can be configured to generate an AAV particle having an AAV-4 serotype. In some embodiments, an AAV vector or system thereof capable of producing AAV particles capable of targeting the liver can be configured to generate an AAV having an AAV-8 serotype. In some embodiments, the AAV vector is a hybrid AAV vector or system thereof. Hybrid AAVs are AAVs that include genomes with elements from one serotype that are packaged into a capsid derived from at least one different serotype. For example, if it is the rAAV2/5 that is to be produced, and if the production method is based on the helper-free, transient transfection method discussed above, the 1st plasmid and the 3rd plasmid (the adeno helper plasmid) will be the same as discussed for rAAV2 production. However, the 2nd plasmid, the pRepCap will be different. In this plasmid, called pRep2/Cap5, the Rep gene is still derived from AAV2, while the Cap gene is derived from AAV5. The production scheme is the same as the above-mentioned approach for AAV2 production. The resulting rAAV is called rAAV2/5, in which the genome is based on recombinant AAV2, while the capsid is based on AAV5. It is assumed the cell or tissue-tropism displayed by this AAV2/5 hybrid virus should be the same as that of AAV5.

A tabulation of certain AAV serotypes as to these cells can be found in Grimm, D. et al, J. Virol. 82: 5887-5911 (2008).

In some embodiments, the AAV vector or system thereof is configured as a "gutless" vector, similar to that described in connection with a retroviral vector. In some embodiments, the "gutless" AAV vector or system thereof can have the cis-acting viral DNA elements involved in genome amplification and packaging in linkage with the heterologous sequences of interest (e.g. the engineered stink bug pheromone synthesis system polynucleotide(s)).

Herpes Simplex Viral Vectors

In some embodiments, the vector can be a Herpes Simplex Viral (HSV)-based vector or system thereof. HSV systems can include the disabled infections single copy (DISC) viruses, which are composed of a glycoprotein H defective mutant HSV genome. When the defective HSV is propagated in complementing cells, virus particles can be generated that are capable of infecting subsequent cells permanently replicating their own genome but are not capable of producing more infectious particles. See e.g. 2009. Trobridge. Exp. Opin. Biol. Ther. 9:1427-1436, whose techniques and vectors described therein can be modified and adapted for use in the engineered stink bug pheromone synthesis system. In some embodiments where an HSV vector or system thereof is utilized, the host cell can be a complementing cell. In some embodiments, HSV vector or system thereof can be capable of producing virus particles capable of delivering a polynucleotide cargo of up to 150 kb. Thus, in some embodiment the engineered stink bug pheromone synthesis system polynucleotide(s) included in the HSV-based viral vector or system thereof can sum from about 0.001 to about 150 kb. HSV-based vectors and systems thereof have been successfully used in several contexts including various models of neurologic disorders. See e.g. Cockrell et al. 2007. Mol. Biotechnol. 36:184-204; Kafri T. 2004. Mol. Biol. 246:367-390; Balaggan and Ali. 2012. Gene Ther. 19:145-153; Wong et al. 2006. Hum. Gen. Ther. 2002. 17:1-9; Azzouz et al. J. Neruosci. 22L10302-10312; and Betchen and Kaplitt. 2003. Curr. Opin. Neurol. 16:487-493, whose techniques and vectors described therein can be modified and adapted for use in the engineered stink bug pheromone synthesis system.

Poxvirus Vectors

In some embodiments, the vector can be a poxvirus vector or system thereof. In some embodiments, the poxvirus vector can result in cytoplasmic expression of one or more engineered stink bug pheromone synthesis system. In some embodiments the capacity of a poxvirus vector or system thereof can be about 25 kb or more. In some embodiments, a poxvirus vector or system thereof can include a one or more engineered stink bug pheromone synthesis system polynucleotides of the present invention.

Vector Construction

The vectors described herein can be constructed using any suitable process or technique. In some embodiments, one or more suitable recombination and/or cloning methods or techniques can be used to the vector(s) described herein. Suitable recombination and/or cloning techniques and/or methods can include, but not limited to, those described in U.S. Application publication No. US 2004-0171156 A1. Other suitable methods and techniques are described elsewhere herein.

Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Any of the techniques and/or methods can be used and/or adapted for constructing an AAV or other vector described herein. nAAV vectors are discussed elsewhere herein.

In some embodiments, the vector can have one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors.

Delivery vehicles, vectors, particles, nanoparticles, formulations and components thereof for expression of one or more elements of an engineered stink bug pheromone synthesis system described herein are as used in the foregoing documents, such as WO 2014/093622 (PCT/US2013/074667) and are discussed in greater detail herein.

Virus Particle Production from Viral Vectors
Retroviral Production

In some embodiments, one or more viral vectors and/or system thereof can be delivered to a suitable cell line for production of virus particles containing the polynucleotide or other payload to be delivered to a host cell. Suitable host cells for virus production from viral vectors and systems thereof described herein are known in the art and are commercially available. For example, suitable host cells include HEK 293 cells and its variants (HEK 293T and HEK 293TN cells). In some embodiments, the suitable host cell for virus production from viral vectors and systems thereof described herein can stably express one or more genes involved in packaging (e.g. pol, gag, and/or VSV-G) and/or other supporting genes.

In some embodiments, after delivery of one or more viral vectors to the suitable host cells for or virus production from viral vectors and systems thereof, the cells are incubated for an appropriate length of time to allow for viral gene expression from the vectors, packaging of the polynucleotide to be delivered (e.g. an engineered stink bug pheromone synthesis system polynucleotide), and virus particle assembly, and secretion of mature virus particles into the culture media. Various other methods and techniques are generally known to those of ordinary skill in the art.

Mature virus particles can be collected from the culture media by a suitable method. In some embodiments, this can involve centrifugation to concentrate the virus. The titer of the composition containing the collected virus particles can be obtained using a suitable method. Such methods can include transducing a suitable cell line (e.g. NIH 3T3 cells) and determining transduction efficiency, infectivity in that cell line by a suitable method. Suitable methods include PCR-based methods, flow cytometry, and antibiotic selection-based methods. Various other methods and techniques are generally known to those of ordinary skill in the art. The concentration of virus particle can be adjusted as needed. In some embodiments, the resulting composition containing virus particles can contain $1 \times 10^1 - 1 \times 10^{20}$ particles/mL.

AAV Particle Production

There are two main strategies for producing AAV particles from AAV vectors and systems thereof, such as those described herein, which depend on how the adenovirus helper factors are provided (helper v. helper free). In some embodiments, a method of producing AAV particles from AAV vectors and systems thereof can include adenovirus infection into cell lines that stably harbor AAV replication and capsid encoding polynucleotides along with AAV vector containing the polynucleotide to be packaged and delivered by the resulting AAV particle (e.g. the engineered stink bug pheromone synthesis system polynucleotide(s)). In some embodiments, a method of producing AAV particles from AAV vectors and systems thereof can be a "helper free" method, which includes co-transfection of an appropriate producing cell line with three vectors (e.g. plasmid vectors): (1) an AAV vector that contains a polynucleotide of interest (e.g. the engineered stink bug pheromone synthesis system polynucleotide(s)) between 2 ITRs; (2) a vector that carries the AAV Rep-Cap encoding polynucleotides; and (helper polynucleotides. One of skill in the art will appreciate various methods and variations thereof that are both helper and –helper free and as well as the different advantages of each system.

Vector and Virus Particle Delivery

A vector (including non-viral carriers) described herein can be introduced into host cells to thereby produce transcripts, proteins, or peptides, including fusion proteins or peptides encoded by nucleic acids as described herein (e.g., engineered stink bug pheromone synthesis system transcripts, proteins, enzymes, mutant forms thereof, fusion proteins thereof, etc.), and virus particles (such as from viral vectors and systems thereof).

One or more engineered stink bug pheromone synthesis system polynucleotides can be delivered using adeno-associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus.

For plasmid delivery, the route of administration, formulation and dose can be as in U.S. Pat. No. 5,846,946 and as in clinical studies involving plasmids. In some embodiments, doses can be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into or otherwise delivered to the tissue or cell of interest.

In terms of in vivo delivery, AAV is advantageous over other viral vectors for a couple of reasons such as low toxicity (this may be due to the purification method not requiring ultra-centrifugation of cell particles that can activate the immune response) and a low probability of causing insertional mutagenesis because it doesn't integrate into the host genome.

The vector(s) and virus particles described herein can be delivered in to a host cell in vitro, in vivo, and/or ex vivo. Delivery can occur by any suitable method including, but not limited to, physical methods, chemical methods, and biological methods. Physical delivery methods are those methods that employ physical force to counteract the membrane barrier of the cells to facilitate intracellular delivery of the vector. Suitable physical methods include, but are not limited to, needles (e.g. injections), ballistic polynucleotides (e.g. particle bombardment, micro projectile gene transfer, and gene gun), electroporation, sonoporation, photoporation, magnetofection, hydroporation, and mechanical massage. Chemical methods are those methods that employ a chemical to elicit a change in the cells membrane permeability or other characteristic(s) to facilitate entry of the vector into the cell. For example, the environmental pH can be altered which can elicit a change in the permeability of the cell membrane. Biological methods are those that rely and capitalize on the host cell's biological processes or biological characteristics to facilitate transport of the vector (with or without a carrier) into a cell. For example, the vector and/or its carrier can stimulate an endocytosis or similar process in the cell to facilitate uptake of the vector into the cell.

Delivery of engineered stink bug pheromone synthesis system components (e.g. polynucleotides encoding engineered stink bug pheromone synthesis system polypeptides) to cells via particles. In some embodiments, any of the engineered stink bug pheromone synthesis system components (e.g. polypeptides, polynucleotides, vectors and combinations thereof described herein) can be attached to, coupled to, integrated with, otherwise associated with one or more particles or component thereof as described herein. The particles described herein can then be administered to a cell or organism by an appropriate route and/or technique. In some embodiments, particle delivery can be selected and be advantageous for delivery of the polynucleotide or vector components. It will be appreciated that in embodiments, particle delivery can also be advantageous for other engineered stink bug pheromone synthesis system molecules and formulations described elsewhere herein.

Modified Cells and Organisms

One or more of the engineered stink bug pheromone synthesis pathway polynucleotides and/or vectors can be delivered to and/or expressed in heterologous cells to produce modified cells. In some embodiments, the cell is a plant cell. In some embodiments, the plant is suitable as a trap crop for management of the brown marmorated and/or harlequin stink bug. As such, also described herein are cells that can include and/or express one or more one or more engineered polynucleotides or vectors capable of producing one or more engineered brown marmorated and/or harlequin pheromone enzymes described herein. Thus, also contemplated herein are organisms that can express in one or more cells one or more one or more engineered polynucleotides or vectors capable of producing one or more engineered brown marmorated and/or harlequin pheromone enzymes described herein. In some instances, the organism is a mosaic. In some instances, the organism can express one or more of the engineered polynucleotides or vectors capable of producing one or more engineered brown marmorated and/or harlequin bug pheromone enzymes described herein in all cells. The polypeptides, polynucleotides, and vectors described herein can be used to modify one or more cells and/or be used to generate organisms to contain one or more modified cells.

As used herein, the term "transgenic cell" refers to a cell, such as a eukaryotic cell, in which one or more of the engineered polynucleotides capable of producing one or more engineered brown marmorated and/or harlequin stink bug pheromone enzymes described herein (the "transgene") has been genomically integrated. The nature, type, or origin of the cell are not particularly limiting according to the present invention. Also, the way the transgene is introduced in the cell can vary and can be any method as is known in the art. In certain embodiments, the transgenic cell is obtained by introducing the transgene in an isolated cell. In certain other embodiments, the transgenic cell is obtained by isolating cells from a transgenic organism.

Modified Cells

In some embodiments the modified cell can be a prokaryotic cell. The prokaryotic cells can be bacterial cells. The bacterial cell can be any suitable strain of bacterial cell.

In some embodiments the modified cell can be a eukaryotic cell. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded.

In certain embodiments, the methods as described herein may comprise providing a transgenic cell in which one or more nucleic acids encoding one or more engineered brown marmorated and/or harlequin stink bug pheromone enzymes described herein are provided or introduced operably connected in the cell with a regulatory element comprising a promoter of one or more gene of interest. By means of example, and without limitation, the transgenic cell as referred to herein may be derived from a transgenic eukaryote, such as a knock-in eukaryote. Any suitable genetic modification method can be used to modify the cells (e.g. convention recombinant techniques and cloning, Cre-Lox systems, Zinc Finger nucleases, TALE nucleases, CRISPR-Cas systems, and the like). Delivery systems for transgenes are well known in the art. By means of example, the transgene may be delivered in for instance eukaryotic cell by means of vector (e.g., AAV, adenovirus, lentivirus) and/or particle and/or nanoparticle delivery, as also described herein elsewhere.

The host cell for modification can be any cell. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, CIR, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr-/-, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In some embodiments, the cell is a plant cell. In some embodiments, the cell is from a plant suitable for use as a trap crop for a stink bug. In some embodiments, the cell is from a plant suitable for use as a trap crop of the brown marmorated and/or harlequin stink bug. In some embodiments, the plant cell is from a sunflower plant, a squash plant, a zucchini plant, a pumpkin plant, a hollyhock plant, buckwheat, triticale, crimson clover, vetch sorghum, and millet. Other plants may be suitable for use as trap crops. Characteristics of suitable trap crops are described in greater detail elsewhere herein.

In some embodiments, a cell transfected with one or more vectors described herein is used to establish a new cell line comprising one or more polynucleotide and/or vector-derived sequences. In some embodiments, a cell transiently transfected with one or more engineered brown marmorated and/or harlequin stink bug pheromone enzymes described herein as described herein (such as by transient transfection of one or more vectors, or transfection with RNA), is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In one embodiment, the invention provides a eukaryotic host cell comprising (a) a first regulatory element operably linked to one or more engineered brown marmorated and/or harlequin stink bug pheromone enzymes described herein, wherein when expressed, produces the one or more enzymes encoded by one or more engineered brown marmorated and/or harlequin stink bug pheromone enzyme polynucleotides described herein.

Modified Organisms

A wide variety of animals, plants, algae, fungi, yeast, etc. and animal, plant, algae, fungus, yeast cell or tissue systems may be engineered for the desired physiological and agronomic characteristics described herein using the nucleic acid constructs of the present disclosure and the various transformation methods mentioned elsewhere herein. In embodiments, one or more cells of a plant, animal, algae, fungus, yeast contain one or more polynucleotides, vectors encoding one or more engineered brown marmorated and/or harlequin stink bug enzymes described herein. In some embodiments, the polynucleotide(s) encoding one or more engineered brown marmorated and/or harlequin stink bug enzymes described herein can be stably or transiently incorporated into one or more cells of a plant, animal, algae, fungus, and/or yeast or tissue system. In some embodiments, one or more engineered brown marmorated and/or harlequin stink bug enzymes described herein are genomically incorporated into one or more cells of a plant, animal, algae, fungus, and/or yeast or tissue system. Further embodiments of the modified organisms and systems are described elsewhere herein.

The engineered brown marmorated and/or harlequin stink bug pheromone enzyme polynucleotides described can be used to confer desired traits (e.g. pheromone and/or pheromone precursor production) on essentially any animal plant, algae, fungus, yeast, etc. A wide variety of animals, plants, algae, fungus, yeast, etc. and plant algae, fungus, yeast cell or tissue systems may be engineered for the desired physiological and agronomic characteristics described herein using the nucleic acid constructs of the present disclosure and the various transformation methods mentioned above.

Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants.

In some embodiments, one or more engineered brown marmorated and/or harlequin stink bug enzymes described herein are expressed in one or more cells of the plant, animal, algae, fungus, yeast, or tissue systems. In some embodiments, one or more engineered brown marmorated and/or harlequin stink bug enzymes described herein can be transcribed and/or translated by a cell to produce one or more engineered brown marmorated and/or harlequin stink bug pheromone enzymes described elsewhere herein. In an embodiment, described herein is a non-human eukaryotic organism (such as a plant); preferably a multicellular eukaryotic organism, comprising a eukaryotic host cell containing one or more components of brown marmorated and/or harlequin stink bug system described herein according to any of the described embodiments.

Thus, the described herein a plant, animal or cell, produced by the present methods and incorporating one or more of the polynucleotides and/or enzymes described herein, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants.

The methods described herein generally result in the generation of "improved animals, plants, algae, fungi, yeast, etc." in that they have one or more desirable traits compared to the wildtype animal, plant, algae, fungi, yeast, etc. In particular embodiments, the plants, algae, fungi, yeast, etc., cells or parts obtained are transgenic plants, comprising an exogenous DNA sequence incorporated into the genome of all or part of the cells. In particular embodiments, non-transgenic genetically modified animals, plants, algae, fungi, yeast, etc., parts or cells are obtained, in that no exogenous DNA sequence is incorporated into the genome of any of the cells of the modified animals, plants, algae, fungi, yeast, etc. In such embodiments, the improved animals, plants, algae, fungi, yeast, etc. are non-transgenic. Accordingly, as used herein, a "non-transgenic" animal, plant, algae, fungi, yeast, etc. or cell thereof is an animal, plant, algae, fungi, yeast, etc. or cell thereof which does not contain a foreign DNA stably integrated into its genome.

Modified Plants and Algae

Described herein are plants cells obtainable and obtained by the methods provided herein. The improved plants obtained by the methods described herein may be useful in food or feed production through expression of genes which, for instance ensure tolerance to plant pests, herbicides, drought, low or high temperatures, excessive water, etc. They can also be used as trap crops, or in other pest management schemes.

The modified plants described herein can be used as trap crops that can be used to control brown marmorated and/or harlequin stink bug infestation. The trap crops can be planted one or more times a year. In some embodiments, the modified trap crop expressing one or more engineered brown marmorated and/or harlequin stink bug polynucleotides vectors and/or enzymes as described elsewhere herein. In some embodiments, the modified trap crop a sunflower plant, a squash plant, a zucchini plant, a pumpkin plant, a hollyhock plant, buckwheat, triticale, crimson clover, vetch sorghum, and millet. Other plants may be suitable for use as trap crops. Suitable trap crops can have one or more of the following characteristics: attracts the target pests (e.g. brown marmorated and/or harlequin stink bug), seeds are readily available, cost effective relative to other management strategies, culture and the management of the plant is well known, the plant is hardy in the geographical location needed and/or time of year needed, has minimal side effects (e.g. it is not invasive, other herbivores on it are benign or beneficial), an optimal maturity time (range is short to long), duration is extendable (by ratooning), the physical properties can be variable (height for barrier; foliage color), is multi-functional (e.g. attracts pollinators, beneficial insects, etc.).

In embodiments more than one type of engineered trap crop can be used in the same area. In embodiments, more than one type of trap crop can be used throughout the year. The physical appearance and height of the engineered trap crop plants can be important and their efficacy as a barrier can be improved by using pole or climbing species or cultivars on a vertical lattice of wire fencing on posts placed in the ground or in portable containers. The default (lack of knowledge) approach relative to placement would be to ring the entire cash crop with the trap crop. Alternatively, to reduce the amount of space and expense required for the trap crop, one may exploit stink bug behavior and use the "source-sink" approach to determine where to strategically place smaller trap crop plots in the most probable pathways that stink bugs will use to arrive at the cash crop from their previous hosts.

In embodiments, the efficiency of the engineered trap crop can be further enhanced by the addition of visual and semiochemical attractants. The yellow pyramid trap baited with the species-specific attractant chemical(s) will attract and capture stink bugs and attract natural enemies. Simple 5-7 gallon plant pots or 3×36 inch mailing tubes painted safety yellow #K7744 will also attract both stink bugs and natural enemies to the trap crops. Stink bugs may be consumed by birds and other animals when exposed off the plant. Specific insect natural enemies include hymenopterous egg parasitoids and parasitic flies (Tachinidae). The mortality exerted on the various stink bug species by these parasitoids is not well documented but it is known that tachinid flies do respond to the semiochemicals released by stink bugs. Thus, the addition of semiochemicals to trap crops may increase natural enemy populations there, bringing them into more frequent contact with stink bugs.

The invention also provides for improved parts of a plant. Plant parts include, but are not limited to, leaves, stems, roots, tubers, seeds, endosperm, ovule, and pollen. Plant parts as envisaged herein may be viable, nonviable, regeneratable, and/or non-regeneratable.

Gametes, seeds, embryos, cither zygotic or somatic, progeny or hybrids of plants comprising the genetic modification, which are produced by traditional breeding methods, are also included within the scope of the present invention. Such plants may contain a heterologous or foreign DNA sequence inserted at or instead of a target sequence. Alternatively, such plants may contain only an alteration (mutation, deletion, insertion, substitution) in one or more nucleotides. As such, such plants will only be different from their progenitor plants by the presence of the particular modification.

In some embodiments, the modified organism is a plant. In general, the term "plant" relates to any various photosynthetic, eukaryotic, unicellular or multicellular organism of the kingdom Plantae characteristically growing by cell division, containing chloroplasts, and having cell walls comprised of cellulose. The term plant encompasses monocotyledonous and dicotyledonous plants. Specifically, the plants are intended to comprise without limitation angiosperm and gymnosperm plants such as acacia, alfalfa, amaranth, apple, apricot, artichoke, ash tree, asparagus, avocado, banana, barley, beans, beet, birch, beech, blackberry, blueberry, broccoli, Brussel's sprouts, cabbage, canola, cantaloupe, carrot, cassava, cauliflower, cedar, a cereal, celery, chestnut, cherry, Chinese cabbage, citrus, clementine, clover, coffee, corn, cotton, cowpea, cucumber, cypress, egg-plant, elm, endive, *eucalyptus*, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm, okra, onion, orange, an ornamental plant or flower or tree, *papaya*, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, yams, yew, and zucchini. The term plant also encompasses Algae, which are mainly photoautotrophs unified primarily by their lack of roots, leaves and other organs that characterize higher plants.

Plants can be modified to express one or more of the engineered brown marmorated and/or harlequin stink bug pheromones using a suitable modification technique, including but not limited to recombinant technology techniques and various genome editing systems, e.g. a CRISPR-Cas system, TALENs, Zinc-finger nucleases, can be used to confer desired traits on essentially any plant. Such methods are known in the art. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., *petunia*, rose, *chrysanthemum*), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, a broad range of plants, such as for example with dicotyledonous plants can be modified belonging to the orders Magnoliales, Illiciales, Laurales, Piperales, Aristochiales, Nymphaeales, Ranunculales, Papaverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, San tales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales; the systems and methods described herein can be used with monocotyledonous plants such as those belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchid ales, or with plants belonging to Gymnospermae, e.g., those belonging to the orders Pinales, Ginkgoales, Cycadales, Araucariales, Cupressales and Gnetales.

Other plants that can be modified as described herein include those in the non-limitative list of dicot, monocot or gymnosperm genera hereunder: *Atropa, Alseodaphne, Anac-*

*ardium, Arachis, Beilschmiedia, Brassica, Carthamus, Cocculus, Croton, Cucumis, Citrus, Citrullus, Capsicum, Catharanthus, Cocos, Coffea, Cucurbita, Daucus, Duguetia, Eschscholzia, Ficus, Fragaria, Glaucium, Glycine, Gossypium, Helianthus, Hevea, Hyoscyamus, Lactuca, Landolphia, Linum, Litsea, Lycopersicon, Lupinus, Manihot, Majorana, Malus, Medicago, Nicotiana, Olea, Parthenium, Papaver, Persea, Phaseolus, Pistacia, Pisum, Pyrus, Prunus, Raphanus, Ricinus, Senecio, Sinomenium, Stephania, Sinapis, Solanum, Theobroma, Trifolium, Trigonella, Vicia, Vinca, Vilis,* and *Vigna*; and the genera *Allium, Andropogon, Eragrostis, Asparagus, Avena, Cynodon, Elaeis, Festuca, Festulolium, Hemerocallis, Hordeum, Lemna, Lolium, Musa, Oryza, Panicum, Pennisetum, Phleum, Poa, Secale, Sorghum, Triticum, Zea, Abies, Cunninghamia, Ephedra, Picea, Pinus,* and *Pseudotsuga.*

As used herein "algae" or "algae cells" that can be modified as described herein include, but are not limited to, algae selected from several eukaryotic phyla, including the Rhodophyta (red algae), Chlorophyta (green algae), Phaeophyta (brown algae), Bacillariophyta (diatoms), Eustigmatophyta and dinoflagellates as well as the prokaryotic phylum Cyanobacteria (blue-green algae). The term "algae" includes for example algae selected from: Amphora, *Anabaena, Ankistrodesmus, Botryococcus, Chaetoceros, Chlamydomonas, Chlorella, Chlorococcum, Cyclotella, Cylindrotheca, Dunaliella, Emiliana, Euglena, Haematococcus, Isochrysis, Monochrysis, Monoraphidium, Nannochloris, Nannochloropsis, Navicula, Neochloris, Nephroselmis, Nitzschia, Nodularia, Nostoc, Ochromonas, Oocystis, Oscillatoria, Pavlova, Phaeodactylum, Playtmonas, Pleurochrysis, Porhyra, Pseudoanabaena, Pyramimonas, Stichococcus, Synechococcus, Synechocystis, Tetraselmis, Thalassiosira,* and *Trichodesmium.*

A part of a plant, i.e., a "plant tissue" may be treated according to the methods of the present invention to produce an improved plant. Plant tissue also encompasses plant cells. The term "plant cell" as used herein refers to individual units of a living plant, either in an intact whole plant or in an isolated form grown in in vitro tissue cultures, on media or agar, in suspension in a growth media or buffer or as a part of higher organized unites, such as, for example, plant tissue, a plant organ, or a whole plant.

A "protoplast" refers to a plant cell that has had its protective cell wall completely or partially removed using, for example, mechanical or enzymatic means resulting in an intact biochemical competent unit of living plant that can reform their cell wall, proliferate and regenerate grow into a whole plant under proper growing conditions.

The term "transformation" broadly refers to the process by which a plant host is genetically modified by the introduction of DNA by means of Agrobacteria or one of a variety of chemical or physical methods. As used herein, the term "plant host" refers to plants, including any cells, tissues, organs, or progeny of the plants. Many suitable plant tissues or plant cells can be transformed and include, but are not limited to, protoplasts, somatic jembryos, pollen, leaves, seedlings, stems, calli, stolons, microtubers, and shoots. A plant tissue also refers to any clone of such a plant, seed, progeny, propagule whether generated sexually or asexually, and descendents of any of these, such as cuttings or seed.

The term "transformed" as used herein, refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is transmitted to the subsequent progeny. In these embodiments, the "transformed" or "transgenic" cell or plant may also include progeny of the cell or plant and progeny produced from a breeding program employing such a transformed plant as a parent in a cross and exhibiting an altered phenotype resulting from the presence of the introduced DNA molecule. Preferably, the transgenic plant is fertile and capable of transmitting the introduced DNA to progeny through sexual reproduction.

The term "progeny", such as the progeny of a transgenic plant, is one that is born of, begotten by, or derived from a plant or the transgenic plant. The introduced DNA molecule may also be transiently introduced into the recipient cell such that the introduced DNA molecule is not inherited by subsequent progeny and thus not considered "transgenic".

The term "plant promoter" as used herein is a promoter capable of initiating transcription in plant cells, whether or not its origin is a plant cell. Exemplary suitable plant promoters include, but are not limited to, those that are obtained from plants, plant viruses, and bacteria such as *Agrobacterium* or *Rhizobium* which comprise genes expressed in plant cells.

In particular embodiments, the DNA construct may be introduced into the plant cell using techniques such as but not limited to electroporation, microinjection, aerosol beam injection of plant cell protoplasts, or the DNA constructs can be introduced directly to plant tissue using biolistic methods, such as DNA particle bombardment (see also Fu et al., Transgenic Res. 2000 February; 9(1):11-9). The basis of particle bombardment is the acceleration of particles coated with gene/s of interest toward cells, resulting in the penetration of the protoplasm by the particles and typically stable integration into the genome. (see e.g. Klein et al, Nature (1987), Klein et ah, Bio/Technology (1992), Casas et ah, Proc. Natl. Acad. Sci. USA (1993).).

In particular embodiments, the DNA constructs containing one or more engineered brown marmorated and/or harlequin stink bug pheromone polynucleotides described herein may be introduced into the plant by *Agrobacterium*-mediated transformation. The DNA constructs may be combined with suitable T-DNA flanking regions and introduced into a conventional *Agrobacterium tumefaciens* host vector. The foreign DNA can be incorporated into the genome of plants by infecting the plants or by incubating plant protoplasts with *Agrobacterium* bacteria, containing one or more Ti (tumor-inducing) plasmids. (see e.g. Fraley et al., (1985), Rogers et al., (1987) and U.S. Pat. No. 5,563,055).

CRISPR or other RNA-guided gene modification systems generally known in the art can be used to introduce targeted double-strand or single-strand breaks and/or to introduce into one or more plant cells or entire plants, gene activator, and/or repressor systems and without being limitative, can be used for gene targeting, gene replacement, targeted mutagenesis, targeted deletions or insertions, targeted inversions and/or targeted translocations. By co-expression of multiple targeting polynucleotides (e.g.) RNAs directed to achieve multiple modifications in a single cell, multiplexed genome modification can be ensured. This technology can be used to high-precision engineering of plants with improved characteristics, including enhanced nutritional quality, increased resistance to diseases and resistance to biotic and abiotic stress, and increased production of commercially valuable plant products or heterologous compounds.

In particular embodiments, the methods described herein are used to modify endogenous genes or to modify their expression without the permanent introduction into the genome of the plant, including those encoding CRISPR system or other targeted nucleic acid modification system components, so as to avoid the presence of foreign DNA in the genome of the plant. This can be of interest as the regulatory requirements for non-transgenic plants are less rigorous.

Chloroplast Targeting

In particular embodiments, it is envisaged that the transgenes are expressed specifically in the chloroplast. For this purpose, use can be made of chloroplast transformation methods or compartmentalization of the engineered vectors or polynucleotides described herein to the chloroplast. For instance, the introduction of genetic modifications in the plastid genome can reduce biosafety issues such as gene flow through pollen. Methods of chloroplast transformation are known in the art and include Particle bombardment, PEG treatment, and microinjection. Additionally, methods involving the translocation of transformation cassettes from the nuclear genome to the plastid can be used as described in WO2010061186.

Alternatively, it is envisaged to target one or more of the engineered vectors or polynucleotides described herein to the plant chloroplast. This is achieved by incorporating in the expression construct a sequence encoding a chloroplast transit peptide (CTP) or plastid transit peptide, operably linked to the 5' region of the sequence encoding the CRISPR-Cas protein. The CTP is removed in a processing step during translocation into the chloroplast. Chloroplast targeting of expressed proteins is well known to the skilled artisan (see for instance Protein Transport into Chloroplasts, 2010, Annual Review of Plant Biology, Vol. 61: 157-180). In such embodiments it is also desired to target the guide RNA to the plant chloroplast. Methods and constructs which can be used for translocating guide RNA into the chloroplast by means of a chloroplast localization sequence are described, for instance, in US20040142476, incorporated herein by reference. Such variations of constructs can be incorporated into the expression systems of the invention to efficiently translocate the CRISPR-Cas-guide RNA.

Introduction of Polynucleotides in Algal Cells

Transgenic algae (or other plants such as rape) may be particularly useful for the expression and/or production of the brown marmorated and/or harlequin stink bug pheromone enzymes described herein. These may be engineered to express or overexpress high levels of oil or alcohols for use in the oil or biofuel industries.

U.S. Pat. No. 8,945,839 describes a method for engineering Micro-Algae (*Chlamydomonas reinhardtii* cells) species) using Cas9. Using similar tools, the methods of the CRISPR-Cas system described herein can be applied on *Chlamydomonas* species and other algae. Electroporation protocols are available to the skilled person such as the standard recommended protocol from the GeneArt *Chlamydomonas* Engineering kit.

Organisms such as microalgae are widely used for synthetic biology. Stovicek et al. (Metab. Eng. Comm., 2015; 2:13 describes genome editing of industrial yeast, for example, *Saccharomyces cerevisiae*, to efficiently produce robust strains for industrial production. Stovicek used a CRISPR—The methods of Stovicek and Hlavová may be applied and/or adapted to produce a modified microalgae expression one or more of the engineered vectors, polynucleotides, and/or polypeptides described herein.

Transient Expression of the Engineered Polynucleotides and/or Vectors in Plant Cells In particular embodiments, it is envisaged that one or more of the engineered vectors or polynucleotides described herein are transiently expressed in the plant cell. In these embodiments, expression of the transgene(s) is transient, plants regenerated from such plant cells typically contain no foreign DNA. In particular embodiments, one or more of the engineered vectors or polynucleotides described herein can be introduced in the plant cells using a plant viral vector (Scholthof et al. 1996, Annu Rev Phytopathol. 1996; 34:299-323). In further particular embodiments, said viral vector is a vector from a DNA virus. For example, gemini-virus (e.g., cabbage leaf curl virus, bean yellow dwarf virus, wheat dwarf virus, tomato leaf curl virus, maize streak virus, tobacco leaf curl virus, or tomato golden mosaic virus) or nanovirus (e.g., *Faba* bean necrotic yellow virus). In other particular embodiments, said viral vector is a vector from an RNA virus. For example, tobravirus (e.g., tobacco rattle virus, tobacco mosaic virus), potexvirus (e.g., potato virus X), or hordeivirus (e.g., barley stripe mosaic virus). The replicating genomes of plant viruses are non-integrative vectors.

In particular embodiments, the vector used for transient expression of the transgene(s) for instance a pEAQ vector, which is tailored for *Agrobacterium*-mediated transient expression (Sainsbury F. et al., Plant Biotechnol J. 2009 September; 7(7):682-93) in the protoplast.

In particular embodiments, double-stranded DNA frag-ments encoding the engineered brown marmorated and/or harlequin stink bug pheromone enzymes described herein can be transiently introduced into the plant cell. In such embodiments, the introduced double-stranded DNA frag-ments are provided in sufficient quantity to modify the cell but do not persist after a contemplated period of time has passed or after one or more cell divisions. Methods for direct DNA transfer in plants are known by the skilled artisan (see for instance Davey et al. Plant Mol Biol. 1989 September; 13(3):273-85.)

In other embodiments, an RNA polynucleotide encoding the engineered brown marmorated and/or harlequin stink bug pheromone enzymes described herein is/are introduced into the plant cell, which is then translated and processed by the host cell generating the protein in sufficient quantity to modify the cell (in the presence of at least one guide RNA) but which does not persist after a contemplated period of time has passed or after one or more cell divisions. Methods for introducing mRNA to plant protoplasts for transient expression are known by the skilled artisan (see for instance in Gallie, Plant Cell Reports (1993), 13; 119-122).

Combinations of the different methods described above are also envisaged. Thus in some embodiments, one or more of the methods or step(s) thereof described herein can be combined or used together.

Delivery of Engineered Polynucleotides, Vectors, and Poly-peptides to a Plant Cell In particular embodiments, it is of interest to deliver one or more engineered polynucleotides, vectors and/or poly-peptides described herein directly to the plant cell. This is of interest, inter alia, for the generation of non-transgenic plants (see e.g. elsewhere herein). In particular embodi-ments, one or more engineered polynucleotides, vectors and/or polypeptides described herein is prepared outside the plant or plant cell and delivered to the cell. For instance, in particular embodiments, the engineered brown marmorated and/or harlequin stink bug pheromone protein(s) is/are pre-pared in vitro prior to introduction to the plant cell. Such protein(s) can be prepared by various methods known by one of skill in the art and include recombinant production. After expression, the engineered protein(s) described herein is/are isolated, refolded if needed, purified and optionally treated to remove any purification tags, such as a His-tag. Once crude, partially purified, or more completely purified engineered protein(s) is/are obtained, the protein may be introduced to the plant cell.

In particular embodiments, the engineered polypeptides, polynucleotides, and/or vectors described herein are intro-duced into the plant cells using nanoparticles. The compo-nents, either as protein or nucleic acid or in a combination thereof, can be uploaded onto or packaged in nanoparticles and applied to the plants (such as for instance described in WO 2008042156 and US 20130185823). In some embodi-ments, cell penetrating peptides can be used to introduce one or more of the engineered polypeptides, polynucleotides, and/or vectors described herein into a plant cell. Accord-ingly, in particular, embodiments the invention comprises compositions comprising a cell penetrating peptide linked to one or more of the engineered protein(s) described herein. In particular embodiments, one or more of the engineered protein(s) described herein is coupled to one or more CPPs to effectively transport them inside plant protoplasts. In other embodiments, the engineered proteins are encoded by one or more circular or non-circular DNA molecule(s) which are coupled to one or more CPPs for plant protoplast delivery. The plant protoplasts are then regenerated to plant cells and further to plants. CPPs are generally described as short peptides of fewer than 35 amino acids either derived from proteins or from chimeric sequences which are capable of transporting biomolecules across cell membrane in a receptor independent manner. CPP can be cationic peptides, peptides having hydrophobic sequences, amphipathic pep-tides, peptides having proline-rich and anti-microbial sequence, and chimeric or bipartite peptides (Pooga and Langel 2005). CPPs are able to penetrate biological mem-branes and as such trigger the movement of various biomo-lecules across cell membranes into the cytoplasm and to improve their intracellular routing, and hence facilitate inter-action of the biomolecule with the target. Examples of CPP include amongst others: Tat, a nuclear transcriptional acti-vator protein required for viral replication by HIV type 1, penetratin, Kaposi fibroblast growth factor (FGF) signal peptide sequence, integrin $\beta3$ signal peptide sequence; pol-yarginine peptide Args sequence, Guanine rich-molecular transporters, sweet arrow peptide, etc.

In particular embodiments, the methods described herein are used to modify endogenous genes or to modify their expression without the permanent introduction into the genome of the plant of any foreign gene, including those one or more of the engineered polypeptides described elsewhere herein, so as to avoid the presence of foreign DNA in the genome of the plant. This can be of interest as the regulatory requirements for non-transgenic plants are less rigorous.

In particular embodiments, the engineered polypeptides, polynucleotides and/or vectors are introduced in the plant cell, protoplast or plant tissue either separately or in mixture, with the aid of particulate delivering molecules such as nanoparticles or CPP molecules as described herein above.

Detecting Modifications in the Plant Genome-Selectable Markers

Where the method involves introduction of a transgene, a transformed plant cell, callus, tissue or plant may be iden-tified and isolated by selecting or screening the engineered plant material for the presence of the transgene or for traits encoded by the transgene. Physical and biochemical meth-ods may be used to identify plant or plant cell transformants containing inserted gene constructs or an endogenous DNA modification. These methods include but are not limited to: 1) Southern analysis or PCR amplification for detecting and determining the structure of the recombinant DNA insert or modified endogenous genes; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct or expression is affected by the genetic modification; 4) protein gel electrophoresis, Western blot techniques, immunoprecipitation, or enzyme-linked immunoassays, where the gene construct or endogenous gene products are proteins. Additional techniques, such as in situ hybridization, enzyme staining, and immunostaining, also may be used to detect the presence or expression of the recombinant construct or detect a modification of endogenous gene in specific plant organs and tissues. The methods for doing all these assays are well known to those skilled in the art.

In some embodiments, the expression system encoding the engineered polypeptides is typically designed to comprise one or more selectable or detectable markers that provide a means to isolate or efficiently select cells that contain and/or have been modified by the transgene system at an early stage and on a large scale.

In the case of *Agrobacterium*-mediated transformation, the marker cassette may be adjacent to or between flanking T-DNA borders and contained within a binary vector. In another embodiment, the marker cassette may be outside of the T-DNA. A selectable marker cassette may also be within or adjacent to the same T-DNA borders as the expression cassette or may be somewhere else within a second T-DNA on the binary vector (e.g., a 2 T-DNA system).

For particle bombardment or with protoplast transformation, the expression system can comprise one or more isolated linear fragments or may be part of a larger construct that might contain bacterial replication elements, bacterial selectable markers or other detectable elements. The expression cassette(s) comprising the engineered polynucleotides described herein may be physically linked to a marker cassette or may be mixed with a second nucleic acid molecule encoding a marker cassette. The marker cassette is comprised of necessary elements to express a detectable or selectable marker that allows for efficient selection of transformed cells.

The selection procedure for the cells based on the selectable marker will depend on the nature of the marker gene. In particular embodiments, use is made of a selectable marker, i.e. a marker which allows a direct selection of the cells based on the expression of the marker. A selectable marker can confer positive or negative selection and is conditional or non-conditional on the presence of external substrates (Miki et al. 2004, 107(3): 193-232). Most commonly, antibiotic or herbicide resistance genes are used as a marker, whereby selection is be performed by growing the engineered plant material on media containing an inhibitory amount of the antibiotic or herbicide to which the marker gene confers resistance. Examples of such genes are genes that confer resistance to antibiotics, such as hygromycin (hpt) and kanamycin (nptII), and genes that confer resistance to herbicides, such as phosphinothricin (bar) and chlorsulfuron (als).

Transformed plants and plant cells may also be identified by screening for the activities of a visible marker, typically an enzyme capable of processing a colored substrate (e.g., the β-glucuronidase, luciferase, B or C1 genes). Such selection and screening methodologies are well known to those skilled in the art.

4. Plant Cultures and Regeneration

In particular embodiments, plant cells which have a modified genome and that are produced or obtained by any of the methods described herein, can be cultured to regenerate a whole plant which possesses the transformed or modified genotype and thus the desired phenotype. Conventional regeneration techniques are well known to those skilled in the art. Particular examples of such regeneration techniques rely on manipulation of certain phytohormones in a tissue culture growth medium, and typically relying on a biocide and/or herbicide marker which has been introduced together with the desired nucleotide sequences. In further particular embodiments, plant regeneration is obtained from cultured protoplasts, plant callus, explants, organs, pollens, embryos or parts thereof (see e.g. Evans et al. (1983), Handbook of Plant Cell Culture, Klee et al (1987) Ann. Rev. of Plant Phys.).

In particular embodiments, transformed or improved plants as described herein can be self-pollinated to provide seed for homozygous improved plants of the invention (homozygous for the DNA modification) or crossed with non-transgenic plants or different improved plants to provide seed for heterozygous plants. Where a recombinant DNA was introduced into the plant cell, the resulting plant of such a crossing is a plant which is heterozygous for the recombinant DNA molecule. Both such homozygous and heterozygous plants obtained by crossing from the improved plants and comprising the genetic modification (which can be a recombinant DNA) are referred to herein as "progeny". Progeny plants are plants descended from the original transgenic plant and containing the genome modification or recombinant DNA molecule introduced by the methods provided herein. Alternatively, genetically modified plants can be obtained by one of the methods described supra using a genome modification technique whereby no foreign DNA is incorporated into the genome. Progeny of such plants, obtained by further breeding may also contain the genetic modification. Breedings are performed by any breeding methods that are commonly used for different crops (e.g., Allard, Principles of Plant Breeding, John Wiley & Sons, NY, U. of CA, Davis, CA, 50-98 (1960).

Modified Fungi

In some embodiments, the modified organism can be a fungus. As used herein, a "fungal cell" refers to any type of eukaryotic cell within the kingdom of fungi. Phyla within the kingdom of fungi include Ascomycota, Basidiomycota, Blastocladiomycota, Chytridiomycota, Glomeromycota, Microsporidia, and Neocallimastigomycota. Fungal cells may include yeasts, molds, and filamentous fungi. In some embodiments, the fungal cell is a yeast cell.

As used herein, the term "yeast cell" refers to any fungal cell within the phyla Ascomycota and Basidiomycota. Yeast cells may include budding yeast cells, fission yeast cells, and mold cells. Without being limited to these organisms, many types of yeast used in laboratory and industrial settings are part of the phylum Ascomycota. In some embodiments, the yeast cell is an *S. cerevisiae, Kluyveromyces marxianus*, or *Issatchenkia orientalis* cell. Other yeast cells may include without limitation *Candida* spp. (e.g., *Candida albicans*), *Yarrowia* spp. (e.g., *Yarrowia lipolytica*), *Pichia* spp. (e.g., *Pichia pastoris*), *Kluyveromyces* spp. (e.g., *Kluyveromyces lactis* and *Kluyveromyces marxianus*), *Neurospora* spp. (e.g., *Neurospora crassa*), *Fusarium* spp. (e.g., *Fusarium oxysporum*), and *Issatchenkia* spp. (e.g., *Issatchenkia orientalis*, a.k.a. *Pichia kudriavzevii* and *Candida acidothermophilum*). In some embodiments, the fungal cell is a filamentous fungal cell. As used herein, the term "filamentous fungal cell" refers to any type of fungal cell that grows in filaments, i.e., hyphae or mycelia. Examples of filamentous fungal cells may include without limitation *Aspergillus* spp. (e.g., *Aspergillus niger*), *Trichoderma* spp. (e.g., *Trichoderma reesei*), *Rhizopus* spp. (e.g., *Rhizopus oryzae*), and *Mortierella* spp. (e.g., *Mortierella isabellina*).

In some embodiments, the fungal cell is an industrial strain. As used herein, "industrial strain" refers to any strain of fungal cell used in or isolated from an industrial process, e.g., production of a product on a commercial or industrial scale. Industrial strain may refer to a fungal species that is typically used in an industrial process, or it may refer to an isolate of a fungal species that may be also used for non-industrial purposes (e.g., laboratory research). Examples of industrial processes may include fermentation (e.g., in production of food or beverage products), distillation, biofuel production, production of a compound, and production of a polypeptide. Examples of industrial strains may include, without limitation, JAY270 and ATCC4124.

In some embodiments, the fungal cell is a polyploid cell. As used herein, a "polyploid" cell may refer to any cell whose genome is present in more than one copy. A polyploid cell may refer to a type of cell that is naturally found in a polyploid state, or it may refer to a cell that has been induced to exist in a polyploid state (e.g., through specific regulation, alteration, activation, or modification of meiosis, cytokinesis, or DNA replication). A polyploid cell may refer to a cell whose entire genome is polyploid, or it may refer to a cell that is polyploid in a particular genomic locus of interest.

In some embodiments, the fungal cell is a diploid cell. As used herein, a "diploid" cell may refer to any cell whose genome is present in two copies. A diploid cell may refer to a type of cell that is naturally found in a diploid state, or it may refer to a cell that has been induced to exist in a diploid state (e.g., through specific regulation, alteration, inactivation, activation, or modification of meiosis, cytokinesis, or DNA replication). For example, the *S. cerevisiae* strain S228C may be maintained in a haploid or diploid state. A diploid cell may refer to a cell whose entire genome is diploid, or it may refer to a cell that is diploid in a particular genomic locus of interest. In some embodiments, the fungal cell is a haploid cell. As used herein, a "haploid" cell may refer to any cell whose genome is present in one copy. A haploid cell may refer to a type of cell that is naturally found in a haploid state, or it may refer to a cell that has been induced to exist in a haploid state (e.g., through specific regulation, alteration, inactivation, activation, or modification of meiosis, cytokinesis, or DNA replication). For example, the *S. cerevisiae* strain S228C may be maintained in a haploid or diploid state. A haploid cell may refer to a cell whose entire genome is haploid, or it may refer to a cell that is haploid in a particular genomic locus of interest.

The yeast can be modified using any suitable technique, which are generally known in the art and can include recombinant engineering techniques, cloning, TALEs, CRISPR-Cas, and the like. Methods for transforming yeast cells which can be used to introduce the engineered polynucleotides described herein are well known to the artisan as can be exemplified are reviewed by Kawai et al., 2010, Bioeng Bugs. 2010 November-December; 1(6): 395-403). Non-limiting examples include transformation of yeast cells by lithium acetate treatment (which may further include carrier DNA and PEG treatment), bombardment or by electroporation.

Modified Microorganisms

In some embodiments, the modified organism is a modified micro-organism.

In particular embodiments, the micro-organism is selected from the genus *Escherichia, Bacillus, Lactobacillus, Rhodococcus, Synechocystis, Synechoystis, Pseudomonas, Aspergillus, Trichoderma, Neurospora, Fusarium, Humicola, Rhizomucor, Kluyveromyces, Pichia, Mucor, Myceliophthora, Penicillium, Phanerochaete, Pleurotus, Trametes, Chrysosporium, Saccharomyces, Stenotrophomonas, Schizosaccharomyces, Yarrowia,* or *Streptomyces.*

Kits

Any of the compounds, compositions, formulations, particles, cells, described herein or a combination thereof can be presented as a combination kit. As used herein, the terms "combination kit" or "kit of parts" refers to the compounds, compositions, formulations, particles, cells and any additional components that are used to package, sell, market, deliver, and/or administer the combination of elements or a single element, such as the active ingredient, contained therein. Such additional components include, but are not limited to, packaging, syringes, blister packages, bottles, and the like. When one or more of the compounds, compositions, formulations, particles, cells, described herein or a combination thereof (e.g., agents) contained in the kit are administered simultaneously, the combination kit can contain the active agents in a single formulation, such as a pharmaceutical formulation or other formulation, (e.g., a tablet, liquid, or gel) or in separate formulations. When the compounds, compositions, formulations, particles, and cells described herein or a combination thereof and/or kit components are not administered simultaneously, the combination kit can contain each agent or other component in separate pharmaceutical formulations. The separate kit components can be contained in a single package or in separate packages within the kit. In some embodiments, the kits can include one or more items that can facilitate planting, plant propagation, seed harvesting, seed storage, and the like. Such items can include planting trays, containers, fertilizers or feed sources, herbicides, fungicides, soil, tags, stakes and the like. Where seeds are provided, the seeds can be coated with one or more layers of protective, water-retention, and/or feed to facilitate e.g. storage, transport, germination and/or early growth.

In some embodiments, the combination kit also includes instructions printed on or otherwise contained in a tangible medium of expression. The instructions can provide information regarding the content of the compounds, compositions, formulations, particles, cells, and/or plants described herein or a combination thereof contained therein, safety information regarding the content of the compounds, compositions, formulations, particles, cells, and/or plants described herein or a combination thereof contained therein, information regarding the dosages, indications for use, and/or recommended dosage and/or planting schedules regimen (s) for the compounds, compositions, formulations, particles, cells, and/or plants described herein or a combination thereof. In some embodiments, the instructions can provide directions for planting a trap crop as described herein to prevent, mitigate, or eliminate infestation of a crop with a stink bug, such as brown marmorated stink bug, harlequin stink bug, or both.

Methods of Controlling Stink Bugs

Any of the enzymes, encoding or other polynucleotides, vectors, cell(s), organism(s) and any system thereof described in greater detail elsewhere herein can be used in a method of controlling pest infestation, particularly infestation by brown marmorated and/or harlequin stink bugs. In some embodiments, a trap crop is produced and planted such that it attracts the brown marmorated and/or harlequin stink bugs away from the important crop. Strategies regarding use of trap crops are described in greater detail herein. In some embodiments, the method includes planting, propagating, feeding, watering, and otherwise caring for the engineered trap crop expressing an engineered brown marmorated and/or harlequin stink bug pheromone pathway. In some embodiments, the engineered plant is planted in a location next to, adjacent to, or with in effective proximity to the crop. As used herein the term "effective proximity" refers to a distance at which the crop can produce a pheromone and is effective to attract a stink bug, such as a brown marmorated stink bug, harlequin stink bug, or both away from a desired crop such that a stink bug infestation of the desired crop is decreased by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to/or 100 fold or more. The ratio of trap crop plant to desired crop plant can range from 0.001 to 1 or more, such as 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1. The trap crop can be planted such that it produces the stink bug pheromone during a suitable time, such as when the desired crop plant is at a stage where stink bug infestation is likely to occur and/or during a time period where stink bugs are present.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1—Terpene Synthases and De Novo Formation of an Aggregation Pheromone Precursor in Harlequin Stink Bug (*Murgantia histrionica*)

Terpene specialized metabolites play important roles in chemical interactions of microbes, plants, and animals (Gershenzon and Dudareva, 2007; Junker et al., 2017; Osbourn et al., 2011; Tholl, 2015). In particular, volatile terpene compounds function as long and short distance semiochemicals in organismal interactions (Byers et al., 2014; Ditengou et al., 2015; Huang et al., 2012; Junker and Tholl, 2013; Raguso, 2016; Rasmann et al., 2005; Robert et al., 2012; Vaughan et al., 2013; Zhou et al., 2017). Insects are well known to release volatile terpenes as inter-specific signals in chemical defense or as alarm, aggregation and sex pheromones in intra-specific communication (Blomquist et al., 2010; Brown et al., 2006; Burse et al., 2009; Muller and Buchbauer, 2011; Pickett et al., 2013; Sobotnik et al., 2010) Despite these important functions, still little is known about the formation of terpene specialized metabolites in insects.

Figures 2A, 2B:
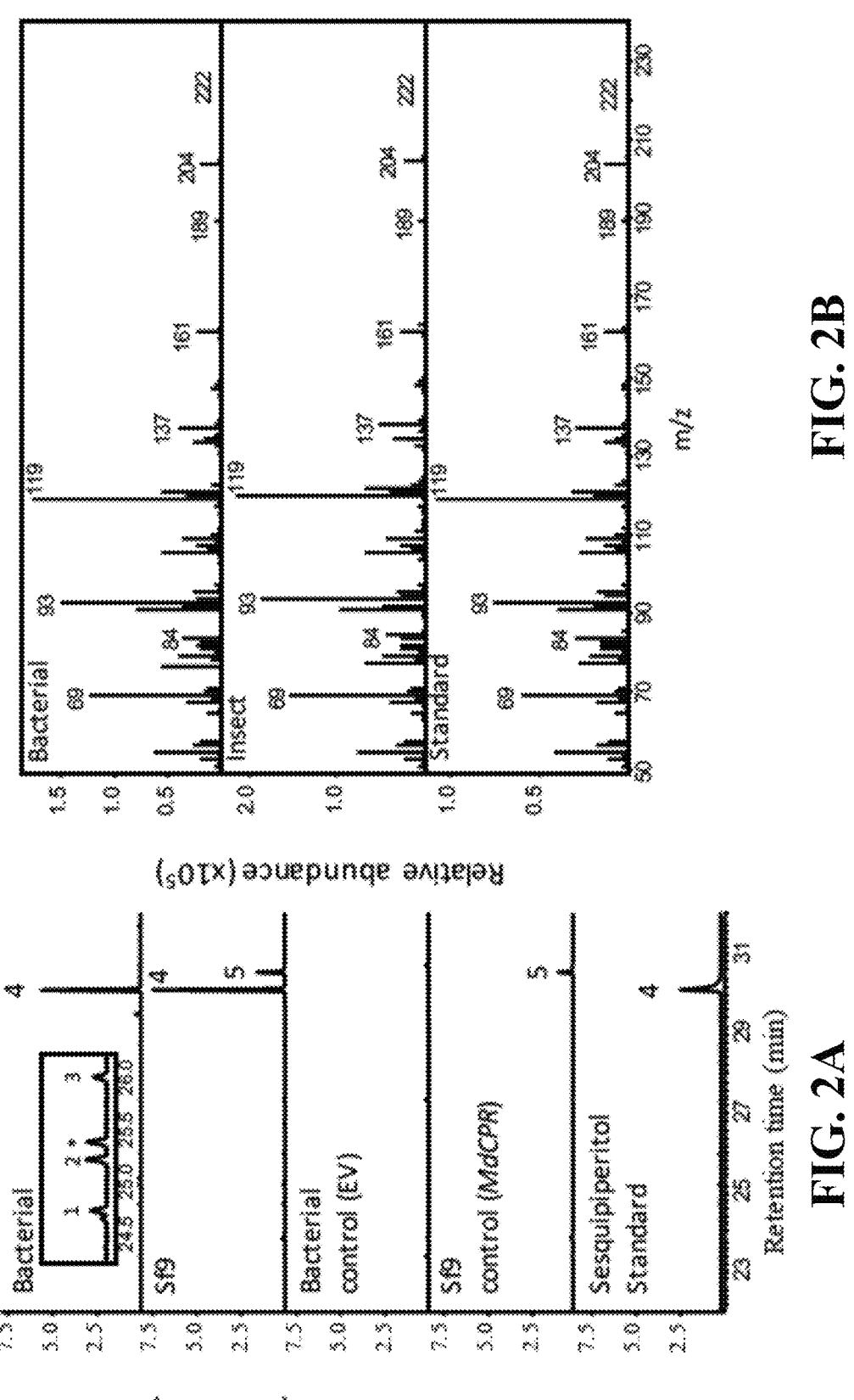
FIGS. 2A-2C—Functional characterization of MhIDS-1 (MhTPS) from *Murgantia histrionica*. Recombinant MhIDS-1 protein was expressed in *E. coli* and Sf9 cells and partially purified by affinity chromatography. Proteins were incubated with (E,E)-FPP in the presence of $Mg^{2+}$ and products were analyzed by GC-MS.
Figure 2C:
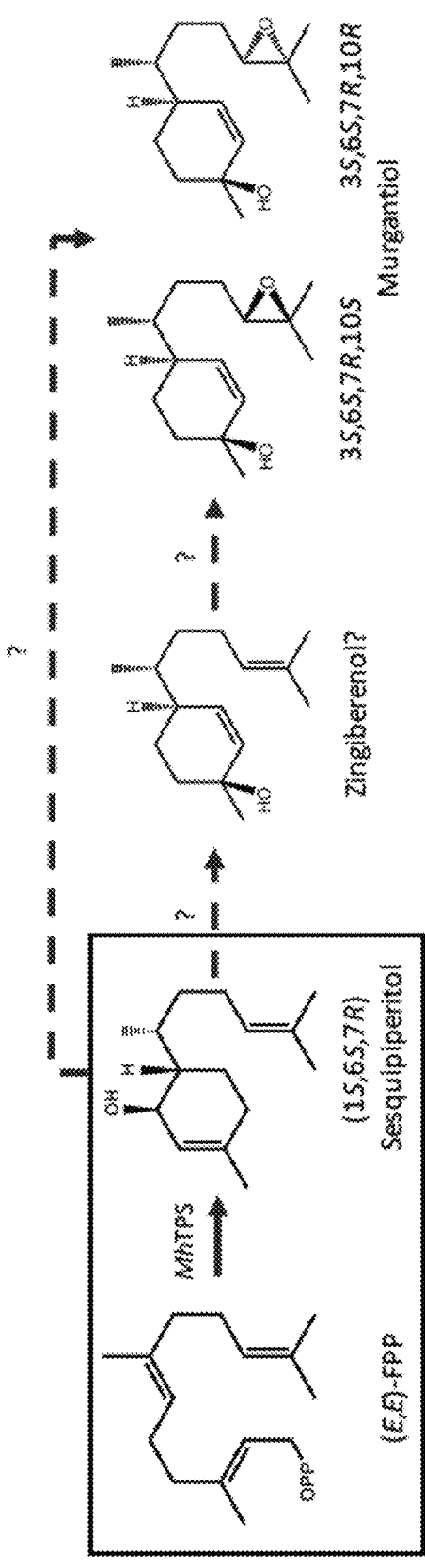

In bacteria, fungi, and plants, volatile terpenes with 10-carbon (monoterpenes) and 15-carbon (sesquiterpene) scaffolds are produced from the isoprenyl diphosphates, geranyl diphosphate (GPP) and farnesyl diphosphate (FPP), respectively, by enzymes called terpene synthases (TPSs) (Chen et al., 2011; Degenhardt et al., 2009; Dickschat, 2016; Jia et al., 2016; Kumar et al., 2016; Quin et al., 2014; Zi et al., 2014). As central intermediates in terpene metabolism, GPP and FPP are assembled by activity of isoprenyl diphosphate synthases (IDSs) that catalyze the condensation of the 5-carbon unit dimethylallyl diphosphate (DMAPP) and one or two molecules of its isomer isopentenyl diphosphate (IPP). Insects have been generally believed to depend on the sequestration of monoterpene or sesquiterpene precursors from their host plants to synthesize pheromone or chemical defense metabolites. This notion was supported by the absence of microbial and plant type terpene synthases in insect genomes. However, studies on the biosynthesis of aggregation pheromones in Coleoptera (beetles) have shown that trans-IDS-like enzymes are able to convert GPP or FPP to terpene pheromones or their respective precursors. Gilg et al. demonstrated that the bark beetle *Ips pini* employs an IDS-like enzyme to produce the monoterpene myrcene from GPP as precursor of the aggregation pheromone ipsdienol (Gilg et al., 2005; Gilg et al., 2009). Recently, a similar finding has been reported from males of the flea beetle *Phyllotreta striolata*, which synthesize the cyclic sesquiterpene aggregation pheromone (6R,7S)-himachala-9,11-diene are from (Z,E)-FPP by an IDS-type enzyme (Beran et al., 2016). From nine IDS-type transcripts in the *P. striolata* transcriptome, two were found to encode bonafide trans- or cis-IDS enzymes, while four transcripts encode terpene synthases suggesting an evolutionary origin of these enzymes from IDS progenitors. Whether other insects, especially those of earlier evolutionary origin, biosynthesize volatile terpenes de novo is unknown This Example can at least demonstrate that among the Hemiptera, stink bugs (Pentatomidae) use IDS-like proteins in pheromone biosynthesis. Several stink bug species release sesquiterpene aggregation/sex pheromones with a bisabolene skeleton (Aldrich et al., 1993; Blassioli-Moraes et al., 2012; Borges et al., 2006; de Oliveira et al., 2013; Khrimian et al., 2014b; McBrien et al., 2002; Moraes et al., 2008). Among these, the harlequin bug *Murgantia histrionica*, a crucifer specialist, produces an isomeric mixture of the sesquiterpene alcohol epoxide murgantiol (10,11-epoxy-1-bisabolen-3-ol) as a male-released aggregation pheromone (Khrimian et al., 2014a; Weber et al., 2014) (FIGS. 2A-2C). We show that an IDS-like enzyme (MhTPS) converts (E,E)-FPP to sesquipiperitol as the presumed stereospecific alcohol precursor of murgantiol, while a second trans-IDS protein (MhFPPS) catalyzes the formation of the MhTPS substrate (E,E)-FPP from IPP and DMAPP. MhTPS is expressed at high levels in males with a predominant localization in the sub-cuticular tissue of the abdominal sternites. A significant role of MhTPS in pheromone biosynthesis was confirmed by RNAi-mediated knockdown of MhTPS mRNA in *M. histrionica* males leading to reduced emission of murgantiol. Phylogenetic comparison of the *M. histrionica* enzymes with other insect IDS proteins suggests that in pierce-sucking true bugs proteins with TPS activity evolved from trans-IDS enzymes and that the emergence of terpene synthases from IDS proteins in insects might have occurred multiple times.

Identification and Functional Characterization of IDS-Like Genes in *M. histrionica*.

Figure 3:
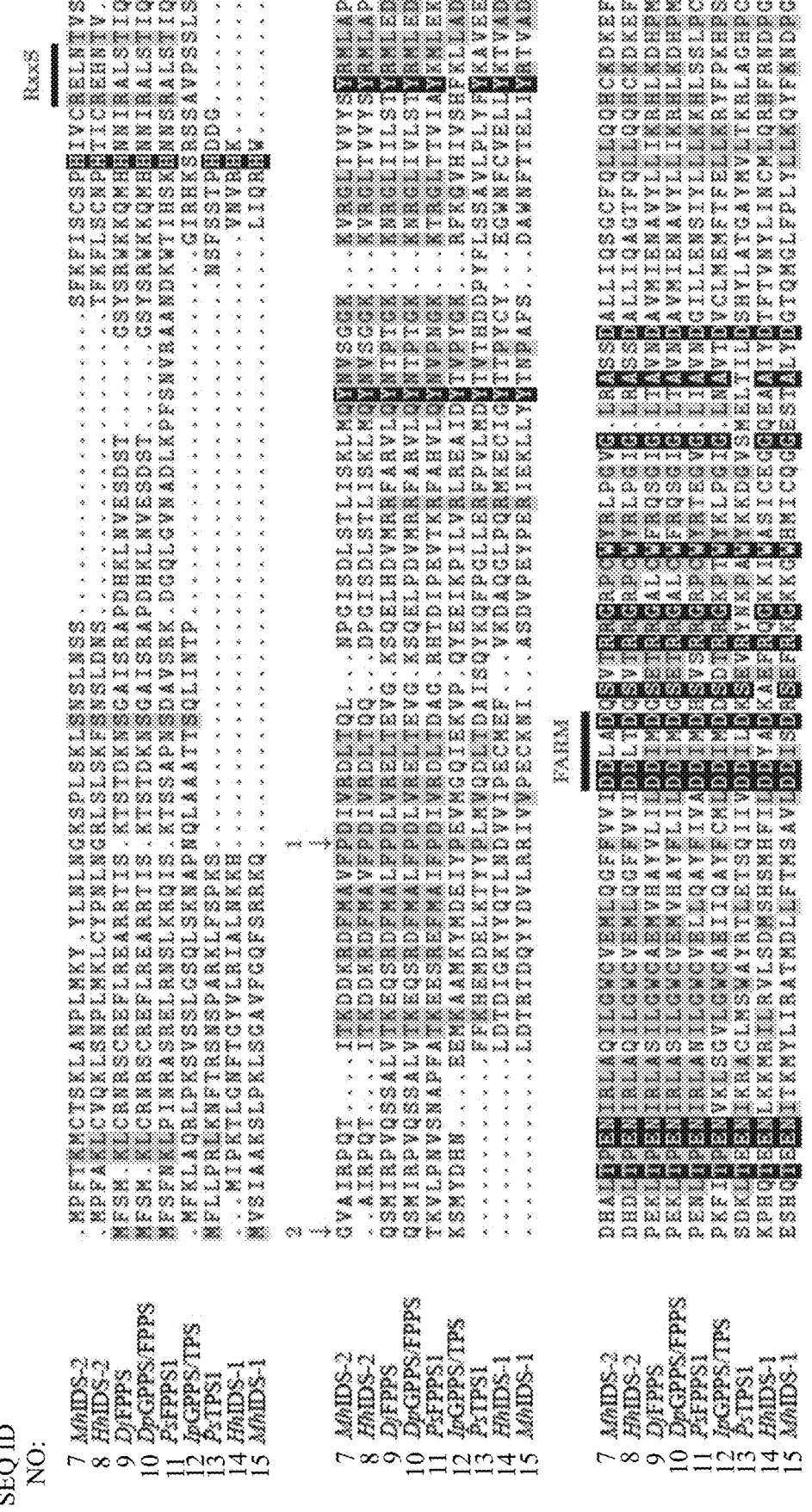
FIG. 3—Amino acid sequence alignment of MhIDS-1 (MhTPS) and MhIDS-2 (MhFPPS) with other functionally confirmed or putative Pentatomid and Coleopteran IDS and TPS proteins. The RxxS motif (labeled) indicates the putative mitochondrial targeting sequence cleavage site. The first aspartate rich motif (FARM) and second aspartate rich motif (SARM) are also labelled. Arrows 1 and 2 represent truncation sites for MhIDS1 and MhIDS2, respectively. Dj, *Dendroctonus jeffreyi*; Dp, *Dendroctonus ponderosae*; Hh, *Halyomorpha halys*; Ip, *Ips pini*; Mh, *Murgantia histrionica*; Ps, *Phyllotreta striolata*.
Figure 3:
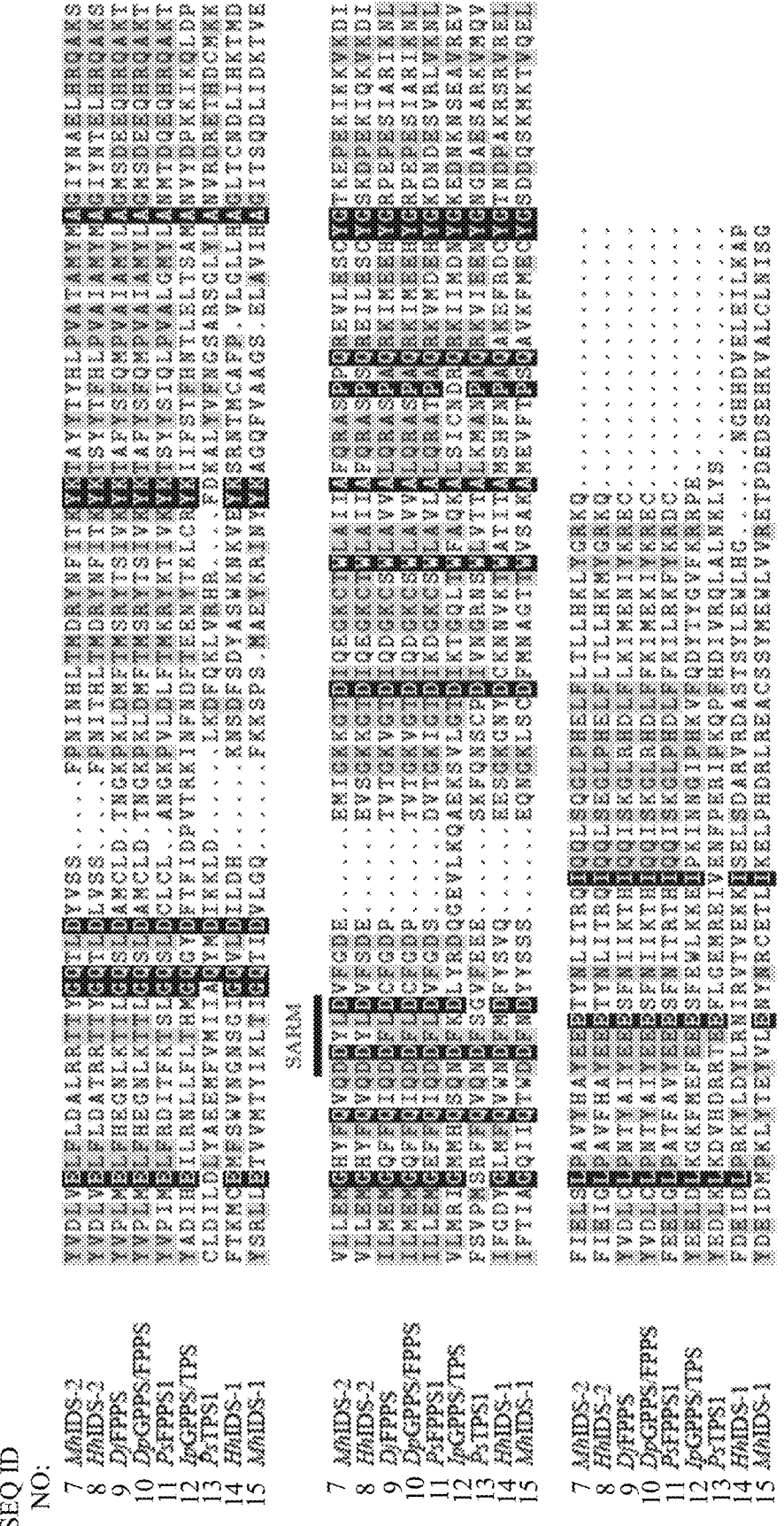

Without being bound by theory it is believed that in the murgantiol biosynthetic pathway of *M. histrionica* an enzyme with terpene synthase activity synthesizes a bisabolene-type hydrocarbon or alcohol terpene precursor, which presumably undergoes further modification(s) including epoxidation to form the pheromone end products (FIGS. 2A-2C). To identify genes involved in the formation of the murgantiol pheromone precursor, a search of two independent transcriptome data sets from different sexes and developmental stages of *M. histrionica* (Sparks et al., 2017) was performed by using plant and microbial type TPS sequences and trans-IDS-type sequences of *Ips pini* FPPS (AAX55631.1) and GPPS/TPS (AAX55632.1), *Bombyx mori* FPPS1 (NP_001036889.1) and FPPS2 (NP_001093301.1), and *Drosophila melanogaster* FPPS (NP_477380). While no genes with sequence similarity to plant or microbial TPSs could be identified, two trans-IDS-like sequences (MhIDS-1, MhIDS-2) annotated to encode FPP synthase (FPPS)-like proteins were retrieved. According to the transcriptome results by Sparks et al. (Sparks et al., 2017), MhIDS-1 (MG662378) was expressed at low levels in mature females but showed an approximately 15 fold higher expression in mature males while MhIDS-2 (MG662379) was expressed equally in both sexes. cDNAs of both genes were amplified from RNA extracted from mature male bugs. MhIDS-1 encodes a 385 aa protein of 44.30 kDa while the MhIDS-2 protein contains 405 aa and has a size of 46.36 kDa (FIG. 3). Another IDS like sequence (IDS-3) with similarity to geranylgeranyl diphosphate (GGPP) synthases (Lai et al., 1998) was found in the transcriptome of adult females (GECQ01397299.1). However, a full-length cDNA of this gene was not able to be amplified.

Figures 4A, 4B:
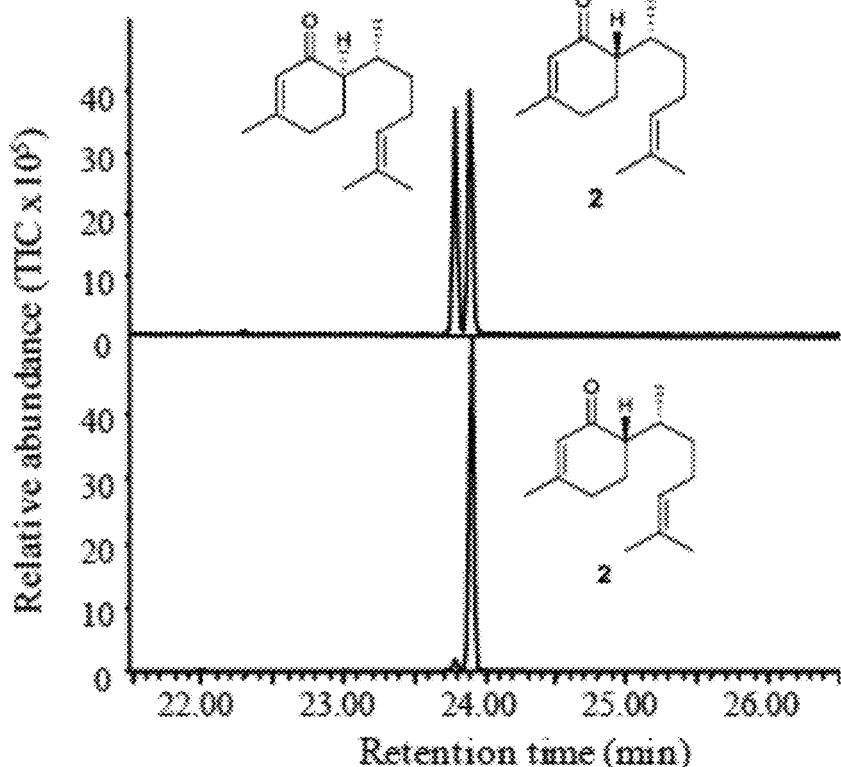
FIGS. 4A-4D—Non-stereospecific identification of sesquipiperitol.

To determine the biochemical function of the detected IDS-like genes, cDNAs encoding full length proteins were cloned in the bacterial protein expression vector pEXP-5 generating an N-terminal histidine-tag fusion. When tested for sesquiterpene synthase activity by using (E,E)-FPP as a substrate, the partially purified recombinant MhIDS-1 protein produced a terpene alcohol as its main product (FIGS. 2A-2C). Using gas chromatography-mass spectrometry (GC-MS), we identified the alcohol product as sesquipiperitol, a sesquiterpene alcohol with a bisabolane skeleton, which has been isolated from different plant species (Bohlmann et al., 1984; Cool, 1996; Sy and Brown, 1997). The identification of sesquipiperitol was performed by comparisons of mass spectra and retention indices and further verified by chemical correlations (SI Results and Material and Methods; FIG. 2A and FIGS. 4A-4D). Sesquipiperitol was also found as the main product in assays upon cleavage of the N-terminal histidine tag (FIG. 5A). In addition to sesquipiperitol, small and varying amounts of the sesquiterpene olefins, γ-curcumene, zingiberene, and β-sesquiphellandrene were detected (FIG. 2A). Hot sample injection contributed to the formation of the olefin products by thermal dehydration of sesquipiperitol as could be shown by cool-on-column injection (FIG. 5B). Sesquipiperitol was also produced, although at lower levels, from (Z,E)-FPP but almost no enzymatic activity was found with (Z,Z)-FPP as the substrate (FIG. 5C). The recombinant enzyme did further convert GPP to several monoterpene olefins (FIG. 5C). However, when incubated with IPP and DMAPP, no formation of terpene products was observed indicating that MhIDS-1 was unable to synthesize prenyl diphosphates for subsequent conversion into terpene products (FIG. 5C). Accordingly, formation of FPP by MhIDS-1 was not observed. Because of its TPS activity and lack of IDS activity, we named MhIDS-1 from here on MhTPS. It was further tested the activity of MhTPS upon expression in insect Sf9 cells (FIG. 2A). Recombinant MhTPS1 protein expressed without a histidine tag under these conditions generated the same enzymatic products upon incubation with (E,E)-FPP as those produced by the bacterially expressed enzyme (FIG. 2A). An alignment of the MhTPS amino acid sequence with those of *I. pini* and *P. striolata* TPS proteins suggested the presence of a putative N-terminal targeting peptide although the RxxS motif indicative of a mitochondrial targeting sequence is absent from the MhTPS protein (FIGS. 2A-2C). Truncation of MhTPS (M1-R45) resulted in the loss of enzymatic activity.

Kinetic analysis of MhTPS1 with (E,E)-FPP as the substrate revealed an apparent $K_m$ value of $4.0\pm0.7$ µM and a $V_{max}$ of $675.3\pm53.7$ pkat/mg. The $k_{cat}$ value was $0.03\pm0.003$ s$^{-1}$ and kcat/Km was $7.5\pm0.478$e-6 s$^{-1}$ mM$^{-1}$. $K_m$, $k_{cat}$ and $k_{cat}/K_m$ values of MhTPS1 were similar to those of other plant sesqui-TPS enzymes such as (E)-β-caryophyllene synthase from *Artemisia annua* (Cai et al., 2002).

Figure 6A:
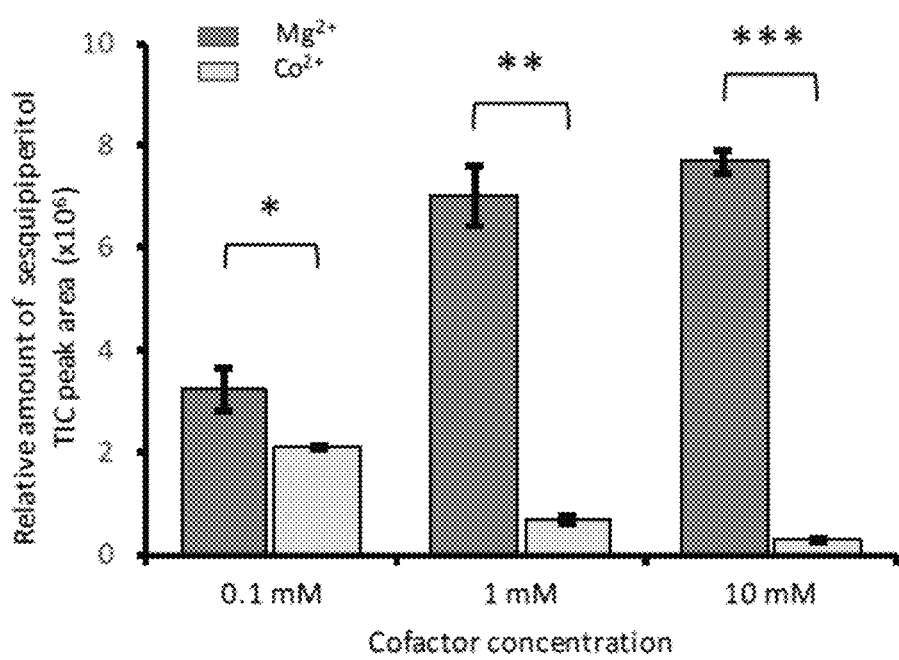
FIGS. 6A-6B—Relative amount of sesquipiperitol produced by MhTPS under various conditions. Relative amount of sesquipiperitol produced by MhTPS under different cofactor (FIG. 6A) and pH conditions (FIG. 6B) using (E,E)-FPP as substrate. Student's t-test, (FIG. 6A) *P<0.05, P<0.005, *P<. 0005, (FIG. 6B) *P<0.05, **P<0.01.
Figure 6B:
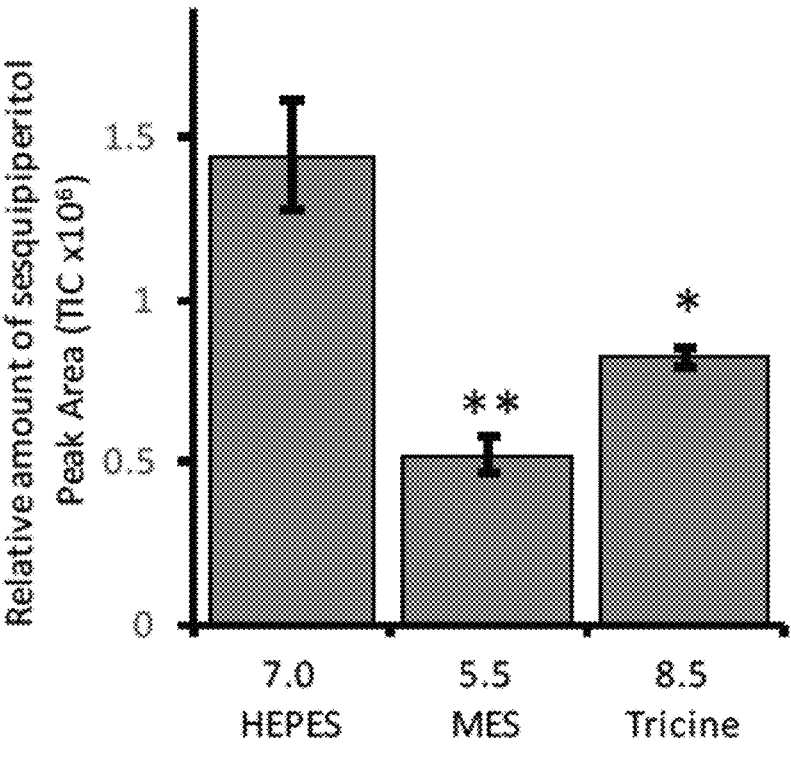

Recombinant MhTPS1 did not produce zingiberenol as a possible precursor of murgantiol. It was tested whether changes in co-factor type or concentration or modifications of pH conditions would modify the enzymatic product profile and activity. No change in product specificity was observed when Mg$^{2+}$ was substituted with Co$^{2+}$, although this metal ion has been found to modify product specificity of a GPP/FPP synthase in the leaf beetle *Phaedon cochleariae* (PcIDS-1) (Frick et al., 2013). Activity increased by approximately 2-fold between 0.1 and 10 mM Mg$^{2+}$ while the opposite was the case for Co$^{2+}$ (FIG. 6A). Activity was highest at pH 7 (FIG. 6B) and no change in product outcome was found under lower or higher pH conditions.

Figure 7:
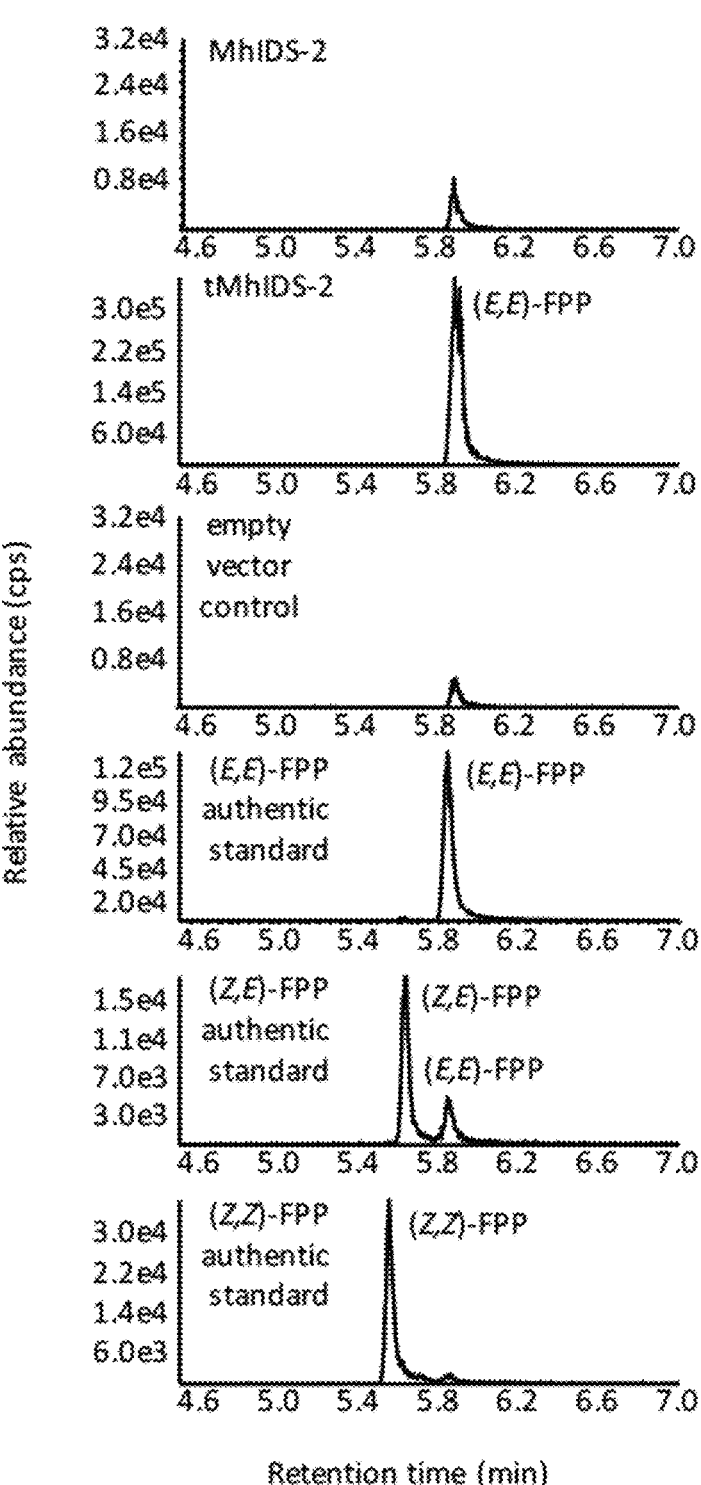
FIG. 7—Prenyltransferase assays of MhIDS-2 and tMhIDS-2. LC-MS chromatograms after functional assays of MhIDS-2 and tMhIDS-2. 50 µM IPP and 50 µM DMAPP were provided as substrates.

In contrast to MhTPS1, partially purified recombinant MhIDS-2 protein did not show any TPS activity when assayed with different isomers of FPP or GPP as substrates. Instead, MhIDS-2 produced (E,E)-FPP from IPP and DMAPP indicating that this protein functions as a trans-IDS (FIG. 7). The enzyme was unable to synthesize any other isomer of FPP, which suggests that (E,E)-FPP is the main isomeric form produced by *M. histrionica* (FIG. 7). Removal of a putative transit peptide (M1-S58) (FIGS. 2A-2C) led to a substantially higher production of (E,E)-FPP by the truncated MhIDS-2 protein (FIG. 7). Because of its FPPS activity, we named IDS-2 hereinafter as MhFPPS. Absolute Configuration of Sesquipiperitol.

Figure 13A:
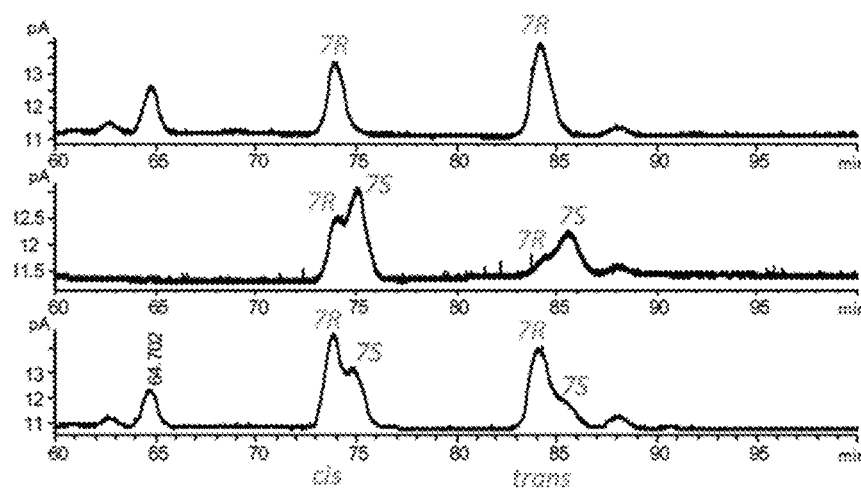
FIGS. 13A-13C—Determination of the absolute configuration of sesquipiperitol.
Figure 13B:
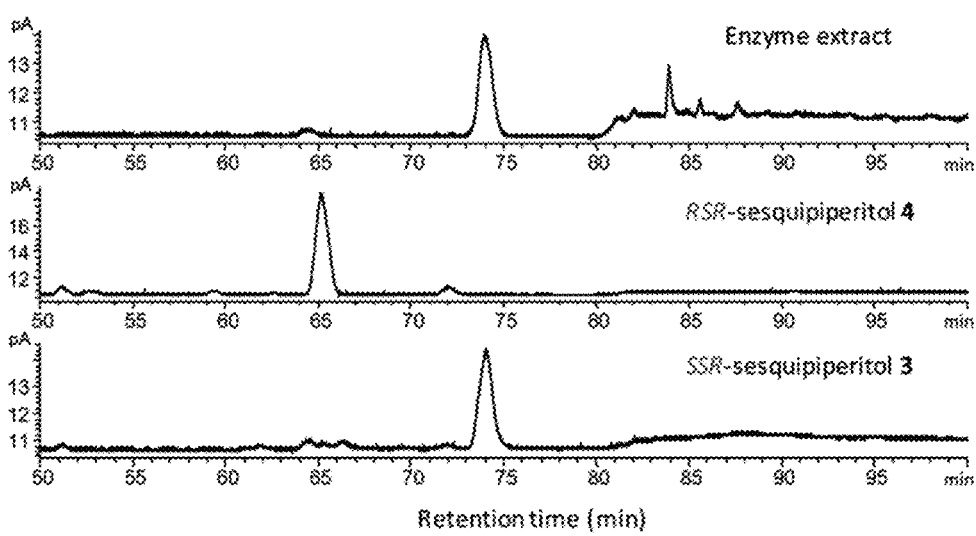

To further support the role of sesquipiperitol as a precursor of murgantiol, the stereospecific configuration of sesquipiperitol at C-6 and C-7 was determined, which was predicted to be the same as that of murgantiol (see also e.g. Methods and FIGS. 4A-4D, 5A-5C and 13A-13C). Oxidation of enzymatically produced sesquipiperitol to sesquipiperitone concluded a relative 6S,7R or 6R,7S configuration (FIG. 6B) Further conversion of sesquipiperitol to bisabolane determined the configuration at C-7 to be (R) (FIG. 13A). This result unambiguously confirmed a 6S,7R configuration of sesquipiperitol, which is identical to the C-6, C-7 configuration of murgantiol. Chiral GC analysis and 2D NMR recordings determined an(S) configuration at C-1 (see e.g., Methods, FIGS. 13B-13C).

Figure 4C:
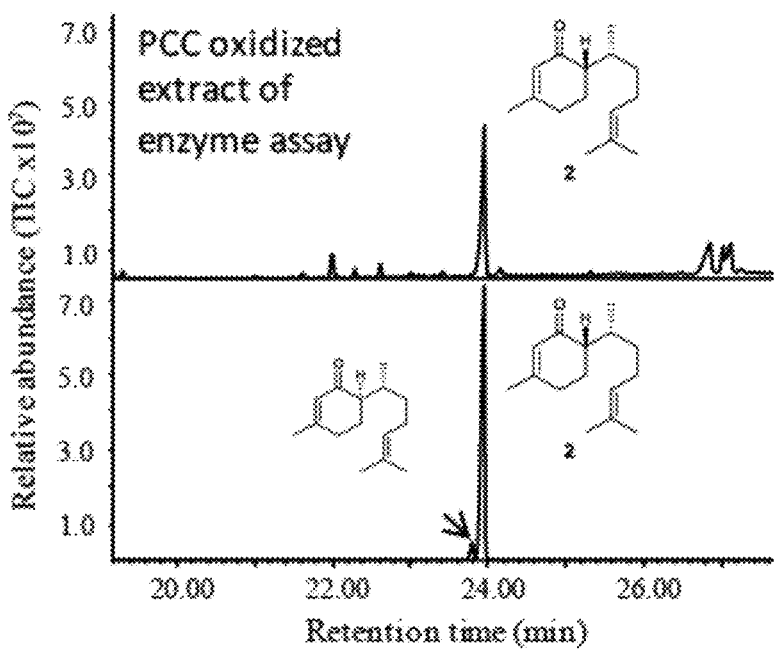
Figure 5A:
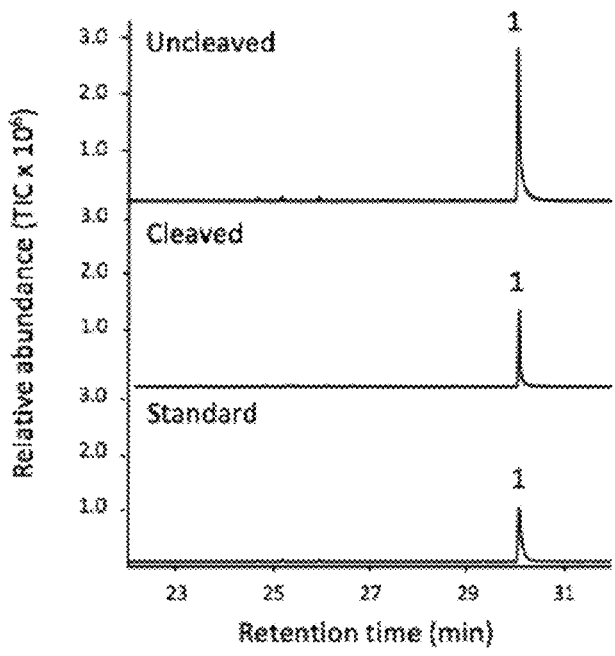
FIGS. 5A-5C—Functional assays of MhTPS.
Figure 5B:
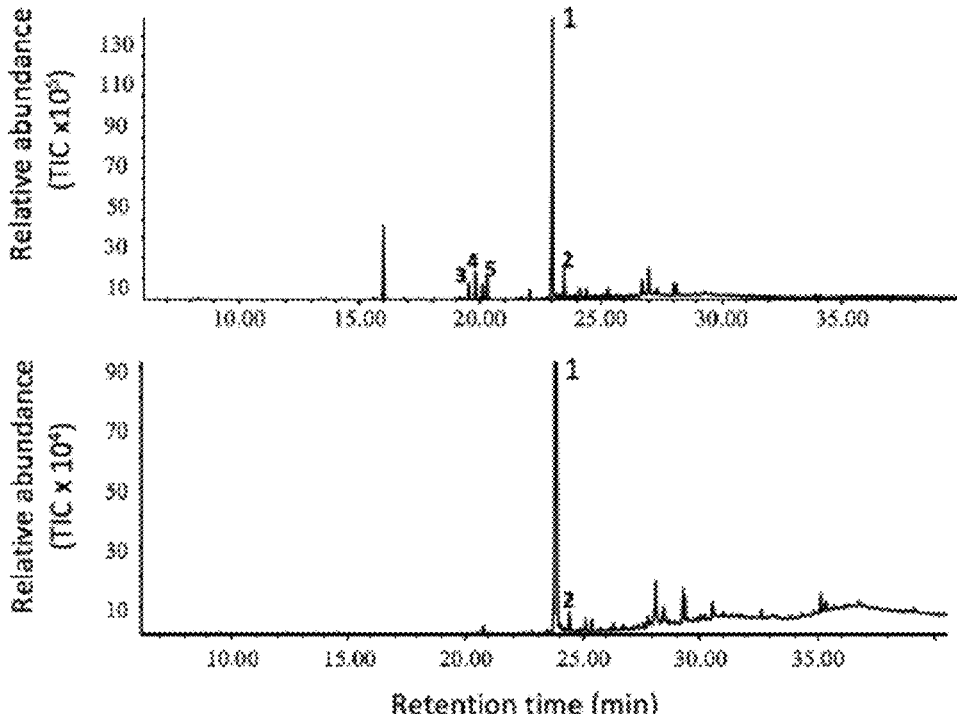
Figure 5C:
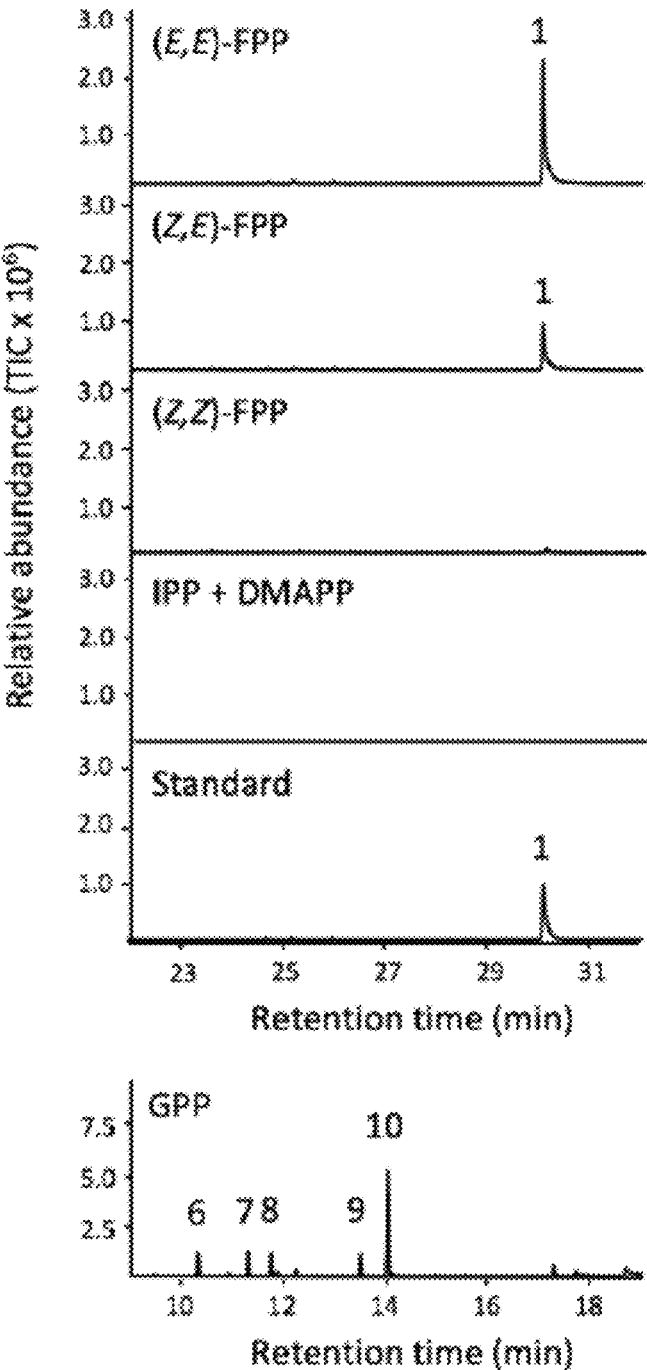

As shown in FIG. 4C, oxidation of sesquipiperitol produced by MhTPS led to 6S,7R-sesquipiperitone 2 but not 6R,7R-sesquipiperitone. However, the oxidation product was indistinguishable by GC retention time and mass-spectrum from 6R,7S-sesquipiperitone prepared analo-gously from 7S-zingiberenol (results not shown). 6S,7R- and 6R,7S-sesquipiperitones were inseparable on chiral Hydrodex-β-6-TBDMS and Lypodex-G columns. To deter-mine the absolute configuration of enzymatically produced sesquipiperitol at C-7 a conversion to bisabolane was per-formed (Borges et al., 2007). Dehydration of sesquipiperitol with phosphorous oxychloride formed bisabolatrienes, which were hydrogenated in the presence of Adams (PtO2) catalyst to bisabolane 5 (FIGS. 4A and 13A). The same dehydration/hydrogenation sequence was conducted with (7R)- and (7S)-zingiberenols (Khrimian et al., 2014b) to make bisabolane standards (FIG. 13A). Chiral GC analysis showed a partial separation of pre-mixed (7R)- and (7S)-bisabolane standards on a Hydrodex β-6TBDM column (dehydration/hydrogenation eliminates chiralities at C-1 and C-6, but creates 1,4-substituted cis/trans-bisabolanes) (FIG. 13A). Co-injection of the bisabolanes derived from enzy-matically produced sesquipiperitol with the bisabolane stan-dards resulted in an alignment with (7R)-bisabolane (FIG. 13A). This result proved a 7R configuration of the MhTPS sesquipiperitol product. Since the relative configuration of this compound was found to be either 6S,7R, or 6R,7S, the absolute configuration at C-6 has to be(S).

MhTPS Expression is Sex-Specific and Localized to the Abdominal Sternites of Mature Male *M. histrionica*.

Figure 8A:
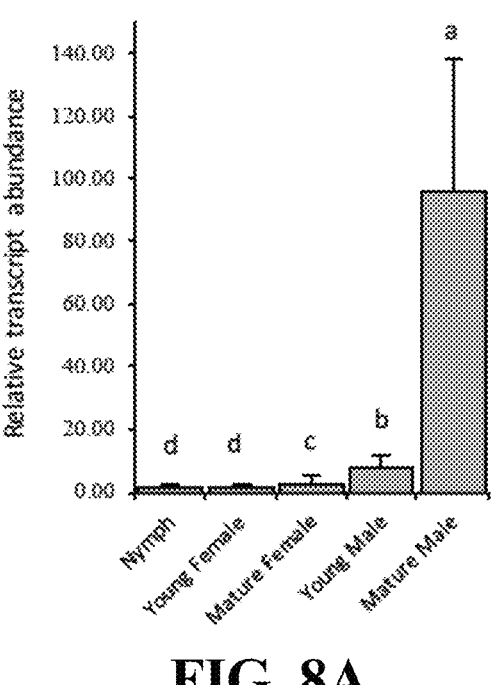
FIGS. 8A-8B—Relative transcript abundance of MhTPS in M. histrionica determined by qRT-PCR.
Figure 8B:
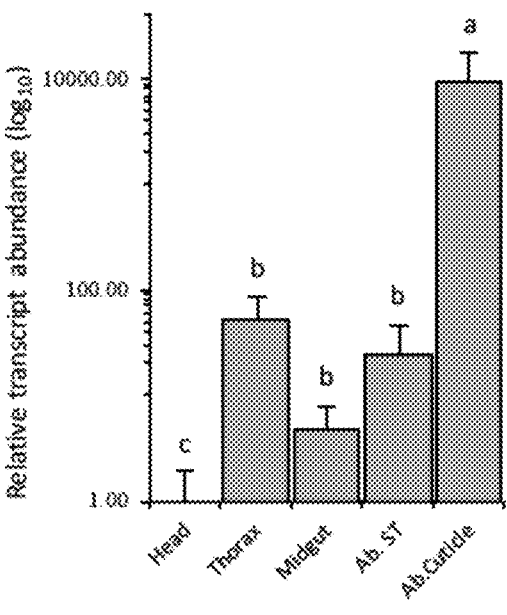

Transcript abundance of MhTPS and MhFPPS was com-pared between different sexes, developmental stages, and tissues by using RT-PCR and quantitative RT-PCR analysis. In agreement with expression levels determined by tran-scriptome analysis (Sparks et al., 2017), MhTPS was expressed at significantly higher levels in mature males than females (FIGS. 8A and 11A). MhTPS transcript abundance also significantly exceeded those of nymphs and immature males, which do not emit murgantiol (FIG. 8A). As expected from transcriptome data (Sparks et al., 2017), MhFPPS showed comparatively higher expression than MhTPS in mature females (FIGS. 8A and 11A). Tissue-specific expres-sion of MhTPS was localized to the tissue lining the cuticle of the abdominal sternites of mature males, while only low expression levels of MhTPS were observed in the fat body and mid gut (FIGS. 8B and 11B).

Figure 13C:
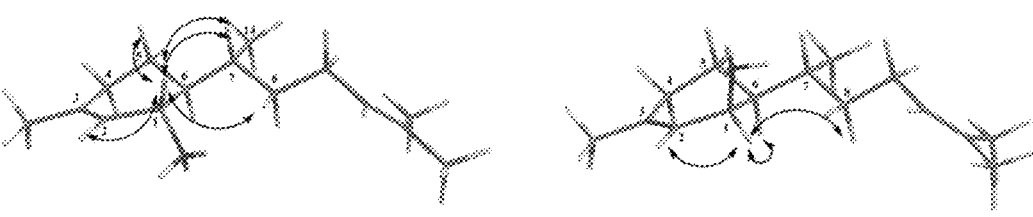

To determine the configuration of enzymatically derived sesquipiperitol at C-1, other chiral GC columns for the separation of epimeric alcohols formed by reduction of the carbonyl group in ketone 2 was examined (FIG. 4A). Retention times of epimeric sesquipiperitol 3 and 4 were substantially different on Hydrodex β-6TBDM (Supplemen-tal FIG. 2.6B) and the late eluting peak matched the enzy-matically produced sesquipiperitol. The stereochemistry of this sesquipiperitol as epimer 3 was proven by NMR record-ings (FIGS. 17 and 13C). NOESY (FIG. 13C) showed cis orientation of H-1 and H-6 in 4 and trans orientation of these protons in alcohol 3. This proved 1S configuration of alcohol 3 and, hence, 1S,6S,7R configuration for synthetic 3 and MhTPS produced sesquipiperitol (FIG. 13C). Thus, the enzymatically derived sesquipiperitol was identified as (−)-(1S,6S,7R)-2,10-bisaboladien-1-ol. $^1$H and $^{13}$C NMR data of sesquipiperitols 3 and 4 were in accord with those of monoterpene analogs, cis- and trans-piperitols (Cantin et al., 2001) providing additional proof for stereochemical assign-ments.

Sesquipiperitol Synthase Activity in *M. histrionica* Protein Extracts.

Figure 9A:
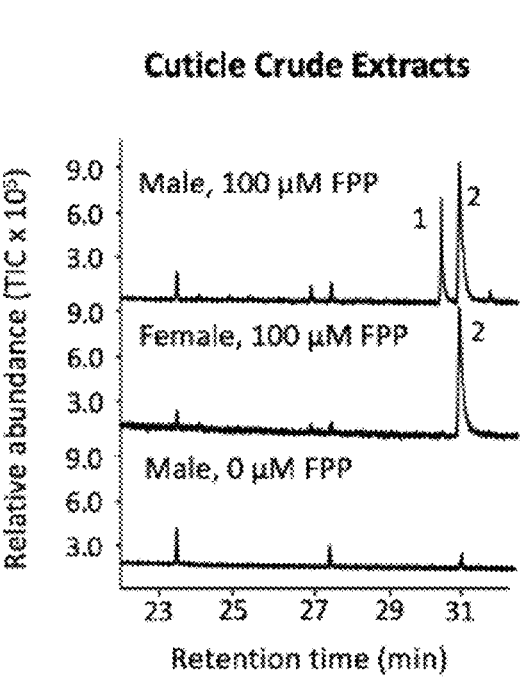
FIGS. 9A-9B—Terpene synthase activity in crude protein extracts of M. histrionica by sex (FIG. 9A) and tissues (FIG. 9B).
Figure 9B:
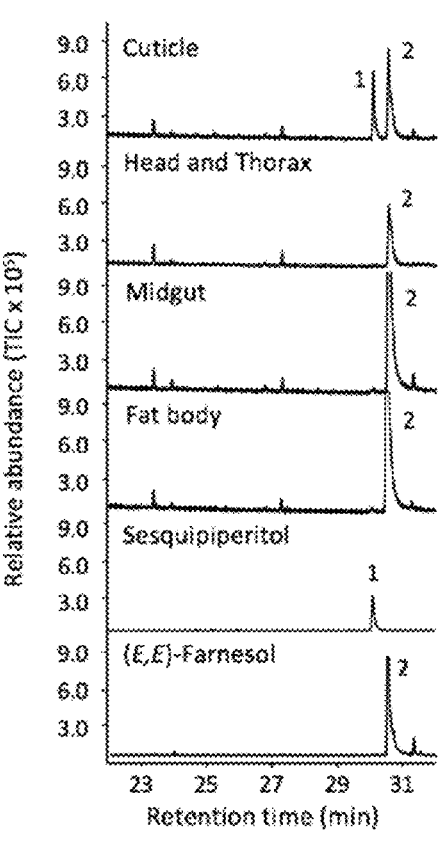

To further confirm that the enzymatic activity for the formation of sesquipiperitol is present in protein lysates of *M. histrionica*, protein was extracted from the cuticle-specific tissue of whole mature male bugs and incubated the lysate with (E,E)-FPP. GC-MS analysis of hexane extracts obtained from the aqueous phase of the assay demonstrated the specific formation of sesquipiperitol in the presence of (E,E)-FPP (FIG. 9A). By contrast, protein extracts from mature females did not produce sesquipiperitol confirming the male specific production of this compound (FIG. 9A). Sesquipiperitol was not synthesized in extracts of the male head and thorax, fat body, or gut tissue when incubated with (E,E)-FPP, which further supports the tissue-specificity of this enzymatic reaction (FIG. 9B). Further conversion of sesquipiperitol or the putative downstream intermediate zingiberenol to murgantiol or other products was found, suggesting that possible downstream enzymatic activities were not supported or potentially inhibited under our selected extraction and assay conditions.

Verification of In Vivo MhTPS Function in Murgantiol Biosynthesis.

To verify the in vivo role of MhTPS in murgantiol biosynthesis, we injected males 3-5 d post eclosion with MhTPS-derived sequence-specific dsRNA. Transcript abun-dance was significantly reduced 13-15 days post injection compared with males injected with lacZ and non-injected males (by >80%; P<0.0001) (FIG. 10A). Pheromone analy-sis of males at the same time post injection showed signifi-cantly lower emission of murgantiol in MhTPS dsRNA males than control males (FIG. 10B) confirming a substan-tial role of MhTPS in murgantiol biosynthesis.

Sequence Comparison and Phylogenetic Analysis of *M. histrionica* TPS and FPPS.

Figure 12:
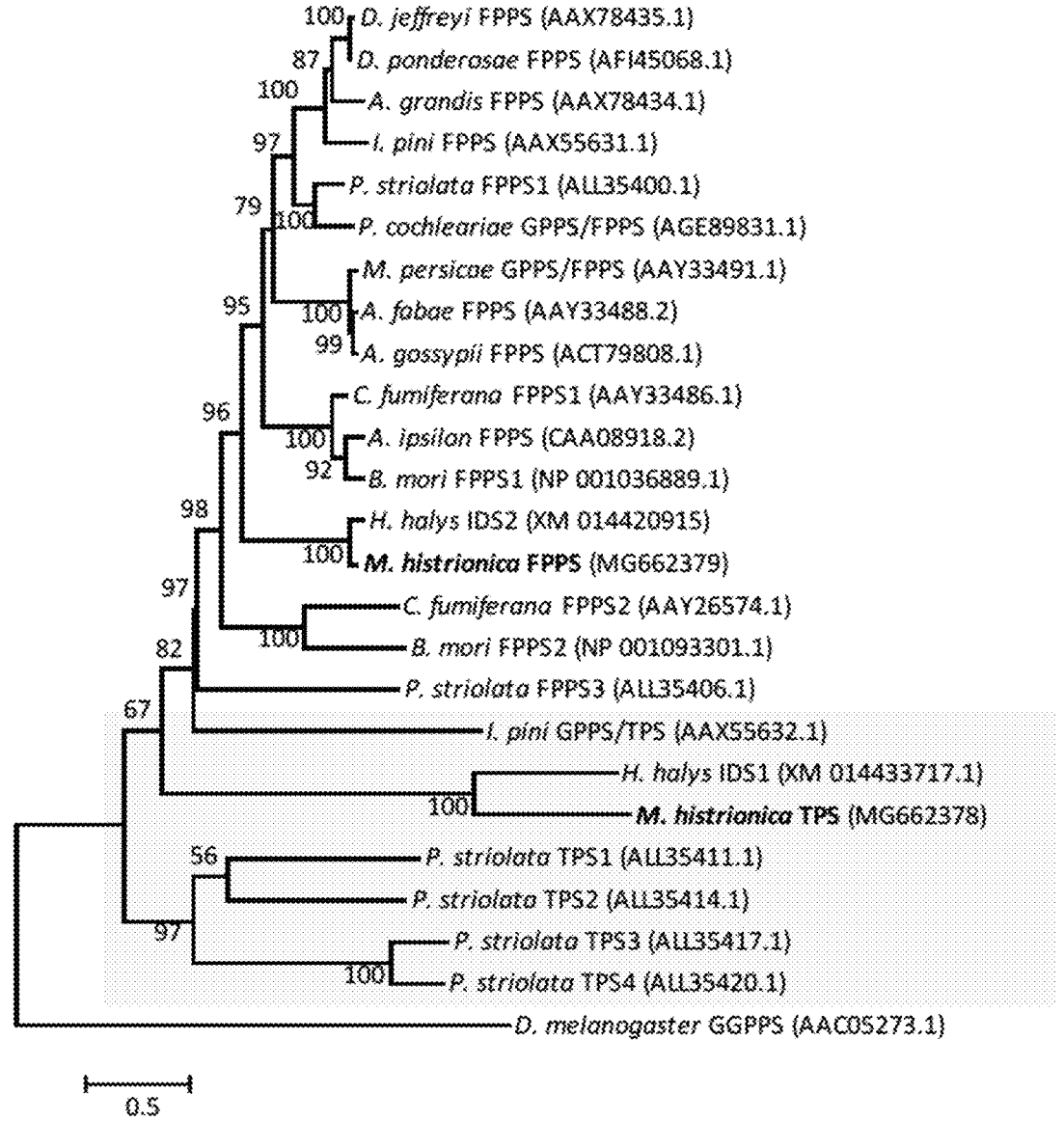
FIG. 12—Majority-rule cladogram inferred from maximum-likelihood analysis of FPPS and TPS enzymes of M. histrionica (bold) with related IDS proteins of H. halys, TPS and IDS proteins of P. striolata, GPPS/TPS of I. pini and other insect trans-(GPPS)/FPPS proteins. The Maximum Likelihood method was based on the Le Gascuel 2008 (LG G+I) model. Bootstrap values (n=1000 replicates) are shown next to each node. The tree is drawn to scale, with branch lengths measured in the number of substitutions per site. Proteins with known or putative TPS activity are highlighted by the grey box. The tree was rooted using a GGPPS from D. melanogaster. Full species names are listed in ∫.
Figure 14:
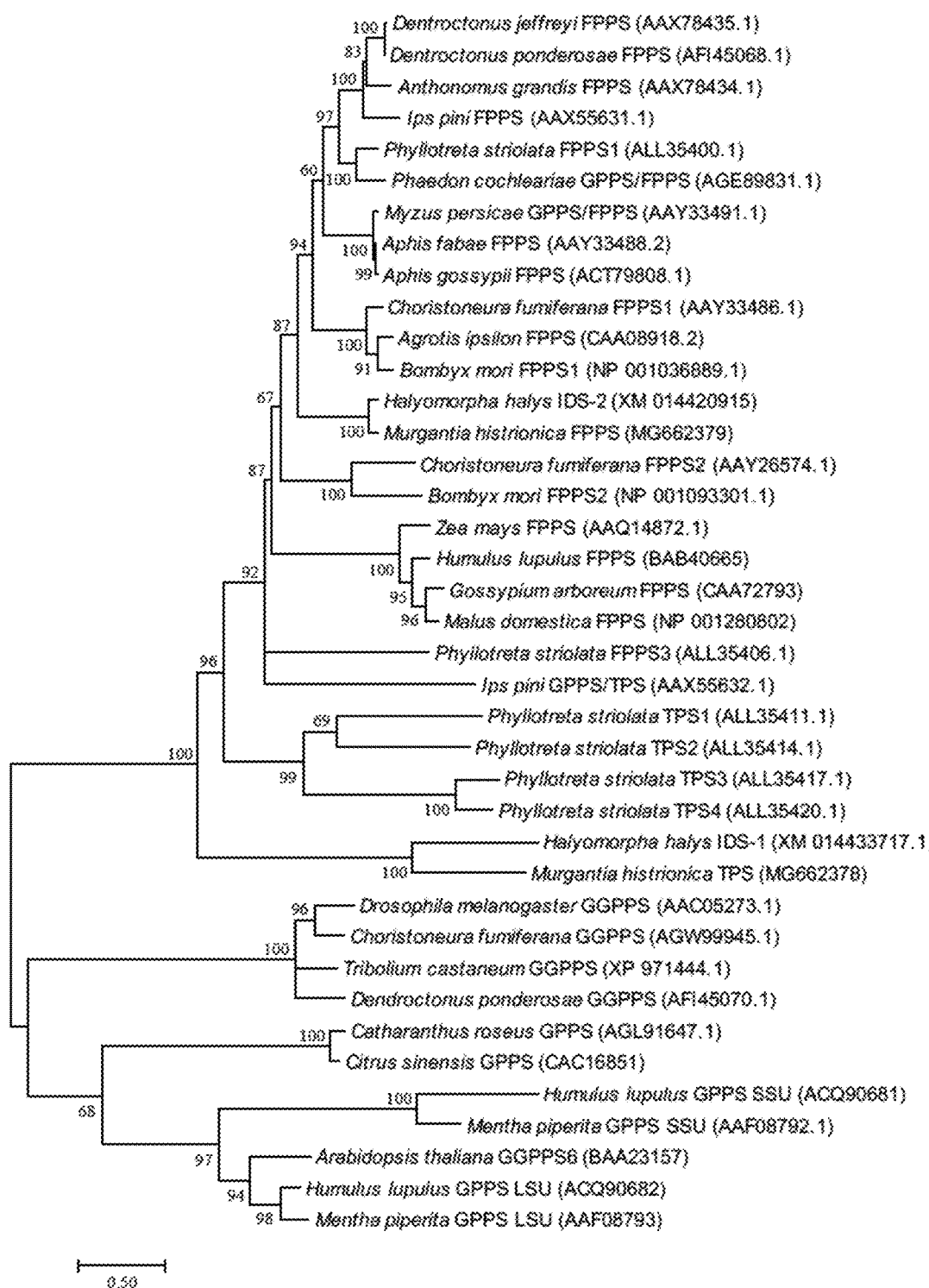
FIG. 14—Majority-rule phylogram inferred from maximum-likelihood analysis of GPPS, FPPS, GGPPS and TPS enzymes of insects and plants. The Maximum Likelihood method was based on the Le Gascuel 2008 (LG G+I) model. Bootstrap values (n=1000 replicates) are shown next to each node. The tree is drawn to scale, with branch lengths measured in the number of substitutions per site.

A phylogenetic analysis based on maximum-likelihood was performed to assess the evolutionary relationship of *M. histrionica* TPS and FPPS with other insect IDS and TPS enzymes (FIG. 12). The data set included trans-IDS proteins from Coleoptera, Lepidoptera, and Hemiptera with known GPPS/FPPS or FPPS activities, the GPPS/TPS from *I. pini*, and the recently characterized IDS and TPS enzymes from *P. striolata*. To compare the relationship of the *M. histri-onica* enzymes with similar enzymes in the Pentatomidae, we retrieved IDS-like sequences from the brown mar-morated stink bug *Halyomorpha halys* based on publicly available transcriptome data sets of this insect (Sparks et al., 2014). For *H. halys* two IDS-like sequences were identified, of which the IDS-1 sequence clusters with *M. histrionica* TPS (MG662378) (38.3% sequence identity) suggesting that *H. halys* IDS-1 might be a functional TPS enzyme. *M. histrionica* TPS and *H. halys* IDS-1 build a clade separated from *I. pini* GPPS/TPS, a cis-IDS (FPPS3) and the TPS clade of *P. striolata* (FIG. 12). *M. histrionica* FPPS and the more closely related *H. halys* IDS-2 protein are positioned in a larger clade of insect proteins with bonafide trans-FPPS or GPPS/FPPS activity including those from Coleoptera, Lepidoptera, and Hemiptera (FIG. 12). A broader phyloge-netic analysis including insect GGPPSs and plant trans-IDS proteins supports an evolutionary origin of the pentatomid TPSs together with the Coleopteran TPSs from a trans-IDS progenitor that gave rise to proteins with GPPS/FPPS or TPS activities (FIG. 14).

Figure 15A:
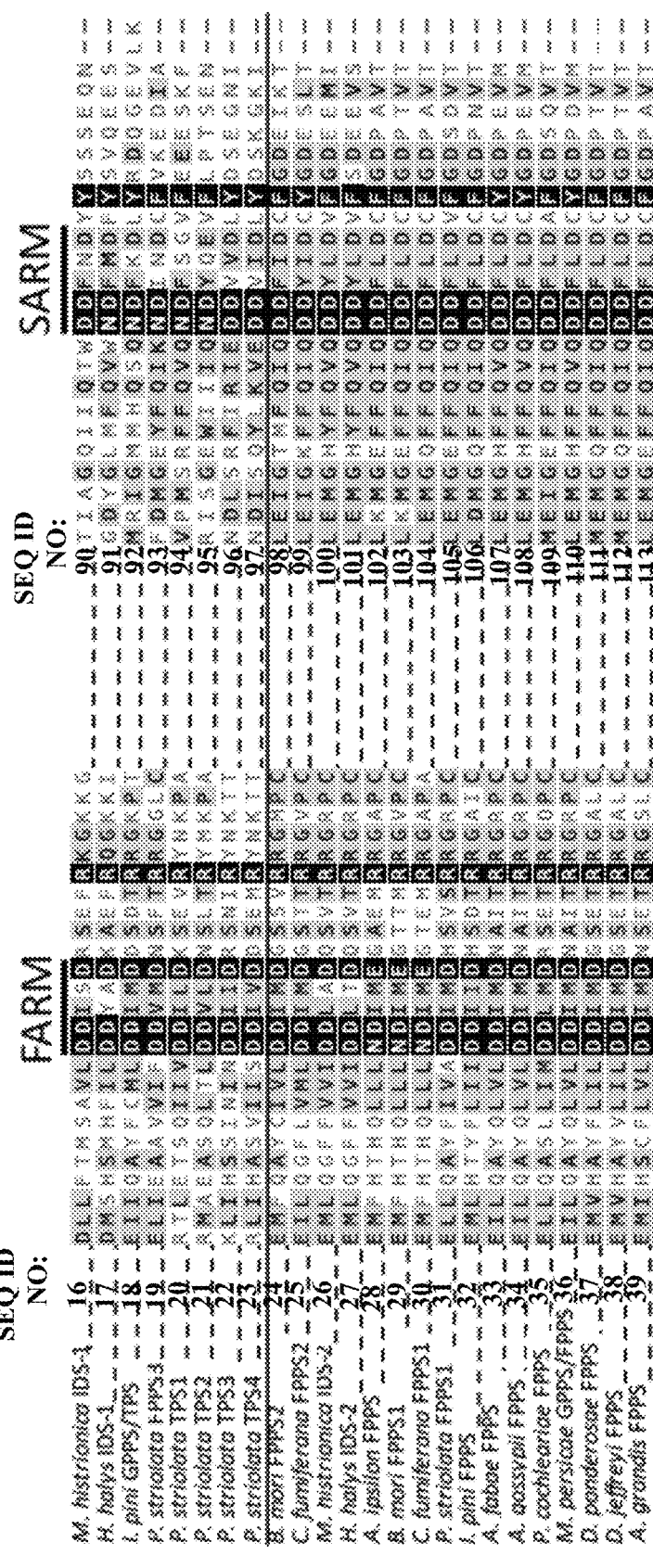

Sequence comparisons between insect IDS and IDS-derived TPS proteins showed distinct variations in the conserved first aspartate rich motif (FARM) and second aspartate rich motif (SARM). Both motifs are involved in the coordinated binding of $Mg^{2+}$ ions with the allylic substrate to initiate catalysis through carbocation formation (FIGS. 15A-15B). In comparison to bona fide trans-IDS proteins, the TPS proteins substitute aromatic with non-aromatic amino acid residues at positions 4 and 5 upstream of the FARM. Additional substitutions were observed for the first or last aspartate residue in the SARM of several TPS enzymes (FIGS. 15A-15B).

Chemical Identification of Sesquipiperitol.

The identification of sesquipiperitol by synthesis and chemical transformations followed the scheme shown in FIG. 4A. Hagiwara et al. (Hagiwara et al., 2002) reported oxidation of zingiberenols to sesquipiperitones by piridinium chlorochromate (PCC) by a virtue of an allylic isomerization of the tertiary alcohol by mildly acidic PCC to a secondary one prior to the oxidation. Application of this procedure starting with a ~1:1 mixture of SSR-zingiberenol and RRR-zingiberenol led to the production of RR- and SR-sesquipiperitones with baseline separation on an HP-MS GC column (FIG. 4B). Oxidation of SSR-zingiberenol 1 of 95:5 diastereomeric ratio resulted in the isolation of SR-sesquipiperitone 2 at approximately the same stereoisomeric purity (FIG. 4B) confirming that during allylic isomerization-oxidation carbons at positions 6 and 7 were unaffected.

PCC oxidation with the hexane extract from recombinant MhIDS-1 (MhTPS) activity assays resulted in the formation of a compound that matched 6S,7R-sesquipiperitone 2 but not 6R,7R-sesquipiperitone based on GC retention time and mass spectral fragmentation (FIG. 4C). Because the compound of interest in the hexane extract was not zingiberenol, an oxidative introduction of an oxo-group at position 1 would arise from the corresponding secondary alcohol, which is sesquipiperitol.

Figure 4D:
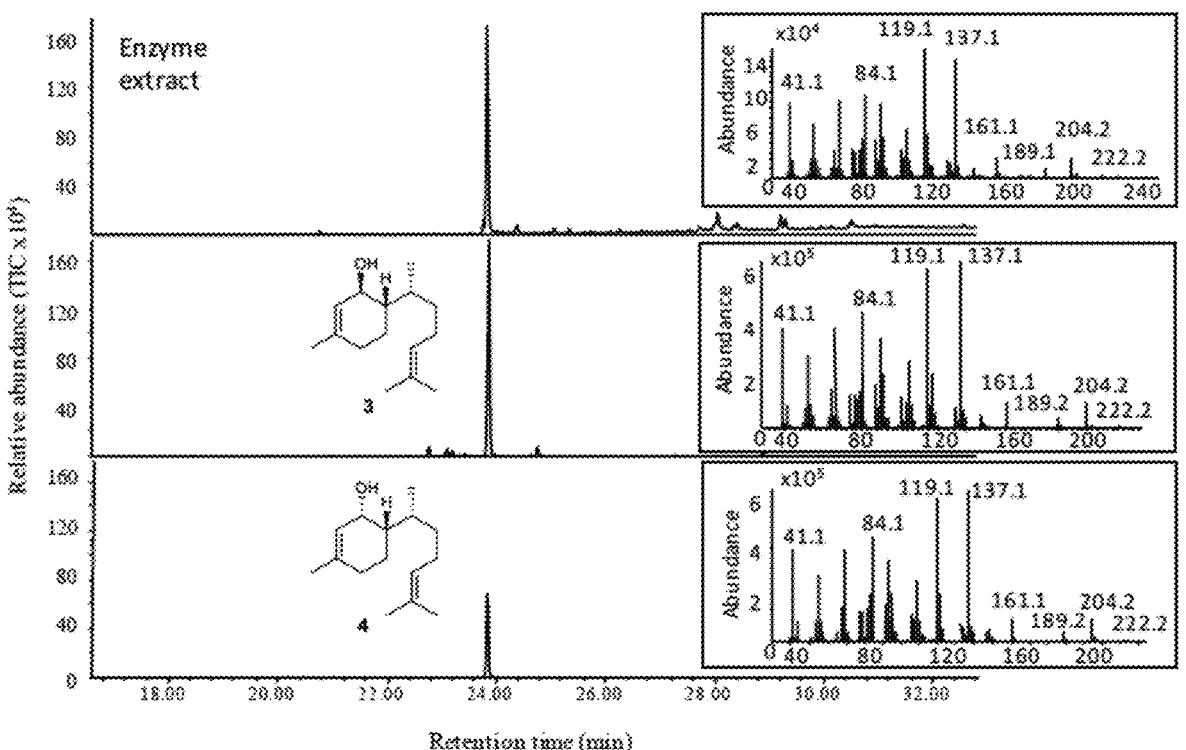

Reduction of the carbonyl group in 2 with lithium aluminum hydride provided a final proof for sesquipiperitol being the major MhIDS-1 (MhTPS) product. Treatment of ketone 2 with lithium aluminum hydride in ether resulted in the formation of epimeric alcohols 3 and 4 (FIGS. 4A and 4D), separated by chromatography on $SiO_2$. GC retention times of these alcohols were almost indistinguishable on the HP-5 MS column, yet matching that of the main MhIDS-1 (MhTPS) product (FIG. 4D). The mass spectrum of this compound was nearly identical to those of alcohols 3 and 4 thus proving its structure as sesquipiperitol (FIG. 4D).

Discussion

IDS-Type Terpene Synthases Evolved in the Hemiptera

This Example can demonstrate that in pentatomids (order Hemiptera) IDS-type proteins with TPS activity are involved in the biosynthesis of aggregation pheromones. To date, IDS-type TPSs with similar functions have only been characterized in the Coleopteran species *I. pini* and *P. striolata* (Beran et al., 2016; Gilg et al., 2005; Gilg et al., 2009). The finding of a functional TPS in *M. histrionica* suggests that adaptations of terpene specialized metabolism for intra-specific communication have occurred in several lineages throughout insect evolution. Phylogenetic analysis indicates that pentatomid and coleopteran TPSs are derived from a trans-IDS progenitor and diverged early from true trans-IDS enzymes. The separate clustering of pentatomid TPSs from *P. striolata* and *I. pini* TPSs (FIG. 12) suggests that proteins with TPS activity might have emerged independently in these and other insect taxa. Phylogenetic comparisons with additional TPSs from other insect lineages will be necessary to further support this hypothesis.

Figures 16A, 16B:
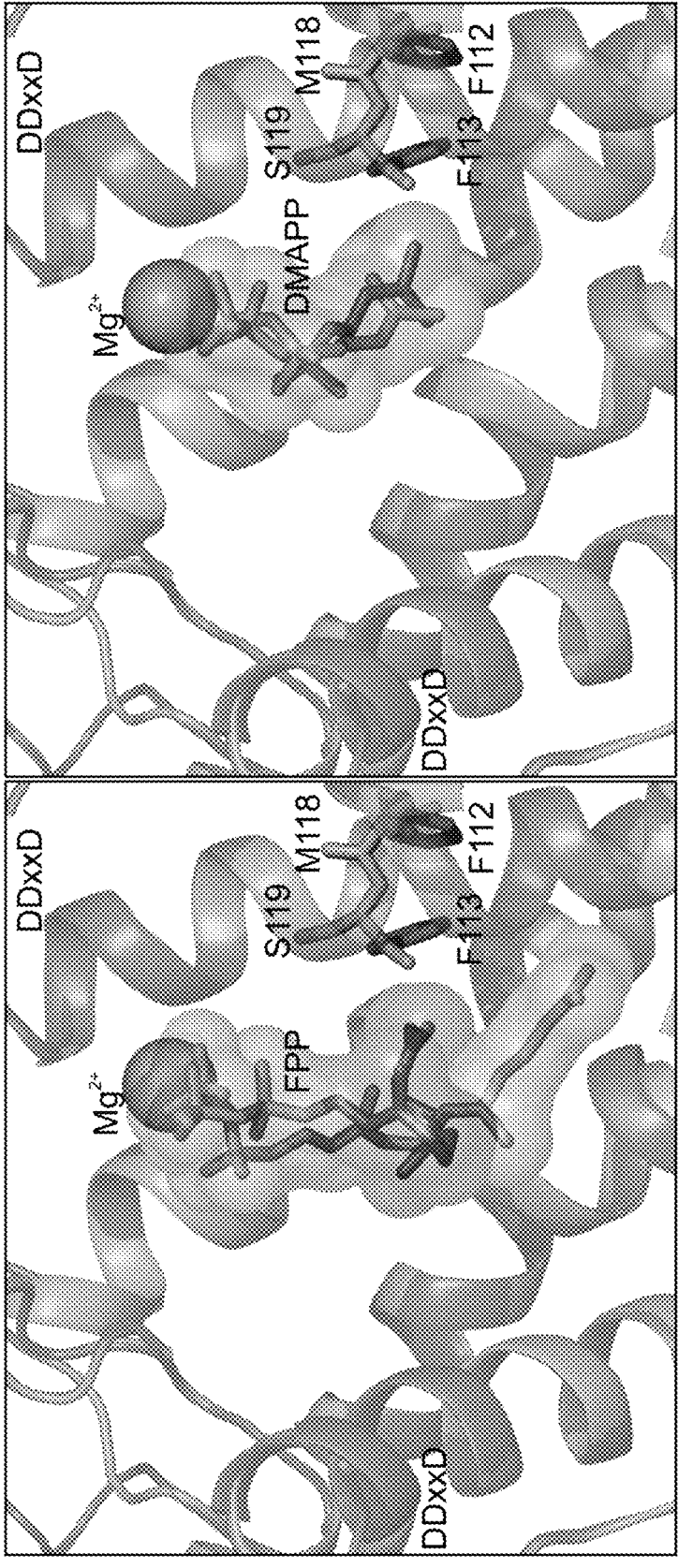
Figure 16C:
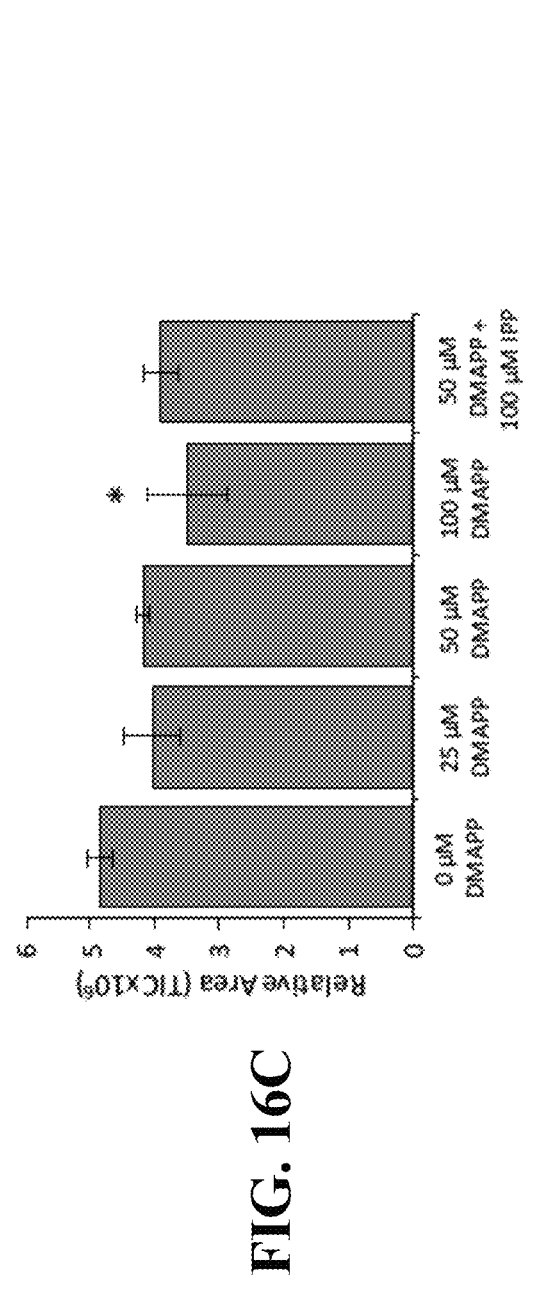

Sequence comparisons were performed between insect IDS and IDS-derived TPS proteins to examine possible structural differences underlying changes in enzyme activity (FIGS. 15A-15B). Substitutions of aromatic with non-aromatic amino acid residues were observed at positions 4 and 5 upstream of the conserved FARM. To further determine whether these substitutions affect the position of (E,E)-FPP as a substrate or product, we positioned (E,E)-FPP in the active site of crystallized *Gallus gallus* FPPS and a *M. histrionica* TPS homology model. This comparative positioning indicates that the substitutions upstream of the FARM (GgFPPS F112, F113-MhTPS M118, S119) are likely to cause a different orientation of the prenyl side chain of the FPP substrate (FIGS. 16A-16D). This repositioning of the substrate may be critical for supporting a subsequent cyclization to terpene products. Docking of DMAPP in both MhTPS and GgFPPS models did not result in different positions of this allylic diphosphate (FIG. 16B). However, no substantial inhibitory effect was observed for DMAPP in the MhTPS-catalyzed reaction of (E,E)-FPP to sesquipiperitol indicating a limited affinity of the enzyme for DMAPP (FIG. 16C). Substitutions of aromatic amino acids upstream of the FARM are also present in long-chain trans-IDS enzymes to facilitate the synthesis of isoprenyl diphosphate products with extended prenyl chains ($\geq$C20) (Wallrapp et al., 2013). However, these modifications alone do not confer terpene cyclase activity. Therefore, the evolutionary transition from trans-IDS to TPS enzymes likely required a combination of modifications at the FARM and/or SARM motifs as observed in the TPS proteins in addition to other residue substitutions to change substrate affinities and specificities for DMAPP and IPP and gain a cyclization function following the binding of (E,E)-FPP as a single allylic substrate.

*M. histrionica* TPS Functions as a Sesquiterpene Alcohol Synthase

Figure 16D:
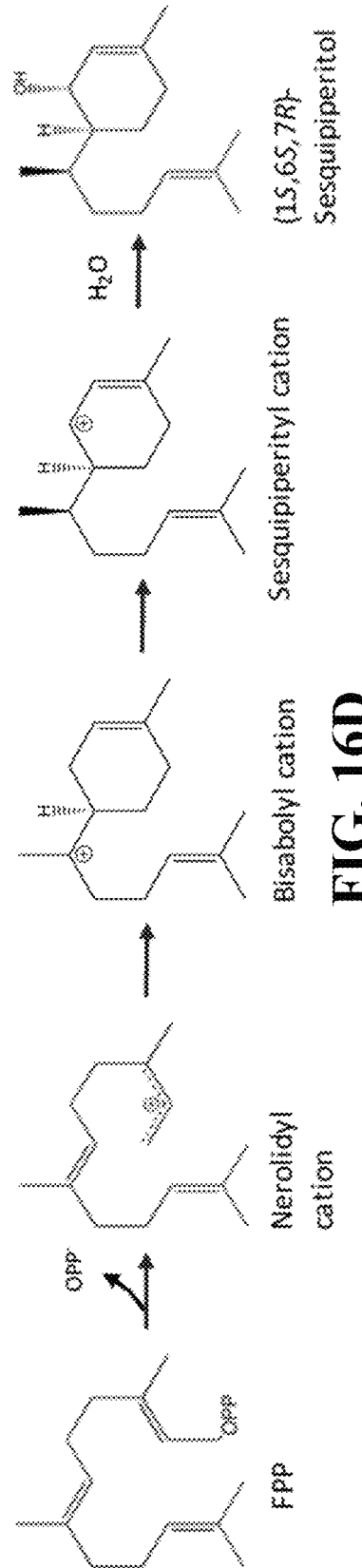

It was observed that the TPS activity associated with the recombinant MhTPS enzyme and with crude lysates of male *M. histrionica* stereospecifically converts (E,E)-FPP to the (1S,6S,7R) isomer of sesquipiperitol. The synthesis of sesquipiperitol most likely proceeds by formation of a bisabolyl cation followed by a hydride shift and subsequent quenching of the carbocation by water (FIG. 16D). The 6S,7R configuration of sesquipiperitol corroborates its function as an intermediate in the formation of the murgantiol stereoisomers. An RNAi-based approach further confirmed the role of the MhTPS-catalyzed reaction in murgantiol biosynthesis. 10,11-Epoxy-1-bisabolen-3-ol stereoisomers also constitute pheromone components of the brown marmorated stink bug *H. halys* (Khrimian et al., 2014b) suggesting that the IDS-1 gene of *H. halys* has a function similar to that of MhTPS. Moreover, related TPS activities presumably operate in other pentatomids to make bisabolene type sex pheromones or their corresponding precursors such as isomers of zingiberenol in the rice stalk stink bug, *Tibraca limbativentris*, and the rice stink bug *Oebalus poecilus* (Borges et al., 2006; de Oliveira et al., 2013), the sesquiterpenes alpha-curcumene, zingiberene, and beta-sesquiphellandrene in the red-shouldered stink bug *Thyanta pallidovirens* (McBrien et al., 2002) or (Z)-α-bisabolene epoxides in the Southern green stink bug *Nezara viridula* (Aldrich et al., 1993; Aldrich et al., 1987). Until our finding of sesquipiperitol as an enzymatic product in *M. histrionica*, this terpenoid and its biosynthesis has not been reported in animals. The occurrence of sesquipiperitol as a natural product in different plant species (Bohlmann et al., 1984; Cool, 1996; Sy and Brown, 1997) suggests convergent biosynthetic evolution of this compound by both plant- and insect derived TPS proteins. Since several terpenes are used as identical semiochemicals by both plants and insects, without being bound by theory it can be that similar processes of convergent evolution occurred in the synthesis of these compounds.

Terpene Formation in *M. histrionica* is Highly Sex- and Tissue-Specific

According to the sex-specific release of murgantiol, the expression of the MhTPS gene and its corresponding enzyme activity was observed to be restricted to mature males. Furthermore, MhTPS activity is specifically localized to tissues lining the cuticle of the abdominal sternites. The formation of the MhTPS product and its conversion to murgantiol at this site would facilitate a direct release of the pheromone through pores in the abdominal cuticle. In *N. viridula*, mature males carry unicellular pheromone glands in cell layers at the ventral tissues of the abdomen, from where bisabolene-epoxides are released via ducts onto the abdominal surface (Cribb et al., 2006). While such glands have not been observed in *M. histrionica*, MhTPS activity may be located in specialized cells as precedented in the Diptera where, for example, oenocyte cells that produce cuticular hydrocarbons are in close association with the epidermis (Martins and Ramalho-Ortigao, 2012; Qiu et al., 2012). The site of synthesis of the terpene pheromone precursor in *M. histrionica* (abdominal cuticle) differs from that in males of the bark beetle Ips *pini* (anterior midgut). Given that pheromone-biosynthesizing genes show elevated expression in male *I. pini* anterior midguts (Blomquist et al., 2010; Gilg et al., 2005) these findings can suggest that the expression of TPS enzymes is closely associated with the site of pheromone biosynthesis, but that the pheromone biosynthetic pathway can occur in different tissues depending on the modes of release of the terpene end product.

Methods for Example 1

Two putative trans-IDS-like genes (MhIDS-1, MhIDS-2) identified in the transcriptome of *M. histrionica* were cloned by amplification of full length cDNAs from RNA extracted from adult males and insertion in the prokaryotic expression vector pEXP5-NT/TOPO, generating an N-terminal histidine tag. A truncated version of MhIDS-2 lacking a putative N-terminal transit peptide was cloned in the same vector, and a truncated version of MhIDS-1 was synthesized and cloned in the pET19b expression vector. For expression in insect cells, the full length MhIDS-1 cDNA was cloned without an N-terminal His-tag into the BaculoDirect vector. Recombinant partially purified MhIDS-1 and MhIDS-2 proteins expressed in *E. coli* and lysates of Sf9 cells expressing MhIDS-1 were tested for TPS and IDS activities and the reaction products analyzed by GC-MS and LC-MS/MS, respectively. Identification and determination of the stereospecific configuration of the main enzymatic product of MhIDS-1 (MhTPS), sesquipiperitol, were performed by synthesis and chemical transformations in combination with chiral GC and NMR analysis. Kinetic properties of MhTPS were examined in assays using [1-3H]-(E,E)-FPP as substrate. Developmental, sex- and tissue-specific expression of the MhTPS transcript or MhTPS activity were determined by quantitative RT-PCR (qRT-PCR) and TPS activity assays of crude lysates, respectively. MhTPS involvement in pheromone production was verified by RNAi by injecting young male *M. histrionica* with dsRNA of MhTPS or lacZ (control) followed by quantitative RT-PCR and pheromone analysis in the headspace. Phylogenetic analysis was performed using Maximum-Likelihood. Further details on organisms, experimental and analytical procedures, data analysis, phylogenetic analysis, protein homology modeling and substrate docking are provided in the Methods. Sequences in this Example have been deposited in the GenBank database (accession nos. MG662378.1-MhTPS and MG662379.1-MhFPPS).

Chemicals and Reagents

Unless otherwise specified, all reagents and solvents were purchased from Aldrich Chemical Co. [1-3H]-FPP (20 Ci/mmol) was obtained from American Radiolabeled Chemicals (St. Louis, MO). Preparation of terpene standards for mass spectral comparisons was performed in the following way: β-Sesquiphellandrene was prepared following McBrien et al. (McBrien et al., 2002). Zingiberene was isolated from ginger oil (Millar, 1998). 4-epi-β-Bisabolol was prepared according to Frater and Müller (Frater and Muller, 1989). γ-Curcumene was prepared by dehydration of 4-epi-β-bisabolol as described (Huang et al., 2000) and was isolated by argentation chromatography on 15% AgNO3-SiO2 eluting with hexane/ether, 20:1. GC-MS (m/z, %): 204 (38), 161 (12), 134 (17), 121 (71), 119 (100), 105 (42), 93 (55), 91 (39), 79 (22), 77 (22), 55 (17), 41 (25). Mass spectral data were in close agreement with those described (Andersen and Syrdal, 1970).

Insects

To establish a *M. histrionica* colony for RNAseq analysis and RNAi treatment, late instar nymphs were collected from insecticide-free vegetable plots in Beltsville, MD. Insects were held in cages (Bioquip) holding potted 4-8 week old collard (*Brassica oleracea* 'Champion') and mustard (*Brassica juncea* 'Southern Curled Giant') plants in climate controlled greenhouses (25+/−5° C., 16:8 h L: D, 65% RH). Newly eclosed adults were removed from cages three times weekly and moved to new cages holding potted plants, isolating males and females. Insects for tissue-specific qRT-PCR analysis were reared on 6-8 week old collard in the greenhouse (Virginia Tech) and in mesh cages (Bioquip) under LD photoperiod at 25° C. Insects were separated by sex and kept until the immature (2-3 day post molt) or mature (14-15 day post molt) adult stage.

Crude Protein Extracts of *M. histrionica*

Fifteen-day old virgin male and female *M. histrionica* were used to prepare crude protein extracts. Extracts were prepared separately for sexes and tissues. Insects were fixed with hexane and dissected in phosphate buffered saline, pH 7. Whole-bugs or tissues (head and thorax, cuticle, midgut, and fat body) were frozen in liquid nitrogen, pulverized with a mortar and pestle, and suspended in 25 mM HEPES, 5 mM MgCl2, 10% glycerol, pH 7. Protein concentration was determined with a Bradford Assay (Bio-rad) according to the manufacturer's instructions.

RNAseq and De Novo Transcriptome Assembly

Total RNA was extracted from individual immature (2-3 days post molt) and mature (14-15 days post molt), male and female *M. histrionica* using TRI Reagent (Ambion) according to the manufacturer's protocol. RNA was DNase treated with RQ1 DNase I (Promega) and purified using the RNeasy Plant Mini Kit (Qiagen). RNA quantity was determined using a Nanodrop ND-1000 spectrophotometer and RNA integrity was analyzed on a Bioanalyzer 2100 (Agilent). RNAseq was performed on an Illumina Genome Analyzer IIx at the Virginia Biocomplexity Institute, Virginia Tech, using paired-end (2×100 bp) reads. Sequences were trimmed using custom Perl scripts for adapter trimming and Btrim (Kong, 2011) for quality trimming resulting in 97-137 million reads per sample. De novo transcriptomes were assembled using Velvet.

Identification and Cloning of IDS Type Genes

Three putative isoprenyl diphosphate synthase like genes (MKIDS1-MhTPS, MhIDS2-MhFPPS, MhIDS3-

MhGGPPS) were identified with tblastn searches of transcriptome data retrieved at the USDA, Beltsville (Sparks et al., 2017) using functionally characterized insect trans-IDS or bifunctional IDS/TPS (*I. pini*) query sequences (FIG. 18). Primers were designed using Geneious (v. 7.1.9) to clone full-length MhTPS (MhTPS_1F/MhTPS_1158R), MhFPPS (MhFPPS_1F/MhFPPS_1218R) and MhGGPPS (MhGGPPS_269F/MhGGPPS_586R) (FIG. 19). Primers were also designed to clone MhFPPS without a predicted transit peptide sequence (tMhFPPS) (primers tMhFPPS_1F/MhFPPS_1218R). cDNAs were generated from total RNA using GoScript reverse transcriptase (Promega). Target sequences were amplified using Q5 proofreading DNA polymerase (New England Biolabs) and purified by gel extraction (New England Biolabs). Purified products were A-tailed using Taq DNA polymerase (New England Biolabs) and ligated into the pGEM-T Easy vector (Promega). Sequences were verified before cloning into expression vectors. The sequences of MhTPS and MhFPPS have been deposited in the Gen-Bank database under accession numbers MG662378 and MG662379 respectively.

Heterologous Expression of Recombinant MhFPPS

Full-length and truncated MhFPPS were amplified from pGEM-T Easy constructs with Q5 DNA polymerase and cloned into the pEXP5-NT/TOPO expression vector containing an N-terminal 6× histidine tag (Invitrogen). pEXP5-NT/TOPO constructs were transformed into *Escherichia coli* strain BL21 (DE3) pLysS (Life Technologies). *E. coli* cultures (50 mL) were grown at 37° C. and 220 rpm and induced with 1 mM IPTG after reaching an OD600 of 0.6. Upon induction, the cells were cultivated at 18° C. for another 18 h prior to collection by centrifugation for 15 min at 5,000 g at 4° C. Pellets were resuspended in 2 mL chilled extraction buffer (50 mM Tris HCl [pH 7.5], 20 mM imidazole, 300 mM NaCl, 10% glycerol (v/v), 5 mM MgCl2, 2 mM DTT) supplemented with 0.3 mg/mL lysozyme (AppliChem), 2.5 U/mL benzonase (Novagen) and proteinase inhibitors (Protease Inhibitor Mix HP, SERVA) and incubated at 4° C. for 30 min on ice. Cells were disrupted by a 4×30 s treatment with a sonicator (Bandelin UW2070, Berlin, Germany; 50%) and lysates centrifuged at 4° C. for 30 min at 15000×g to obtain soluble fractions. Recombinant proteins were purified using Ni-NTA Spin Columns (Qiagen, Hilden, Germany) according to the manufacturer's instructions. For enzymatic assays, the buffer was exchanged with 25 mM 3-(N-morpholino)-2-hydroxypropanesulfonic acid (MOPSO, pH 7.2, 10% [v/v] glycerol, 1 mM DTT, 5 mM $MgCl_2$) using PD-10 Desalting Columns (GE Healthcare Life Sciences).

Heterologous Expression of Recombinant MhTPS

For bacterial expression, the full-length MhTPS cDNA was amplified from the pGEM-T Easy construct (primers MhTPS_1F/MhTPS_1158R) and cloned into the pEXP5-NT/TOPO (Invitrogen) expression vector containing an N-terminal 6× histidine tag. A truncated form of MhTPS (stMhTPS, bp 136-1158) was designed and synthesized by GenScript (Piscataway, NJ) with codon optimization for *E. coli* and cloned into pET19b. Following transformation into *E. coli* BL21 (DE3) pLysS cells (Invitrogen), single colonies were selected at 18° C. on LB with ampicillin (100 µg/mL) and chloramphenicol (34 µg/mL). Expression cultures were started in 5 ml LB plus antibiotics prior to inoculation of 200 mL of the same medium and cultivation at 18° C. for 4-8 hours. Expression was induced at an OD600 of 0.50 with 0.5 mM IPTG. Following cultivation of 48 h, cells were washed in 100 mL wash buffer (20 mM Tris-HCl, 50 mM KCl, pH 7), pelleted and resuspended in 15 mL cell lysis buffer (50 mM NaH2PO4, 300 mM NaCl, 5 mM imidazole, 0.5 mM PMSF, 2 mM DTT, pH 8). Cells were lysed on ice for 2×30 s (1 min interval) at 20% amplitude (Branson Digital Sonifier) and the supernatant was partially purified with Ni-NTA agarose (Qiagen) using three washes of 30 mM imidazole. The target protein was eluted in a single 1 mL fraction with 250 mM imidazole and desalted into TPS assay buffer (25 mM HEPES, 10 mM MgCl2, 10% glycerol, pH 7) using PD MiniTrap G-25 desalting columns (GE Healthcare).

For expression in insect cells (Sf9), a cDNA encoding MhTPS protein (without an N-terminal His-tag) was produced for cloning into the pENTR4NcoI– (Sandstrom et al., 2006) vector by Gibson assembly using the In-Fusion HD Cloning Kit (Clontech). Briefly, the ORF was amplified using MhTPS_FusF1 and MhTPS_FusR1 primers. pENTR4NcoI– was amplified using pENTRF4 and pENTRR5 primers as described previously (Song et al., 2013). Recombinant plasmids were transformed into *E. coli* Stellar™ DH5α and confirmed by sequencing.

Recombinant MhTPS was produced in Sf9 cells using the BaculoDirect Expression System (Invitrogen). Briefly, the coding region was transferred from pENTR4NcoI– into the linearized BaculoDirect vector by LR recombination. High-titer P3 viral stocks were prepared by successive amplifications of P1 and P2 stocks. Serum-adapted cells were infected with P3 viral stock and incubated for 72 h in 50 mL cultures in Sf900 II serum-free media (Invitrogen) supplemented with 10% (vol/vol) FBS (Atlas Biologicals). Optimal viral doses and infection times were determined by monitoring recombinant protein production by SDS-PAGE. For MhTPS, cells were harvested in 100 mM sodium phosphate buffer, pH 7.6, and resuspended in assay buffer (25 mM HEPES, 5 mM MgCl2, 5 mM KCl, 10% glycerol, pH 7) with 500 µM PMSF and Protease Inhibitor Cocktail (Sigma). Lysates were prepared as previously described (Sandstrom et al., 2006).

IDS Activity Assay and Analysis

For enzyme assays, 96 µl of partially purified protein were mixed with 2 µl 50 µM isopentenyl diphosphate (IPP; Sigma) and 2 µl 50 µM dimethylallyl diphosphate (DMAPP; Sigma) and incubated at 30° C. for 2 h. Analysis of IDS enzyme products was done using an Agilent 1260 HPLC system (Agilent Technologies) coupled to an API 5000 triple-quadrupole mass spectrometer (AB Sciex Instruments) according to the protocol described by Beran et al. (Beran et al., 2016).

TPS Activity Assay

Enzyme activity was assessed in crude protein extracts from whole male and female bugs and from the cuticle, head and thorax, midgut, and fat body tissues of male bugs. Enzyme assays were performed by administering 50 µM (E,E)-FPP to protein extracts (50 µg total protein) in 25 mM HEPES, 5 mM MgCl2, 5 mM KCl, 10% glycerol, pH 7 at a final volume of 200 µL. An equal volume of hexane was overlaid on each preparation to collect volatiles using a 6 h incubation period at 30° C. Products were extracted by vigorously mixing preparations for 15 sec and the organic phase was separated by centrifugation at 4000×g for 10 min.

Assays with heterologously expressed protein were performed in assay buffer (see above) in a total volume of 250 µl with partially purified protein, 1 mM DTT, and 50 M allylic substrate [(E,E)-, (Z,E)- or (Z,Z)-FPP] and incubated at 30° C. for 1 h with a 250 µL hexane overlay. Assays were stopped on ice and compounds extracted by mixing (vortex) at maximum speed for . . . 15 sec. Phases were separated by centrifugation at 4000×g for 10 min and the hexane phase was removed and dried over MgSO4 One µl of liquid sample was injected in splitless mode and analyzed by GC-MS. For identification of the MhTPS product, assays were scaled up by incubating 1 mL protein in a 7 mL screw top test tube and the obtained hexane extract was used for further analysis. To determine enzyme kinetic parameters, assays were performed in a final volume of 50 µL with 0.3 µg partially purified, *E. coli* expressed MhTPS enzyme and increasing concentrations of [1-3H]-(E,E)-FPP (64 uCi mmol-1). Assays were incubated in triplicate at 30° C. for 5 min prior to extraction of the reaction product with 250 µl hexane. Quantification of the radioactive product were as described by Tholl et al. (Tholl et al., 2005). Calculation of Km and Vmax values was performed by rectangular hyperbolic regression analysis using the Hyperbolic Regression Analysis (HYPER 1.01) software (J. S. Easterby, University of Liverpool).

Gas Chromatography-Mass Spectrometry Analysis of MhTPS Products

GC-MS analysis was performed by liquid injection at 240° C. running in split 5 mode and separated on a GC-2010 gas chromatograph (Shimadzu, Kyoto, Japan) using a 30 m×0.25 mm i.d.×0.25 µm film Zebron ZB-XLB column coupled with a QP2010S mass spectrometer (Shimadzu). The GC program was as follows: 40° C. with 2 min hold, then raised to 220° C. at 5° C./min, then raised to 240° C. at 70° C./min followed by a 2 min hold time. Mass spectrometry was performed with an ion source temperature of 240° C., interface temperature of 280° C., electron ionization (EI) potential of 70 eV and scan range of 50 to 400 atomic mass units. Helium was used as a carrier gas at 1.9 mL/min. Terpene olefin products were identified by comparison of retention times and mass spectra with those of authentic standards.

Comparative hot injection and cool-on column GC-MS analyses of the TPS assay products were performed at the USDA, Beltsville in electron impact (EI) ionization mode at 70 eV with an Agilent Technologies 5973 mass selective detector interfaced with a 6890 N GC system equipped with a 30 m×0.25 mm i.d.×0.25 µm film HP-5 MS Agilent J&W column. The column temperature was maintained at 40 degrees C. for 5 min, and then raised to 240 degrees C. at 7 degrees C./min, then to 270 at 15 degrees C./min. Helium was used as a carrier gas at 1 ml/min. Injections of 1 µl hexane extract were done either splitless at 260 degrees C., or cool-on-column at 70 degrees C.

An HP-5 MS column was also used for GC-MS analysis (see above) of pheromone emissions from the RNAi-mediated knockdown experiment. Injections were done splitless at 260 degrees C. and the column temperature was maintained at 400C for 5 min, and then raised to 270 degrees C. at 10 degrees C./min. Helium was used as a carrier gas at 1 ml/min.

GC Analyses of Chemical Modification Products

GC analyses were performed on an Agilent Technologies 6890N instrument equipped with a flame ionization detector and a 25 m×0.25 mm ID Hydrodex β-6TBDM capillary column (Macherey-Nagel GmbH & Co. KG, Düren, Germany). Hydrogen was used as a carrier gas at 1.5 ml/min. The temperature program for bisabolanes was: 50 (5) to 90 (111) at 10 degrees C./min. The temperature program for sesquipiperitols was: 50 (5) to 130 (67) at 10 degrees C., then to 160 degrees C. at 15 degrees C./min. Splitless injections were conducted at the injector temperature 260 degrees C. and detector temperature 270 degrees C. GC-HRMS analysis was performed in TOF EI mode on a Waters GCT Premier instrument equipped with a DB5-MS column. Identification of the MhTPS Product Sesquipiperitol Various stereoisomers for chemical correlations were produced according to Supplemental FIG. 2.2A. For these procedures, flash chromatography was performed with 230-400 mesh silica gel (Fisher Scientific). TLC analyses were conducted on Whatman AL SIL G/UV plates using 20% ethanol solution of phosphomolybdic acid, and/or UV for visualization of spots. Optical rotations were obtained using a Perkin-Elmer 241 polarimeter with a 1.0 mL cell.

(3S,6S,7R)-1,10-bisaboladien-1-ol (SSR-zingiberenol) was prepared as described in Khrimian et al. (Khrimian et al., 2014a). An approximate 1:1 mixture of cis-(7R)-1,10-bisaboladien-3-ols (SSR-zingiberenol and RRR-zingiberenol) was synthesized as described in Leskey et. al. (Leskey et al., 2015).

A mixture of (6R,7R)-2,10-bisaboladien-1-one and (6S,7R)-2,10-bisaboladien-1-one (RR- and SR-sesquipiperitones) was prepared following Hagiwara et al. (Hagiwara et al., 2002). Briefly, an approximately 1:1 mixture of SSR-zingiberenol and RRR-zingiberenol (107 mg, 0.48 mol), pyridinium chlorochromate (PCC, 310 mg, 1.40 mmol), and dichloromethane (2 ml) was stirred at 0 degrees C. for 15 min, then at 25 degrees C. for 2 h. The mixture was poured into ether (10 ml) and washed consecutively with 5% NaOH, 5% HCl, 0.1 M $NaHCO_3$, brine, then dried with sodium sulfate. Flash chromatography with hexane/ethyl acetate, 10:1, afforded an approximate 1:1 mixture of sesquipiperitones (73 mg, 69%) almost baseline separated on a HP-5 MS GC column. The late eluting peak was identified as SR-sesquipiperitone 2 based on oxidation of SSR-zingiberenol.

(6S,7R)-2,10-Bisaboladien-1-one (SR-sesquipiperitone 2) was prepared analogously to the above experiment from SSR-zingiberenol 1 (154 mg, 0.69 mol, 95:5 dr), PCC (446 mg, 2 mmol) in $CH_2Cl_2$ (3 ml). GC-MS analysis showed 93:7 and NMR 95:5 ratios of (6S,7R)- and (6R,7R)-2,10-bisaboladien-1-ones. $[\alpha]D^{20}$ +43.8 (c 2.65, $CHCl_3$). Lit. (Hagiwara et al., 2002) $[\alpha]D^{20}$ +37.1 (c 3.7, CHCl3). $^1$H NMR (600 MHz, $CDCl_3$): 0.78 (d, J=6.6 Hz, 3H), 1.26 (m, 2H), 1.57 (s, 3H), 1.66 (s, 3H), 1.74 (m, 1H), 1.91 (s, 3H), 1.92 (m, 2H), 1.99 (m, 1H), 2.13 (dt, J=12.6, 4.2 Hz, 1H), 2.28 (m, 2H), 2.32 (m, 1H), 5.09 (tm, J=7.2 Hz, 1H), 5.84 (m, 1H). 95:5 Diastereomeric ratio was found by integration of methyl groups at 0.78 (6S,7R) and 0.91 (6R,7R). $^{13}$C NMR (151 MHz, $CDCl_3$): 15.6, 17.6, 22.4, 24.1, 25.7, 26.0, 30.3, 30.9, 34.7, 49.8, 124.5, 127.2, 131.4, 161.1, 201.1. 13C NMR data were in a close agreement with those reported (Hagiwara et al., 2002).

For the oxidation of the MhTPS assay product with PCC, a hexane solution (50 µl) of the MhTPS assay extract was stirred in an open conic vial till dryness. Dichloromethane (70 µl) was added followed by PCC (1-2 mg) and the mixture was stirred for 2 h. Ether (1 ml) was added and the content of the vial was filtered through a short pad of SiO2. The solution was analyzed by GC-MS by splitless injection vs. SR-sesquipiperitone 2.

The reduction of SR-sesquipiperitone 2 was performed by adding lithium aluminum hydride (210 µl of 1.0 M in ether; 0.21 mmol) at −25 degrees C. to a solution of the ketone (42 mg, 0.19 mmol) in ether (2.0 ml). The temperature was allowed to rise to −100C, and the mixture was stirred for 2 h. Water (8 µl) was added to the mixture, followed by 15% NaOH (8 µl), and again water (24 µl). The crystalline residue was filtered, the ether solution was concentrated, and the residue was flash chromatographed with hexane/ethyl acetate, 11:1. RSR-Sesquipiperitol 4 (5 mg, 12%) was isolated as a faster-eluting product, $[\alpha]D20$ +168.4 (c 0.38, $CHCl_3$), followed by a mixture of SSR-sesquipiperitol 3 and RSR-Sesquipiperitol 4 (9 mg, 21%), then SSR-sesquipiperitol 3 (19 mg, 45%), $[\alpha]D^{20}$ −15.4 (c 0.91, CHCl3). $^1$H and $^{13}$C NMR data of the alcohols are presented in FIG. 17. $^1$H NMR data of 3 and 4 were in agreement with those published for their enantiomers (Bohlmann et al., 1984). $^1$H and $^{13}$C NMR data of 3 were in good agreement with those reported by Sy and Brown (Sy and Brown, 1997) and $_{13}$C NMR data of 3 matched those reported by Cool (Cool, 1996).

Dehydration/hydrogenation of sesquipiperitol was done in the following way: An aliquot of the MhTPS assay extract (50 µl) containing ~10 µg sesquipiperitol was concentrated with a gentle stream of $N_2$ and taken into 50 µl dichloromethane. The solution was cooled to 0 degrees C. and treated with 2 µl of a premixed solution of $POCl_3$ (1.2 µl) and pyridine (20 µl). The mixture was stirred at 25 degrees C. for 16 h, further diluted with 200 µl $CH_2Cl_2$ and treated with 30 µl water. The organic layer was separated and washed with water (30 µl) and 5% sodium bicarbonate (10 µl). The dichloromethane solution was made up to 300 µl volume by adding fresh solvent and filtered through a small cartridge of $Na_2SO_4$ before analyzing by GC to confirm the presence of zingiberene, β-sesquiphellandrene and other dehydration products. This solution was hydrogenated in the presence of a $PtO_2$ (Adams) catalyst until the complete hydrogenation of bisabolatrienes to bisabolane 5, which appears on HP-5 MS GC column as a mixture of well-separated cis and trans isomers (at para position of the cyclohexane ring) on the background of piperidine formed by co-hydrogenation of pyridine. The mixture was washed with 0.05 M HCl (2×10 µl), water (2×20 µl), 5% $NaHCO_3$ and dried with Na2SO4. This mixture was analyzed on a Hydrodex-β-6-TBDMS GC column against standards of 7S- and 7R-bisabolanes prepared analogously by dehydration/hydrogenation of 7S- and 7R-zingiberenols (Khrimian et al., 2014b).

NMR Analysis $^1$H NMR spectra were obtained at 600 MHz and $^{13}$C spectrum at 151 MHz on a Bruker AVIII-600 MHz spectrometer. Chemical shifts are reported in δ units and referenced to the residual CDCl3 solvent signal; coupling constants are reported in Hz. COSY, $^{13}$C-DEPT, HSQC, and NOESY spectra were also recorded to assign protons and carbons and stereochemistries of compounds 3 and 4 (FIG. 13C).

Gene Expression Analysis

Insects used for tissue and sex-specific gene expression analysis were killed with hexane vapor in a screw top jar and dissected in PBS (137 mM NaCl, 8.1 mM Na2HPO4, 1.5 mM NaH2PO4, 2.7 mM KCl, pH 7.2). Insects were dissected in groups of five and tissues frozen in liquid nitrogen. Three rounds of dissections were performed for a total of three replicates for five tissue groups (head, thorax, midgut, soft tissue minus midgut and abdominal cuticle including attached epithelial cells. All samples were kept at −80° C. before RNA extraction. cDNAs were generated from total RNA as described above. Relative transcript abundance was measured by quantitative (Real Time)-Reverse Transcription PCR (qRT-PCR) using the ddCt method and normalized to 18S (Livak and Schmittgen, 2001). Primers were designed using Geneious (v. 7.1.9) to amplify a fragment of approximately 100 bp (FIG. 19) and tested for non-specific binding using the *M. histrionica* transcriptome data. Primer efficiencies were measured to be between 90-105%. Reaction plates contained 1 µL cDNA (25 ng), 0.6 µL each primer, 7.8 µL dH2O and 10 µL PowerSYBR Green PCR Master Mix (Applied Biosystems) per well. The samples were analyzed on an Applied Biosystems 7300 using 40 cycles of 50° C. 2 min, 95° C. 20 mins, 95° C. 15 sec, 60° C. 1 min. Primers were tested for non-specific amplification by analyzing the dissociation curve after PCR. Significance was measured using one-way analysis of variance (ANOVA) and means grouped by Tukey's HSD.

RNAi Treatment dsRNA was prepared using the MEGAscript RNAi kit (Ambion) per manufacturer's instructions. Adult males were injected 3-5 d post eclosion (n=6 per group) with 400 ng dsRNA in PBS (16) (pH 7) using a 31 ga Hamilton syringe (10 µL 1701SN, 2 inch, pt 2; Hamilton Company, Reno NV) inserted 3 mm between the pygophore and connexivum. Changes in transcript abundance were measured using qRT-PCR at 12 days post injection as above.

Volatile Collection from RNAi Treated Insects

Treated insects were allowed to recover on potted collards (*Brassica oleracea* 'Champion') for 3 d before cohorts of 3 males were moved to each volatile collection chamber. Volatile collection chambers were 1 L glass jars (Wide Mouth Quart Mason Jars; Ball Jar Company, Muncie, Indiana) with Teflon lids (Savillex, Minneapolis, MN). Insects were fed with organic cauliflower florets, which were replaced every other day (16 L:8 D photoperiod). Headspace from each cohort was collect by drawing humidified air into the container through 6-14 mesh activated charcoal (Fisher Scientific) and out of the container by vacuum (~1 L/min), through traps (15 cm×4 mm i.d.) containing HayeSep Q (200 mg each; Hayes Separations Inc., Bandera, TX). After 48 h of collection, the adsorbents were eluted with $CH_2Cl_2$ (1 mL/sample). The solutions were stored at 10° C. before analyses. Three cohorts of each treatment were sampled for each experimental bout, and this experiment was repeated three times so that collections were taken from 9 cohorts of each treatment total. Because the data from headspace collections was non-normal and did not respond to transformation, we compared the amount of murgantiol detected in treated and control cohorts by conducting a generalized log-linear analysis assuming a Poisson distribution, followed by contrast tests for mean separation (alpha=0.05).

Amino Acid Sequence Analysis of MhTPS and MhFPPS

Amino acid sequence alignment of MhTPS and MhFPPS with other insect TPS and IDS proteins was made in Geneious (v. 7.1.9) using MUSCLE with full end gap penalty. Sequence logos were generated using Berkley Weblogo Server (v. 2.8.2) (Crooks et al., 2004; Schneider and Stephens, 1990).

Sequence Analysis and Tree Reconstruction

Multiple sequence alignments were computed using MAFFT and default parameters (www.ebi.ac.uk). Based on these alignments, trees were reconstructed with MEGA6 (Tamura et al., 2011) using a maximum likelihood algorithm. All positions with <80% site coverage were eliminated. A bootstrap resampling analysis with 1000 replicates was performed to evaluate the topology of the generated trees. A substitution model test was performed with MEGA6 to identify the best-fit substitution model for each dataset. The substitution models used for tree reconstructions are described in the respective figure legend.

Homology Modeling and Substrate Docking

A homology model of MhTPS was generated using the SWISS-MODEL server (swissmodel.expasy.org) and the crystal structure of avian FPP synthase (PDB-ID: 1FPS) (Tarshis et al., 1994) as a template. The generated model was subject to energy minimization with the YASARA force field (www.yasara.org) and assessed for stereochemical correctness on the basis of Ramachandran plots using ProCheck (Laskowski, 2001). Ligand docking of FPP and DMAPP was performed using the Molegro Virtual Docker software (www.clcbio.com) with ligand structures obtained from available co-crystallized structures of avian FPP synthase (PDB-ID: 1UBX and 1UBY) (Tarshis et al., 1996) and subsequent visualization in PyMOL.

EXAMPLE 1 REFERENCES

Aldrich, J. R., Numata, H., Borges, M., Bin, F., Waite, G. K. and Lusby, W. R. (1993). Artifacts and pheromone blends from *Nezara* spp. and other stink bugs (Heteroptera, Pentatomidae). Z. Naturforsch. C Bio. Sci. 48, 73-79.:

Aldrich, J. R., Oliver, J. E., Lusby, W. R., Kochansky, J. P. and Lockwood, J. A. (1987). Pheromone strains of the cosmopolitan pest, *Nezara viridula* (Heteroptera, Pentatomidae). J Exp Zool 244, 171-175.

Andersen, N. H. and Syrdal, D. D. (1970). Terpenes and sesquiterpenes of *Chamaecyparis nootkatensis* leaf oil. Phytochemistry 9, 1325-1340.

Beran, F., Rahfeld, P., Luck, K., Nagel, R., Vogel, H., Wielsch, N., Irmisch, S., Ramasamy, S., Gershenzon, J., Heckel, D. G. and Kollner, T. G. (2016)! Novel family of terpene synthases evolved from trans-isoprenyl diphosphate synthases in a flea beetle. Proc. Natl. Acad. Sci. USA 113, 2922-2927.

Blassioli-Moraes, M. C., Laumann, R. A., Oliveira, M. W. M., Woodcock, C. M., Mayon, P., Hooper, A., Pickett, J. A., Birkett, M. A. and Borges, M. (2012). Sex pheromone communication in two sympatric neotropical stink bug species *Chinavia ubica* and *Chinavia impicticornis*. J. Chem. Ecol. 38, 836-845.

Blomquist, G. J., Figueroa-Teran, R., Aw, M., Song, M. M., Gorzalski, A., Abbott, N. L., Chang, E. and Tittiger, C. (2010). Pheromone production in bark beetles. Insect Biochem Mol Biol 40, 699-712.

Bohlmann, F., Tsankova, E. and Jakupovic, J. (1984). Sesquiterpenes and acetylenes from *Argyranthemum adauctum* ssp *jacobaeifolium*. Phytochemistry 23, 1103-1104.

Borges, M., Birkett, M., Aldrich, J. R., Oliver, J. E., Chiba, M., Murata, Y., Laumann, R. A., Barrigossi, J. A., Pickett, J. A. and Moraes, M. C. B. (2006). Sex attractant pheromone from the rice stalk stink bug, *Tibraca limbativentris* Stal. J. Chem. Ecol. 32, 2749-2761.

Borges, M., Millar, J. G., Laumann, R. A. and Moraes, M. C. (2007). A male-produced sex pheromone from the neotropical redbanded stink bug, *Piezodorus guildinii*. J Chem Ecol 33, 1235-1248.

Brown, A. E., Riddick, E. W., Aldrich, J. R. and Holmes, W. E. (2006). Identification of (−)-beta-caryophyllene as a gender-specific terpene produced by the multicolored Asian lady beetle. J. Chem. Ecol. 32, 2489-2499.

Burse, A., Frick, S., Discher, S., Tolzin-Banasch, K., Kirsch, R., Strauss, A., Kunert, M. and Boland, W. (2009). Always being well prepared for defense: The production of deterrents by juvenile Chrysomelina beetles (Chrysomelidae). Phytochemistry 70, 1899-1909.

Byers, K., Vela, J. P., Peng, F., Riffell, J. A. and Bradshaw, H. D. (2014). Floral volatile alleles can contribute to pollinator-mediated reproductive isolation in monkeyflowers (Mimulus). Plant J. 80, 1031-1042.

Cai, Y., Jia, J. W., Crock, J., Lin, Z. X., Chen, X. Y. and Croteau, R. (2002). A cDNA clone for beta-caryophyllene synthase from *Artemisia annua*. Phytochemistry 61, 523-529.

Cantin, A., Lull, C., Primo, J., Miranda, M. A. and Primo-Yufera, P. (2001). Isolation, structural assignment and insecticidal activity of (−)-(1S,2R,3R,4S)-1,2-epoxy-1-methyl-4-(1-methylethyl)-cyclohex-3-yl acetate, a natural product from *Minthostachys tomentosa*. Tetrahedron-Asymmetry 12, 677-683.

Chen, F., Tholl, D., Bohlmann, J. and Pichersky, E. (2011). The family of terpene synthases in plants: a mid-size family of genes for specialized metabolism that is highly diversified throughout the kingdom. Plant J. 66, 212-229.

Cool, L. G. (1996). Sesquiterpene alcohols from foliage of *Fitzroya cupressoides*. Phytochemistry 42, 1015-1019.

Cribb, B. W., Siriwardana, K. N. and Walter, G. H. (2006). Unicellular pheromone glands of the pentatomid bug *Nezara viridula* (Heteroptera: Insecta): ultrastructure, classification, and proposed function. J Morphol 267, 831-840.

Crooks, G. E., Hon, G., Chandonia, J. M. and Brenner, S. E. (2004). WebLogo: a sequence logo generator. Genome Res 14, 1188-1190.

de Oliveira, M. W. M., Borges, M., Andrade, C. K. Z., Laumann, R. A., Barrigossi, J. A. F. and Blassioli-Moraes, M. C. (2013). Zingiberenol, (1S,4R,1'S)-4-(1',5'-Dimethylhex-4'-enyl)-1-methylcyclohex-2-en-1-ol, identified as the sex pheromone produced by males of the rice stink bug *Oebalus poecilus* (Heteroptera: Pentatomidae). J. Agric. Food Chem. 61, 7777-7785.

Degenhardt, J., Kollner, T. G. and Gershenzon, J. (2009). Monoterpene and sesquiterpene synthases and the origin of terpene skeletal diversity in plants. Phytochemistry 70, 1621-1637.

Dickschat, J. S. (2016). Bacterial terpene cyclases. Nat. Prod. Rep. 33, 87-110.

Ditengou, F. A., Muller, A., Rosenkranz, M., Felten, J., Lasok, H., van Doorn, M. M., Legue, V., Palme, K., Schnitzler, J. P. and Polle, A. (2015). Volatile signalling by sesquiterpenes from ectomycorrhizal fungi reprogrammes root architecture. Nat. Commun. 6, Frater, G. and Muller, U. (1989). Synthesis of (+)-(4S,8R)-8-epi-beta-bisabolol and (−)-(4R,8S)-4-epi-beta-bisabolol. Helv Chim Acta 72, 653-658.

Frick, S., Nagel, R., Schmidt, A., Bodemann, R. R., Rahfeld, P., Pauls, G., Brandt, W., Gershenzon, J., Boland, W. and Burse, A. (2013). Metal ions control product specificity of isoprenyl diphosphate synthases in the insect terpenoid pathway. Proc Natl Acad Sci USA 110, 56-61.

Gershenzon, J. and Dudareva, N. (2007). The function of terpene natural products in the natural world. Nat. Chem. Biol. 3, 408-414.

Gilg, A. B., Bearfield, J. C., Tittiger, C., Welch, W. H. and Blomquist, G. J. (2005). Isolation and functional expression of an animal geranyl diphosphate synthase and its role in bark beetle pheromone biosynthesis. Proc. Natl. Acad. Sci. USA 102, 9760-9765.

Gilg, A. B., Tittiger, C. and Blomquist, G. J. (2009). Unique animal prenyltransferase with monoterpene synthase activity. Naturwissenschaften 96, 731-735.

Hagiwara, H., Okabe, T., Ono, H., Kamat, V. P., Hoshi, T., Suzuki, T. and Ando, M. (2002). Total synthesis of bisabolane sesquiterpenoids, alpha-bisabol-1-one, curcumene, curcuphenol and elvirol: utility of catalytic enamine reaction in cyclohexenone synthesis. J Chem Soc Perk T 1 895-900.

Harris, C. S. (1938). The anatomy and histology of the alimentary system of the harlequin cabbage bug, *Murgantia histrionica* Hahn. (Hemiptera: Pentatomidae). Ohio J Sci 38, 316-331.

Huang, M., Sanchez-Moreiras, A. M., Abel, C., Sohrabi, R., Lee, S., Gershenzon, J. and Tholl, D. (2012). The major volatile organic compound emitted from *Arabidopsis*

*thaliana* flowers, the sesquiterpene (E)-β-caryophyllene, is a defense against a bacterial pathogen. New Phytol. 193, 997-1008.

Huang, Q. L., Williams, H. J., Roessner, C. A. and Scott, A. I. (2000). Sesquiterpenes produced by truncated taxadiene synthase. Tetrahedron Letters 41, 9701-9704.

Jia, Q., Li, G., Kollner, T. G., Fu, J., Chen, X., Xiong, W., Crandall-Stotler, B. J., Bowman, J. L., Weston, D. J., Zhang, Y., Chen, L., Xie, Y., Li, F.-W., Rothfels, C. J., Larsson, A., Graham, S. W., Stevenson, D. W., Wong, G. K.-S., Gershenzon, J. and Chen, F. (2016). Microbial-type terpene synthase genes occur widely in nonseed land plants, but not in seed plants. Proc. Natl. Acad. Sci. USA 113, 12328-12333.

Junker, R. R., et. al . . . (2017). Covariation and phenotypic integration in chemical communication displays: biosynthetic constraints and ecoevolutionary implications. New Phytol. DOI: 10.1111/nph.14505.

Junker, R. R. and Tholl, D. (2013). Volatile organic compound mediated interactions at the plantmicrobe interface. J. Chem. Ecol. 39, 810-825.

Khrimian, A., Shirali, S., Vermillion, K. E., Siegler, M. A., Guzman, F., Chauhan, K., Aldrich, J. R. and Weber, D. C. (2014a). Determination of the stereochemistry of the aggregation pheromone of harlequin bug, *Murgantia histrionica*. J. Chem. Ecol. 40, 1260-1268.

Khrimian, A., Zhang, A. J., Weber, D. C., Ho, H. Y., Aldrich, J. R., Vermillion, K. E., Siegler, M. A., Shirali, S., Guzman, F. and Leskey, T. C. (2014b). Discovery of the aggregation pheromone of the brown marmorated stink bug (*Halyomorpha halys*) through the creation of stereoisomeric libraries of 1-bisabolen-3-ols. J. Nat. Prod. 77, 1708-1717.

Kong, Y. (2011). Btrim: a fast, lightweight adapter and quality trimming program for next generation sequencing technologies. Genomics 98, 152-153.

Kumar, S., et al . . . (2016). Molecular diversity of terpene synthases in the liverwort Marchantia *polymorpha*. Plant *Cell* 28, 2632-2650.

Lai, C. Q., McMahon, R., Young, C., Mackay, T. F. C. and Langley, C. H. (1998). quemao, a *Drosophila* bristle locus, encodes geranylgeranyl pyrophosphate synthase. Genetics 149, 1051-1061. Laskowski, R. A. (2001). PDBsum: summaries and analyses of PDB structures. Nucleic Acids Res. 29, 221-222.

Leskey, T. C., Khrimian, A., Weber, D. C., Aldrich, J. C., Short, B. D., Lee, D. H. and Morrison, W. R., 3rd (2015). Behavioral responses of the invasive *Halyomorpha halys* (Stal) to traps baited with stereoisomeric mixtures of 10,11-epoxy-1-bisabolen-3-ol. J Chem Ecol 41, 418-429.

Livak, K. J. and Schmittgen, T. D. (2001). Analysis of relative gene expression data using realtime quantitative PCR and the 2(−Delta Delta C(T)) Method. Methods 25, 402-408. Martins, G. F. and Ramalho-Ortigao, J. M. (2012). Oenocytes in insects. Invert Surviv J 9, 139-152.

McBrien, H. L., Millar, J. G., Rice, R. E., McElfresh, J. S., Cullen, E. and Zalom, F. G. (2002). Sex attractant pheromone of the red-shouldered stink bug *Thyanta pallidovirens*: A pheromone blend with multiple redundant components. J. Chem. Ecol. 28, 1797-1818.

Millar, J. G. (1998). Rapid and simple isolation of zingiberene from ginger essential Oil. J Nat Prod 61, 1025-1026.

Moraes, M. C. B., Pareja, M., Laumann, R. A. and Borges, M. (2008). The chemical volatiles (semiochemicals) produced by neotropical stink bugs (Hemiptera: Pentatomidae). Neotrop. Entomol. 37, 489-505.

Muller, M. and Buchbauer, G. (2011). Essential oil components as pheromones. A review. Flavour Frag J 26, 357-377.

Osbourn, A., Goss, R. J. M. and Field, R. A. (2011). The saponins-polar isoprenoids with important and diverse biological activities. Nat. Prod. Rep. 28, 1261-1268.

Pickett, J. A., Allemann, R. K. and Birkett, M. A. (2013). The semiochemistry of aphids. Nat. Prod. Rep. 30, 1277-1283.

Qiu, Y., et al. (2012). An insect-specific P450 oxidative decarbonylase for cuticular hydrocarbon biosynthesis. Proc Natl Acad Sci USA 109, 14858-14863.

Quin, M. B., Flynn, C. M. and Schmidt-Dannert, C. (2014). Traversing the fungal terpenome. Nat. Prod. Rep. 31, 1449-1473.

Raguso, R. A. (2016). More lessons from linalool: insights gained from a ubiquitous floral volatile. Curr. Opin. Plant Biol. 32, 31-36.

Rasmann, S., Kollner, T. G., Degenhardt, J., Hiltpold, I., Toepfer, S., Kuhlmann, U., Gershenzon, J. and Turlings, T. C. J. (2005). Recruitment of entomopathogenic nematodes by insect-damaged maize roots. Nature 434, 732-737.

Robert, C. A. M., Erb, M., Duployer, M., Zwahlen, C., Doyen, G. R. and Turlings, T. C. J. (2012). Herbivore-induced plant volatiles mediate host selection by a root herbivore. New Phytol. 194, 1061-1069.

Sandstrom, P., Welch, W. H., Blomquist, G. J. and Tittiger, C. (2006). Functional expression of a bark beetle cytochrome P450 that hydroxylates myrcene to ipsdienol. Insect Biochem Mol Biol 36, 835-845.

Schneider, T. D. and Stephens, R. M. (1990). Sequence logos: a new way to display consensus sequences. Nucleic Acids Res 18, 6097-6100.

Sobotnik, J., Jirosova, A. and Hanus, R. (2010). Chemical warfare in termites. J. Insect Physiol. 56, 1012-1021.

Song, M. M., et al. (2013). Functional characterization of myrcene hydroxylases from two geographically distinct Ips *pini* populations. Insect Biochem Mol Biol 43, 336-343.

Sparks, M. E., et al. (2017). A transcriptome survey spanning life stages and sexes of the harlequin bug, *Murgantia histrionica*. Insects 8, 55.

Sparks, M. E., Shelby, K. S., Kuhar, D. and Gundersen-Rindal, D. E. (2014). Transcriptome of the invasive brown marmorated stink bug, *Halyomorpha halys* (Stal) (Heteroptera: Pentatomidae). Plos One 9, 1-13.

Staddon, B. W. and Edmunds, M. G. (1991). Gland regional and spatial patterns in the abdominal sternites of some pentatomoid Heteroptera. Ann. Soc. Ent. Fr. 27, 189-203.

Sy, L. K. and Brown, G. D. (1997). Oxygenated bisabolanes from *Alpinia densibracteata*. Phytochemistry 45, 537-544.

Tarshis, L. C., Proteau, P. J., Kellogg, B. A., Sacchettini, J. C. and Poulter, C. D. (1996). Regulation of product chain length by isoprenyl diphosphate synthases. Proc. Natl. Acad. Sci. USA 93, 15018-15023.

Tarshis, L. C., Yan, M. J., Poulter, C. D. and Sacchettini, J. C. (1994). Crystal structure of recombinant farnesyl diphosphate synthase at 2.6 Angstrom resolution Biochemistry 33, 10871-10877.

Tholl, D., Chen, F., Petri, J., Gershenzon, J. and Pichersky, E. (2005). Two sesquiterpene synthases are responsible for the complex mixture of sesquiterpenes emitted from *Arabidopsis* flowers. Plant J. 42, 757-771.

Vaughan, M. M., et al. (2013). Formation of the unusual semivolatile diterpene rhizathalene by the *Arabidopsis* class I terpene synthase TPS08 in the root stele is involved in defense against belowground herbivory. Plant Cell 25, 1108-1125.

Wallrapp, F. H., et al. (2013). Prediction of function for the polyprenyl transferase subgroup in the isoprenoid synthase superfamily. Proc. Natl. Acad. Sci. USA 110, E1196-E1202.

Weber, D. C., Walsh, G. C., DiMeglio, A. S., Athanas, M. M., Leskey, T. C. and Khrimian, A. (2014). Attractiveness of harlequin bug, Murgantia histrionica, aggregation pheromone: Field response to isomers, ratios, and dose. J. Chem. Ecol. 40, 1251-1259.

Zhou, W. W., et al. (2017). Tissue-Specific Emission of (E)-alpha-Bergamotene Helps Resolve the Dilemma When Pollinators Are Also Herbivores. Curr Biol 27, 1336-1341.

Zi, J., Mafu, S. and Peters, R. J. (2014). To gibberellins and beyond! Surveying the evolution of (di) terpenoid metabolism. Annu. Rev. Plant Biol. 65, 259-286.

Example 2—A Sesquiterpene Synthase Produces the Pheromone Precursor Sesquipiperitol in the Brown Marmorated Stink Bug *Halyomorpha halys*

The majority of stink bugs (Pentatomidae) produce terpene based aggregation or sex pheromones (Weber et al., 2018). These pheromones have been of particular interest for pest management of stink bugs such as the brown marmorated stink bug *Halyomorpha halys*. *H. halys* was first detected in North America in Allentown, Pennsylvania in 1996 where it is believed to have arrived in a shipping container from China (Hoebeke and Carter, 2003; Xu et al., 2013). Since then it has been found outside the United States in Canada and European countries like Switzerland, Germany and Liechtenstein (Haye et al., 2015). Like many Pentatomidae, *H. halys* produces 15-carbon sesquiterpene aggregation pheromones with a bisabolene backbone (Weber et al., 2018). In 2014, the aggregation pheromone of *H. halys* was identified as a blend of (3S,6S,7R,10S)- and (3R,6S,7R,10S)-10,11-epoxy-1-bisabolen-3-ol (Khrimian et al., 2014b). Interestingly, the harlequin bug (*Murgantia histrionica*), a crucifer specialist native to South America and a common pest in the US South (McPherson and Ahmad, 2008), shares the SSRS-10,11-epoxy-1-bisabolen-3-ol stereoisomer of its aggregation pheromone murgantiol (Example 1) with that of *H. halys* indicating a common biosynthetic origin or convergent evolutionary trajectories in the pheromone production of these stink bugs.

Terpenes are derived from the 5-carbon isoprenyl diphosphate precursors, isopentenyl diphosphate (IPP) and its isomer dimethylallyl diphosphate (DMAPP). Two or more of these C5 units are combined by isoprenyl diphosphate synthases (IDS) in head-to-tail condensation reactions to synthesize the diphosphate substrates used by terpene synthases (TPS) to form a large number of structurally diverse terpene compounds (Thulasiram et al., 2007). TPSs are named according to the number of carbon atoms of their products with mono- ($C_{10}$), sesqui- ($C_{15}$) and diterpenes ($C_{20}$) being the most abundant and widely studied (Sacchettini and Poulter, 1997). IDSs typically have two characteristic aspartate-rich motifs for the binding of their substrates, while TPSs have one aspartate-rich motif and an NSE/DTE motif (Christianson, 2006).

Whether stink bugs produce their terpene pheromones de novo and which enzymes could be involved has been largely unknown. Only a few studies in beetles and a recent investigation of pheromone biosynthesis in *M. histrionica* have shown that insect terpene biosynthesis appears to rely on terpene synthases with IDS-like amino acid sequences (Beran et al., 2016; Gilg et al., 2009) (Example 1). These IDS-like TPSs are so far unique to insects. *M. histrionica* was found to have an IDS type sesquiterpene synthase that produces the pheromone precursor (1S,6S,7R)-sesquipiperitol (Example 1). Without being bound by theory, it was believed that *H. halys* can synthesize the same pheromone precursors by activity of a sesquiterpene synthase.

In this Example, it can be at least demonstrated that *H. halys* produces the cyclic sesquiterpene alcohol sesquipiperitol in a single enzymatic step as a putative pheromone precursor. Out of seven IDS type genes found in the *H. halys* genome, one encodes a functional sesquipiperitol synthase. A second IDS protein was found to have sesquiterpene synthase activity while a third functions as an IDS protein, which makes farnesyl diphosphate (FPP). The sesquipiperitol synthases from *H. halys* and *M. histrionica* share high sequence similarity and our phylogenetic analysis indicates that both stink bugs share a common enzymatic progenitor and have undergone convergent evolution in the production of their sesquiterpene pheromones.

Results

Determination of Terpene Synthase Activity in *H. halys*

To determine a possible sesquiterpene synthase activity related to pheromone production in *H. halys*, enzyme activity was measured in crude protein extracts from whole male and female bugs using (E,E)-FPP as a substrate. Supernatants of homogenized bugs were incubated 6 h in the presence of the substrate and products extracted by hexane and analyzed by GC-MS. An enzymatic product with the retention time and mass spectrum similar to that of the previously identified sesquiterpene alcohol, sesquipiperitol (Chapter II) was detected in crude protein extracts of males but not females (FIGS. 20A-20B).

Identification and Functional Characterization of IDS-like Genes in *H. halys*

To identify the gene(s) responsible for sesquipiperitol synthesis in *H. halys*, we a tblastn search in GenBank was performed with 'organism' restricted to *H. halys* and using query sequences MhTPS (MG662378.1) and MhFPPS (MG662379.1) from HB (Example 1) as well as *I. pini* GPPS/TPS (AAX55632.1) and FPPS (AAX55631.1) and *P. striolata* TPS1 (KT959248). Seven IDS-like sequences were found (HhIDS1-7, FIG. 27) in the RefSeq genome assembly (acc. no. PRJNA298780) and transcriptome (SRA acc. no. SRP040652) (Sparks et al., 2014). Transcriptomic data showed two of the sequences were highly expressed in both males and females (HhIDS2 and HhIDS7), one showed low but differential expression in males (HhIDS1), and a fourth (HhIDS6) was lowly expressed in both sexes (FIG. 31) (Sparks et al., 2017). Full length cDNAs could only be amplified for HhIDS1, HhIDS2 and HhIDS7 (FIG. 21). HhIDS1 is a 43.78 kDa protein containing 377 amino acids, HhIDS2 is a 46.31 kDa protein containing 403 amino acids and HhIDS7 is a 41.98 kDa protein containing 368 amino acids, HhIDS3-6 could not be amplified.

To functionally characterize these genes, cDNAs encoding full-length proteins were cloned into the bacterial expression vector pEXP5 with an N-terminal histidine fusion tag. Due to difficulties in cloning and expressing HhIDS1 and HhIDS7, these cDNAs were codon optimized for *E. coli*, synthesized and ligated into pET19b by GenScript (Piscataway, NJ) which provided an N-terminal histidine tag. As analyzed by GC-MS, HhIDS7 produced high amounts of the sesquiterpene alcohol sesquipiperitol when given (E,E)-FPP, lower amounts when exposed to (Z,E)-FPP and no product when give (Z,Z)-FPP (FIGS. 22A-22B and 29A). HhIDS1 produced several sesquiterpene olefins and alcohols at low abundance when provided with either (E,E)- FPP or (Z,E)-FPP as substrates, the most prominent being elemol (FIG. 29B).

Sesquipiperitol was identified by matching the retention time and mass spectra to a (1S,6S,7R)-sesquipiperitol standard. The absolute configuration of the product still remains to be determined. Assays with HhIDS7 also showed trace amounts of sesquiterpene olefins y-curcumene, a-zingiberene and B-sesquiphellandrene, which were also seen in assays with recombinant HB TPS (see FIG. 3) and are most likely thermal dehydration products of sesquipiperitol from exposure to the high temperature (240° C.) of the GC injection port (see Example 1). The stereoisomer of the sesquipiperitol product has not yet been identified. When assayed with FPP isomers as substrate, HhIDS2 did not produce a terpene product (data not shown) but when assayed with prenyl diphosphate precursors isopentenyl diphosphate (IPP) and dimethyl allyl diphosphate (DMAPP) the protein produced only (E,E)-FPP (FIG. 23). Due to the TPS activity of HhIDS1 and HhIDS7 we have designated these HhTPS2 and HhTPS1, respectively. Due to the lack of TPS activity and the ability to function as an IDS enzyme, we designate HhIDS2 as HhFPPS.

Expression of HhTPS1 in Mature *H. halys* Occurs in the Fat Body

To determine the location of HhTPS1 expression, five adult males were dissected into midgut, fat body along with other abdominal soft tissues and abdominal cuticle including sternites with attached epithelial cells and transcript abundance was measured in these tissues by RT-PCR. HhTPS1 transcript abundance appeared highest in the fat body and lowest in abdominal sternites (FIG. 24).

HhTPS1 Accepts (E,E)-FPP as Substrate

Recombinant, codon optimized HhTPS1 and HhTPS2 were assayed with 50 μM (E,E)-, (Z,E)- and (Z,Z)-FPP substrates and product extracted with hexane. HhTPS1 accepts (E,E)-FPP as the primary substrate and produces an isomer of sesquipiperitol. HhTPS2 does not seem to prefer any substrate and makes multiple sesquiterpene products, the most abundant being elemol.

Discussion

HhTPS1 Produces the Sesquiterpene Sesquipiperitol

*H. halys* is perhaps the most significant stink bug pest in the United States. A greater understanding of how *H. halys* terpenoid pheromones are produced could provide novel and better pest management solutions. Emerging research on insect terpene biosynthesis suggests many insects rely on IDS-like terpene synthases for pheromone production (Beran et al., 2016; Gilg et al., 2009).

The *H. halys* genome contains a family of seven IDS-like sequences, of which three were successfully amplified from cDNA. It was shown that two of these IDS-type genes (HhTPS1, HhTPS2) function as TPS enzymes in vitro, while the third (HhFPPS) represents a bona fide IDS enzyme making (E,E)-FPP. HhTPS1 produces an isomer of sesquipiperitol, which was also detected as a product of terpene synthase activity in crude protein extracts of males. By contrast, none of the enzymatic products produced by HhTPS2 were found in the crude protein assays. Both TPS enzymes have highest activity with (E,E)-FPP as substrate, the sole product of HhFPPS. An IDS/TPS type family similar to that in *H. halys* has recently been reported from the striped flea beetle, *Phyllotreta striolata* (Beran et al., 2016). Here, a single TPS enzyme was found to produce the predominant sesquiterpene aggregation pheromone himachaladiene, while three out of five recombinant TPS enzymes made low amounts of sesquiterpenes unrelated to the pheromone and absent in crude protein assays (Beran et al., 2016).

Retention time and mass spectral comparisons of the terpene product of *M. histrionica* TPS and HhTPS1 assayed with (E,E)-FPP show that both enzymes make sesquipiperitol (FIGS. 25A-25B). Although the absolute configuration of sesquipiperitol synthesized by HhTPS1 has not been identified, we assume that it shares the same 6S,7R configuration with sesquipiperitol made by MhTPS as a precursor of the (3S,6S,7R,10S)-10,11-epoxy-1-bisabolen-3-ol or (3R,6S,7R,10S)-10,11-epoxy-1-bisabolen-3-ol pheromone compounds (Khrimian et al., 2014a; Khrimian et al., 2014b).

HhTPS1 and *Murgantia histrionica* TPS are Highly Similar Proteins

Sequence and phylogenetic comparisons of the IDS-type TPS enzymes of *H. halys* with IDS and TPS proteins from other insects suggests that the *H. halys* proteins arose from trans-IDS progenitors similarly to TPS enzymes from *M. histrionica* and *P. striolata* (FIG. 26). Coleopteran and pentatomid TPS form separate clades from FPPS with Coleoptera diverging earlier. Within Pentatomidae, HhFPPS groups in a clade with MhFPPS while the remaining *H. halys* IDS-like proteins group with HhTPS1, HhTPS2 and MhTPS. A search of the current genome assembly shows *H. halys* IDS and TPS genes group on three separate scaffolds but in close proximity within scaffolds (FIG. 32). These same gene clusters are reflected in the clades of the phylogenetic analysis. This grouping along with clades shown in phylogenetic analysis suggests gene duplication and neo-functionalization in pentatomid TPS genes and likely other insects. Why some TPS such as HhTPS2 produce terpenes in vitro that are not readily detected in vivo is currently unknown but might be the result of tissue specific regulation, posttranslational modifications, or substrate availability.

Remarkably, the HhTPS1 and MhTPS enzymes of both stink bugs, despite their different geographic origins, share 80.4% amino acid sequence identity and 89.9% sequence similarity (FIG. 30) (BLOSUM62). By contrast, the sequence identity between HhFPPS and HhTPS1 is only 24.6%. Similarly, low sequence identities are seen between IDS (FPPS) and TPS enzymes from *M. histrionica*. Phylogenetic analysis, placement in the genome and sequence differences further supports the hypothesis that true IDS enzymes most likely diverged early from IDS-like proteins which adopted TPS function. High sequence similarity between HhTPS1 and MhTPS suggests residues that have diverged from their respective FPPS but are similar between the two TPS may play a role in their shared biochemistry and could aid in positional characterizations.

A sequence alignment of HhFPPS, HhTPS1 and HhTPS2 proteins shows that all proteins contain the first aspartate-rich motif and second aspartate-rich motif of IDS type proteins (FIG. 21). HhFPPS appears to contain a putative transit peptide as evidenced by the extended N-terminus. HhFPPS also carries aromatic amino acids in position 4 and 5 upstream of the first aspartate-rich motif, which typically limit chain-elongation in short chain IDS enzymes (Kellogg and Poulter, 1997; Vandermoten et al., 2009). By contrast, in HhTPS1 and HhTPS2 these residues are replaced by non-aromatic amino acids. Similar residue changes have been observed in TPS proteins from *M. histrionica* and *P. striolata* (Example 1) and likely cause a change in the position of the FPP substrate facilitating a conversion of FPP to a terpene product. Further structural analysis will be required to support this hypothesis.

Expression of HhTPS1 and Site of Pheromone Production

Remarkably, *H. halys* shows high transcript levels of HhTPS1 in males and females (FIG. 31) (Sparks et al., 2017) and yet sesquipiperitol is not produced from crude protein extracts from females when assayed with the substrate (E,E)-FPP. This could be a result of post-transcriptional regulation. A lack of correlation between transcript and enzyme activity was also observed for the *P. striolata* TPS1 gene, which the authors suggest may be due to a post-transcriptional modification (Beran et al., 2016). Alternatively, the substrate (E,E)-FPP may be hydrolyzed before it can be converted to sesquipiperitol. This hypothesis may be supported by the finding of a second farnesol isomer in crude protein extract of female.

Transcript of HhTPS1 does not appear to be localized to one tissue but is found throughout the abdomen and is highest in the fat body and other soft tissues. This finding is in contrast to the tissue specific expression of MhTPS in the epithelial cells of the sternites (Example 1). An examination of the abdominal cuticle shows males and females both have a layer of epithelial cells but with different coloration. It is possible that male epithelial cells represent the specific site of pheromone storage or release even though the precursor and/or the pheromone end products could be made in the fat body.

Functions of several of the other IDS-like genes (HhIDS3-6) are not known. However, a recent study in rice showed geranylgeranyl diphosphate synthase (GGPPS) binds to the structurally similar GGPPS recruiting protein (OsGRP) and directs flow of GGPP to the thylakoid for chlorophyll biosynthesis (Zhou et al., 2017). In a separate study, active and inactive forms of farnesyl diphosphate synthase (FPPS) were found in the spruce budworm (*Choristoneura fumiferana*). When inactive enzyme CfFPPS1 was combined with the active enzyme CfFPPS2, a sharp increase in production of ethyl-branched juvenile hormone occurred (Sen et al., 2007). Given that insect TPS genes appear to be paralogs of IDS genes, a similar heterodimer formation could be possible in *H. halys*, directing subcellular trafficking and/or facilitating pheromone production.

Follow up studies in *H. halys* include qRT-PCR to measure tissue and sex expression differences, positive identification of the stereoisomer of sesquipiperitol (Ashot Khrimian, USDA, Beltsville, MD) and kinetics. If HhTPS1 does not produce a racemic mixture of sesquipiperitol, further enzymes in the pathway will need to be characterized to determine which is responsible to the natural pheromone ratio of 3.5:1 (SSRS:RSRS) (Khrimian et al., 2014b).

Methods

Insects

A greenhouse colony of *H. halys* was started from late instar nymphs collected from insecticide-free vegetable plots in Beltsville, MD. Insects were reared in cages (Bioquip) on a diet of organic green beans and shelled raw sunflower seeds and buckwheat seeds (2:1 w/w), glued onto squares of brown wrapping paper with wheat-based wallpaper paste and distilled water supplied in two cotton-stopped 7 cm×2 cm o.d. shell vials held together with a rubber band. Insects were reared in a climate controlled growth chamber (25+/−5° C., 16:8 h L: D, 65% RH). Newly eclosed adults were removed from cages three times weekly and moved to new cages, isolating males and females. Insects were kept until the immature (2-3 day post molt) or mature (14-15 day post molt) adult stage.

Crude Protein Extracts of *H. halys*

Fifteen-day old virgin male and female *H. halys* were used to prepare crude protein extracts. Whole bugs were frozen in liquid nitrogen, pulverized with a mortar and pestle, and suspended in assay buffer (25 mM HEPES, 5 mM MgCl$_2$, 10% glycerol, 0.5 mM PMSF, 1 mM DTT, pH 7). Samples were centrifuged for 15 mins at 16000×g and supernatant collected. Protein concentration was determined with a Bradford Assay (Bio-rad) according to the manufacturer's instructions.

Identification and Cloning of IDS Type Genes

Seven putative isoprenyl diphosphate synthase like genes (HhIDS1-HhIDS7) were identified by tblastn search in NCBI with organism restricted to *H. halys* and using functionally characterized insect trans-IDS query sequences from harlequin bug (*M. histrionica*) TPS and FPPS, bifunctional IDS/TPS from bark beetle (*I. pini*) or TPS from flea beetle (*P. striolata*) (FIG. 27). Primers were designed using Geneious (v. 7.1.9) to clone full-length HhIDS1-HhIDS7 genes (FIG. 28). cDNAs for HhIDS1, HhIDS2 and HhIDS7 were generated from total RNA using GoScript reverse transcriptase (Promega). Target sequences were amplified using Q5 proofreading DNA polymerase (New England Biolabs) and purified by gel extraction (New England Biolabs). Purified products were A-tailed using Taq DNA polymerase (New England Biolabs) and ligated into the pGEM-T Easy vector (Promega). Sequences were verified before cloning into expression vectors. cDNAs for HhIDS3, HhIDS4, HhIDS5 and HhIDS6 could not be amplified. Sequences for HhIDS1 (HhTPS2), HhIDS2 (HhFPPS) and HhIDS7 (HhTPS1) were verified by Sanger sequencing and have been deposited in the GenBank database under accession numbers MG870387 (HhTPS1), MG917093 (HhTPS2) and MG870389 (HhFPPS).

Heterologous Expression of Recombinant HhFPPS

Full-length HhFPPS was amplified from pGEM-T Easy construct with Q5 DNA polymerase and cloned into the pEXP5-NT/TOPO expression vector containing an N-terminal 6× histidine tag (Invitrogen). pEXP5-NT/TOPO construct was transformed into *Escherichia coli* strain BL21 (DE3) pLysS (Life Technologies). *E. coli* cultures (50 mL) were grown at 37° C. and 220 rpm and induced with 1 mM IPTG after reaching an OD600 of 0.6. Upon induction, the cells were cultivated at 18° C. for another 18 h prior to collection by centrifugation for 15 min at 5,000 g at 4° C. Pellets were resuspended in 2 mL chilled extraction buffer (50 mM Tris HCl [pH 7.5], 20 mM imidazole, 300 mM NaCl, 10% glycerol (v/v), 5 mM MgCl2, 2 mM DTT) supplemented with 0.3 mg/mL lysozyme (AppliChem), 2.5 U/mL benzonase (Novagen) and proteinase inhibitors (Protease Inhibitor Mix HP, SERVA) and incubated at 4° C. for 30 min on ice. Cells were disrupted by a 4×30 s treatment with a sonicator (Bandelin UW2070, Berlin, Germany; 50%) and lysates centrifuged at 4° C. for 30 min at 15000×g to obtain soluble fractions. Recombinant proteins were purified using Ni-NTA Spin Columns (Qiagen, Hilden, Germany) according to the manufacturer's instructions. For enzymatic assays, the buffer was exchanged with 25 mM 3-(N-morpholino)-2-hydroxypropanesulfonic acid (MOPSO, pH 7.2, 10% [v/v] glycerol, 1 mM DTT, 5 mM MgCl$_2$) using PD-10 Desalting Columns (GE Healthcare Life Sciences).

Heterologous Expression of Recombinant HhTPS1 and HhTPS2

Due to difficulties in the cloning process, HhTPS1 and HhTPS2 were designed and synthesized by GenScript (Piscataway, NJ) with codon optimization for *E. coli* and cloned into pET19b. Following transformation into *E. coli* BL21 (DE3) pLysS cells (Invitrogen), single colonies were selected at 18° C. on LB with ampicillin (100 µg/mL) and chloramphenicol (34 ug/mL). Expression cultures were started in 5 ml LB plus antibiotics prior to inoculation of 200 mL of the same medium and cultivation at 18° C. for 4-8 hours. Expression was induced at an OD600 of 0.50 with 0.5 mM IPTG. Following cultivation of 48 h, cells were washed in 100 mL wash buffer (20 mM Tris-HCl, 50 mM KCl, pH 7), pelleted and resuspended in 15 mL cell lysis buffer (50 mM NaH2PO4, 300 mM NaCl, 5 mM imidazole, 0.5 mM PMSF, 2 mM DTT, pH 8). Cells were lysed on ice for 2×30 s (1 min interval) at 20% amplitude (Branson Digital Sonifier) and the supernatant was partially purified with Ni-NTA agarose (Qiagen) using three washes of 30 mM imidazole. The target protein was eluted in a single 1 mL fraction with 250 mM imidazole and desalted into TPS assay buffer (25 mM HEPES, 10 mM MgCl2, 10% glycerol, pH 7) using PD MiniTrap G-25 desalting columns (GE Healthcare).

IDS Activity Assay and Analysis

For enzyme assays, 96 µl of partially purified protein were mixed with 2 µl 50 µM isopentenyl diphosphate (IPP; Sigma) and 2 µl 50 M dimethylallyl diphosphate (DMAPP; Sigma) and incubated at 30° C. for 2 h. Analysis of IDS enzyme products was done using an Agilent 1260 HPLC system (Agilent Technologies) coupled to an API 5000 triple-quadrupole mass spectrometer (AB Sciex Instruments) according to the protocol described by Beran et al. (2016).

TPS Activity Assay

Enzyme activity was assessed in crude protein extracts from whole male and female bugs. Enzyme assays were performed by administering 100 µM (E,E)-FPP to protein extracts (100 ug total protein) in 25 mM HEPES, 5 mM MgCl2, 10% glycerol, pH 7 at a final volume of 200 µL. An equal volume of hexane was overlaid on each preparation to collect volatiles using a 6 h incubation period at 30° C. Products were extracted by vigorously mixing preparations for 15 sec and the organic phase was separated by centrifugation at 4000×g for 10 min.

Assays with heterologously expressed protein were performed in assay buffer (see above) in a total volume of 100 µl with partially purified protein, 1 mM DTT, and 50 µM allylic substrate [(E,E)-, (Z,E)- or (Z,Z)-FPP] and incubated at 30° C. for 1 h with a 100 µL hexane overlay. Assays were stopped on ice and compounds extracted by mixing (vortex) at maximum speed for 15 sec. Phases were separated by centrifugation at 4000×g for 10 min and the hexane phase was removed and dried over MgSO4. One µl of liquid sample was injected in splitless mode and analyzed by GC-MS.

Gene Expression Analysis

Insects used for tissue-specific gene expression analysis were killed with hexane vapor in a screw top jar and dissected in PBS (137 mM NaCl, 8.1 mM Na2HPO4, 1.5 mM NaH2PO4, 2.7 mM KCl, pH 7.2). Five insects were dissected and tissues frozen in liquid nitrogen between dissections. Tissues were pooled from all five stink bugs so there was one replicate for each group. Tissue groups were midgut, abdominal soft tissue minus midgut and abdominal cuticle including attached epithelial cells. All samples were kept at −80° C. before RNA extraction. cDNAs were generated from total RNA as described above. Relative transcript abundance was measured by PCR and visualized on agarose gel. Primers were designed using Geneious (v. 7.1.9) (FIG. 28).

Gas Chromatography-Mass Spectrometry Analysis of Enzyme Products

GC-MS analysis was performed by liquid injection at 240° C. running in split 5 mode and separated on a GC-2010 gas chromatograph (Shimadzu, Kyoto, Japan) using a 30 m×0.25 mm i.d.×0.25 µm film Zebron ZB-XLB column coupled with a QP2010S mass spectrometer (Shimadzu). The GC program was as follows: 40° C. with 2 min hold, then raised to 220° C. at 5° C./min, then raised to 240° C. at 70° C./min followed by a 2 min hold time. Mass spectrometry was performed with an ion source temperature of 240° C., interface temperature of 280° C., electron ionization (EI) potential of 70 eV and scan range of 50 to 400 atomic mass units. Helium was used as a carrier gas at 1.9 mL/min. Terpene olefin products were identified by comparison of retention times and mass spectra with those of authentic standards.

Amino Acid Sequence Analysis

Amino acid sequence alignment of HhTPS1, HhTPS2 and HhFPPS was made in Geneious (v. 7.1.9) using MUSCLE with full end gap penalty.

REFERENCES FOR EXAMPLE 2

Beran, F., et al. (2016). Novel family of terpene synthases evolved from trans-isoprenyl diphosphate synthases in a flea beetle. Proc Natl Acad Sci USA 113, 2922-2927.

Christianson, D. W. (2006). Structural biology and chemistry of the terpenoid cyclases. Chem Rev 106, 3412-3442.

Gilg, A. B., Tittiger, C. and Blomquist, G. J. (2009). Unique animal prenyltransferase with monoterpene synthase activity. Naturwissenschaften 96, 731-735.

Haye, T., Gariepy, T., Hoelmer, K., Rossi, J. P., Streito, J. C., Tassus, X. and Desneux, N. (2015). Range expansion of the invasive brown marmorated stinkbug, *Halyomorpha halys*: an increasing threat to field, fruit and vegetable crops worldwide. J Pest Sci 88, 665-673.

Hoebeke, E. R. and Carter, M. E. (2003). *Halyomorpha halys* (Stal) (Heteroptera: Pentatomidae): A polyphagous plant pest from Asia newly detected in North America. P Entomol Soc Wash 105, 225-237.

Kellogg, B. A. and Poulter, C. D. (1997). Chain elongation in the isoprenoid biosynthetic pathway. Curr Opin Chem Biol 1, 570-578.

Khrimian, A., et al . . . (2014a). Determination of the stereochemistry of the aggregation pheromone of harlequin bug, *Murgantia histrionica*. J Chem Ecol 40, 1260-1268.

Khrimian, A., et al. (2014b). Discovery of the aggregation pheromone of the brown marmorated stink bug (*Halyomorpha halys*) through the creation of stereoisomeric libraries of 1-bisabolen-3-ols. J Nat Prod 77, 1708-1717.

McPherson, J. E. and Ahmad, I. (2008). Comparison of male genitalia of *Murgantia histrionica, M. varicolor*, and *M. violascens* (Hemiptera: Heteroptera: Pentatomidae). P Entomol Soc Wash 110, 1028-1033.

Sacchettini, J. C. and Poulter, C. D. (1997). Biochemistry—Creating isoprenoid diversity. Science 277, 1788-1789.

Sen, S. E., et al. (2007). Purification, properties and heteromeric association of type-1 and type-2 lepidopteran farnesyl diphosphate synthases. Insect Biochem Mol Biol 37, 819-828.

Sparks, M. E., et al. (2017). A transcriptome survey spanning life stages and sexes of the harlequin bug, *Murgantia histrionica*. Insects 8, 55.

Sparks, M. E., Shelby, K. S., Kuhar, D. and Gundersen-Rindal, D. E. (2014).

Transcriptome of the invasive brown marmorated stink bug, *Halyomorpha halys* (Stal) (Heteroptera: Pentatomidae). Plos One 9, 1-13.

Thulasiram, H. V., Erickson, H. K. and Poulter, C. D. (2007). Chimeras of two isoprenoid synthases catalyze all four coupling reactions in isoprenoid biosynthesis. Science 316, 73-76.

Vandermoten, S., Haubruge, E. and Cusson, M. (2009). New insights into short-chain prenyltransferases: structural features, evolutionary history and potential for selective inhibition. Cell Mol Life Sci 66, 3685-3695.123

Xu, J., Fonseca, D. M., Hamilton, G. C., Hoelmer, K. A. and Nielsen, A. L. (2013). Tracing the origin of US brown marmorated stink bug, *Halyomorpha halys*. Biol Inv 16, 153-166.

Zhou, W., et al. (2017). Tissue-specific emission of (E)-alpha-bergamotene helps resolve the dilemma when pollinators are also herbivores. Curr Biol 27, 1336-1341.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

Further attributes, features, and embodiments of the present invention can be understood by reference to the following numbered embodiments of the disclosed invention. Reference to disclosure in any of the preceding embodiments is applicable to any preceding numbered embodiment and to any combination of any number of preceding embodiments, as recognized by appropriate antecedent disclosure in any combination of preceding embodiments that can be made. The following numbered embodiments are provided:

1. An engineered polynucleotide comprising:
   one or more polynucleotides that is about 50-100% identical to SEQ ID NO: 3, SEQ ID NO: 4, or both.

2. The engineered polynucleotide of embodiment 1, wherein the engineered polynucleotide encodes a polypeptide that is about 50-100% identical to SEQ ID NO: 1, SEQ ID NO: 2, or both.

3. The engineered polynucleotide of any one of embodiments 1-2, further comprising a polynucleotide capable of encoding a cytochrome P450 enzyme.

4. The engineered polynucleotide of any one of embodiments 1-3, wherein the cytochrome P450 enzyme is a cytochrome P450 enzyme that is expressed by a brown marmorated stink bug, a harlequin stink bug, or both.

5. The engineered polynucleotide of any one of embodiments 1-4, further comprising a polynucleotide capable of encoding an isomerase.

6. The engineered polynucleotide of any one of embodiments 1-5, wherein the isomerase is an isomerase that is expressed by a brown marmorated stink bug, a harlequin stink bug, or both.

7. An engineered polynucleotide capable of encoding two or more of the following polypeptides:
   (a) a polypeptide that is about 50-100% identical to SEQ ID NO: 1;
   (b) a polypeptide that is about 50-100% identical to SEQ ID NO: 2;
   (c) a cytochrome P450 enzyme; and
   (d) an isomerase.

8. A vector system comprising:
   one or more polynucleotides as in any one of embodiments 1-7; and
   optionally, one or more regulatory elements, wherein one or more of the one or more regulatory elements is operably coupled to the polynucleotide.

9. The vector system of any one of embodiments 7-8, wherein the regulatory element is a plant-specific regulatory element.

10. The vector system of any one of embodiments 7-9, wherein the vector system comprises 2 or more vectors, where at least one of the vectors comprises one or more polynucleotides as in any one of embodiments 1-7.

11. An engineered stink bug pheromone synthesis system comprising:
   one or more TPS polypeptides, wherein each TPS polypeptide is about 50-100% identical to SEQ ID NO: 1, SEQ ID NO: 2, or both; and
   one or both of a cytochrome P450 polypeptide and an isomerase polypeptide.

12. The engineered stink bug pheromone synthesis system of embodiment 11, wherein the system is capable of producing
   (a) a brown marmorated stink bug pheromone;
   (b) a brown marmorated stink bug pheromone intermediate;
   (c) a harlequin stink bug pheromone;
   (d) a harlequin stink bug pheromone intermediate; or
   (e) any combination thereof.

13. The engineered stink bug pheromone synthesis system of any one of embodiments 11-12, wherein the system is capable of producing
   (a) a brown marmorated stink bug sesquipiperitol or isomer thereof;
   (b) a harlequin stink bug sesquipiperitol or isomer thereof;
   (c) a brown marmorated stink bug zingiberenol;
   (d) a harlequin stink bug zingiberenol;
   (e) a brown marmorated stink bug murgantiol;
   (f) a harlequin stink bug murgantiol; or
   (g) any combination thereof.

14. A cell comprising:
   (a) one or more engineered polynucleotide as in any one of embodiments 1-7;
   (b) a vector system as in any one of embodiments 8-10;
   (c) an engineered stink bug pheromone synthesis system of any one of embodiments 11-13; or
   (d) any combination thereof.

15. The cell of embodiment 14, wherein the cell is a plant cell.

16. The cell of embodiment 15, wherein the plant cell is of a plant species that is suitable for use as a trap crop for management of a brown marmorated stink bug, a harlequin stink bug, or both.

17. The cell of any one of embodiments 14-16, wherein the cell is capable of producing
   (a) a brown marmorated stink bug pheromone;
   (b) a brown marmorated stink bug pheromone intermediate;
   (c) a harlequin stink bug pheromone;
   (d) a harlequin stink bug pheromone intermediate; or
   (e) any combination thereof.

18. The cell of any of embodiments 14-17, wherein the cell is capable of producing
   (a) a brown marmorated stink bug sesquipiperitol or isomer thereof;
   (b) a harlequin stink bug sesquipiperitol or isomer thereof;
   (c) a brown marmorated stink bug zingiberenol;
   (d) a harlequin stink bug zingiberenol;
   (e) a brown marmorated stink bug murgantiol;
   (f) a harlequin stink bug murgantiol; or
   (g) any combination thereof.

19. An engineered plant comprising:
   (a) one or more engineered polynucleotide as in any one of embodiments 1-7;
   (b) a vector system as in any one of embodiments 8-10;
   (c) an engineered stink bug pheromone synthesis system of any one of embodiments 11-13;
   (d) a cell as in any one of embodiments 14-18; or
   (e) any combination thereof.

20. The engineered plant of embodiment 19, wherein the plant is a plant species effective as a trap crop for management of the brown marmorated stink bug, harlequin stink bug, or both.

21. The engineered plant of any one of embodiments 19-20, wherein the engineered plant expresses in one or more of its cells:
   (a) one or more engineered polynucleotide as in any one of embodiments 1-7;
   (b) an engineered stink bug pheromone synthesis system of any one of embodiments 11-13; or
   (c) both.

22. The engineered plant of any one of embodiments 19-21, wherein the engineered plant is capable of producing a brown marmorated stink bug pheromone, a harlequin stink bug pheromone, or both.

23. The engineered plant any one of embodiments 19-22, wherein the plant is capable of producing in one, some, or all of it cells;
   (a) a brown marmorated stink bug pheromone;
   (b) a brown marmorated stink bug pheromone intermediate;
   (c) a harlequin stink bug pheromone;
   (d) a harlequin stink bug pheromone intermediate; or
(e) any combination thereof.

24. The engineered plant of any one of embodiments 19-23, wherein the engineered plant is capable of producing
   (a) a brown marmorated stink bug sesquipiperitol or isomer thereof;
   (b) a harlequin stink bug sesquipiperitol or isomer thereof;
   (c) a brown marmorated stink bug zingiberenol;
   (d) a harlequin stink bug zingiberenol;
   (e) a brown marmorated stink bug murgantiol;
   (f) a harlequin stink bug murgantiol; or
   (g) any combination thereof.

25. A kit comprising:
   (a) one or more engineered polynucleotide as in any one of embodiments 1-7;
   (b) a vector system as in any one of embodiments 8-10;
   (c) an engineered stink bug pheromone synthesis system of any one of embodiments 11-13;
   (d) a cell as in any one of embodiments 14-18;
   (e) a plant as in any one of embodiments 19-24; or
   (f) any combination thereof.

26. A method of managing brown stink bug infestation, harlequin stink bug infestation, or both of a crop, comprising:
   planting an engineered plant as in any one of embodiments 19-24.

27. The method of embodiment 26, wherein the engineered plant is planted in a location next to, adjacent to, or with in effective proximity to the crop.

---

What is claimed is:

1. An engineered polynucleotide comprising: a polynucleotide that is 100% identical to SEQ ID NO: 4; and a heterologous regulatory element operatively coupled to the polynucleotide.

2. The engineered polynucleotide of claim 1, wherein the engineered polynucleotide encodes a polypeptide that is 100% identical to SEQ ID NO: 2.

* * * * *